US007217807B2

(12) United States Patent
Bentwich

(10) Patent No.: US 7,217,807 B2
(45) Date of Patent: May 15, 2007

(54) BIOINFORMATICALLY DETECTABLE GROUP OF NOVEL HIV REGULATORY GENES AND USES THEREOF

(75) Inventor: Itzhak Bentwich, Kfar Daniel (IL)

(73) Assignee: Rosetta Genomics Ltd, Rehovot (IL)

( * ) Notice: Subject to any disclaimer, the term of this patent is extended or adjusted under 35 U.S.C. 154(b) by 244 days.

(21) Appl. No.: 10/604,944

(22) Filed: Aug. 28, 2003

(65) Prior Publication Data

US 2004/0219515 A1 Nov. 4, 2004

Related U.S. Application Data

(63) Continuation-in-part of application No. 10/604,945, filed on Aug. 27, 2003, which is a continuation-in-part of application No. 10/604,943, filed on Aug. 28, 2003, and a continuation-in-part of application No. 10/604,942, filed on Aug. 28, 2003, which is a continuation of application No. 10/303,778, filed on Nov. 26, 2002, now abandoned.

(60) Provisional application No. 60/441,241, filed on Jan. 17, 2003, provisional application No. 60/441,230, filed on Jan. 16, 2003.

(51) Int. Cl.
C07H 21/00 (2006.01)
C12Q 1/68 (2006.01)
C12N 7/00 (2006.01)
G06F 19/00 (2006.01)

(52) U.S. Cl. ...................... 536/23.1; 435/6; 435/235.1; 536/24.3; 702/20

(58) Field of Classification Search ...................... None
See application file for complete search history.

(56) References Cited

U.S. PATENT DOCUMENTS

| 6,573,099 | B2 | 6/2003 | Graham | |
|---|---|---|---|---|
| 6,720,138 | B2 | 4/2004 | Sharma | |
| 6,753,139 | B1 | 6/2004 | Baulcombe | |
| 6,989,442 | B2 | 1/2006 | Vargeese | |
| 2002/0086356 | A1 | 7/2002 | Tuschl | |
| 2003/0108923 | A1 | 6/2003 | Tuschl | |
| 2003/0175950 | A1* | 9/2003 | McSwiggen | ................ 435/325 |
| 2003/0228691 | A1 | 12/2003 | Lewis | |
| 2004/0086884 | A1 | 5/2004 | Beach | |
| 2004/0106566 | A1 | 6/2004 | Lin | |
| 2004/0268441 | A1 | 12/2004 | Vance | |
| 2005/0059011 | A1 | 3/2005 | Sin | |

FOREIGN PATENT DOCUMENTS

| WO | WO 01/68836 | 9/2001 |
|---|---|---|
| WO | WO 01/75164 | 10/2001 |
| WO | WO 02/44321 | 6/2002 |
| WO | WO 02/094165 | 11/2002 |
| WO | WO 03/029459 | 4/2003 |
| WO | WO 03/070884 | 8/2003 |
| WO | WO 03/070903 | 8/2003 |
| WO | WO 03/070918 | 8/2003 |
| WO | WO 03/074654 | 9/2003 |
| WO | WO 2004/009779 | 1/2004 |

OTHER PUBLICATIONS

Brander et al. "Lack of Strong Immune Selection Pressure by the Immunodominant HLA-A*0201-restricted Cytotoxic T Lymphocyte Response in Chronic Human Immunodeficiency Virus-1 Infection" J. Clin. Invest. (Jun. 1998) vol. 101, No. 11, pp. 2559-2566.*
Elbashir, S., et al., "Duplexes of 21-Nucleotide RNAs Mediate RNA Interference in Cultured Mammalian Cells," Nature, vol. 411, pp. 494-498 (2001).
Carrington, J., et al., "Role of MicroRNAs in Plant and Animal Development," Science, vol. 301, pp. 336-338 (2003).
Coburn, Glen, et al., "Potent and Specific Inhibition of Human Immunodeficiency Virus Type 1 Replication by RNA Intereference," Journal of Virology, vol. 76, No. 18, pp. 9225-9231 (2002).
Hutvágner, G., et al., "A Cellular Function for the RNA-Interference Enzyme Dicer in the Maturation of the let-7 Small Temporal RNA," Science, vol. 293, pp. 834-838 (2001).
Mallory, A., et al., "A Viral Suppressor of RNA Silencing Differentially Regulates the Accumulation of Short Interfering RNAs and Micro-RNAs in Tobacco," PINAS, vol. 99, No. 23, pp. 15228-15233 (2002).
Li, H., et al., "Induction and Suppression of RNA Silencing by an Animal Virus," Science, vol. 296, pp. 1319-1321 (2002).
Llave, C., et al., "Virus-Encoded Suppressor of Posttranscriptional Gene Silencing Targets a Maintenance Step in the Silencing Pathway," PNAS, vol. 97, No. 24, pp. 13401-13406 (2000).
Novina, C., et al., "siRNA-Directed Inhibition of HIV-1 Infection," Nature Medicine, vol. 8, No. 7, pp. 681-686 (2002).
Provost, P., et al., "Ribonuclease Activity and RNA Binding of Recombinant Human Dicer," EMBO Journal, vol. 21, No. 21, pp. 5864-5874 (2002).
Pomerantz, R., "RNA Interference Meets HIV-1: Will Silence be Golden?" Nature Medicine, vol. 8, No. 7, pp. 659-660 (2002).
Ryo, A., et al., "Serial Analysis of Gene Expression in HIV-1 Infected T Cell Lines," FEBS Letters 462, pp. 182-186 (1999).
Smith, N., et al., "Total Silencing by Intron-Spliced Hairpin RNAs," Nature, vol. 407, pp. 319-320 (2000).

(Continued)

Primary Examiner—John S. Brusca
Assistant Examiner—Eric S. DeJong
(74) Attorney, Agent, or Firm—Polsinelli Shalton Welte Suelthaus PC; Teddy C. Scott, Jr.

(57) ABSTRACT

The present invention relates to a group of novel viral RNA regulatory genes, here identified as "viral genomic address messenger genes" or "VGAM genes", and as "genomic record" or "GR" genes. VGAM genes selectively inhibit translation of known host target genes, and are believed to represent a novel pervasive viral attack mechanism. GR genes encode an operon-like cluster of VGAM genes. VGAM and viral GR genes may therefore be useful in diagnosing, preventing and treating viral disease. Several nucleic acid molecules are provided respectively encoding several VGAM genes, as are vectors and probes, both comprising the nucleic acid molecules, and methods and systems for detecting VGAM genes, and for counteracting their activity.

5 Claims, 17 Drawing Sheets

OTHER PUBLICATIONS

Waterhouse, P., et al., "Virus Resistance and Gene Silencing in Plants can be Induced by Simultaneous Expression of Sense and Antisense RNA," Proc. Natl. Acad. Sci. USA, vol. 95, pp. 13959-13964 (1998).

Ayash-Rashkovsky, M., et al., "Generation of Th1 Immune Responses to Inactivated, gp120-Depleted HIV-1 in Mice with a Dominant Th2 Biased Immune Profile via Imunostimulatory Oligonucleotides-Relevance to AIDS Vaccines in Developing Countries," Vaccine vol. 20, pp. 2684-2692 (2002).

Jacque, J., et al., "Modulation of HIV-1 Replication by RNA Interference," Nature, vol. 418, pp. 435-438 (2002).

Merkle, I., et al., "Biological Significance of a Human Enterovirus B-Specific RNA Element in the 3' Nontranslated Region," Journal of Virology, vol. 76, No. 19, pp. 9900-9909 (2002).

Schramke, V., et al., "Hairpin RNAs and Retrotransposon LTRs Effect RNAi and Chromatin-Based Gene Silencing," Science, vol. 301, pp. 1069-1074 (2003).

Ryo, A., et al., "Identification and Characterization of Differentially Expressed mRNAs in HIV Type 1-Infected Human T Cells," Aids Research and Human Retroviruses, vol. 16, No. 10, pp. 995-1005 (2000).

Ambros, V., "MicroRNAs: Tiny Regulators with Great Potential," Cell, vol. 107, pp. 823-826 (2001).

Ambros, V., "MicroRNA Pathways in Flies and Worms: Growth, Death, Fat, Stress, and Timing," Cell, vol. 113, pp. 673-676 (2003).

Reinhart, B., et al., "The 21-Nucleotide *let-7* RNA Regulates Developmental Timing in *Caenorhabditis elegans*," Nature, vol. 403, pp. 901-906 (2000).

Lagos-Quintana, M., et al., "Identification of Novel Genes Coding for Small Expressed RNAs," Science, vol. 294, pp. 853-858 (2001).

Lee, N., et al., "Expression of Small Interfering RNAs Targeted Against HIV-1 *rev* Transcripts in Human Cells," Nature Biotechnology, vol. 19, pp. 500-505 (2002).

Morel, J., et al., "Fertile Hypomorphic ARGONAUTE (ago1) Mutants Impaired in Post-Transcriptional Gene Silencing and Virus Resistance," The Plant Cell, vol. 14, pp. 629-639 (2002).

Zhang, M., "Large-Scale Gene Expression Data Analysis: A New Challenge to Computational Biologists," Genome Research, vol. 9, pp. 681-688 (1999).

Fire, A. et al.; Nature 1998;391:806-811; Macmillan Publishers Ltd, London, United Kingdom.

\* cited by examiner

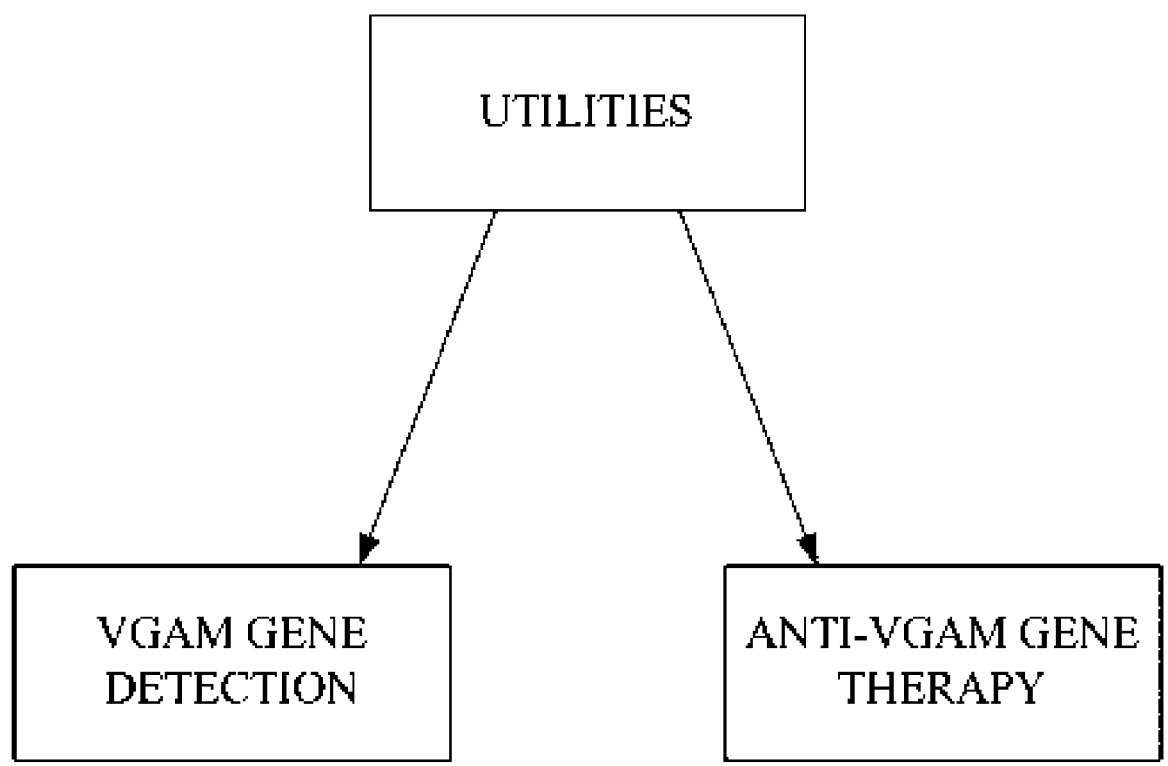

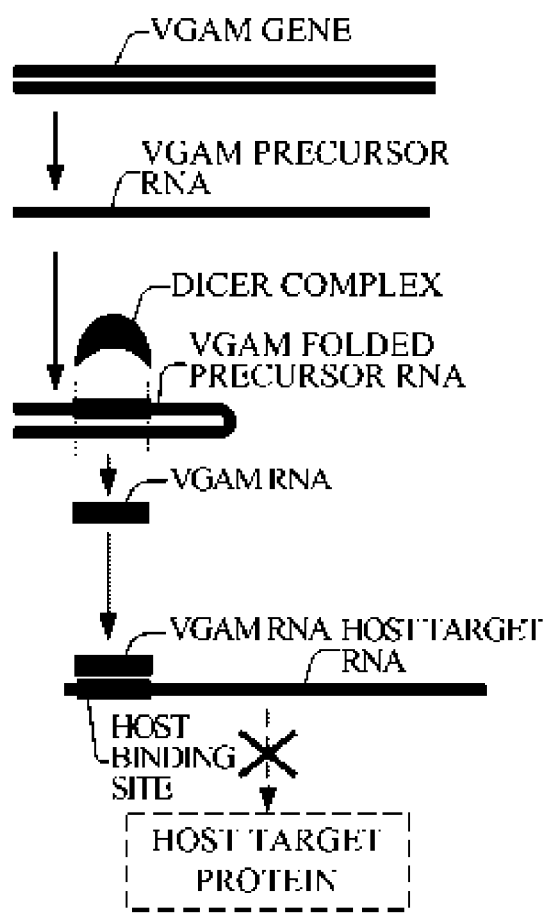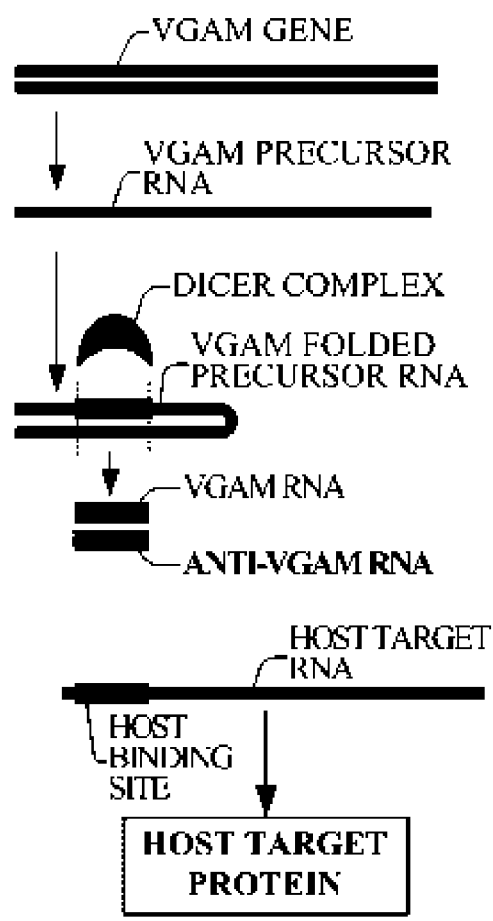

EST72223 sequence:

FIG. 12A

CCCTTATTAGAGGATTCTGCTCATGCCAGG**GTGAGGTAGTAAGTTGT
ATTGTTGTGGGGTAGGGATATTAGGCCCCAATTAGAAGATAACTAT
ACAACTTACTACTTTCCC**TGGTGTGTGGCATATTCACACTTAGTCTTA
GCAGTGTTGCCTCCATCAGACAAAGTTGTAGATGTTCCTTGGATAATT
TGGACTGGAAGAAAAGAGACATGGAAGGGGACAGATGGTGTTTAGG
GTGAGGCAGATGTCATTATAAAGTGACTTGTCTTTCATTAATTGGAGC
ATATAATTATTTTACCTTTGGGCATGAACTCATTTTGCTATTCTTCAAC
TGTGTAATGATTGCATTTTATTAGTAATAGAACAGGAATGTGTGCAAG
GGAATGGAAAGCATACTTTAAGAATTTTGGGCCAGGCGCGGTGGTTC
ATGCCTGTAATCCCAGCATTTTTGGGAGGCCGAGGCGGGTGGATCA
CCTGAGGTCAGGAGTTCGAGACCAACCTGGCCAACACGGCGAAACC
CCGCCTCTACTCAAATACAAAAATTAGCCAGGCTTGGTGACACTCGC
CTGTGGTCCCAGCTACTCAGGAGGCTGAGGCAGGAG**AATTGCTTGA
ACCCAGGAAGTGGAGGCTTCAGTGAGCTGAGAACACGCCACTGCA**
CTCCAGTCCTGGGCAACAGAGCAAGACTCTGTCTCAGGAAAAAAA
AG

MIR98

GAM24

FIG. 12B

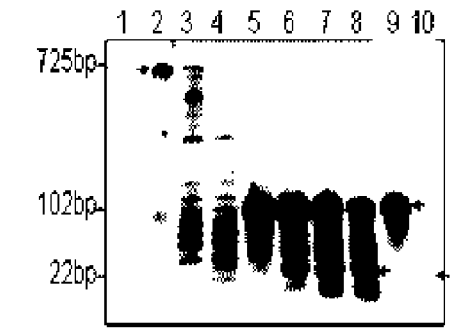

MIR98

FIG. 12C

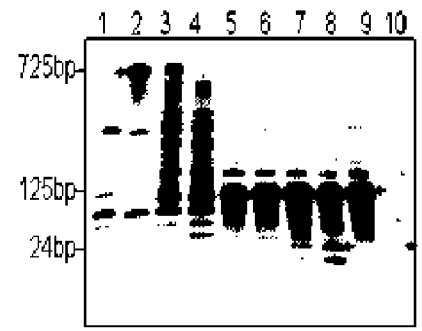

GAM24

FIG. 12D

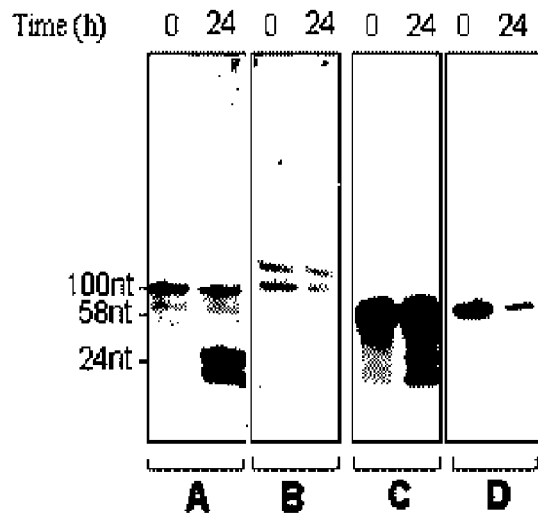

FIG. 13A

```
dbEST Id.7929020(Image4514344) sequence:
GCAAAACTGGAAGCATTCCCTTTGAAAACTGGCACAAGACAGGGATGCCCTCT
CTCACCCTCCTATTCAACATAGTGTTGGAAGTTCTGCCCAGGGCAATTAGGCA
GGAGAAGGAAATAAAGGGTATTCAATTAGGAAAAGAGCAAGTCAAATTGTTCCT
GTTTGCAGATGACATGATTGTATATCTAGAAAACCCCATTGTCTCAGCCCCAAA
TCTCCTTAAGCTGATAAGCAACTTCAGCAAAGTCTCAGGATACAAAATAAATGT
ACAAAAATCACAAGCATTCTTACACACCAACAGAAAAACAGAGCCAAATCA
TGAGTGAACTCCCATTCACAATTGCTTCAAAGAGAATAAAATACCTAGGAATCC
AACTTACAAGGATCTGAAGCACCTCTTCAAGGAGAACTACAAACCACTGCTCA
AGGAAATAAAAGAGGATACAAACAAATGGAAGAACATTCCATGCTCATGGGTAG
GAAGAATCAATATTGTGAAAATGGCCATACTGCCCAAGGTAATTTACAGATTCA
ATCCATCCCCATCAAGCTACCAATGACTTTCTTCACAGAATTCCAAAAAACTA
CTTTAAAGTTCATATGGAACCAAAAAAGAGCCCGCATCGCCAAGTCAATCCTAA
GCCAAAAGAACAAAGCTGGAGGCATCACACTACCTGACTTCAAACTTTACTACA  GAM23
AGGCTACAGTAACCAAAACAGGATGGTACTGGTACCAAAACAGACATATAGATC
AATGGAACAGAACAGAGCCCTCAGAAATAACGCCGAATACCTACAACTATCTGA
TCTTTGACAAACCTGAGAAAACAAGCAATGGGGAAGGATTCCCTATTTAATA
AATGGTGCTGGGAAAACTGACTAGCCATATGTACAAAGCTGAAACTGGATCCCT
TCCTTACACCTTATACAAAAATCAATTCAAGATGGATTAAAGATTTAAACGTTA
GACCTAAAACCATAAAAACCCTAGAAGAAAACCTAGGCATTACCATTCAGGACA
TAGGCATGGGCAAGGACTTCATGTCCAAAACACCAAAAGCAATGGCAACAAAAG
ACAAAATTGACAAATGGGATCTAATTAAACTAAAGAGCTTCTGCACAGCAAAAG
AAACTACCATCAGAGTGAACAGGCAACCTACAAAATGGGAGAAAATTTTCGCAA  GAM2
CCTACTCATCTGACAAAGGGCTAATATCCAGAATCTACAATGAACTCAAACAAA     5
TTTACAAAAAAAAAAAAAAAA
```

FIG. 13B

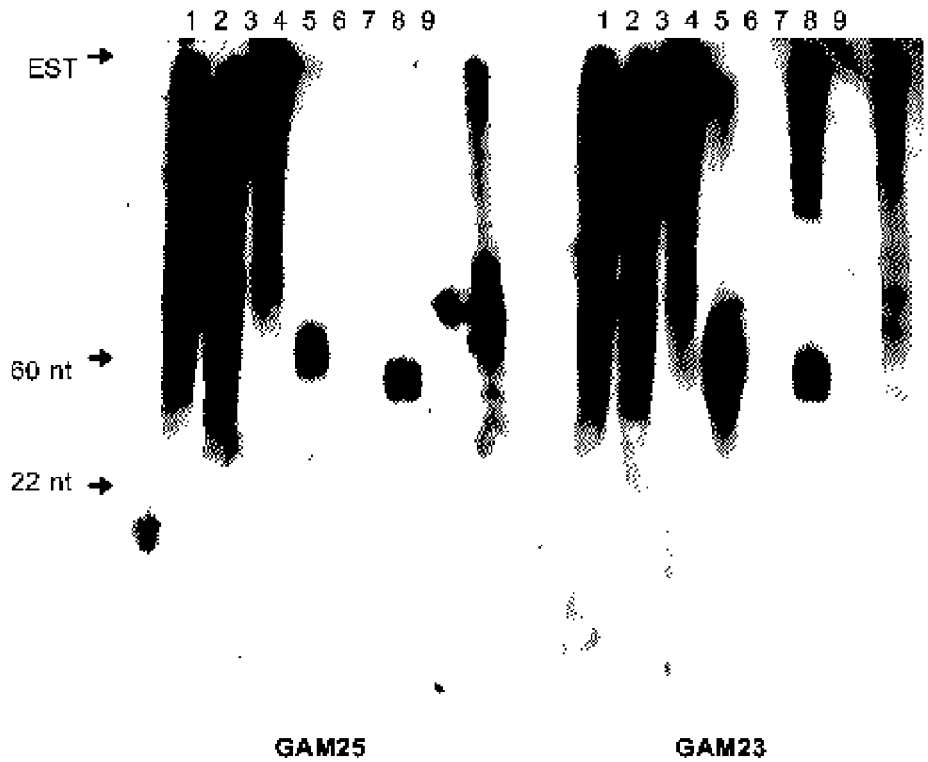

GAM25                                    GAM23

GAM25

FIG. 14A dbEST Id.1388749 (Image1020185) Sequence:
ACTCCTATCAACAGTGTAAAAGCATTCCTGTTTCTCCATAATCTTGCCAGCATCTT
TTCATTTTTTTGAATTATAGCCATTCTGACTGTTGTGACATGGTGTCTCATTGTCG
TTTTGATTTGCATTTCTCAGATGATCAGTGATGTTGAAGTTTTTTTGTTTGTTGGC
TGCATGTATGCCTTCTTTTGAAAAGTGTCTGTTTGTGTCCTTTGACCACTTTCTAA
TGGGGTTCAGTTTTTTTTTCTTGTAAATTTGTTTAAGTTCCTTGTAGATGCTGGAT
ATTAGACCTTTGTCAGATGGATAGAGTGCAAAAATTTTCTCCCATTCTGTAGGTTG
TCGGTTTACTCTGTTGATAGGTTCTTAATGCTGTGCAGAAGCTCTTTAGTTTAATT
AGATCCCATTTGTCAATTTTGCCTTTTGTTGCAATTGCTTTTGGCATCTTCGTCAT
GAAATCTTTGCCCTTGCCTGTGTCCTGAATGGCATTGCCTAGGTTTTCTTCCAGGA
TTTTTATAGTTTTGGGTTGTAGATTTAAGTCTTTAATCCATCTTGAGTTAACTTTT
GTATATGGGTTAAGGAAGGGGCCCGTTTCAATTTGCTGCAAATGGCTAGCCAGTTC
TCCCAGCACCATTTATTAAATAGGGAATCTTTTCCCCATTGCTTCCTTTTGTCAGG
TTTGTCAAAGATCACATGGTTGTAGGTGTGTGGTCTTATTTCTGGGTTCTCTATTC
TGTTCCATTGGGCTATGGGCCGGTTCTGTACCACCACTATGCTGTTTGGGTACCA
TAGTCTTGTAGAATGTTTGAAGCTGGGTAGCATGATGCCTCTAGCTTTGCTCTTCT
TGCTAAGAAATGTCTTGGCTATTTGGGCTCTTTTTGGTTCCATATGAATTTTAAA
ATAGCTTTTCTAGGTCTGTAAAGAATGTGAATAGTAGTTTAATGGGCCTAGCATT
TAATTTACAGATTGCCTTGGGCAGTGTGGTCATTTTCAGGATATTGATCCTTCCTG
TCTGTGAGCATATGTTTTCCATTTGTTTGTGTCATCTCTGATTTCTTTGAATAAT
GGTTTATAGTTATCCTTGAAAAGGTCCTTCACTTTTCTTGTTAGCTGTATTCCTAG
ATATTATACTCTTCTTGTGGCAATTGTGAATGGGAGTTAATTCATGAGTTTTCTCT
CGGCTTGCCTGTTGTTGGTGTATAGGAATGCTAGTGACTTTGCACATTGATTTTG
TATCCTGAGACTTTGTTGAAGTTCCTTATCAGCTAACAAGTTTTTGAGCTGAGATG
ATGGAGTTTTCTAGATATAGGATCATATCATCTGCAAACAAAGATAGTTTGACTTC
CTGTCTTCCTATTTGAATAGCTTTTCTTTCTTTCTCTTGCCTGATTGCCTTGGTGA
CAATTTCTAATACTGTGTTGAATAGGAGTGGTGAGCTCCTGCCAA

GAM 26

FIG. 14B

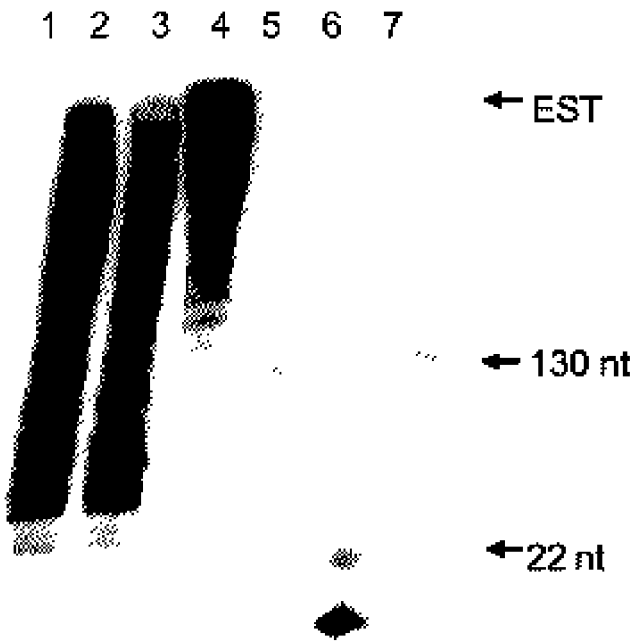

GAM26

& 1

SEQUENCE LISTING

<160> NUMBER OF SEQ ID NOS: 406

<210> SEQ ID NO 1
<211> LENGTH: 51
<212> TYPE: DNA
<213> ORGANISM: Human immunodeficiency virus 1

<400> SEQUENCE: 1
caatgagtcc gagatcttca gacctggagg aggagatatg agggacaatt g       51

<210> SEQ ID NO 2
<211> LENGTH: 52
<212> TYPE: DNA
<213> ORGANISM: Human immunodeficiency virus 1

<400> SEQUENCE: 2
catatgtatg tttcagggaa agctagggga tggttttata gacatcacta tg      52

<210> SEQ ID NO 3
<211> LENGTH: 59
<212> TYPE: DNA
<213> ORGANISM: Human immunodeficiency virus 1

<400> SEQUENCE: 3
ccactctatt ttgtgcatca gatgctaaag catatgatac agaggtacat aatgtttgg    59

<210> SEQ ID NO 4
<211> LENGTH: 64
<212> TYPE: DNA
<213> ORGANISM: Human immunodeficiency virus 1

<400> SEQUENCE: 4
ccataatgat gcagagaggc aattttagga accaaagaaa gattgttaag tgtttcaatt   60
gtgg       64

<210> SEQ ID NO 5
<211> LENGTH: 52
<212> TYPE: DNA
<213> ORGANISM: Human immunodeficiency virus 1

<400> SEQUENCE: 5
ccattgacag aagaaaaaat aaaagcatta gtagaaattt gtacagagat gg      52

<210> SEQ ID NO 6
<211> LENGTH: 65
<212> TYPE: DNA
<213> ORGANISM: Human immunodeficiency virus 1

<400> SEQUENCE: 6
cctctattgt gtgcatcaaa ggatagagat aaaagacacc aaggaagctt tagacaagat   60
agagg      65

<210> SEQ ID NO 7
<211> LENGTH: 52
<212> TYPE: DNA
<213> ORGANISM: Human immunodeficiency virus 1

<400> SEQUENCE: 7
gaatagtttt tgctgtactt tctatagtga atagagttag gcagggatat tc    52

<210> SEQ ID NO 8
<211> LENGTH: 67
<212> TYPE: DNA
<213> ORGANISM: Human immunodeficiency virus 1

<400> SEQUENCE: 8
gccacatacc tagaagaata agacagggct tggaaaggat tttgctataa gatgggtggc    60
aagtggt    67

<210> SEQ ID NO 9
<211> LENGTH: 52
<212> TYPE: DNA
<213> ORGANISM: Human immunodeficiency virus 1

<400> SEQUENCE: 9
ggagacagcg acgaagagct catcagaaca gtcagactca tcaagcttct ct    52

<210> SEQ ID NO 10
<211> LENGTH: 51
<212> TYPE: DNA
<213> ORGANISM: Human immunodeficiency virus 1

<400> SEQUENCE: 10
ggtccaaaat gcgaacccag attgtaagac tattttaaaa gcattgggac c    51

<210> SEQ ID NO 11
<211> LENGTH: 69
<212> TYPE: DNA
<213> ORGANISM: Human immunodeficiency virus 1

<400> SEQUENCE: 11
gtactgggtc tctctggtta gaccagatct gagcctggga gctctctggc taactaggga    60
acccactgc    69

<210> SEQ ID NO 12
<211> LENGTH: 54
<212> TYPE: DNA
<213> ORGANISM: Human immunodeficiency virus 1

<400> SEQUENCE: 12
taattggaag aaatctgttg actcagattg gttgcacttt aaattttccc atta    54

<210> SEQ ID NO 13
<211> LENGTH: 50
<212> TYPE: DNA
<213> ORGANISM: Human immunodeficiency virus 1

<400> SEQUENCE: 13
tctttggcaa cgacccctcg tcacaataaa gatagggggg caactaaagg    50

<210> SEQ ID NO 14
<211> LENGTH: 77
<212> TYPE: DNA

<213> ORGANISM: Human immunodeficiency virus 1

<400> SEQUENCE: 14
ttaccctata gtgcagaaca tccagggggca aatggtacat caggccatat cacctagaac    60
tttaaatgca tgggtaa    77

<210> SEQ ID NO 15
<211> LENGTH: 55
<212> TYPE: DNA
<213> ORGANISM: Human immunodeficiency virus 1

<400> SEQUENCE: 15
ttcattgcca gtttgtttc ataacaaaag ccttaggcat ctcctatggc aggaa    55

<210> SEQ ID NO 16
<211> LENGTH: 24
<212> TYPE: DNA
<213> ORGANISM: Human immunodeficiency virus 1

<400> SEQUENCE: 16
tgagtccgag atcttcagac ctgg    24

<210> SEQ ID NO 17
<211> LENGTH: 19
<212> TYPE: DNA
<213> ORGANISM: Human immunodeficiency virus 1

<400> SEQUENCE: 17
ttttatagac atcactatg    19

<210> SEQ ID NO 18
<211> LENGTH: 24
<212> TYPE: DNA
<213> ORGANISM: Human immunodeficiency virus 1

<400> SEQUENCE: 18
tatgatacag aggtacataa tgtt    24

<210> SEQ ID NO 19
<211> LENGTH: 19
<212> TYPE: DNA
<213> ORGANISM: Human immunodeficiency virus 1

<400> SEQUENCE: 19
ttaagtgttt caattgtgg    19

<210> SEQ ID NO 20
<211> LENGTH: 24
<212> TYPE: DNA
<213> ORGANISM: Human immunodeficiency virus 1

<400> SEQUENCE: 20
tgacagaaga aaaaataaaa gcat    24

<210> SEQ ID NO 21
<211> LENGTH: 24
<212> TYPE: DNA
<213> ORGANISM: Human immunodeficiency virus 1

<400> SEQUENCE: 21
tattgtgtgc atcaaaggat agag    24

```
<210> SEQ ID NO 22
<211> LENGTH: 24
<212> TYPE: DNA
<213> ORGANISM: Human immunodeficiency virus 1

<400> SEQUENCE: 22
tagtttttgc tgtactttct atag                                          24

<210> SEQ ID NO 23
<211> LENGTH: 20
<212> TYPE: DNA
<213> ORGANISM: Human immunodeficiency virus 1

<400> SEQUENCE: 23
taagatgggt ggcaagtggt                                               20

<210> SEQ ID NO 24
<211> LENGTH: 20
<212> TYPE: DNA
<213> ORGANISM: Human immunodeficiency virus 1

<400> SEQUENCE: 24
cagactcatc aagcttctct                                               20

<210> SEQ ID NO 25
<211> LENGTH: 24
<212> TYPE: DNA
<213> ORGANISM: Human immunodeficiency virus 1

<400> SEQUENCE: 25
tccaaaatgc gaacccagat tgta                                          24

<210> SEQ ID NO 26
<211> LENGTH: 24
<212> TYPE: DNA
<213> ORGANISM: Human immunodeficiency virus 1

<400> SEQUENCE: 26
tctctggtta gaccagatct gagc                                          24

<210> SEQ ID NO 27
<211> LENGTH: 24
<212> TYPE: DNA
<213> ORGANISM: Human immunodeficiency virus 1

<400> SEQUENCE: 27
ttggttgcac tttaaatttt ccca                                          24

<210> SEQ ID NO 28
<211> LENGTH: 24
<212> TYPE: DNA
<213> ORGANISM: Human immunodeficiency virus 1

<400> SEQUENCE: 28
tggcaacgac ccctcgtcac aata                                          24

<210> SEQ ID NO 29
<211> LENGTH: 24
<212> TYPE: DNA
<213> ORGANISM: Human immunodeficiency virus 1

<400> SEQUENCE: 29
tatagtgcag aacatccagg ggca                                          24
```

```
<210> SEQ ID NO 30
<211> LENGTH: 24
<212> TYPE: DNA
<213> ORGANISM: Human immunodeficiency virus 1

<400> SEQUENCE: 30
agccttaggc atctcctatg gcag                                          24

<210> SEQ ID NO 31
<211> LENGTH: 20
<212> TYPE: DNA
<213> ORGANISM: Human immunodeficiency virus 1

<400> SEQUENCE: 31
atgctttcat tttttcactg                                               20

<210> SEQ ID NO 32
<211> LENGTH: 19
<212> TYPE: DNA
<213> ORGANISM: Human immunodeficiency virus 1

<400> SEQUENCE: 32
ttttattctt tcttcttca                                                19

<210> SEQ ID NO 33
<211> LENGTH: 22
<212> TYPE: DNA
<213> ORGANISM: Human immunodeficiency virus 1

<400> SEQUENCE: 33
gaaaattgaa aagtacaact aa                                            22

<210> SEQ ID NO 34
<211> LENGTH: 18
<212> TYPE: DNA
<213> ORGANISM: Human immunodeficiency virus 1

<400> SEQUENCE: 34
accacttgcc acgctgtt                                                 18

<210> SEQ ID NO 35
<211> LENGTH: 21
<212> TYPE: DNA
<213> ORGANISM: Human immunodeficiency virus 1

<400> SEQUENCE: 35
ggaaaaaaag actgcaacca a                                             21

<210> SEQ ID NO 36
<211> LENGTH: 17
<212> TYPE: DNA
<213> ORGANISM: Human immunodeficiency virus 1

<400> SEQUENCE: 36
agagaagtgt gaccctg                                                  17

<210> SEQ ID NO 37
<211> LENGTH: 22
<212> TYPE: DNA
<213> ORGANISM: Human immunodeficiency virus 1

<400> SEQUENCE: 37
ccaggtctaa acagctgacc ca                                            22
```

-continued

<210> SEQ ID NO 38
<211> LENGTH: 19
<212> TYPE: DNA
<213> ORGANISM: Human immunodeficiency virus 1

<400> SEQUENCE: 38
agagaagctg gtaattctg                                                  19

<210> SEQ ID NO 39
<211> LENGTH: 19
<212> TYPE: DNA
<213> ORGANISM: Human immunodeficiency virus 1

<400> SEQUENCE: 39
gggaaaagca gtaaaccaa                                                  19

<210> SEQ ID NO 40
<211> LENGTH: 17
<212> TYPE: DNA
<213> ORGANISM: Human immunodeficiency virus 1

<400> SEQUENCE: 40
gcttttctct tctgtca                                                    17

<210> SEQ ID NO 41
<211> LENGTH: 18
<212> TYPE: DNA
<213> ORGANISM: Human immunodeficiency virus 1

<400> SEQUENCE: 41
accacttgaa acatttta                                                   18

<210> SEQ ID NO 42
<211> LENGTH: 18
<212> TYPE: DNA
<213> ORGANISM: Human immunodeficiency virus 1

<400> SEQUENCE: 42
ccaggtgttc tacactca                                                   18

<210> SEQ ID NO 43
<211> LENGTH: 20
<212> TYPE: DNA
<213> ORGANISM: Human immunodeficiency virus 1

<400> SEQUENCE: 43
atgctttcat tttttcactg                                                 20

<210> SEQ ID NO 44
<211> LENGTH: 20
<212> TYPE: DNA
<213> ORGANISM: Human immunodeficiency virus 1

<400> SEQUENCE: 44
atgctttcat tttttcactg                                                 20

<210> SEQ ID NO 45
<211> LENGTH: 20
<212> TYPE: DNA
<213> ORGANISM: Human immunodeficiency virus 1

<400> SEQUENCE: 45
atgctttcat tttttcactg                                              20

<210> SEQ ID NO 46
<211> LENGTH: 20
<212> TYPE: DNA
<213> ORGANISM: Human immunodeficiency virus 1

<400> SEQUENCE: 46
atgctttcat tttttcactg                                              20

<210> SEQ ID NO 47
<211> LENGTH: 20
<212> TYPE: DNA
<213> ORGANISM: Human immunodeficiency virus 1

<400> SEQUENCE: 47
atgctttcat tttttcactg                                              20

<210> SEQ ID NO 48
<211> LENGTH: 20
<212> TYPE: DNA
<213> ORGANISM: Human immunodeficiency virus 1

<400> SEQUENCE: 48
agactgacct tgatgagctg                                              20

<210> SEQ ID NO 49
<211> LENGTH: 17
<212> TYPE: DNA
<213> ORGANISM: Human immunodeficiency virus 1

<400> SEQUENCE: 49
ttgggttcca cttcgga                                                 17

<210> SEQ ID NO 50
<211> LENGTH: 18
<212> TYPE: DNA
<213> ORGANISM: Human immunodeficiency virus 1

<400> SEQUENCE: 50
caggcagatc tcagactc                                                18

<210> SEQ ID NO 51
<211> LENGTH: 17
<212> TYPE: DNA
<213> ORGANISM: Human immunodeficiency virus 1

<400> SEQUENCE: 51
accacttgcc tctttct                                                 17

<210> SEQ ID NO 52
<211> LENGTH: 18
<212> TYPE: DNA
<213> ORGANISM: Human immunodeficiency virus 1

<400> SEQUENCE: 52
agagaagcca tgcgttcc                                                18

<210> SEQ ID NO 53
<211> LENGTH: 16
<212> TYPE: DNA
<213> ORGANISM: Human immunodeficiency virus 1

<400> SEQUENCE: 53

```
accactacat ccatct                                                16

<210> SEQ ID NO 54
<211> LENGTH: 16
<212> TYPE: DNA
<213> ORGANISM: Human immunodeficiency virus 1

<400> SEQUENCE: 54
agggagggat gggtct                                                16

<210> SEQ ID NO 55
<211> LENGTH: 17
<212> TYPE: DNA
<213> ORGANISM: Human immunodeficiency virus 1

<400> SEQUENCE: 55
agagaagctg atgcctc                                               17

<210> SEQ ID NO 56
<211> LENGTH: 19
<212> TYPE: DNA
<213> ORGANISM: Human immunodeficiency virus 1

<400> SEQUENCE: 56
agagaaacga gtgagtttg                                             19

<210> SEQ ID NO 57
<211> LENGTH: 16
<212> TYPE: DNA
<213> ORGANISM: Human immunodeficiency virus 1

<400> SEQUENCE: 57
cgcaccaccc atttta                                                16

<210> SEQ ID NO 58
<211> LENGTH: 18
<212> TYPE: DNA
<213> ORGANISM: Human immunodeficiency virus 1

<400> SEQUENCE: 58
agagaagctg gaagcctg                                              18

<210> SEQ ID NO 59
<211> LENGTH: 17
<212> TYPE: DNA
<213> ORGANISM: Human immunodeficiency virus 1

<400> SEQUENCE: 59
agaaagccat gagtttg                                               17

<210> SEQ ID NO 60
<211> LENGTH: 20
<212> TYPE: DNA
<213> ORGANISM: Human immunodeficiency virus 1

<400> SEQUENCE: 60
tttttttttt tcttctgcca                                            20

<210> SEQ ID NO 61
<211> LENGTH: 17
<212> TYPE: DNA
<213> ORGANISM: Human immunodeficiency virus 1
```

```
<400> SEQUENCE: 61
accacttctt ttcatct                                              17

<210> SEQ ID NO 62
<211> LENGTH: 19
<212> TYPE: DNA
<213> ORGANISM: Human immunodeficiency virus 1

<400> SEQUENCE: 62
ccataaatga aacacttga                                            19

<210> SEQ ID NO 63
<211> LENGTH: 16
<212> TYPE: DNA
<213> ORGANISM: Human immunodeficiency virus 1

<400> SEQUENCE: 63
agggtagctg agtctg                                               16

<210> SEQ ID NO 64
<211> LENGTH: 21
<212> TYPE: DNA
<213> ORGANISM: Human immunodeficiency virus 1

<400> SEQUENCE: 64
tacaattgtc ccagttcgca t                                         21

<210> SEQ ID NO 65
<211> LENGTH: 18
<212> TYPE: DNA
<213> ORGANISM: Human immunodeficiency virus 1

<400> SEQUENCE: 65
accacttgaa ttgatctt                                             18

<210> SEQ ID NO 66
<211> LENGTH: 18
<212> TYPE: DNA
<213> ORGANISM: Human immunodeficiency virus 1

<400> SEQUENCE: 66
agagaagctt catgtttg                                             18

<210> SEQ ID NO 67
<211> LENGTH: 21
<212> TYPE: DNA
<213> ORGANISM: Human immunodeficiency virus 1

<400> SEQUENCE: 67
tacagatgat tacgcatttt g                                         21

<210> SEQ ID NO 68
<211> LENGTH: 20
<212> TYPE: DNA
<213> ORGANISM: Human immunodeficiency virus 1

<400> SEQUENCE: 68
agagaagctt gatcttggag                                           20

<210> SEQ ID NO 69
<211> LENGTH: 17
<212> TYPE: DNA
<213> ORGANISM: Human immunodeficiency virus 1
```

```
<400> SEQUENCE: 69
accacctgcc cccacct                                               17

<210> SEQ ID NO 70
<211> LENGTH: 21
<212> TYPE: DNA
<213> ORGANISM: Human immunodeficiency virus 1

<400> SEQUENCE: 70
ccagacctag ggctggactc a                                          21

<210> SEQ ID NO 71
<211> LENGTH: 20
<212> TYPE: DNA
<213> ORGANISM: Human immunodeficiency virus 1

<400> SEQUENCE: 71
gctcagagtt gttaaccaga                                            20

<210> SEQ ID NO 72
<211> LENGTH: 19
<212> TYPE: DNA
<213> ORGANISM: Human immunodeficiency virus 1

<400> SEQUENCE: 72
catagtgacg tcctgaaga                                             19

<210> SEQ ID NO 73
<211> LENGTH: 19
<212> TYPE: DNA
<213> ORGANISM: Human immunodeficiency virus 1

<400> SEQUENCE: 73
agaaaagctt gagcaagtc                                             19

<210> SEQ ID NO 74
<211> LENGTH: 19
<212> TYPE: DNA
<213> ORGANISM: Human immunodeficiency virus 1

<400> SEQUENCE: 74
agaaaagctt gagcaagtc                                             19

<210> SEQ ID NO 75
<211> LENGTH: 19
<212> TYPE: DNA
<213> ORGANISM: Human immunodeficiency virus 1

<400> SEQUENCE: 75
agaaaagctt gagcaagtc                                             19

<210> SEQ ID NO 76
<211> LENGTH: 20
<212> TYPE: DNA
<213> ORGANISM: Human immunodeficiency virus 1

<400> SEQUENCE: 76
catagtgaaa gtttataaga                                            20

<210> SEQ ID NO 77
<211> LENGTH: 19
<212> TYPE: DNA
```

<213> ORGANISM: Human immunodeficiency virus 1

<400> SEQUENCE: 77
ccacaattga aatttttaa					19

<210> SEQ ID NO 78
<211> LENGTH: 17
<212> TYPE: DNA
<213> ORGANISM: Human immunodeficiency virus 1

<400> SEQUENCE: 78
ccattggaaa catttaa					17

<210> SEQ ID NO 79
<211> LENGTH: 21
<212> TYPE: DNA
<213> ORGANISM: Human immunodeficiency virus 1

<400> SEQUENCE: 79
tgcccctgga tctaccagca t					21

<210> SEQ ID NO 80
<211> LENGTH: 21
<212> TYPE: DNA
<213> ORGANISM: Human immunodeficiency virus 1

<400> SEQUENCE: 80
attgtgacaa gaattgttac c					21

<210> SEQ ID NO 81
<211> LENGTH: 17
<212> TYPE: DNA
<213> ORGANISM: Human immunodeficiency virus 1

<400> SEQUENCE: 81
cattttgaaa tacttaa					17

<210> SEQ ID NO 82
<211> LENGTH: 18
<212> TYPE: DNA
<213> ORGANISM: Human immunodeficiency virus 1

<400> SEQUENCE: 82
accctgcccc acccatct					18

<210> SEQ ID NO 83
<211> LENGTH: 21
<212> TYPE: DNA
<213> ORGANISM: Human immunodeficiency virus 1

<400> SEQUENCE: 83
ccacagggag caaacactta g					21

<210> SEQ ID NO 84
<211> LENGTH: 25
<212> TYPE: DNA
<213> ORGANISM: Human immunodeficiency virus 1

<400> SEQUENCE: 84
atgctcatat cattttctt cttca				25

<210> SEQ ID NO 85
<211> LENGTH: 18

-continued

```
<212> TYPE: DNA
<213> ORGANISM: Human immunodeficiency virus 1

<400> SEQUENCE: 85
agagaagcag gggagctc                                                 18

<210> SEQ ID NO 86
<211> LENGTH: 17
<212> TYPE: DNA
<213> ORGANISM: Human immunodeficiency virus 1

<400> SEQUENCE: 86
aggggagcga tgagctg                                                  17

<210> SEQ ID NO 87
<211> LENGTH: 19
<212> TYPE: DNA
<213> ORGANISM: Human immunodeficiency virus 1

<400> SEQUENCE: 87
agagaagctc ataagtgtg                                                19

<210> SEQ ID NO 88
<211> LENGTH: 18
<212> TYPE: DNA
<213> ORGANISM: Human immunodeficiency virus 1

<400> SEQUENCE: 88
accacttata tcaactta                                                 18

<210> SEQ ID NO 89
<211> LENGTH: 17
<212> TYPE: DNA
<213> ORGANISM: Human immunodeficiency virus 1

<400> SEQUENCE: 89
agagaagcag gagtctg                                                  17

<210> SEQ ID NO 90
<211> LENGTH: 18
<212> TYPE: DNA
<213> ORGANISM: Human immunodeficiency virus 1

<400> SEQUENCE: 90
ccctggatcc tcacacta                                                 18

<210> SEQ ID NO 91
<211> LENGTH: 16
<212> TYPE: DNA
<213> ORGANISM: Human immunodeficiency virus 1

<400> SEQUENCE: 91
ccagggagac acttaa                                                   16

<210> SEQ ID NO 92
<211> LENGTH: 17
<212> TYPE: DNA
<213> ORGANISM: Human immunodeficiency virus 1

<400> SEQUENCE: 92
agaaaggtat gagtttg                                                  17

<210> SEQ ID NO 93
```

```
-continued

<211> LENGTH: 19
<212> TYPE: DNA
<213> ORGANISM: Human immunodeficiency virus 1

<400> SEQUENCE: 93
ccacaaaaga aacacttaa                                              19

<210> SEQ ID NO 94
<211> LENGTH: 22
<212> TYPE: DNA
<213> ORGANISM: Human immunodeficiency virus 1

<400> SEQUENCE: 94
atgcttcttt tttcttctgt ta                                          22

<210> SEQ ID NO 95
<211> LENGTH: 19
<212> TYPE: DNA
<213> ORGANISM: Human immunodeficiency virus 1

<400> SEQUENCE: 95
tgcaggtttt tcttcttca                                              19

<210> SEQ ID NO 96
<211> LENGTH: 22
<212> TYPE: DNA
<213> ORGANISM: Human immunodeficiency virus 1

<400> SEQUENCE: 96
agaaaagcgg gttttgggtc tg                                          22

<210> SEQ ID NO 97
<211> LENGTH: 22
<212> TYPE: DNA
<213> ORGANISM: Human immunodeficiency virus 1

<400> SEQUENCE: 97
tgcccctgga catgtttcct ac                                          22

<210> SEQ ID NO 98
<211> LENGTH: 18
<212> TYPE: DNA
<213> ORGANISM: Human immunodeficiency virus 1

<400> SEQUENCE: 98
accactcgac tcatcttg                                               18

<210> SEQ ID NO 99
<211> LENGTH: 18
<212> TYPE: DNA
<213> ORGANISM: Human immunodeficiency virus 1

<400> SEQUENCE: 99
aggcgcctga tgagttca                                               18

<210> SEQ ID NO 100
<211> LENGTH: 18
<212> TYPE: DNA
<213> ORGANISM: Human immunodeficiency virus 1

<400> SEQUENCE: 100
tacaatctgg acttggta                                               18
```

```
<210> SEQ ID NO 101
<211> LENGTH: 20
<212> TYPE: DNA
<213> ORGANISM: Human immunodeficiency virus 1

<400> SEQUENCE: 101
acatctgggt tcaaattctg                                               20

<210> SEQ ID NO 102
<211> LENGTH: 16
<212> TYPE: DNA
<213> ORGANISM: Human immunodeficiency virus 1

<400> SEQUENCE: 102
tgggaaagta aaccaa                                                   16

<210> SEQ ID NO 103
<211> LENGTH: 18
<212> TYPE: DNA
<213> ORGANISM: Human immunodeficiency virus 1

<400> SEQUENCE: 103
catggtggta tcttaaaa                                                 18

<210> SEQ ID NO 104
<211> LENGTH: 23
<212> TYPE: DNA
<213> ORGANISM: Human immunodeficiency virus 1

<400> SEQUENCE: 104
tgcccccaga tgttcctggg ctg                                           23

<210> SEQ ID NO 105
<211> LENGTH: 16
<212> TYPE: DNA
<213> ORGANISM: Human immunodeficiency virus 1

<400> SEQUENCE: 105
aggggagatg agtttg                                                   16

<210> SEQ ID NO 106
<211> LENGTH: 19
<212> TYPE: DNA
<213> ORGANISM: Human immunodeficiency virus 1

<400> SEQUENCE: 106
ctgccataga taccctaag                                                19

<210> SEQ ID NO 107
<211> LENGTH: 21
<212> TYPE: DNA
<213> ORGANISM: Human immunodeficiency virus 1

<400> SEQUENCE: 107
atgctagttt ttttttctct t                                             21

<210> SEQ ID NO 108
<211> LENGTH: 18
<212> TYPE: DNA
<213> ORGANISM: Human immunodeficiency virus 1

<400> SEQUENCE: 108
agagaagcca ggaggtct                                                 18
```

```
<210> SEQ ID NO 109
<211> LENGTH: 20
<212> TYPE: DNA
<213> ORGANISM: Human immunodeficiency virus 1

<400> SEQUENCE: 109
accacttggt cagaatttta                                               20

<210> SEQ ID NO 110
<211> LENGTH: 22
<212> TYPE: DNA
<213> ORGANISM: Human immunodeficiency virus 1

<400> SEQUENCE: 110
cccctggatg cccctaacca ct                                            22

<210> SEQ ID NO 111
<211> LENGTH: 17
<212> TYPE: DNA
<213> ORGANISM: Human immunodeficiency virus 1

<400> SEQUENCE: 111
agaggagctt gtgaatc                                                  17

<210> SEQ ID NO 112
<211> LENGTH: 17
<212> TYPE: DNA
<213> ORGANISM: Human immunodeficiency virus 1

<400> SEQUENCE: 112
accacctcct tcatctt                                                  17

<210> SEQ ID NO 113
<211> LENGTH: 22
<212> TYPE: DNA
<213> ORGANISM: Human immunodeficiency virus 1

<400> SEQUENCE: 113 tgccccttttg gaattctgca ct                                           22

<210> SEQ ID NO 114
<211> LENGTH: 19
<212> TYPE: DNA
<213> ORGANISM: Human immunodeficiency virus 1

<400> SEQUENCE: 114
agaggagtgg atgagcctg                                                19

<210> SEQ ID NO 115
<211> LENGTH: 18
<212> TYPE: DNA
<213> ORGANISM: Human immunodeficiency virus 1

<400> SEQUENCE: 115
gggaagatgc acaaccaa                                                 18

<210> SEQ ID NO 116
<211> LENGTH: 19
<212> TYPE: DNA
<213> ORGANISM: Human immunodeficiency virus 1

<400> SEQUENCE: 116
gctctagaat ctaaccaga                                                19
```

<210> SEQ ID NO 117
<211> LENGTH: 18
<212> TYPE: DNA
<213> ORGANISM: Human immunodeficiency virus 1

<400> SEQUENCE: 117
aaagtacagc aaaaccta                                                 18

<210> SEQ ID NO 118
<211> LENGTH: 18
<212> TYPE: DNA
<213> ORGANISM: Human immunodeficiency virus 1

<400> SEQUENCE: 118
ttatcttttc ttctgtta                                                 18

<210> SEQ ID NO 119
<211> LENGTH: 23
<212> TYPE: DNA
<213> ORGANISM: Human immunodeficiency virus 1

<400> SEQUENCE: 119
ctgttgtgag aaatgcccag gct                                           23

<210> SEQ ID NO 120
<211> LENGTH: 19
<212> TYPE: DNA
<213> ORGANISM: Human immunodeficiency virus 1

<400> SEQUENCE: 120
ctcagacctg aatcagaga                                                19

<210> SEQ ID NO 121
<211> LENGTH: 22
<212> TYPE: DNA
<213> ORGANISM: Human immunodeficiency virus 1

<400> SEQUENCE: 121
atgtgagctt tttcttctgt ta                                            22

<210> SEQ ID NO 122
<211> LENGTH: 16
<212> TYPE: DNA
<213> ORGANISM: Human immunodeficiency virus 1

<400> SEQUENCE: 122
cgcaccaccc atttta                                                   16

<210> SEQ ID NO 123
<211> LENGTH: 16
<212> TYPE: DNA
<213> ORGANISM: Human immunodeficiency virus 1

<400> SEQUENCE: 123
cgcaccaccc atttta                                                   16

<210> SEQ ID NO 124
<211> LENGTH: 15
<212> TYPE: DNA
<213> ORGANISM: Human immunodeficiency virus 1

<400> SEQUENCE: 124

-continued

```
aggactgtga gtctg                                                    15

<210> SEQ ID NO 125
<211> LENGTH: 17
<212> TYPE: DNA
<213> ORGANISM: Human immunodeficiency virus 1

<400> SEQUENCE: 125
ttattttttc cttgtca                                                  17

<210> SEQ ID NO 126
<211> LENGTH: 17
<212> TYPE: DNA
<213> ORGANISM: Human immunodeficiency virus 1

<400> SEQUENCE: 126
accacttgct atggtct                                                  17

<210> SEQ ID NO 127
<211> LENGTH: 22
<212> TYPE: DNA
<213> ORGANISM: Human immunodeficiency virus 1

<400> SEQUENCE: 127 cttttttctta atgcatacaa ta                                           22

<210> SEQ ID NO 128
<211> LENGTH: 17
<212> TYPE: DNA
<213> ORGANISM: Human immunodeficiency virus 1

<400> SEQUENCE: 128
ttgggctcca ttctgga                                                  17

<210> SEQ ID NO 129
<211> LENGTH: 19
<212> TYPE: DNA
<213> ORGANISM: Human immunodeficiency virus 1

<400> SEQUENCE: 129
tctatcccct tgtcacata                                                19

<210> SEQ ID NO 130
<211> LENGTH: 20
<212> TYPE: DNA
<213> ORGANISM: Human immunodeficiency virus 1

<400> SEQUENCE: 130
accaggagac caccatctta                                               20

<210> SEQ ID NO 131
<211> LENGTH: 18
<212> TYPE: DNA
<213> ORGANISM: Human immunodeficiency virus 1

<400> SEQUENCE: 131
agaggaccgc gatgagtc                                                 18

<210> SEQ ID NO 132
<211> LENGTH: 19
<212> TYPE: DNA
<213> ORGANISM: Human immunodeficiency virus 1

<400> SEQUENCE: 132
```

-continued tgctgtgttc tttctgtca                                              19

<210> SEQ ID NO 133
<211> LENGTH: 16
<212> TYPE: DNA
<213> ORGANISM: Human immunodeficiency virus 1

<400> SEQUENCE: 133
agagaagcat cagtct                                                 16

<210> SEQ ID NO 134
<211> LENGTH: 18
<212> TYPE: DNA
<213> ORGANISM: Human immunodeficiency virus 1

<400> SEQUENCE: 134
ccacttgatg cacaaata                                               18

<210> SEQ ID NO 135
<211> LENGTH: 19
<212> TYPE: DNA
<213> ORGANISM: Human immunodeficiency virus 1

<400> SEQUENCE: 135
agagaattgt gtgagtctg                                              19

<210> SEQ ID NO 136
<211> LENGTH: 21
<212> TYPE: DNA
<213> ORGANISM: Human immunodeficiency virus 1

<400> SEQUENCE: 136
atgtttactc tccttctgtc a                                           21

<210> SEQ ID NO 137
<211> LENGTH: 21
<212> TYPE: DNA
<213> ORGANISM: Human immunodeficiency virus 1

<400> SEQUENCE: 137
atgcttttat tccctttgtt a                                           21

<210> SEQ ID NO 138
<211> LENGTH: 18
<212> TYPE: DNA
<213> ORGANISM: Human immunodeficiency virus 1

<400> SEQUENCE: 138
agacagtaga tgagtctg                                               18

<210> SEQ ID NO 139
<211> LENGTH: 22
<212> TYPE: DNA
<213> ORGANISM: Human immunodeficiency virus 1

<400> SEQUENCE: 139
accacccagc aagcccgcct ta                                          22

<210> SEQ ID NO 140
<211> LENGTH: 18
<212> TYPE: DNA
<213> ORGANISM: Human immunodeficiency virus 1

```
<400> SEQUENCE: 140
ccattgtgaa acacttaa                                                      18

<210> SEQ ID NO 141
<211> LENGTH: 17
<212> TYPE: DNA
<213> ORGANISM: Human immunodeficiency virus 1

<400> SEQUENCE: 141
accacctccc tatctta                                                       17

<210> SEQ ID NO 142
<211> LENGTH: 24
<212> TYPE: DNA
<213> ORGANISM: Human immunodeficiency virus 1

<400> SEQUENCE: 142
ccaggtctga agaactgttg ccca                                               24

<210> SEQ ID NO 143
<211> LENGTH: 17
<212> TYPE: DNA
<213> ORGANISM: Human immunodeficiency virus 1

<400> SEQUENCE: 143
cccctgggcc ctgccta                                                       17

<210> SEQ ID NO 144
<211> LENGTH: 20
<212> TYPE: DNA
<213> ORGANISM: Human immunodeficiency virus 1

<400> SEQUENCE: 144
ctgtaatttg atgtacacaa                                                    20

<210> SEQ ID NO 145
<211> LENGTH: 18
<212> TYPE: DNA
<213> ORGANISM: Human immunodeficiency virus 1

<400> SEQUENCE: 145
cataatggtg tcttaaaa                                                      18

<210> SEQ ID NO 146
<211> LENGTH: 18
<212> TYPE: DNA
<213> ORGANISM: Human immunodeficiency virus 1

<400> SEQUENCE: 146 agaaccttg atgagact                                                       18

<210> SEQ ID NO 147
<211> LENGTH: 19
<212> TYPE: DNA
<213> ORGANISM: Human immunodeficiency virus 1

<400> SEQUENCE: 147
agagaagcct agatatctg                                                     19

<210> SEQ ID NO 148
<211> LENGTH: 18
<212> TYPE: DNA
<213> ORGANISM: Human immunodeficiency virus 1
```

-continued

<400> SEQUENCE: 148
accacattcc cattttta                                              18

<210> SEQ ID NO 149
<211> LENGTH: 16
<212> TYPE: DNA
<213> ORGANISM: Human immunodeficiency virus 1

<400> SEQUENCE: 149
acctgaccac ccattt                                                16

<210> SEQ ID NO 150
<211> LENGTH: 18
<212> TYPE: DNA
<213> ORGANISM: Human immunodeficiency virus 1

<400> SEQUENCE: 150
aaagtacagc aaaaccta                                              18

<210> SEQ ID NO 151
<211> LENGTH: 18
<212> TYPE: DNA
<213> ORGANISM: Human immunodeficiency virus 1

<400> SEQUENCE: 151
ttatcttttc ttctgtta                                              18

<210> SEQ ID NO 152
<211> LENGTH: 24
<212> TYPE: DNA
<213> ORGANISM: Human immunodeficiency virus 1

<400> SEQUENCE: 152
tgggaaaacc agtctatgca ccaa                                       24

<210> SEQ ID NO 153
<211> LENGTH: 16
<212> TYPE: DNA
<213> ORGANISM: Human immunodeficiency virus 1

<400> SEQUENCE: 153
agagaagcct gtggct                                                16

<210> SEQ ID NO 154
<211> LENGTH: 17
<212> TYPE: DNA
<213> ORGANISM: Human immunodeficiency virus 1

<400> SEQUENCE: 154
agatgttgat gaggctg                                               17

<210> SEQ ID NO 155
<211> LENGTH: 17
<212> TYPE: DNA
<213> ORGANISM: Human immunodeficiency virus 1

<400> SEQUENCE: 155
acctctgcca cccatct                                               17

<210> SEQ ID NO 156
<211> LENGTH: 19
<212> TYPE: DNA

<213> ORGANISM: Human immunodeficiency virus 1

<400> SEQUENCE: 156
ttgggagtcc cattttgga                    19

<210> SEQ ID NO 157
<211> LENGTH: 20
<212> TYPE: DNA
<213> ORGANISM: Human immunodeficiency virus 1

<400> SEQUENCE: 157
ctgccatctg ctgcctaggc                   20

<210> SEQ ID NO 158
<211> LENGTH: 17
<212> TYPE: DNA
<213> ORGANISM: Human immunodeficiency virus 1

<400> SEQUENCE: 158
ccagagacac ctgaggc                      17

<210> SEQ ID NO 159
<211> LENGTH: 17
<212> TYPE: DNA
<213> ORGANISM: Human immunodeficiency virus 1

<400> SEQUENCE: 159
ccagagacac ctgaggc                      17

<210> SEQ ID NO 160
<211> LENGTH: 23
<212> TYPE: DNA
<213> ORGANISM: Human immunodeficiency virus 1

<400> SEQUENCE: 160
ctgcccccag ggacacctaa ggc               23

<210> SEQ ID NO 161
<211> LENGTH: 22
<212> TYPE: DNA
<213> ORGANISM: Human immunodeficiency virus 1

<400> SEQUENCE: 161
agaagcttct gttttgggtc tg                22

<210> SEQ ID NO 162
<211> LENGTH: 22
<212> TYPE: DNA
<213> ORGANISM: Human immunodeficiency virus 1

<400> SEQUENCE: 162
tacaaggatt tcgcattctg gg                22

<210> SEQ ID NO 163
<211> LENGTH: 18
<212> TYPE: DNA
<213> ORGANISM: Human immunodeficiency virus 1

<400> SEQUENCE: 163
acaatgagtt tgcatttt                     18

<210> SEQ ID NO 164
<211> LENGTH: 18

```
<212> TYPE: DNA
<213> ORGANISM: Human immunodeficiency virus 1

<400> SEQUENCE: 164
gcttttattt tctcctct                                                 18

<210> SEQ ID NO 165
<211> LENGTH: 16
<212> TYPE: DNA
<213> ORGANISM: Human immunodeficiency virus 1

<400> SEQUENCE: 165
acaattccgc attttg                                                   16

<210> SEQ ID NO 166
<211> LENGTH: 20
<212> TYPE: DNA
<213> ORGANISM: Human immunodeficiency virus 1

<400> SEQUENCE: 166
tggcattact ctgcactata                                               20

<210> SEQ ID NO 167
<211> LENGTH: 18
<212> TYPE: DNA
<213> ORGANISM: Human immunodeficiency virus 1

<400> SEQUENCE: 167
accctggacc acccatct                                                 18

<210> SEQ ID NO 168
<211> LENGTH: 18
<212> TYPE: DNA
<213> ORGANISM: Human immunodeficiency virus 1

<400> SEQUENCE: 168
agaaactttg gatgagtt                                                 18

<210> SEQ ID NO 169
<211> LENGTH: 17
<212> TYPE: DNA
<213> ORGANISM: Human immunodeficiency virus 1

<400> SEQUENCE: 169
agagaagtta gatcctg                                                  17

<210> SEQ ID NO 170
<211> LENGTH: 20
<212> TYPE: DNA
<213> ORGANISM: Human immunodeficiency virus 1

<400> SEQUENCE: 170
tgcccctggc tgtgctctac                                               20

<210> SEQ ID NO 171
<211> LENGTH: 17
<212> TYPE: DNA
<213> ORGANISM: Human immunodeficiency virus 1

<400> SEQUENCE: 171
agagaagcct tggaatc                                                  17

<210> SEQ ID NO 172
```

```
<211> LENGTH: 17
<212> TYPE: DNA
<213> ORGANISM: Human immunodeficiency virus 1

<400> SEQUENCE: 172
ccacaattgg gttctta                                                17

<210> SEQ ID NO 173
<211> LENGTH: 22
<212> TYPE: DNA
<213> ORGANISM: Human immunodeficiency virus 1

<400> SEQUENCE: 173
ccaggtctaa acagctgacc ca                                          22

<210> SEQ ID NO 174
<211> LENGTH: 22
<212> TYPE: DNA
<213> ORGANISM: Human immunodeficiency virus 1

<400> SEQUENCE: 174
ccaggtctaa acagctgacc ca                                          22

<210> SEQ ID NO 175
<211> LENGTH: 20
<212> TYPE: DNA
<213> ORGANISM: Human immunodeficiency virus 1

<400> SEQUENCE: 175
gctttactct ttcttctgtc                                             20

<210> SEQ ID NO 176
<211> LENGTH: 18
<212> TYPE: DNA
<213> ORGANISM: Human immunodeficiency virus 1

<400> SEQUENCE: 176 gccctctgt ctctgcac                                                18

<210> SEQ ID NO 177
<211> LENGTH: 17
<212> TYPE: DNA
<213> ORGANISM: Human immunodeficiency virus 1

<400> SEQUENCE: 177
agagaagttg gggtctg                                                17

<210> SEQ ID NO 178
<211> LENGTH: 18
<212> TYPE: DNA
<213> ORGANISM: Human immunodeficiency virus 1

<400> SEQUENCE: 178
agagaccctg tgagtctg                                               18

<210> SEQ ID NO 179
<211> LENGTH: 22
<212> TYPE: DNA
<213> ORGANISM: Human immunodeficiency virus 1

<400> SEQUENCE: 179
ccaggtctaa acagctgacc ca                                          22
```

```
<210> SEQ ID NO 180
<211> LENGTH: 18
<212> TYPE: DNA
<213> ORGANISM: Human immunodeficiency virus 1

<400> SEQUENCE: 180
ccacacgtaa acacttga                                                  18

<210> SEQ ID NO 181
<211> LENGTH: 19
<212> TYPE: DNA
<213> ORGANISM: Human immunodeficiency virus 1

<400> SEQUENCE: 181
accacttgca ctattctta                                                 19

<210> SEQ ID NO 182
<211> LENGTH: 18
<212> TYPE: DNA
<213> ORGANISM: Human immunodeficiency virus 1

<400> SEQUENCE: 182
gaaaatttaa aggagcaa                                                  18

<210> SEQ ID NO 183
<211> LENGTH: 21
<212> TYPE: DNA
<213> ORGANISM: Human immunodeficiency virus 1

<400> SEQUENCE: 183
catagcaggg cgtctgtaaa a                                              21

<210> SEQ ID NO 184
<211> LENGTH: 22
<212> TYPE: DNA
<213> ORGANISM: Human immunodeficiency virus 1

<400> SEQUENCE: 184
ctcagacctg gtttgagata ga                                             22

<210> SEQ ID NO 185
<211> LENGTH: 18
<212> TYPE: DNA
<213> ORGANISM: Human immunodeficiency virus 1

<400> SEQUENCE: 185
accacttgtt gtacatct                                                  18

<210> SEQ ID NO 186
<211> LENGTH: 16
<212> TYPE: DNA
<213> ORGANISM: Human immunodeficiency virus 1

<400> SEQUENCE: 186
ccaggagaaa cactta                                                    16

<210> SEQ ID NO 187
<211> LENGTH: 17
<212> TYPE: DNA
<213> ORGANISM: Human immunodeficiency virus 1

<400> SEQUENCE: 187
agagaagaaa tgggtct                                                   17
```

```
<210> SEQ ID NO 188
<211> LENGTH: 20
<212> TYPE: DNA
<213> ORGANISM: Human immunodeficiency virus 1

<400> SEQUENCE: 188
catgaagaaa tgcctgaagc                                           20

<210> SEQ ID NO 189
<211> LENGTH: 19
<212> TYPE: DNA
<213> ORGANISM: Human immunodeficiency virus 1

<400> SEQUENCE: 189
tttatttttt atcctgtca                                            19

<210> SEQ ID NO 190
<211> LENGTH: 19
<212> TYPE: DNA
<213> ORGANISM: Human immunodeficiency virus 1

<400> SEQUENCE: 190
accagggccg catccatct                                            19

<210> SEQ ID NO 191
<211> LENGTH: 22
<212> TYPE: DNA
<213> ORGANISM: Human immunodeficiency virus 1

<400> SEQUENCE: 191
cagtctggac cagcaccttg ga                                        22

<210> SEQ ID NO 192
<211> LENGTH: 23
<212> TYPE: DNA
<213> ORGANISM: Human immunodeficiency virus 1

<400> SEQUENCE: 192
ccaggcctga atggatggac tca                                       23

<210> SEQ ID NO 193
<211> LENGTH: 18
<212> TYPE: DNA
<213> ORGANISM: Human immunodeficiency virus 1

<400> SEQUENCE: 193
agagaagctg gaagcctg                                             18

<210> SEQ ID NO 194
<211> LENGTH: 19
<212> TYPE: DNA
<213> ORGANISM: Human immunodeficiency virus 1

<400> SEQUENCE: 194
gctttcatga attctgtca                                            19

<210> SEQ ID NO 195
<211> LENGTH: 18
<212> TYPE: DNA
<213> ORGANISM: Human immunodeficiency virus 1

<400> SEQUENCE: 195
accactgcta tccatctt                                             18
```

<210> SEQ ID NO 196
<211> LENGTH: 20
<212> TYPE: DNA
<213> ORGANISM: Human immunodeficiency virus 1

<400> SEQUENCE: 196
accacttgcc aatgcctctc                                              20

<210> SEQ ID NO 197
<211> LENGTH: 18
<212> TYPE: DNA
<213> ORGANISM: Human immunodeficiency virus 1

<400> SEQUENCE: 197
accgcgccca gcccatct                                                18

<210> SEQ ID NO 198
<211> LENGTH: 17
<212> TYPE: DNA
<213> ORGANISM: Human immunodeficiency virus 1

<400> SEQUENCE: 198
agagaagttg tgacctg                                                 17

<210> SEQ ID NO 199
<211> LENGTH: 19
<212> TYPE: DNA
<213> ORGANISM: Human immunodeficiency virus 1

<400> SEQUENCE: 199
agagaagcag aacggcctg                                               19

<210> SEQ ID NO 200
<211> LENGTH: 20
<212> TYPE: DNA
<213> ORGANISM: Human immunodeficiency virus 1

<400> SEQUENCE: 200
agagaaacca gctgagtctg                                              20

<210> SEQ ID NO 201
<211> LENGTH: 18
<212> TYPE: DNA
<213> ORGANISM: Human immunodeficiency virus 1

<400> SEQUENCE: 201
accacttgcc ctgcctca                                                18

<210> SEQ ID NO 202
<211> LENGTH: 25
<212> TYPE: DNA
<213> ORGANISM: Human immunodeficiency virus 1

<400> SEQUENCE: 202
ctctaccctc tcccaccaca cagta                                        25

<210> SEQ ID NO 203
<211> LENGTH: 19
<212> TYPE: DNA
<213> ORGANISM: Human immunodeficiency virus 1

<400> SEQUENCE: 203

```
catgaaaatg tctatagaa                                                19
```

<210> SEQ ID NO 204
<211> LENGTH: 16
<212> TYPE: DNA
<213> ORGANISM: Human immunodeficiency virus 1

<400> SEQUENCE: 204

```
agagaagcta gaagtc                                                   16
```

<210> SEQ ID NO 205
<211> LENGTH: 20
<212> TYPE: DNA
<213> ORGANISM: Human immunodeficiency virus 1

<400> SEQUENCE: 205

```
agagaagcag ttggcatctg                                               20
```

<210> SEQ ID NO 206
<211> LENGTH: 18
<212> TYPE: DNA
<213> ORGANISM: Human immunodeficiency virus 1

<400> SEQUENCE: 206

```
ctgggttcac attttgga                                                 18
```

<210> SEQ ID NO 207
<211> LENGTH: 24
<212> TYPE: DNA
<213> ORGANISM: Human immunodeficiency virus 1

<400> SEQUENCE: 207

```
tgagaaaatt taaagtgttt ctag                                          24
```

<210> SEQ ID NO 208
<211> LENGTH: 22
<212> TYPE: DNA
<213> ORGANISM: Human immunodeficiency virus 1

<400> SEQUENCE: 208

```
agagaagaaa tatttgagtc tg                                            22
```

<210> SEQ ID NO 209
<211> LENGTH: 21
<212> TYPE: DNA
<213> ORGANISM: Human immunodeficiency virus 1

<400> SEQUENCE: 209

```
atgccatttt ttttcttctg t                                             21
```

<210> SEQ ID NO 210
<211> LENGTH: 19
<212> TYPE: DNA
<213> ORGANISM: Human immunodeficiency virus 1

<400> SEQUENCE: 210

```
agagagggta ttgagtctg                                                19
```

<210> SEQ ID NO 211
<211> LENGTH: 19
<212> TYPE: DNA
<213> ORGANISM: Human immunodeficiency virus 1

<400> SEQUENCE: 211

```
agagaagctc tttgaagtt                                              19

<210> SEQ ID NO 212
<211> LENGTH: 20
<212> TYPE: DNA
<213> ORGANISM: Human immunodeficiency virus 1

<400> SEQUENCE: 212
gcttttattt ttattttatc                                             20

<210> SEQ ID NO 213
<211> LENGTH: 17
<212> TYPE: DNA
<213> ORGANISM: Human immunodeficiency virus 1

<400> SEQUENCE: 213
agagaagctg gtggatc                                                17

<210> SEQ ID NO 214
<211> LENGTH: 19
<212> TYPE: DNA
<213> ORGANISM: Human immunodeficiency virus 1

<400> SEQUENCE: 214
ctgtggtaag aacacttaa                                              19

<210> SEQ ID NO 215
<211> LENGTH: 22
<212> TYPE: DNA
<213> ORGANISM: Human immunodeficiency virus 1

<400> SEQUENCE: 215
ctgccatttc tgtgcctagg ct                                          22

<210> SEQ ID NO 216
<211> LENGTH: 17
<212> TYPE: DNA
<213> ORGANISM: Human immunodeficiency virus 1

<400> SEQUENCE: 216
accacagact catctta                                                17

<210> SEQ ID NO 217
<211> LENGTH: 18
<212> TYPE: DNA
<213> ORGANISM: Human immunodeficiency virus 1

<400> SEQUENCE: 217
ggagaaaact gcaaccaa                                               18

<210> SEQ ID NO 218
<211> LENGTH: 18
<212> TYPE: DNA
<213> ORGANISM: Human immunodeficiency virus 1

<400> SEQUENCE: 218
accactaatt gccactca                                               18

<210> SEQ ID NO 219
<211> LENGTH: 16
<212> TYPE: DNA
<213> ORGANISM: Human immunodeficiency virus 1
```

```
<400> SEQUENCE: 219
agaggctgtg agtctg                                                   16

<210> SEQ ID NO 220
<211> LENGTH: 18
<212> TYPE: DNA
<213> ORGANISM: Human immunodeficiency virus 1

<400> SEQUENCE: 220
gaaagaaagc gcagccaa                                                 18

<210> SEQ ID NO 221
<211> LENGTH: 19
<212> TYPE: DNA
<213> ORGANISM: Human immunodeficiency virus 1

<400> SEQUENCE: 221
ccagagagat gccaaaggc                                                19

<210> SEQ ID NO 222
<211> LENGTH: 18
<212> TYPE: DNA
<213> ORGANISM: Human immunodeficiency virus 1

<400> SEQUENCE: 222
agaagctttg agagcctg                                                 18

<210> SEQ ID NO 223
<211> LENGTH: 30
<212> TYPE: DNA
<213> ORGANISM: Human immunodeficiency virus 1

<400> SEQUENCE: 223
atacaacctg atgtcatatt ccattttgga                                    30

<210> SEQ ID NO 224
<211> LENGTH: 30
<212> TYPE: DNA
<213> ORGANISM: Human immunodeficiency virus 1

<400> SEQUENCE: 224
atacaacctg atgtcatatt ccattttgga                                    30

<210> SEQ ID NO 225
<211> LENGTH: 21
<212> TYPE: DNA
<213> ORGANISM: Human immunodeficiency virus 1

<400> SEQUENCE: 225
tgcccctgga tctaccagca t                                             21

<210> SEQ ID NO 226
<211> LENGTH: 22
<212> TYPE: DNA
<213> ORGANISM: Human immunodeficiency virus 1

<400> SEQUENCE: 226
accactcggg gcccccatct tg                                            22

<210> SEQ ID NO 227
<211> LENGTH: 21
<212> TYPE: DNA
<213> ORGANISM: Human immunodeficiency virus 1
```

```
<400> SEQUENCE: 227
ccacagggag caaacactta g                                              21

<210> SEQ ID NO 228
<211> LENGTH: 20
<212> TYPE: DNA
<213> ORGANISM: Human immunodeficiency virus 1

<400> SEQUENCE: 228
ctgatggaga tgctcaaggc                                                20

<210> SEQ ID NO 229
<211> LENGTH: 17
<212> TYPE: DNA
<213> ORGANISM: Human immunodeficiency virus 1

<400> SEQUENCE: 229
agaggctgat gtgtctg                                                   17

<210> SEQ ID NO 230
<211> LENGTH: 18
<212> TYPE: DNA
<213> ORGANISM: Human immunodeficiency virus 1

<400> SEQUENCE: 230
aagctttcta tgagtttg                                                  18

<210> SEQ ID NO 231
<211> LENGTH: 16
<212> TYPE: DNA
<213> ORGANISM: Human immunodeficiency virus 1

<400> SEQUENCE: 231
agagaagcat cagtct                                                    16

<210> SEQ ID NO 232
<211> LENGTH: 16
<212> TYPE: DNA
<213> ORGANISM: Human immunodeficiency virus 1

<400> SEQUENCE: 232
agagaagcat cagtct                                                    16

<210> SEQ ID NO 233
<211> LENGTH: 23
<212> TYPE: DNA
<213> ORGANISM: Human immunodeficiency virus 1

<400> SEQUENCE: 233
gcccaggcac gcccgaccag aga                                            23

<210> SEQ ID NO 234
<211> LENGTH: 18
<212> TYPE: DNA
<213> ORGANISM: Human immunodeficiency virus 1

<400> SEQUENCE: 234
cataggattt ctatagaa                                                  18

<210> SEQ ID NO 235
<211> LENGTH: 16
<212> TYPE: DNA
```

<213> ORGANISM: Human immunodeficiency virus 1

<400> SEQUENCE: 235
ccaggagaaa cactta                                          16

<210> SEQ ID NO 236
<211> LENGTH: 18
<212> TYPE: DNA
<213> ORGANISM: Human immunodeficiency virus 1

<400> SEQUENCE: 236
aggcgcctga tgagttca                                        18

<210> SEQ ID NO 237
<211> LENGTH: 18
<212> TYPE: DNA
<213> ORGANISM: Human immunodeficiency virus 1

<400> SEQUENCE: 237
aggcgcctga tgagttca                                        18

<210> SEQ ID NO 238
<211> LENGTH: 18
<212> TYPE: DNA
<213> ORGANISM: Human immunodeficiency virus 1

<400> SEQUENCE: 238
aggcgcctga tgagttca                                        18

<210> SEQ ID NO 239
<211> LENGTH: 21
<212> TYPE: DNA
<213> ORGANISM: Human immunodeficiency virus 1

<400> SEQUENCE: 239
accactcatc acggccatct t                                    21

<210> SEQ ID NO 240
<211> LENGTH: 18
<212> TYPE: DNA
<213> ORGANISM: Human immunodeficiency virus 1

<400> SEQUENCE: 240
ccctggatcc tcacacta                                        18

<210> SEQ ID NO 241
<211> LENGTH: 22
<212> TYPE: DNA
<213> ORGANISM: Human immunodeficiency virus 1

<400> SEQUENCE: 241
gcccagatct ggtcccttgc ag                                   22

<210> SEQ ID NO 242
<211> LENGTH: 20
<212> TYPE: DNA
<213> ORGANISM: Human immunodeficiency virus 1

<400> SEQUENCE: 242
accacctgct cctcatctta                                      20

<210> SEQ ID NO 243
<211> LENGTH: 22

```
<212> TYPE: DNA
<213> ORGANISM: Human immunodeficiency virus 1

<400> SEQUENCE: 243
ctttggtttg atgcatacaa ta                                      22

<210> SEQ ID NO 244
<211> LENGTH: 23
<212> TYPE: DNA
<213> ORGANISM: Human immunodeficiency virus 1

<400> SEQUENCE: 244
tgcttttatt tcctcctcct tca                                     23

<210> SEQ ID NO 245
<211> LENGTH: 20
<212> TYPE: DNA
<213> ORGANISM: Human immunodeficiency virus 1

<400> SEQUENCE: 245
ctccccatcc caaccagaga                                         20

<210> SEQ ID NO 246
<211> LENGTH: 18
<212> TYPE: DNA
<213> ORGANISM: Human immunodeficiency virus 1

<400> SEQUENCE: 246
agagaagctt catgtttg                                           18

<210> SEQ ID NO 247
<211> LENGTH: 18
<212> TYPE: DNA
<213> ORGANISM: Human immunodeficiency virus 1

<400> SEQUENCE: 247
atgacttgcc acccacct                                           18

<210> SEQ ID NO 248
<211> LENGTH: 17
<212> TYPE: DNA
<213> ORGANISM: Human immunodeficiency virus 1

<400> SEQUENCE: 248
ctatctgatg cacagaa                                            17

<210> SEQ ID NO 249
<211> LENGTH: 22
<212> TYPE: DNA
<213> ORGANISM: Human immunodeficiency virus 1

<400> SEQUENCE: 249
gctcagatct gatgcttcaa ga                                      22

<210> SEQ ID NO 250
<211> LENGTH: 22
<212> TYPE: DNA
<213> ORGANISM: Human immunodeficiency virus 1

<400> SEQUENCE: 250
ctcagatctg aaaagcacaa ga                                      22

<210> SEQ ID NO 251
```

```
<211> LENGTH: 18
<212> TYPE: DNA
<213> ORGANISM: Human immunodeficiency virus 1

<400> SEQUENCE: 251
accaccacgc ccagctta                                              18

<210> SEQ ID NO 252
<211> LENGTH: 18
<212> TYPE: DNA
<213> ORGANISM: Human immunodeficiency virus 1

<400> SEQUENCE: 252
ttgggttcac attctgga                                              18

<210> SEQ ID NO 253
<211> LENGTH: 18
<212> TYPE: DNA
<213> ORGANISM: Human immunodeficiency virus 1

<400> SEQUENCE: 253
caaatctggt tctgaaag                                              18

<210> SEQ ID NO 254
<211> LENGTH: 20
<212> TYPE: DNA
<213> ORGANISM: Human immunodeficiency virus 1

<400> SEQUENCE: 254
agagaagtag gaagagcctg                                            20

<210> SEQ ID NO 255
<211> LENGTH: 21
<212> TYPE: DNA
<213> ORGANISM: Human immunodeficiency virus 1

<400> SEQUENCE: 255
gcccctggac gtttctgccg c                                          21

<210> SEQ ID NO 256
<211> LENGTH: 18
<212> TYPE: DNA
<213> ORGANISM: Human immunodeficiency virus 1

<400> SEQUENCE: 256
accacattgt acccattt                                              18

<210> SEQ ID NO 257
<211> LENGTH: 17
<212> TYPE: DNA
<213> ORGANISM: Human immunodeficiency virus 1

<400> SEQUENCE: 257
accagtaacc tatctta                                               17

<210> SEQ ID NO 258
<211> LENGTH: 20
<212> TYPE: DNA
<213> ORGANISM: Human immunodeficiency virus 1

<400> SEQUENCE: 258
accacccagt tcttcatctt                                            20
```

```
<210> SEQ ID NO 259
<211> LENGTH: 19
<212> TYPE: DNA
<213> ORGANISM: Human immunodeficiency virus 1

<400> SEQUENCE: 259
accacttaaa attatctta                                                    19

<210> SEQ ID NO 260
<211> LENGTH: 17
<212> TYPE: DNA
<213> ORGANISM: Human immunodeficiency virus 1

<400> SEQUENCE: 260
ccacaattgg gttctta                                                      17

<210> SEQ ID NO 261
<211> LENGTH: 17
<212> TYPE: DNA
<213> ORGANISM: Human immunodeficiency virus 1

<400> SEQUENCE: 261
agatgttgat gaggctg                                                      17

<210> SEQ ID NO 262
<211> LENGTH: 18
<212> TYPE: DNA
<213> ORGANISM: Human immunodeficiency virus 1

<400> SEQUENCE: 262
agagaagcct gtgccctg                                                     18

<210> SEQ ID NO 263
<211> LENGTH: 24
<212> TYPE: DNA
<213> ORGANISM: Human immunodeficiency virus 1

<400> SEQUENCE: 263
ccaggtctga agaactgttg ccca                                              24

<210> SEQ ID NO 264
<211> LENGTH: 20
<212> TYPE: DNA
<213> ORGANISM: Human immunodeficiency virus 1

<400> SEQUENCE: 264
ctcagatcca gggacagagg                                                   20

<210> SEQ ID NO 265
<211> LENGTH: 18
<212> TYPE: DNA
<213> ORGANISM: Human immunodeficiency virus 1

<400> SEQUENCE: 265
caggtctagc cgggccca                                                     18

<210> SEQ ID NO 266
<211> LENGTH: 17
<212> TYPE: DNA
<213> ORGANISM: Human immunodeficiency virus 1

<400> SEQUENCE: 266
accttcacct catctta                                                      17
```

```
<210> SEQ ID NO 267
<211> LENGTH: 18
<212> TYPE: DNA
<213> ORGANISM: Human immunodeficiency virus 1

<400> SEQUENCE: 267
atagaaagta gccaaaaa                                                    18

<210> SEQ ID NO 268
<211> LENGTH: 18
<212> TYPE: DNA
<213> ORGANISM: Human immunodeficiency virus 1

<400> SEQUENCE: 268
accacccctg tgcccatc                                                    18

<210> SEQ ID NO 269
<211> LENGTH: 23
<212> TYPE: DNA
<213> ORGANISM: Human immunodeficiency virus 1

<400> SEQUENCE: 269
ctctatcctt gtatatcaca ata                                              23

<210> SEQ ID NO 270
<211> LENGTH: 25
<212> TYPE: DNA
<213> ORGANISM: Human immunodeficiency virus 1

<400> SEQUENCE: 270
atgctttgct tttttcttta tgtca                                            25

<210> SEQ ID NO 271
<211> LENGTH: 21
<212> TYPE: DNA
<213> ORGANISM: Human immunodeficiency virus 1

<400> SEQUENCE: 271
gccacaggag atgcccaaag c                                                21

<210> SEQ ID NO 272
<211> LENGTH: 18
<212> TYPE: DNA
<213> ORGANISM: Human immunodeficiency virus 1

<400> SEQUENCE: 272
ttattctatc ttctgtca                                                    18

<210> SEQ ID NO 273
<211> LENGTH: 21
<212> TYPE: DNA
<213> ORGANISM: Human immunodeficiency virus 1

<400> SEQUENCE: 273
tttttatttc tttttctgtc a                                                21

<210> SEQ ID NO 274
<211> LENGTH: 16
<212> TYPE: DNA
<213> ORGANISM: Human immunodeficiency virus 1

<400> SEQUENCE: 274
agaagagatg agtttg                                                      16
```

```
<210> SEQ ID NO 275
<211> LENGTH: 24
<212> TYPE: DNA
<213> ORGANISM: Human immunodeficiency virus 1

<400> SEQUENCE: 275
aacattatgt actgtatata tcat                                              24

<210> SEQ ID NO 276
<211> LENGTH: 18
<212> TYPE: DNA
<213> ORGANISM: Human immunodeficiency virus 1

<400> SEQUENCE: 276 accactttc agccattt                                                      18

<210> SEQ ID NO 277
<211> LENGTH: 22
<212> TYPE: DNA
<213> ORGANISM: Human immunodeficiency virus 1

<400> SEQUENCE: 277
gtggccattt tttcttctgt ca                                                22

<210> SEQ ID NO 278
<211> LENGTH: 17
<212> TYPE: DNA
<213> ORGANISM: Human immunodeficiency virus 1

<400> SEQUENCE: 278
agagaatgtg atgagtt                                                      17

<210> SEQ ID NO 279
<211> LENGTH: 20
<212> TYPE: DNA
<213> ORGANISM: Human immunodeficiency virus 1

<400> SEQUENCE: 279
agagagtggg ggtgagtctg                                                   20

<210> SEQ ID NO 280
<211> LENGTH: 17
<212> TYPE: DNA
<213> ORGANISM: Human immunodeficiency virus 1

<400> SEQUENCE: 280
accacctccc tatctta                                                      17

<210> SEQ ID NO 281
<211> LENGTH: 21
<212> TYPE: DNA
<213> ORGANISM: Human immunodeficiency virus 1

<400> SEQUENCE: 281
atgctttata acctcttctg t                                                 21

<210> SEQ ID NO 282
<211> LENGTH: 19
<212> TYPE: DNA
<213> ORGANISM: Human immunodeficiency virus 1

<400> SEQUENCE: 282
```

―continued

| | |
|---|---|
| tgcccagagg cctaaggct | 19 |

<210> SEQ ID NO 283
<211> LENGTH: 20
<212> TYPE: DNA
<213> ORGANISM: Human immunodeficiency virus 1

<400> SEQUENCE: 283

| | |
|---|---|
| agagggtga tgataaactg | 20 |

<210> SEQ ID NO 284
<211> LENGTH: 19
<212> TYPE: DNA
<213> ORGANISM: Human immunodeficiency virus 1

<400> SEQUENCE: 284

| | |
|---|---|
| agagaagctt gtgttttg | 19 |

<210> SEQ ID NO 285
<211> LENGTH: 19
<212> TYPE: DNA
<213> ORGANISM: Human immunodeficiency virus 1

<400> SEQUENCE: 285

| | |
|---|---|
| agagaagcct aggtgggct | 19 |

<210> SEQ ID NO 286
<211> LENGTH: 19
<212> TYPE: DNA
<213> ORGANISM: Human immunodeficiency virus 1

<400> SEQUENCE: 286

| | |
|---|---|
| atgcttttat tgtaccttc | 19 |

<210> SEQ ID NO 287
<211> LENGTH: 16
<212> TYPE: DNA
<213> ORGANISM: Human immunodeficiency virus 1

<400> SEQUENCE: 287

| | |
|---|---|
| agaagcaatg ggtctg | 16 |

<210> SEQ ID NO 288
<211> LENGTH: 17
<212> TYPE: DNA
<213> ORGANISM: Human immunodeficiency virus 1

<400> SEQUENCE: 288

| | |
|---|---|
| tgcatctttt cttctgt | 17 |

<210> SEQ ID NO 289
<211> LENGTH: 21
<212> TYPE: DNA
<213> ORGANISM: Human immunodeficiency virus 1

<400> SEQUENCE: 289

| | |
|---|---|
| gtggttgaga tgcccacggc t | 21 |

<210> SEQ ID NO 290
<211> LENGTH: 20
<212> TYPE: DNA
<213> ORGANISM: Human immunodeficiency virus 1

<400> SEQUENCE: 290

```
aacattatgc ttactgcatc                                              20

<210> SEQ ID NO 291
<211> LENGTH: 18
<212> TYPE: DNA
<213> ORGANISM: Human immunodeficiency virus 1

<400> SEQUENCE: 291
accacttgtt gaaatcca                                                18

<210> SEQ ID NO 292
<211> LENGTH: 20
<212> TYPE: DNA
<213> ORGANISM: Human immunodeficiency virus 1

<400> SEQUENCE: 292
agagaagctg cctcagtctg                                              20

<210> SEQ ID NO 293
<211> LENGTH: 19
<212> TYPE: DNA
<213> ORGANISM: Human immunodeficiency virus 1

<400> SEQUENCE: 293
ctgtattttg atgcaacaa                                               19

<210> SEQ ID NO 294
<211> LENGTH: 16
<212> TYPE: DNA
<213> ORGANISM: Human immunodeficiency virus 1

<400> SEQUENCE: 294
ccacatgtaa cactta                                                  16

<210> SEQ ID NO 295
<211> LENGTH: 18
<212> TYPE: DNA
<213> ORGANISM: Human immunodeficiency virus 1

<400> SEQUENCE: 295
ccacaattgt ctgaacat                                                18

<210> SEQ ID NO 296
<211> LENGTH: 18
<212> TYPE: DNA
<213> ORGANISM: Human immunodeficiency virus 1

<400> SEQUENCE: 296
acagtattcc attttgga                                                18

<210> SEQ ID NO 297
<211> LENGTH: 19
<212> TYPE: DNA
<213> ORGANISM: Human immunodeficiency virus 1

<400> SEQUENCE: 297
acatatgcct ctactcata                                               19

<210> SEQ ID NO 298
<211> LENGTH: 18
<212> TYPE: DNA
<213> ORGANISM: Human immunodeficiency virus 1
```

```
<400> SEQUENCE: 298
agagaagcgt gaagtttg                                                18

<210> SEQ ID NO 299
<211> LENGTH: 20
<212> TYPE: DNA
<213> ORGANISM: Human immunodeficiency virus 1

<400> SEQUENCE: 299
accacttgat aagcatcttg                                              20

<210> SEQ ID NO 300
<211> LENGTH: 15
<212> TYPE: DNA
<213> ORGANISM: Human immunodeficiency virus 1

<400> SEQUENCE: 300
agaaggatga gtttg                                                   15

<210> SEQ ID NO 301
<211> LENGTH: 21
<212> TYPE: DNA
<213> ORGANISM: Human immunodeficiency virus 1

<400> SEQUENCE: 301
ggagtattaa agtggaacca a                                            21

<210> SEQ ID NO 302
<211> LENGTH: 20
<212> TYPE: DNA
<213> ORGANISM: Human immunodeficiency virus 1

<400> SEQUENCE: 302
ctctcgggcg atgcacacaa                                              20

<210> SEQ ID NO 303
<211> LENGTH: 20
<212> TYPE: DNA
<213> ORGANISM: Human immunodeficiency virus 1

<400> SEQUENCE: 303
ccacaactgg aaacacttga                                              20

<210> SEQ ID NO 304
<211> LENGTH: 21
<212> TYPE: DNA
<213> ORGANISM: Human immunodeficiency virus 1

<400> SEQUENCE: 304
ctgataaaga tttcagactc a                                            21

<210> SEQ ID NO 305
<211> LENGTH: 18
<212> TYPE: DNA
<213> ORGANISM: Human immunodeficiency virus 1

<400> SEQUENCE: 305 gccctgggc acactgta                                                 18

<210> SEQ ID NO 306
<211> LENGTH: 23
<212> TYPE: DNA
<213> ORGANISM: Human immunodeficiency virus 1
```

-continued

```
<400> SEQUENCE: 306
tacttcttgg ttcacattttt gga                                          23

<210> SEQ ID NO 307
<211> LENGTH: 20
<212> TYPE: DNA
<213> ORGANISM: Human immunodeficiency virus 1

<400> SEQUENCE: 307
acctctcctc acccatctta                                               20

<210> SEQ ID NO 308
<211> LENGTH: 17
<212> TYPE: DNA
<213> ORGANISM: Human immunodeficiency virus 1

<400> SEQUENCE: 308
cagccctggc tggactc                                                  17

<210> SEQ ID NO 309
<211> LENGTH: 18
<212> TYPE: DNA
<213> ORGANISM: Human immunodeficiency virus 1

<400> SEQUENCE: 309
gcagtgggtc tgttgcca                                                 18

<210> SEQ ID NO 310
<211> LENGTH: 21
<212> TYPE: DNA
<213> ORGANISM: Human immunodeficiency virus 1

<400> SEQUENCE: 310
agaatggaca agcgcaacca a                                             21

<210> SEQ ID NO 311
<211> LENGTH: 20
<212> TYPE: DNA
<213> ORGANISM: Human immunodeficiency virus 1

<400> SEQUENCE: 311
tgctctaaag ctctgcacta                                               20

<210> SEQ ID NO 312
<211> LENGTH: 19
<212> TYPE: DNA
<213> ORGANISM: Human immunodeficiency virus 1

<400> SEQUENCE: 312
agagaagccc aggatggtc                                                19

<210> SEQ ID NO 313
<211> LENGTH: 18
<212> TYPE: DNA
<213> ORGANISM: Human immunodeficiency virus 1

<400> SEQUENCE: 313
agagaagcac atgacctg                                                 18

<210> SEQ ID NO 314
<211> LENGTH: 20
<212> TYPE: DNA
```

```
<213> ORGANISM: Human immunodeficiency virus 1

<400> SEQUENCE: 314
ctacagacca tagcaaaaac                                              20

<210> SEQ ID NO 315
<211> LENGTH: 19
<212> TYPE: DNA
<213> ORGANISM: Human immunodeficiency virus 1

<400> SEQUENCE: 315
catagaatgt gtctataaa                                               19

<210> SEQ ID NO 316
<211> LENGTH: 21
<212> TYPE: DNA
<213> ORGANISM: Human immunodeficiency virus 1

<400> SEQUENCE: 316
tattgtttct gggtgttgcc a                                            21

<210> SEQ ID NO 317
<211> LENGTH: 18
<212> TYPE: DNA
<213> ORGANISM: Human immunodeficiency virus 1

<400> SEQUENCE: 317
ccaagggatg cccaaagc                                                18

<210> SEQ ID NO 318
<211> LENGTH: 18
<212> TYPE: DNA
<213> ORGANISM: Human immunodeficiency virus 1

<400> SEQUENCE: 318
tgccataagc tcaaggct                                                18

<210> SEQ ID NO 319
<211> LENGTH: 18
<212> TYPE: DNA
<213> ORGANISM: Human immunodeficiency virus 1

<400> SEQUENCE: 319
tgccacaggc ctaaggct                                                18

<210> SEQ ID NO 320
<211> LENGTH: 20
<212> TYPE: DNA
<213> ORGANISM: Human immunodeficiency virus 1

<400> SEQUENCE: 320
accaccagct gcacccatct                                              20

<210> SEQ ID NO 321
<211> LENGTH: 17
<212> TYPE: DNA
<213> ORGANISM: Human immunodeficiency virus 1

<400> SEQUENCE: 321
ctatatgaaa catttaa                                                 17

<210> SEQ ID NO 322
<211> LENGTH: 20
```

```
<212> TYPE: DNA
<213> ORGANISM: Human immunodeficiency virus 1

<400> SEQUENCE: 322
ctatagaaca atgcaaaaac                                              20

<210> SEQ ID NO 323
<211> LENGTH: 22
<212> TYPE: DNA
<213> ORGANISM: Human immunodeficiency virus 1

<400> SEQUENCE: 323
ccaggtgacc tacccggact ca                                           22

<210> SEQ ID NO 324
<211> LENGTH: 19
<212> TYPE: DNA
<213> ORGANISM: Human immunodeficiency virus 1

<400> SEQUENCE: 324
accacctgcc ctaccattt                                               19

<210> SEQ ID NO 325
<211> LENGTH: 20
<212> TYPE: DNA
<213> ORGANISM: Human immunodeficiency virus 1

<400> SEQUENCE: 325
agagaagctg gcaagagctg                                              20

<210> SEQ ID NO 326
<211> LENGTH: 16
<212> TYPE: DNA
<213> ORGANISM: Human immunodeficiency virus 1

<400> SEQUENCE: 326
agaaaagttt gaagtc                                                  16

<210> SEQ ID NO 327
<211> LENGTH: 19
<212> TYPE: DNA
<213> ORGANISM: Human immunodeficiency virus 1

<400> SEQUENCE: 327
agagaagctc agtagaatc                                               19

<210> SEQ ID NO 328
<211> LENGTH: 19
<212> TYPE: DNA
<213> ORGANISM: Human immunodeficiency virus 1

<400> SEQUENCE: 328
agagaagcct gaggaattt                                               19

<210> SEQ ID NO 329
<211> LENGTH: 20
<212> TYPE: DNA
<213> ORGANISM: Human immunodeficiency virus 1

<400> SEQUENCE: 329
ccatcaaaag aaacacttaa                                              20

<210> SEQ ID NO 330
```

```
<211> LENGTH: 17
<212> TYPE: DNA
<213> ORGANISM: Human immunodeficiency virus 1

<400> SEQUENCE: 330
accacttctg gccatct                                                    17

<210> SEQ ID NO 331
<211> LENGTH: 19
<212> TYPE: DNA
<213> ORGANISM: Human immunodeficiency virus 1

<400> SEQUENCE: 331
agagaagcat gtctgagtt                                                  19

<210> SEQ ID NO 332
<211> LENGTH: 16
<212> TYPE: DNA
<213> ORGANISM: Human immunodeficiency virus 1

<400> SEQUENCE: 332
ccatagggag cctaag                                                     16

<210> SEQ ID NO 333
<211> LENGTH: 20
<212> TYPE: DNA
<213> ORGANISM: Human immunodeficiency virus 1

<400> SEQUENCE: 333
acctgccggc cacccattca                                                 20

<210> SEQ ID NO 334
<211> LENGTH: 20
<212> TYPE: DNA
<213> ORGANISM: Human immunodeficiency virus 1

<400> SEQUENCE: 334
ctatcatgtg gatgcacaca                                                 20

<210> SEQ ID NO 335
<211> LENGTH: 18
<212> TYPE: DNA
<213> ORGANISM: Human immunodeficiency virus 1

<400> SEQUENCE: 335
ggattaaagt ggaaccaa                                                   18

<210> SEQ ID NO 336
<211> LENGTH: 18
<212> TYPE: DNA
<213> ORGANISM: Human immunodeficiency virus 1

<400> SEQUENCE: 336
accccccagc ccatctta                                                   18

<210> SEQ ID NO 337
<211> LENGTH: 20
<212> TYPE: DNA
<213> ORGANISM: Human immunodeficiency virus 1

<400> SEQUENCE: 337
agagaagctc tttgtatctg                                                 20
```

<210> SEQ ID NO 338
<211> LENGTH: 20
<212> TYPE: DNA
<213> ORGANISM: Human immunodeficiency virus 1

<400> SEQUENCE: 338
catagtggct gcctatagaa                                              20

<210> SEQ ID NO 339
<211> LENGTH: 18
<212> TYPE: DNA
<213> ORGANISM: Human immunodeficiency virus 1

<400> SEQUENCE: 339
ttgggtctgc attttgga                                                18

<210> SEQ ID NO 340
<211> LENGTH: 19
<212> TYPE: DNA
<213> ORGANISM: Human immunodeficiency virus 1

<400> SEQUENCE: 340
ggaaaaataa tgtaaccaa                                               19

<210> SEQ ID NO 341
<211> LENGTH: 23
<212> TYPE: DNA
<213> ORGANISM: Human immunodeficiency virus 1

<400> SEQUENCE: 341
accacttata atgcctcatc tta                                          23

<210> SEQ ID NO 342
<211> LENGTH: 20
<212> TYPE: DNA
<213> ORGANISM: Human immunodeficiency virus 1

<400> SEQUENCE: 342
agagagtggg ggtgagtctg                                              20

<210> SEQ ID NO 343
<211> LENGTH: 17
<212> TYPE: DNA
<213> ORGANISM: Human immunodeficiency virus 1

<400> SEQUENCE: 343
accactgctg gccatct                                                 17

<210> SEQ ID NO 344
<211> LENGTH: 22
<212> TYPE: DNA
<213> ORGANISM: Human immunodeficiency virus 1

<400> SEQUENCE: 344
ggaaattata aatggcaacc aa                                           22

<210> SEQ ID NO 345
<211> LENGTH: 21
<212> TYPE: DNA
<213> ORGANISM: Human immunodeficiency virus 1

<400> SEQUENCE: 345
aagtttattg taatgagtct g                                            21

```
<210> SEQ ID NO 346
<211> LENGTH: 18
<212> TYPE: DNA
<213> ORGANISM: Human immunodeficiency virus 1

<400> SEQUENCE: 346
ctcaaatccc accagaga                                                   18

<210> SEQ ID NO 347
<211> LENGTH: 20
<212> TYPE: DNA
<213> ORGANISM: Human immunodeficiency virus 1

<400> SEQUENCE: 347
agagaagctc cgtgggcctg                                                 20

<210> SEQ ID NO 348
<211> LENGTH: 20
<212> TYPE: DNA
<213> ORGANISM: Human immunodeficiency virus 1

<400> SEQUENCE: 348
aggcctcttt ggtgagcctg                                                 20

<210> SEQ ID NO 349
<211> LENGTH: 19
<212> TYPE: DNA
<213> ORGANISM: Human immunodeficiency virus 1

<400> SEQUENCE: 349
agagaagctg ggtgatctg                                                  19

<210> SEQ ID NO 350
<211> LENGTH: 16
<212> TYPE: DNA
<213> ORGANISM: Human immunodeficiency virus 1

<400> SEQUENCE: 350
agagaagctt gtggtc                                                     16

<210> SEQ ID NO 351
<211> LENGTH: 21
<212> TYPE: DNA
<213> ORGANISM: Human immunodeficiency virus 1

<400> SEQUENCE: 351
agagtatttc ttgatgaatt t                                               21

<210> SEQ ID NO 352
<211> LENGTH: 22
<212> TYPE: DNA
<213> ORGANISM: Human immunodeficiency virus 1

<400> SEQUENCE: 352
aacatcaatg gactctgtat ca                                              22

<210> SEQ ID NO 353
<211> LENGTH: 18
<212> TYPE: DNA
<213> ORGANISM: Human immunodeficiency virus 1

<400> SEQUENCE: 353
gcccttacat tctgcact                                                   18
```

<210> SEQ ID NO 354
<211> LENGTH: 22
<212> TYPE: DNA
<213> ORGANISM: Human immunodeficiency virus 1

<400> SEQUENCE: 354
ctctatccct ctgtggccaa ta                                            22

<210> SEQ ID NO 355
<211> LENGTH: 18
<212> TYPE: DNA
<213> ORGANISM: Human immunodeficiency virus 1

<400> SEQUENCE: 355
ggaattcagc attttgga                                                 18

<210> SEQ ID NO 356
<211> LENGTH: 19
<212> TYPE: DNA
<213> ORGANISM: Human immunodeficiency virus 1

<400> SEQUENCE: 356
agagaagctg caggagctg                                                19

<210> SEQ ID NO 357
<211> LENGTH: 17
<212> TYPE: DNA
<213> ORGANISM: Human immunodeficiency virus 1

<400> SEQUENCE: 357
accacccagt catttta                                                  17

<210> SEQ ID NO 358
<211> LENGTH: 18
<212> TYPE: DNA
<213> ORGANISM: Human immunodeficiency virus 1

<400> SEQUENCE: 358
agagggcgaa atgagtct                                                 18

<210> SEQ ID NO 359
<211> LENGTH: 16
<212> TYPE: DNA
<213> ORGANISM: Human immunodeficiency virus 1

<400> SEQUENCE: 359
ccactgaaac atttaa                                                   16

<210> SEQ ID NO 360
<211> LENGTH: 23
<212> TYPE: DNA
<213> ORGANISM: Human immunodeficiency virus 1

<400> SEQUENCE: 360
tgcccctgga tatcagcaat ata                                           23

<210> SEQ ID NO 361
<211> LENGTH: 19
<212> TYPE: DNA
<213> ORGANISM: Human immunodeficiency virus 1

<400> SEQUENCE: 361
accacttgcc gagctccta          19

<210> SEQ ID NO 362
<211> LENGTH: 22
<212> TYPE: DNA
<213> ORGANISM: Human immunodeficiency virus 1

<400> SEQUENCE: 362
gctcagatcc atgtgccagg ga          22

<210> SEQ ID NO 363
<211> LENGTH: 21
<212> TYPE: DNA
<213> ORGANISM: Human immunodeficiency virus 1

<400> SEQUENCE: 363
agagagcaag gattgagtct g          21

<210> SEQ ID NO 364
<211> LENGTH: 20
<212> TYPE: DNA
<213> ORGANISM: Human immunodeficiency virus 1

<400> SEQUENCE: 364
atgcttttac tttttctttt          20

<210> SEQ ID NO 365
<211> LENGTH: 19
<212> TYPE: DNA
<213> ORGANISM: Human immunodeficiency virus 1

<400> SEQUENCE: 365
agagaagctc gtgaatgtt          19

<210> SEQ ID NO 366
<211> LENGTH: 23
<212> TYPE: DNA
<213> ORGANISM: Human immunodeficiency virus 1

<400> SEQUENCE: 366
ctctatcctt gtatatcaca ata          23

<210> SEQ ID NO 367
<211> LENGTH: 17
<212> TYPE: DNA
<213> ORGANISM: Human immunodeficiency virus 1

<400> SEQUENCE: 367
accactactg gccatct          17

<210> SEQ ID NO 368
<211> LENGTH: 17
<212> TYPE: DNA
<213> ORGANISM: Human immunodeficiency virus 1

<400> SEQUENCE: 368
tgcttttatt ttccttc          17

<210> SEQ ID NO 369
<211> LENGTH: 20
<212> TYPE: DNA
<213> ORGANISM: Human immunodeficiency virus 1

<400> SEQUENCE: 369
agagaagccc gaggggctg                                      20

<210> SEQ ID NO 370
<211> LENGTH: 16
<212> TYPE: DNA
<213> ORGANISM: Human immunodeficiency virus 1

<400> SEQUENCE: 370
agaaaggcgg tgagtc                                         16

<210> SEQ ID NO 371
<211> LENGTH: 16
<212> TYPE: DNA
<213> ORGANISM: Human immunodeficiency virus 1

<400> SEQUENCE: 371
agaaaggcgg tgagtc                                         16

<210> SEQ ID NO 372
<211> LENGTH: 17
<212> TYPE: DNA
<213> ORGANISM: Human immunodeficiency virus 1

<400> SEQUENCE: 372
agagatgatt gagtctg                                        17

<210> SEQ ID NO 373
<211> LENGTH: 19
<212> TYPE: DNA
<213> ORGANISM: Human immunodeficiency virus 1

<400> SEQUENCE: 373
agagaagcca ggccagctg                                      19

<210> SEQ ID NO 374
<211> LENGTH: 17
<212> TYPE: DNA
<213> ORGANISM: Human immunodeficiency virus 1

<400> SEQUENCE: 374
ccacaattgg gttctta                                        17

<210> SEQ ID NO 375
<211> LENGTH: 18
<212> TYPE: DNA
<213> ORGANISM: Human immunodeficiency virus 1

<400> SEQUENCE: 375
ccacttgatg cacaaata                                       18

<210> SEQ ID NO 376
<211> LENGTH: 20
<212> TYPE: DNA
<213> ORGANISM: Human immunodeficiency virus 1

<400> SEQUENCE: 376
agagagtggg ggtgagtctg                                     20

<210> SEQ ID NO 377
<211> LENGTH: 20
<212> TYPE: DNA
<213> ORGANISM: Human immunodeficiency virus 1

-continued

```
<400> SEQUENCE: 377
agagaaatcc tagatgagtc                                              20

<210> SEQ ID NO 378
<211> LENGTH: 24
<212> TYPE: DNA
<213> ORGANISM: Human immunodeficiency virus 1

<400> SEQUENCE: 378
ccaggtctga agaactgttg ccca                                         24

<210> SEQ ID NO 379
<211> LENGTH: 20
<212> TYPE: DNA
<213> ORGANISM: Human immunodeficiency virus 1

<400> SEQUENCE: 379
gaaatggcaa gtgcaaccaa                                              20

<210> SEQ ID NO 380
<211> LENGTH: 18
<212> TYPE: DNA
<213> ORGANISM: Human immunodeficiency virus 1

<400> SEQUENCE: 380 tgccttttt ttctgtca                                                 18

<210> SEQ ID NO 381
<211> LENGTH: 18
<212> TYPE: DNA
<213> ORGANISM: Human immunodeficiency virus 1

<400> SEQUENCE: 381
aggtgcttga tgaatctg                                                18

<210> SEQ ID NO 382
<211> LENGTH: 18
<212> TYPE: DNA
<213> ORGANISM: Human immunodeficiency virus 1

<400> SEQUENCE: 382
agagaagatg aaagtttg                                                18

<210> SEQ ID NO 383
<211> LENGTH: 17
<212> TYPE: DNA
<213> ORGANISM: Human immunodeficiency virus 1

<400> SEQUENCE: 383
gcccctgtgt cccacta                                                 17

<210> SEQ ID NO 384
<211> LENGTH: 17
<212> TYPE: DNA
<213> ORGANISM: Human immunodeficiency virus 1

<400> SEQUENCE: 384
accactactg gccatct                                                 17

<210> SEQ ID NO 385
<211> LENGTH: 17
<212> TYPE: DNA
<213> ORGANISM: Human immunodeficiency virus 1
```

```
<400> SEQUENCE: 385
accactactg gccatct                                                  17

<210> SEQ ID NO 386
<211> LENGTH: 24
<212> TYPE: DNA
<213> ORGANISM: Human immunodeficiency virus 1

<400> SEQUENCE: 386
ctacagaaca tggagcaaaa acta                                          24

<210> SEQ ID NO 387
<211> LENGTH: 18
<212> TYPE: DNA
<213> ORGANISM: Human immunodeficiency virus 1

<400> SEQUENCE: 387 agagggagg taagtctg                                                  18

<210> SEQ ID NO 388
<211> LENGTH: 18
<212> TYPE: DNA
<213> ORGANISM: Human immunodeficiency virus 1

<400> SEQUENCE: 388
agagaagcca gaggtgtg                                                 18

<210> SEQ ID NO 389
<211> LENGTH: 18
<212> TYPE: DNA
<213> ORGANISM: Human immunodeficiency virus 1

<400> SEQUENCE: 389
agagaagctt gggagcct                                                 18

<210> SEQ ID NO 390
<211> LENGTH: 17
<212> TYPE: DNA
<213> ORGANISM: Human immunodeficiency virus 1

<400> SEQUENCE: 390
ccactgtgct tgcacta                                                  17

<210> SEQ ID NO 391
<211> LENGTH: 17
<212> TYPE: DNA
<213> ORGANISM: Human immunodeficiency virus 1

<400> SEQUENCE: 391
gaagataatg caaccaa                                                  17

<210> SEQ ID NO 392
<211> LENGTH: 19
<212> TYPE: DNA
<213> ORGANISM: Human immunodeficiency virus 1

<400> SEQUENCE: 392
agagaagccc aggatggtc                                                19

<210> SEQ ID NO 393
<211> LENGTH: 19
<212> TYPE: DNA
```

<213> ORGANISM: Human immunodeficiency virus 1

<400> SEQUENCE: 393
ggaagtgatg cctaaagct                                          19

<210> SEQ ID NO 394
<211> LENGTH: 20
<212> TYPE: DNA
<213> ORGANISM: Human immunodeficiency virus 1

<400> SEQUENCE: 394
tggcattact ctgcactata                                         20

<210> SEQ ID NO 395
<211> LENGTH: 26
<212> TYPE: DNA
<213> ORGANISM: Human immunodeficiency virus 1

<400> SEQUENCE: 395
gctcagatct ggttaaacat cagaga                                  26

<210> SEQ ID NO 396
<211> LENGTH: 20
<212> TYPE: DNA
<213> ORGANISM: Human immunodeficiency virus 1

<400> SEQUENCE: 396
tgctctaaag ctctgcacta                                         20

<210> SEQ ID NO 397
<211> LENGTH: 19
<212> TYPE: DNA
<213> ORGANISM: Human immunodeficiency virus 1

<400> SEQUENCE: 397
agagaagttt gtaaatttg                                          19

<210> SEQ ID NO 398
<211> LENGTH: 18
<212> TYPE: DNA
<213> ORGANISM: Human immunodeficiency virus 1

<400> SEQUENCE: 398
cataagagca cctaaggc                                           18

<210> SEQ ID NO 399
<211> LENGTH: 18
<212> TYPE: DNA
<213> ORGANISM: Human immunodeficiency virus 1

<400> SEQUENCE: 399
agaaaggggg tgagtctg                                           18

<210> SEQ ID NO 400
<211> LENGTH: 17
<212> TYPE: DNA
<213> ORGANISM: Human immunodeficiency virus 1

<400> SEQUENCE: 400
atgcttttct tctatca                                            17

<210> SEQ ID NO 401
<211> LENGTH: 18

```
<212> TYPE: DNA
<213> ORGANISM: Human immunodeficiency virus 1

<400> SEQUENCE: 401
agagaagctg caggtttg                                              18

<210> SEQ ID NO 402
<211> LENGTH: 20
<212> TYPE: DNA
<213> ORGANISM: Human immunodeficiency virus 1

<400> SEQUENCE: 402
ctggcacctg atgcacacaa                                            20

<210> SEQ ID NO 403
<211> LENGTH: 17
<212> TYPE: DNA
<213> ORGANISM: Human immunodeficiency virus 1

<400> SEQUENCE: 403
agagaagccg agctctg                                               17

<210> SEQ ID NO 404
<211> LENGTH: 18
<212> TYPE: DNA
<213> ORGANISM: Human immunodeficiency virus 1

<400> SEQUENCE: 404
acaatctgaa cgtctggg                                              18

<210> SEQ ID NO 405
<211> LENGTH: 24
<212> TYPE: DNA
<213> ORGANISM: Human immunodeficiency virus 1

<400> SEQUENCE: 405
ctacagaaca tggagcaaaa acta                                       24

<210> SEQ ID NO 406
<211> LENGTH: 24
<212> TYPE: DNA
<213> ORGANISM: Human immunodeficiency virus 1

<400> SEQUENCE: 406
ctacagaaca tggagcaaaa acta                                       24
```

BIOINFORMATICALLY DETECTABLE GROUP OF NOVEL HIV REGULATORY GENES AND USES THEREOF

CROSS-REFERENCE TO RELATED APPLICATIONS

This application is a continuation-in-part of U.S. application Ser. No. 10/604,943, filed Aug. 28, 2003, and this application claims the benefit of U.S. Provisional Application No. 60/441,230, filed Jan. 17, 2003; and U.S. application Ser. No. 10/604,943 is a continuation-in-part of U.S. application Ser. No. 10/604,942, filed Aug. 28, 2003, and U.S. application Ser. No. 10/604,943 claims the benefit of U.S. Provisional Application No. 60/441,241, filed Jan. 17, 2003; and U.S. application Ser. No. 10/604,942 is a continuation-in-part of U.S. application Ser. No. 10/604,945, filed Aug. 27, 2003, which is a continuation of U.S. application Ser. No. 10/303,778, filed Nov. 26, 2002.

BACKGROUND OF INVENTION

1. Field of the Invention

The present invention relates to a group of bioinformatically detectable novel viral RNA regulatory genes, here identified as "viral genomic address messenger" or "VGAM" genes.

2. Description of Prior Art

Small RNAs are known to perform diverse cellular functions, including post-transcriptional gene expression regulation. The first two such RNA genes, Lin-4 and Let-7, were identified by genetic analysis of *Caenorhabditis Elegans* (*Elegans*) developmental timing, and were termed short temporal RNA (stRNA) (Wightman, B., Ha, I., Ruvkun, G., Cell 75, 855 (1993); Erdmann, V. A. et al., Nucleic Acids Res. 29, 189 (2001); Lee, R. C., Feinbaum, R. L., Ambros, V., Cell 75, 843 (1993); Reinhart, B. et al., Nature 403, 901 (2000)).

Lin-4 and Let-7 each transcribe a ~22 nucleotide (nt) RNA, which acts a post transcriptional repressor of target mRNAs, by binding to elements in the 3"-untranslated region (UTR) of these target mRNAs, which are complimentary to the 22 nt sequence of Lin-4 and Let-7 respectively. While Lin-4 and Let-7 are expressed at different developmental stage, first larval stage and fourth larval stage respectively, both specify the temporal progression of cell fates, by triggering post-transcriptional control over other genes (Wightman, B., Ha, I., Ruvkun, G., Cell 75, 855 (1993); Slack et al., Mol. Cell 5,659 (2000)). Let-7 as well as its temporal regulation have been demonstrated to be conserved in all major groups of bilaterally symmetrical animals, from nematodes, through flies to humans (Pasquinelli, A., et al. Nature 408,86 (2000)).

The initial transcription product of Lin-4 and Let-7 is a ~60–80 nt RNA, the nucleotide sequence of the first half of which is partially complimentary to that of its second half, therefore allowing this RNA to fold onto itself, forming a "hairpin structure". The final gene product is a ~22 nt RNA, which is "diced" from the above mentioned "hairpin structure", by an enzyme called Dicer, which also apparently also mediates the complimentary binding of this ~22 nt segment to a binding site in the 3" UTR of its target gene.

Recent studies have uncovered 93 new genes in this class, now referred to as micro RNA or miRNA genes, in genomes of *Elegans, Drosophilea*, and Human (Lagos-Quintana, M., Rauhut, R., Lendeckel, W., Tuschl, T., Science 294, 853 (2001); Lau, N. C., Lim, L. P., Weinstein, E. G., Bartel, D. P., Science 294, 858 (2001); Lee, R. C., Ambros, V., Science 294, 862 (2001). Like the well studied Lin-4 and Let-7, all newly found MIR genes produce a ~60–80 nt RNA having a nucleotide sequence capable of forming a "hairpin structure". Expressions of the precursor ~60–80 nt RNA and of the resulting diced ~22 nt RNA of most of these newly discovered MIR genes have been detected.

Based on the striking homology of the newly discovered MIR genes to their well-studied predecessors Lin-4 and Let-7, the new MIR genes are believed to have a similar basic function as that of Lin-4 and Let-7: modulation of target genes by complimentary binding to the UTR of these target genes, with special emphasis on modulation of developmental control processes. This is despite the fact that the above mentioned recent studies did not find target genes to which the newly discovered MIR genes complementarily bind. While existing evidence suggests that the number of regulatory RNA genes "may turn out to be very large, numbering in the hundreds or even thousands in each genome", detecting such genes is challenging (Ruvkun G., "Perspective: Glimpses of a tiny RNA world", Science 294, 779 (2001)).

The ability to detect novel RNA genes is limited by the methodologies used to detect such genes. All RNA genes identified so far either present a visibly discernable whole body phenotype, as do Lin-4 and Let-7 (Wightman et. al., Cell 75, 855 (1993); Reinhart et al., Nature 403, 901 (2000)), or produce significant enough quantities of RNA so as to be detected by the standard biochemical genomic techniques, as do the 93 recently detected miRNA genes. Since a limited number clones were sequenced by the researchers discovering these genes, 300 by Bartel and 100 by Tuschl (Bartel et. al., Science 294, 858 (2001); Tuschl et. al., Science 294, 853 (2001)), the RNA genes found can not be much rarer than 1% of all RNA genes. The recently detected miRNA genes therefore represent the more prevalent among the miRNA gene family.

Current methodology has therefore been unable to detect RNA genes which either do not present a visually discernable whole body phenotype, or are rare (e.g. rarer than 0.1% of all RNA genes), and therefore do not produce significant enough quantities of RNA so as to be detected by standard biochemical technique. To date, miRNA have not been detected in viruses.

SUMMARY OF INVENTION

The present invention relates to a novel group of bioinformatically detectable, viral regulatory RNA genes, which repress expression of host target host genes, by means of complementary hybridization to binding sites in untranslated regions of these host target host genes. It is believed that this novel group of viral genes represent a pervasive viral mechanism of attacking hosts, and that therefore knowledge of this novel group of viral genes may be useful in preventing and treating viral diseases.

In various preferred embodiments, the present invention seeks to provide improved method and system for detection and prevention of viral disease, which is mediated by this group of novel viral genes.

Accordingly, the invention provides several substantially pure nucleic acids (e.g., genomic nucleic acid, cDNA or synthetic nucleic acid) each encoding a novel viral gene of the VGAM group of gene, vectors comprising the nucleic acids, probes comprising the nucleic acids, a method and system for selectively modulating translation of known "target" genes utilizing the vectors, and a method and system for detecting expression of known "target" genes utilizing the probe.

By "substantially pure nucleic acid" is meant nucleic acid that is free of the genes which, in the naturally-occurring genome of the organism from which the nucleic acid of the invention is derived, flank the genes discovered and isolated by the present invention. The term therefore includes, for example, a recombinant nucleic acid which is incorporated into a vector, into an autonomously replicating plasmid or virus, or into the genomic nucleic acid of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant nucleic acid which is part of a hybrid gene encoding additional polypeptide sequence.

"Inhibiting translation" is defined as the ability to prevent synthesis of a specific protein encoded by a respective gene, by means of inhibiting the translation of the mRNA of this gene. "Translation inhibiter site" is defined as the minimal nucleic acid sequence sufficient to inhibit translation.

There is thus provided in accordance with a preferred embodiment of the present invention a bioinformatically detectable novel viral gene encoding substantially pure nucleic acid wherein: RNA encoded by the bioinformatically detectable novel viral gene is about 18 to about 24 nucleotides in length, and originates from an RNA precursor, which RNA precursor is about 50 to about 120 nucleotides in length, a nucleotide sequence of a first half of the RNA precursor is a partial inversed-reversed sequence of a nucleotide sequence of a second half thereof, a nucleotide sequence of the RNA encoded by the novel viral gene is a partial inversed-reversed sequence of a nucleotide sequence of a binding site associated with at least one host target gene, and a function of the novel viral gene is bioinformatically deducible.

There is further provided in accordance with another preferred embodiment of the present invention a method for anti-viral treatment comprising neutralizing said RNA.

Further in accordance with a preferred embodiment of the present invention the neutralizing comprises: synthesizing a complementary nucleic acid molecule, a nucleic sequence of which complementary nucleic acid molecule is a partial inversed-reversed sequence of said RNA, and transfecting host cells with the complementary nucleic acid molecule, thereby complementarily binding said RNA.

Further in accordance with a preferred embodiment of the present invention the neutralizing comprises immunologically neutralizing.

There is still further provided in accordance with another preferred embodiment of the present invention a bioinformatically detectable novel viral gene encoding substantially pure nucleic acid wherein: RNA encoded by the bioinformatically detectable novel viral gene includes a plurality of RNA sections, each of the RNA sections being about 50 to about 120 nucleotides in length, and including an RNA segment, which RNA segment is about 18 to about 24 nucleotides in length, a nucleotide sequence of a first half of each of the RNA sections encoded by the novel viral gene is a partial inversed-reversed sequence of nucleotide sequence of a second half thereof, a nucleotide sequence of each of the RNA segments encoded by the novel viral gene is a partial inversed-reversed sequence of the nucleotide sequence of a binding site associated with at least one target host gene, and a function of the novel viral gene is bioinformatically deducible from the following data elements: the nucleotide sequence of the RNA encoded by the novel viral gene, a nucleotide sequence of the at least one target host gene, and function of the at least one target host gene.

Further in accordance with a preferred embodiment of the present invention the function of the novel viral gene is bioinformatically deducible from the following data elements: the nucleotide sequence of the RNA encoded by the bioinformatically detectable novel viral gene, a nucleotide sequence of the at least one target host gene, and a function of the at least one target host gene.

Still further in accordance with a preferred embodiment of the present invention the RNA encoded by the novel viral gene complementarily binds the binding site associated with the at least one target host gene, thereby modulating expression of the at least one target host gene.

Additionally in accordance with a preferred embodiment of the present invention the binding site associated with at least one target host gene is located in an untranslated region of RNA encoded by the at least one target host gene.

Moreover in accordance with a preferred embodiment of the present invention the function of the novel viral gene is selective inhibition of translation of the at least one target host gene, which selective inhibition includes complementary hybridization of the RNA encoded by the novel viral gene to the binding site.

Further in accordance with a preferred embodiment of the present invention the invention includes a vector including the DNA.

Still further in accordance with a preferred embodiment of the present invention the invention includes a method of selectively inhibiting translation of at least one gene, including introducing the vector.

Moreover in accordance with a preferred embodiment of the present invention the introducing includes utilizing RNAi pathway.

Additionally in accordance with a preferred embodiment of the present invention the invention includes a gene expression inhibition system including: the vector, and a vector inserter, functional to insert the vector into a cell, thereby selectively inhibiting translation of at least one gene.

Further in accordance with a preferred embodiment of the present invention the invention includes a probe including the DNA.

Still further in accordance with a preferred embodiment of the present invention the invention includes a method of selectively detecting expression of at least one gene, including using the probe.

Additionally in accordance with a preferred embodiment of the present invention the invention includes a gene expression detection system including: the probe, and a gene expression detector functional to selectively detect expression of at least one gene.

Further in accordance with a preferred embodiment of the present invention the invention includes an anti-viral substance capable of neutralizing the RNA.

Still further in accordance with a preferred embodiment of the present invention the neutralizing includes complementarily binding the RNA.

Additionally in accordance with a preferred embodiment of the present invention the neutralizing includes immunologically neutralizing.

Moreover in accordance with a preferred embodiment of the present invention the invention includes a method for anti-viral treatment including neutralizing the RNA.

Further in accordance with a preferred embodiment of the present invention the neutralizing includes: synthesizing a complementary nucleic acid molecule, a nucleic sequence of which complementary nucleic acid molecule is a partial inversed-reversed sequence of the RNA, and transfecting host cells with the complementary nucleic acid molecule, thereby complementarily binding the RNA.

Still further in accordance with a preferred embodiment of the present invention the neutralizing includes immunologically neutralizing.

BRIEF DESCRIPTION OF DRAWINGS

FIG. 10 is a block diagram illustrating different utilities of genes of a novel group of genes, and operons of a novel group of operons, both of the present invention;

FIGS. 11A and 11B are simplified diagrams, which when taken together illustrate a mode of gene therapy applicable to genes of the novel group of genes of the present invention;

FIG. 12A is an annotated sequence of EST72223 (SEQ ID NO: 415) comprising novel gene GAM24 (SEQ ID NO: 419) detected by the gene detection system of the present invention;

FIGS. 12B and 12C are pictures of laboratory results, which when taken together demonstrate laboratory confirmation of expression of the bioinformatically detected novel gene GAM24 of FIG. 12A;

FIG. 12D provides pictures of laboratory results, which when taken together demonstrate further laboratory confirmation of expression of the bioinformatically detected novel gene GAM24 of FIG. 12A;

FIG. 13A is an annotated sequence of an EST7929020 (SEQ ID NO: 416) comprising novel genes GAM23 (SEQ ID NO: 420) and GAM25 (SEQ ID NO: 421) detected by the gene detection system of the present invention;

FIG. 13B is a picture of laboratory results, which confirm expression of bioinformatically detected novel genes GAM23 and GAM25 of FIG. 13A;

FIG. 14A is an annotated sequence of an EST1388749 (SEQ ID NO: 417) comprising novel gene GAM26 (SEQ ID NO: 422) detected by the gene detection system of the present invention;

FIG. 14B is a picture of laboratory results, which confirm expression of the bioinformatically detected novel gene GAM26 of FIG. 14A;

FIGS. 15A through 29D are schematic diagrams illustrating sequences, functions and utilities of 15 specific viral genes of the novel group of viral regulatory genes of the present invention, detected using the bioinformatic gene detection system described hereinabove with reference to FIGS. 1 through 8; and FIGS. 30 through 31 are schematic diagrams illustrating sequences, functions and utilities of 2 specific viral genes of a group of novel regulatory "operon-like" viral genes of the present invention, detected using the bioinformatic gene detection system described hereinabove with reference to FIGS. 9 through 14.

BRIEF DESCRIPTION OF SEQUENCES

A Sequence Listing of genomic sequences of the present invention designated SEQ ID:1 through SEQ ID:406 is attached to this application, enclosed in computer readable form on CD-ROM. The genomic listing comprises the following nucleotide sequences: Genomic sequences designated SEQ ID:1 through SEQ ID:15 are nucleotide sequences of 15 gene precursors of respective novel genes of the present invention; Genomic sequences designated SEQ ID:16 through SEQ ID:30 are nucleotide sequences of 15 genes of the present invention; and Genomic sequences designated SEQ ID:31 through SEQ ID:406 are nucleotide sequences of 376 gene precursors of respective novel genes of the present invention.

DETAILED DESCRIPTION

Figure 1:
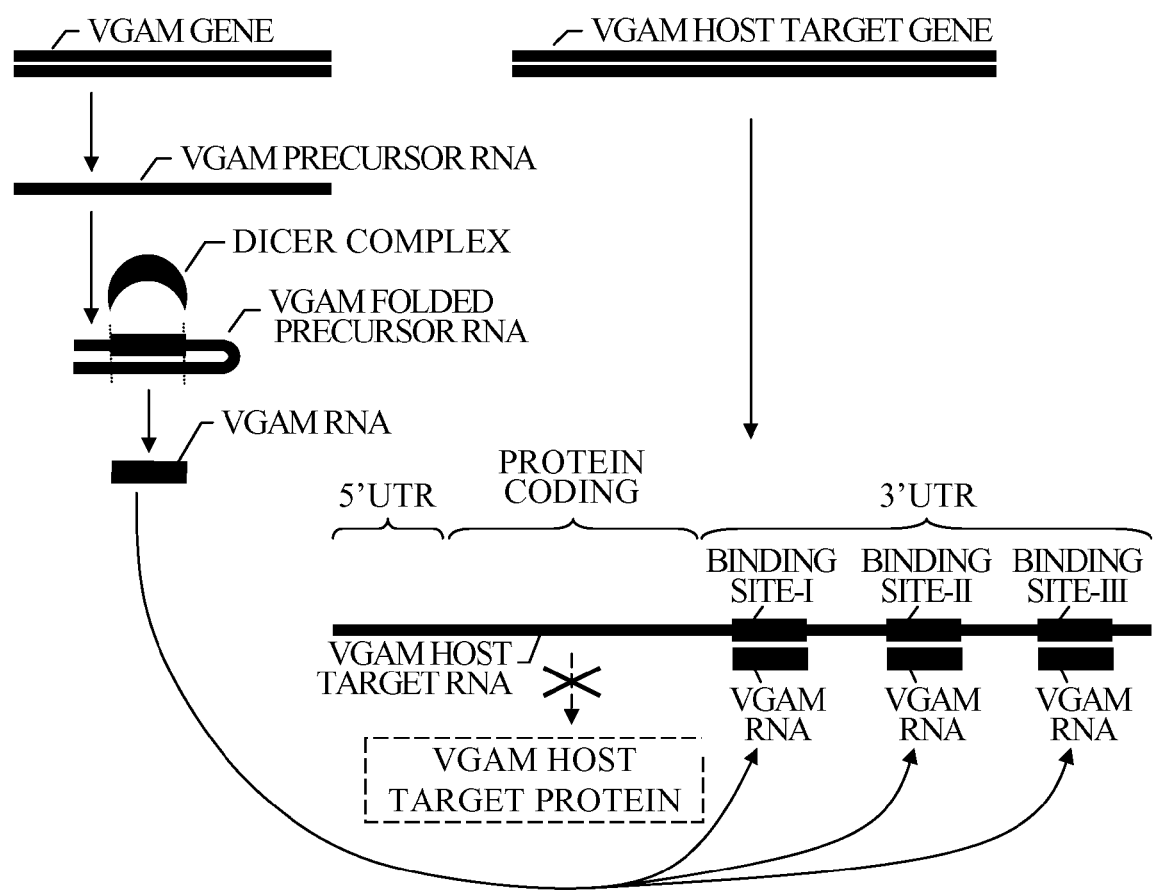
FIG. 1 is a simplified diagram illustrating a mode by which viral genes of a novel group of viral genes of the present invention, modulate expression of known host target genes.

Reference is now made to FIG. 1 which is a simplified diagram illustrating a mode by which genes of a novel group of genes of the present invention, modulate expression of known host target.

The novel genes of the present invention are micro RNA (miRNA)-like, regulatory RNA genes, modulating expression of known host target. This mode of modulation is common to other known miRNA genes, as described hereinabove with reference to the background of the invention section.

VGAM GENE and TARGET GENE are two human genes contained in the DNA of the human genome.

VGAM GENE encodes a VGAM PRECURSOR RNA. However, similar to other miRNA genes, and unlike most ordinary genes, its RNA, VGAM PRECURSOR RNA, does not encode a protein.

Figure 8:
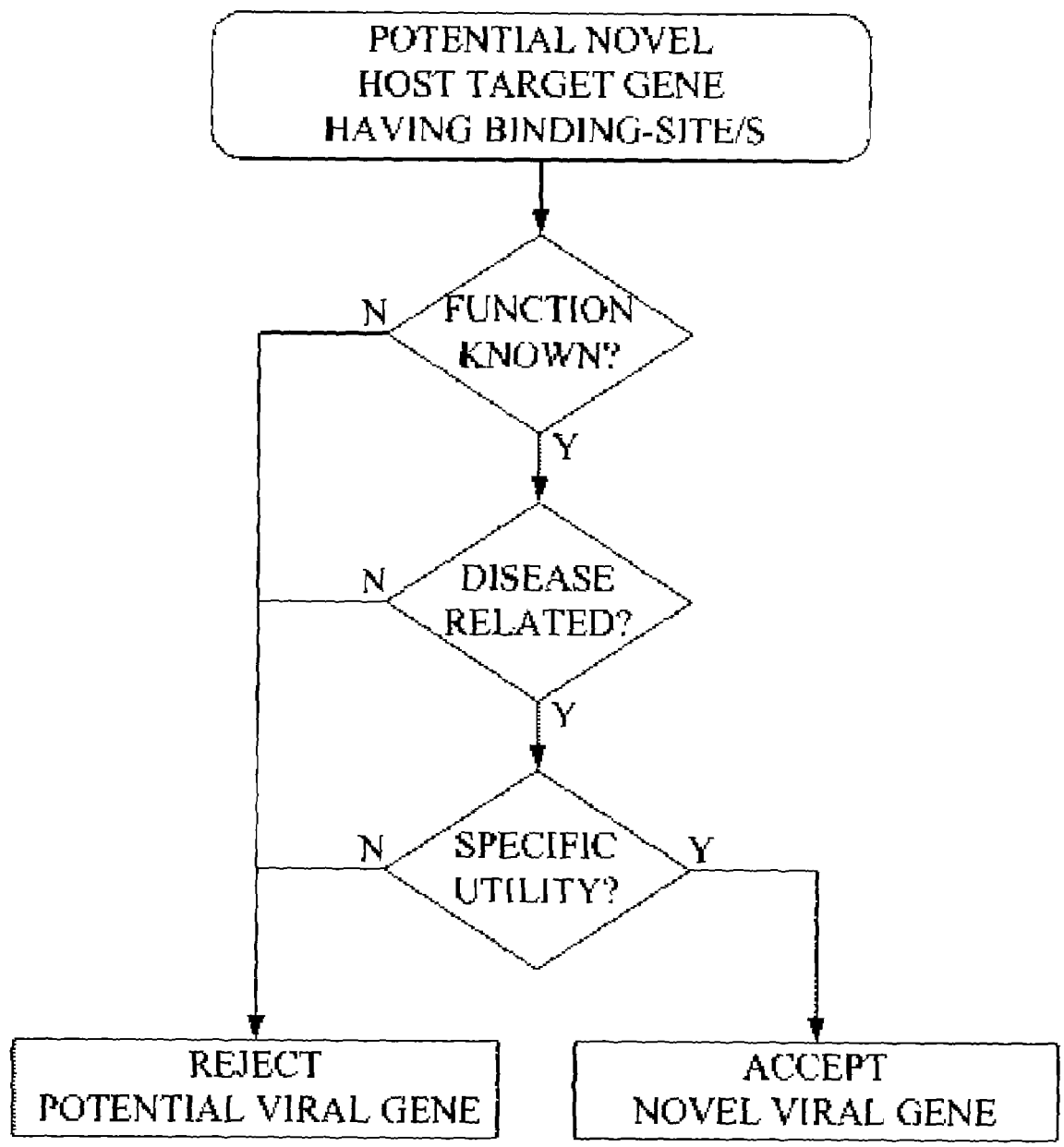
FIG. 8 is a simplified flowchart illustrating operation of a function & utility analyzer constructed and operative in accordance with a preferred embodiment of the present invention.

VGAM PRECURSOR RNA folds onto itself, forming VGAM FOLDED PRECURSOR RNA. As FIG. 8 illustrates, VGAM FOLDED PRECURSOR RNA forms a "hairpin structure", folding onto itself. As is well known in the art, this "hairpin structure", is typical genes of the miRNA genes, and is due to the fact that nucleotide sequence of the first half of the RNA of a gene in this group is an accurate or partial inversed-reversed sequence of the nucleotide sequence of its second half. By "inversed-reversed" is meant a sequence which is reversed and wherein each nucleotide is replaced by a complimentary nucleotide, as is well known in the art (e.g. ATGGC [SEQ ID NO: 407] is the inversed-reversed sequence of GCCAT [SEQ ID NO: 408]).

An enzyme complex, designated DICER COMPLEX, "dices" the VGAM FOLDED PRECURSOR RNA into a single stranded RNA segment, about 22 nucleotides long, designated VGAM RNA. As is known in the art, "dicing" of the hairpin structured RNA precursor into shorter RNA segments about 22 nucleotides long by a Dicer type enzyme is catalyzed by an enzyme complex comprising an enzyme called Dicer together with other necessary proteins.

TARGET GENE encodes a corresponding messenger RNA, designated TARGET RNA. This TARGET RNA comprises 3 regions: a 5" untranslated region, a protein coding region and a 3" untranslated region, designated 5"UTR, PROTEIN CODING and 3"UTR respectively.

VGAM RNA binds complementarily a BINDING SITE, located on the 3"UTR segment of TARGET RNA. This complementarily binding is due to the fact that the nucleotide sequence of VGAM RNA is an accurate or partial inversed-reversed sequence of the nucleotide sequence of BINDING SITE.

The complimentary binding of VGAM RNA to BINDING SITE inhibits translation of TARGET RNA into TARGET PROTEIN. TARGET PROTEIN is therefore outlined by a broken line.

It is appreciated by one skilled in the art that the mode of transcriptional inhibition illustrated by FIG. 1 with specific reference to VGAM genes of the present invention, is in fact common to all other miRNA genes. A specific complimentary binding site has been demonstrated only for Lin-4 and Let-7. All the other 93 newly discovered miRNA genes are also believed by those skilled in the art to modulate expression of other genes by complimentary binding, although specific complimentary binding sites for these genes have not yet been found (Ruvkun G., "Perspective: Glimpses of a tiny RNA world", Science 294, 779 (2001)). The present invention discloses a novel group of genes, the VGAM genes, belonging to the miRNA genes group, and for which a specific an complimentary binding has been determined.

Figure 2:
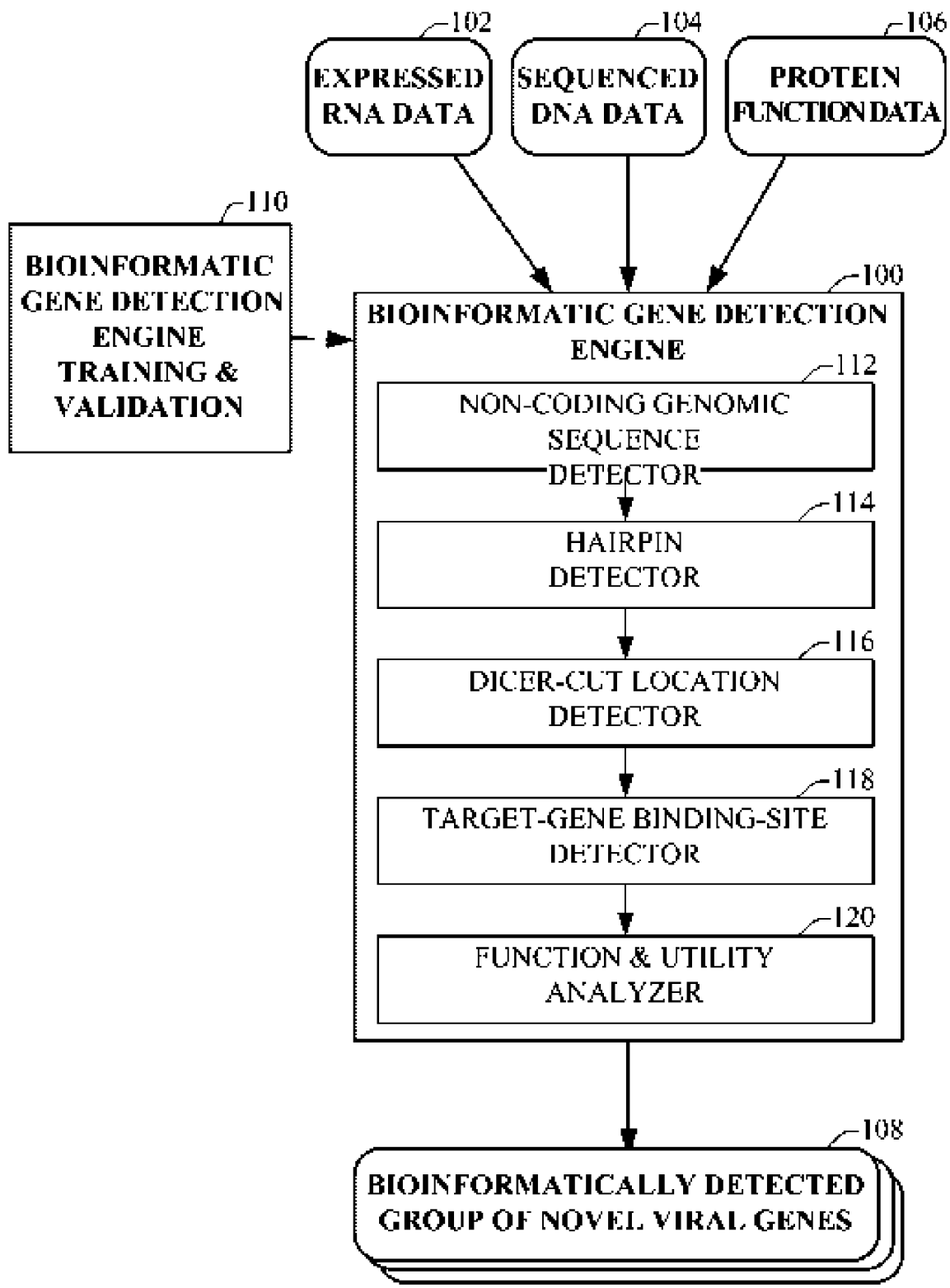
FIG. 2 is a simplified block diagram illustrating a bioinformatic gene detection system capable of detecting genes of the novel group of genes of the present invention, which system is constructed and operative in accordance with a preferred embodiment of the present invention.

Reference is now made to FIG. 2 which is a simplified block diagram illustrating a bioinformatic gene detection system capable of detecting genes of the novel group of genes of the present invention, which system is constructed and operative in accordance with a preferred embodiment of the present invention.

A centerpiece of the present invention is a bioinformatic gene detection engine 100, which is a preferred implementation of a mechanism capable of bioinformatically detecting genes of the novel group of genes of the present invention.

The function of the bioinformatic gene detection engine 100 is as follows: it receives three types of input, expressed RNA data 102, sequenced DNA data 104, and protein function data 106, performs a complex process of analysis of this data as elaborated below, and based on this analysis produces output of a bioinformatically detected group of novel genes designated 108.

Expressed RNA data 102 comprises published expressed sequence tags (EST) data, published mRNA data, as well as other sources of published RNA data. Sequenced DNA data 104 comprises alphanumeric data describing sequenced genomic data, which preferably includes annotation data such as location of known protein coding regions relative to the sequenced data. Protein function data 106 comprises scientific publications reporting studies which elucidated physiological function known proteins, and their connection, involvement and possible utility in treatment and diagnosis of various diseases. Expressed RNA data 102, sequenced DNA data 104 may preferably be obtained from data published by the National Center for Bioinformatics (NCBI) at the National Institute of Health (NIH), as well as from various other published data sources. Protein function data 106 may preferably be obtained from any one of numerous relevant published data sources, such as the Online Mendelian Inherited Disease In Man (OMIM) database developed by John Hopkins University, and also published by NCBI.

Prior to actual detection of bioinformatically detected novel genes 108 by the bioinformatic gene detection engine 100, a process of bioinformatic gene detection engine training & validation designated 110 takes place. This process uses the known miRNA genes as a training set (some 200 such genes have been found to date using biological laboratory means), to train the bioinformatic gene detection engine 100 to bioinformatically recognize miRNA-like genes, and their respective potential target binding sites. Bioinformatic gene detection engine training & validation 110 is further describe hereinbelow with reference to FIG. 3.

The bioinformatic gene detection engine 100 comprises several modules which are preferably activated sequentially, and are described as follows:

A non-coding genomic sequence detector 112 operative to bioinformatically detect non-protein coding genomic sequences. The non-coding genomic sequence detector 112 is further described hereinbelow with reference to FIGS. 4A and 4B.

A hairpin detector 114 operative to bioinformatically detect genomic "hairpin-shaped" sequences, similar to VGAM FOLDED PRECURSOR of FIG. 1. The hairpin detector 114 is further described hereinbelow with reference to FIGS. 5A and 5B.

A dicer-cut location detector 116 operative to bioinformatically detect the location on a hairpin shaped sequence which is enzymatically cut by DICER COMPLEX of FIG. 1. The dicer-cut location detector 116 is further described hereinbelow with reference to FIG. 6A.

A target-gene binding-site detector 118 operative to bioinformatically detect host target having binding sites, the nucleotide sequence of which is partially complementary to that of a given genomic sequence, such as a sequence cut by DICER COMPLEX of FIG. 1. The target-gene binding-site detector 118 is further described hereinbelow with reference to FIGS. 7A and 7B.

A function & utility analyzer 120 operative to analyze function and utility of host target, in order to identify host target which have a significant clinical function and utility. The function & utility analyzer 120 is further described hereinbelow with reference to FIG. 8.

Hardware implementation of the bioinformatic gene detection engine 100 is important, since significant computing power is preferably required in order to perform the computation of bioinformatic gene detection engine 100 in reasonable time and cost. As an example, it is estimated that using one powerful 8-processor PC Server, over 30 months of computing time (at 24 hours per day) would be required in order to detect all miRNA genes in human EST data, and their respective binding sites.

For example, in order to address this challenge at reasonable time and cost, a preferred embodiment of the present invention may comprise a cluster of a large number of personal computers (PCs), such as 100 PCs (Pentium IV, 1.7 GHz, with 40 GB storage each), connected by Ethernet to several strong servers, such as 4 servers (2-CPU, Xeon 2.2 GHz, with 200 GB storage each), combined with an 8-processor server (8-CPU, Xeon 550 Mhz w/8 GB RAM) connected via 2 HBA fiber-channels to an EMC Clariion 100-disks, 3.6 Terabyte storage device. Additionally, preferably an efficient database computer program, such as Microsoft (TM) SQL-Server database computer program is used and is optimized to the specific requirements of bioinformatic gene detection engine 100. Furthermore, the PCs are preferably optimized to operate close to 100% CPU usage continuously, as is known in the art. Using suitable hardware and software may preferably reduce the required calculation time in the abovementioned example from 30 months to 20 days.

It is appreciated that the abovementioned hardware configuration is not meant to be limiting, and is given as an illustration only. The present invention may be implemented in a wide variety of hardware and software configurations.

The present invention discloses 15 novel viral genes of the VGAM group of genes, which have been detected bioinformatically, as described hereinbelow with reference to FIGS. 15 through 29. Laboratory confirmation of 4 genes of the GAM group of genes is described hereinbelow with reference to FIGS. 12 through 14.

Figure 3:
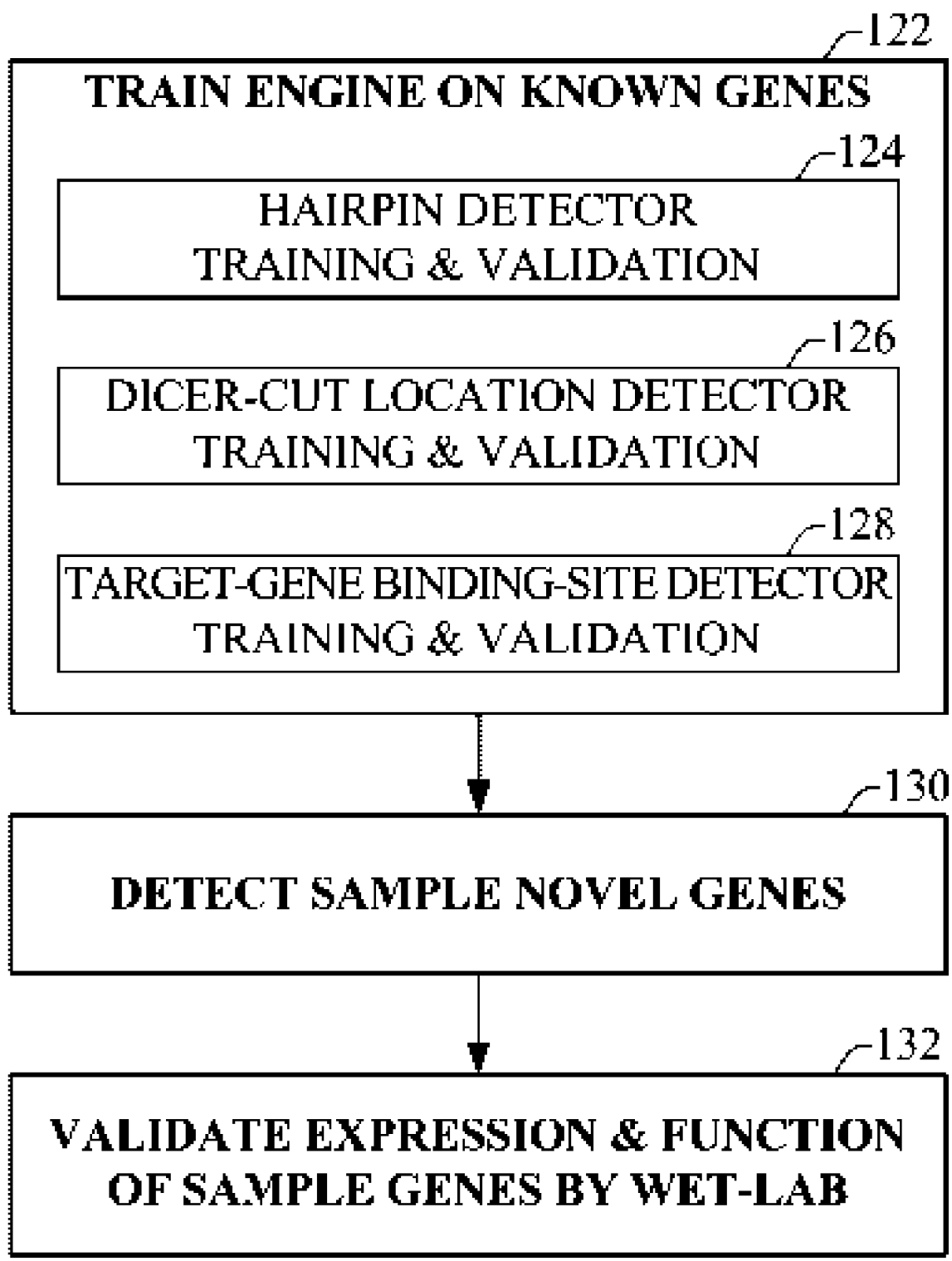
FIG. 3 is a simplified flowchart illustrating operation of a mechanism for training of a computer system to recognize the novel genes of the present invention, which mechanism is constructed and operative in accordance with a preferred embodiment of the present invention.

Reference is now made to FIG. 3 which is a simplified flowchart illustrating operation of a mechanism for training of a computer system to recognize the novel genes of the present invention. This mechanism is a preferred implementation of the bioinformatic gene detection engine training & validation 110 described hereinabove with reference to FIG. 2.

Bioinformatic gene detection engine training & validation 110 of FIG. 2 begins by training the bioinformatic gene detection engine to recognize known miRNA genes, as designated by numeral 122. This training step comprises hairpin detector training & validation 124, further described hereinbelow with reference to FIG. 12A, dicer-cut location detector training & validation 126, further described hereinbelow with reference to FIGS. 6A and 6B, and target-gene binding-site detector training & validation 128, further described hereinbelow with reference to FIG. 7A.

Next, the bioinformatic gene detection engine 100 is used to bioinformatically detect sample novel genes, as designated by numeral 130. An example of a sample novel gene thus detected is described hereinbelow with reference to FIG. 12.

Finally, wet lab experiments are preferably conducted in order to validate expression and preferably function the sample novel genes detected by the bioinformatic gene detection engine 100 in the previous step. An example of wet-lab validation of the abovementioned sample novel gene bioinformatically detected by the system is described hereinbelow with reference to FIGS. 13A and 13B.

Figure 4A:
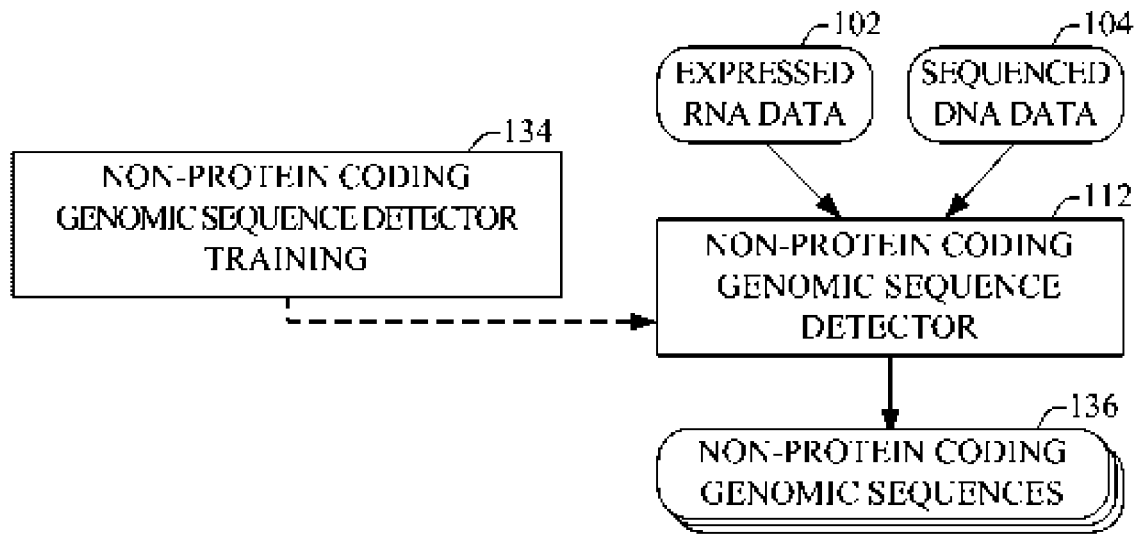
FIG. 4A is a simplified block diagram of a non-coding genomic sequence detector constructed and operative in accordance with a preferred embodiment of the present invention.

Reference is now made to FIG. 4A which is a simplified block diagram of a preferred implementation of the noncoding genomic sequence detector 112 described hereinabove with reference to FIG. 2. Non-protein coding genomic sequence detector 112 of FIG. 2 preferably receives as input at least two types of published genomic data: expressed RNA data 102, including EST data and mRNA data, and sequenced DNA data 104. After its initial training, indicated by numeral 134, and based on the abovementioned input data, the non-protein coding genomic sequence detector 112 produces as output a plurality of non-protein coding genomic sequences 136. Preferred operation of the non-protein coding genomic sequence detector 112 is described hereinbelow with reference to FIG. 4B.

Figure 4B:
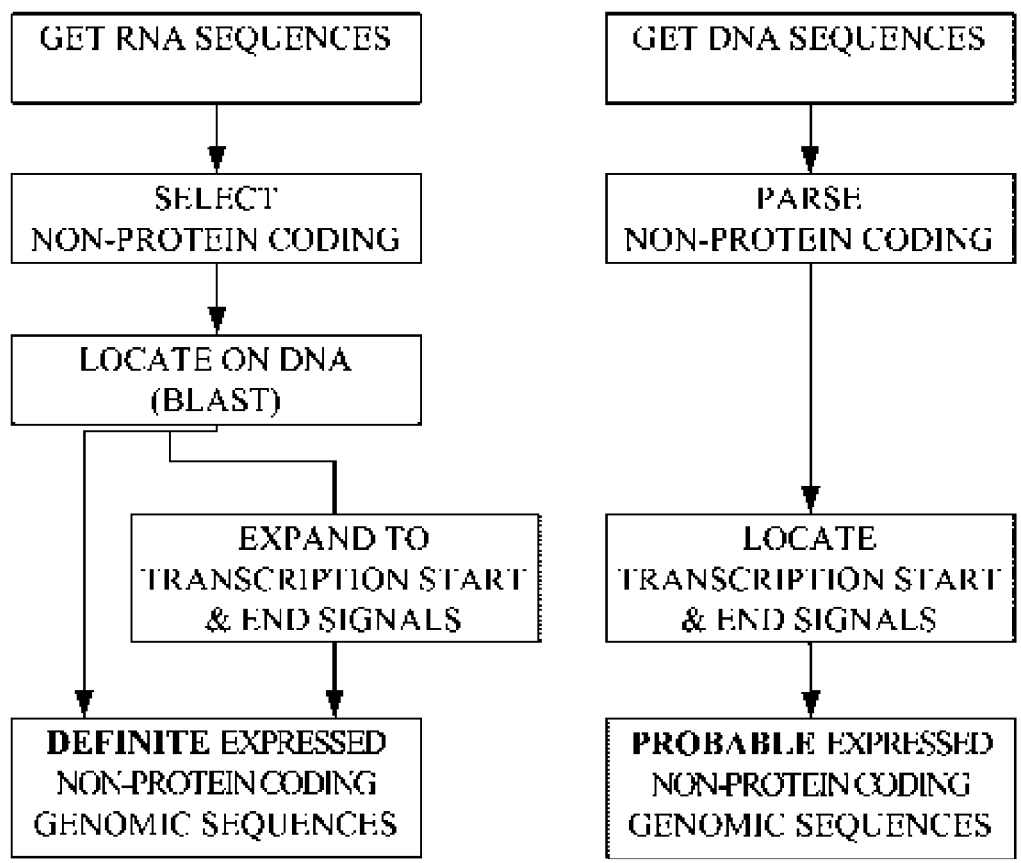
FIG. 4B is a simplified flowchart illustrating operation of a non-coding genomic sequence detector constructed and operative in accordance with a preferred embodiment of the present invention.

Reference is now made to FIG. 4B which is a simplified flowchart illustrating a preferred operation of the noncoding genomic sequence detector 112 of FIG. 2. Detection of non-protein coding genomic sequences to be further analyzed by the system generally preferably progresses in one of the following two paths.

A first path for detecting non-protein coding genomic sequences begins by receiving a plurality of known RNA sequences, such as EST data. Each RNA sequence is first compared to all known protein-coding sequences, in order to select only those RNA sequences which are non-protein coding. This can preferably be performed by BLAST comparison of the RNA sequence to known protein coding sequences. The abovementioned BLAST comparison to the DNA preferably also provides the localization of the RNA on the DNA.

Optionally, an attempt may be made to "expand" the non-protein RNA sequences thus found, by searching for transcription start and end signals, upstream and downstream of location of the RNA on the DNA respectively, as is well known in the art.

A second path for detecting non-protein coding genomic sequences starts by receiving DNA sequences. The DNA sequences are parsed into non protein coding sequences, based on published DNA annotation data: extracting those DNA sequences which are between known protein coding sequences. Next, transcription start and end signals are sought. If such signals are found, and depending on their "strength", probable expressed non-protein coding genomic sequences are yielded.

Figure 5A:
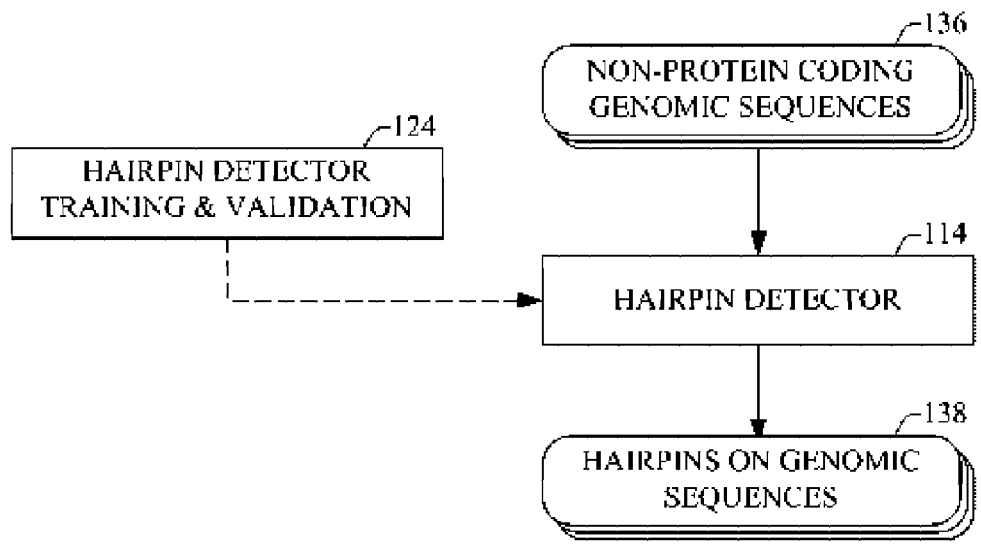
FIG. 5A is a simplified block diagram of a hairpin detector constructed and operative in accordance with a preferred embodiment of the present invention.

Reference is now made to FIG. 5A which is a simplified block diagram of a preferred implementation of the hairpin detector 114 described hereinabove with reference to FIG. 2.

The goal of the hairpin detector 114 is to detect "hairpin" shaped genomic sequences, similar to those of known miRNA genes. As mentioned hereinabove with reference to FIG. 1, a "hairpin" genomic sequence refers to a genomic sequence which "folds onto itself" forming a hairpin like shape, due to the fact that nucleotide sequence of the first half of the nucleotide sequence is an accurate or The hairpin detector 114 of FIG. 2 receives as input a plurality of non-protein coding genomic sequences 136 of FIG. 4A, and after a phase of hairpin detector training & validation 124 of FIG. 3, is operative to detect and output "hairpin shaped" sequences found in the input expressed non-protein coding sequences, designated by numeral 138.

The phase of hairpin detector training & validation 124 is an iterative process of applying the hairpin detector 114 to known hairpin shaped miRNA genes, calibrating the hairpin detector 114 such that it identifies the training set of known hairpins, as well as sequences which are similar thereto. Preferred operation of the hairpin detector 114 is described hereinbelow with reference to FIG. 5B.

Figure 5B:
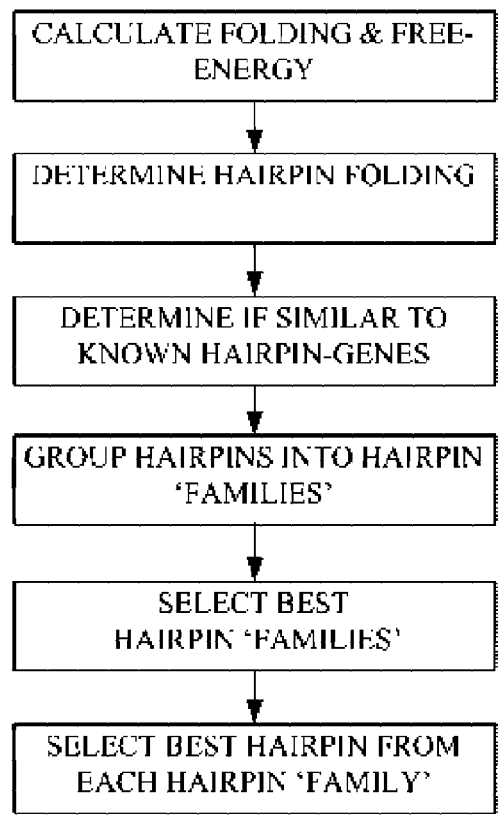
FIG. 5B is a simplified flowchart illustrating operation of a hairpin detector constructed and operative in accordance with a preferred embodiment of the present invention.

Reference is now made to FIG. 5B which is a simplified flowchart illustrating a preferred operation of the hairpin detector 114 of FIG. 2.

A hairpin structure is a two dimensional folding structure, resulting from the nucleotide sequence pattern: the nucleotide sequence of the first half of the hairpin sequence is an inversed-reversed sequence of the second half thereof. Different methodologies are known in the art for detection of various two dimensional and three dimensional hairpin structures.

In a preferred embodiment of the present invention, the hairpin detector 114 initially calculates possible 2-dimensional (2D) folding patterns of a given one of the non-protein coding genomic sequences 136, preferably using a 2D folding algorithm based on free-energy calculation, such as the Zucker algorithm, as is well known in the art.

Next, the hairpin detector 114 analyzes the results of the 2D folding, in order to determine the presence, and location of hairpin structures. A 2D folding algorithm typically provides as output a listing of the base-pairing of the 2D folded shape, i.e. a listing of which all two pairs of nucleotides in the sequence which will bond. The goal of this second step, is to asses this base-pairing listing, in order to determine if it describes a hairpin type bonding pattern.

The hairpin detector 114 then assess those hairpin structures found by the previous step, comparing them to hairpins of known miRNA genes, using various parameters such as length, free-energy, amount and type of mismatches, etc. Only hairpins that bear statistically significant resemblance of the population of hairpins of known miRNAs, according to the abovementioned parameters are accepted.

Lastly, the hairpin detector 114 attempts to select those hairpin structures which are as stable as the hairpins of know miRNA genes. This may be achieved in various manners. A preferred embodiment of the present invention utilizes the following methodology comprising three steps:

First, the hairpin detector 114 attempts to group potential hairpins into "families" of closely related hairpins. As is known in the art, a free-energy calculation algorithm, typically provides multiple "versions" each describing a different possible 2D folding pattern for the given genomic sequence, and the free energy of such possible folding. The hairpin detector 114 therefore preferably assesses all hairpins found on all "versions", grouping hairpins which appear in different versions, but which share near identical locations into a common "family" of hairpins. For example, all hairpins in different versions, the center of which is within 7 nucleotides of each other may preferably be grouped to a single "family".

Next, hairpin "families" are assessed, in order to select only those families which represent hairpins that are as stable as those of known miRNA hairpins. For example, preferably only families which are represented in at least 65% of the free-energy calculation 2D folding versions, are considered stable.

Finally, an attempt is made to select the most suitable hairpin from each selected family. For example, preferably the hairpin which appears in more versions than other hairpins, and in versions the free-energy of which is lower, may be selected.

Figure 6A:
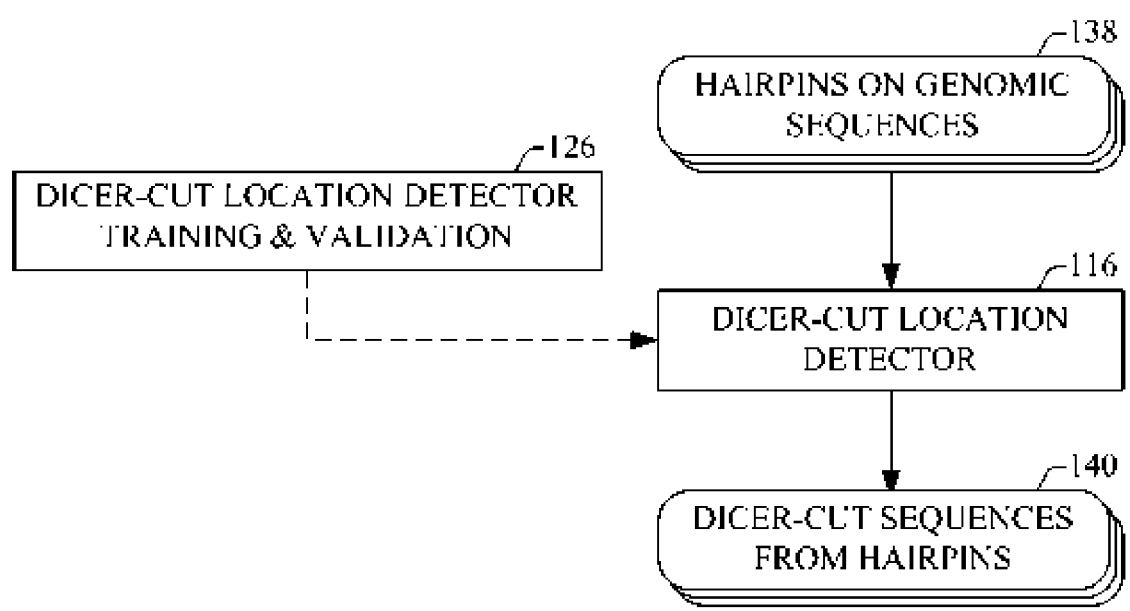
FIG. 6A is a simplified block diagram of a dicer-cut location detector constructed and operative in accordance with a preferred embodiment of the present invention.

Reference is now made to FIG. 6A which is a simplified block diagram of a preferred implementation of the dicer-cut location detector 116 described hereinabove with reference to FIG. 2.

The goal of the dicer-cut location detector 116 is to detect the location in which DICER COMPLEX of FIG. 1, comprising the enzyme Dicer, would "dice" the given hairpin sequence, similar to VGAM FOLDED PRECURSOR RNA, yielding VGAM RNA both of FIG. 1.

The dicer-cut location detector 116 of FIG. 2 therefore receives as input a plurality of hairpins on genomic sequences 138 of FIG. 5A, which were calculated by the previous step, and after a phase of dicer-cut location detector training & validation 126 of FIG. 3, is operative to detect a respective plurality of dicer-cut sequences from hairpins 140, one for each hairpin.

In a preferred embodiment of the present invention, the dicer-cut location detector 116 preferably uses a combination of neural networks, Bayesian networks, Markovian modeling, and Support Vector Machines (SVMs) trained on the known dicer-cut locations of known miRNA genes, in order to detect dicer-cut locations. Dicer-cut location detector training & validation 126, which is further described hereinbelow with reference to FIG. 6B.

Figure 6B:
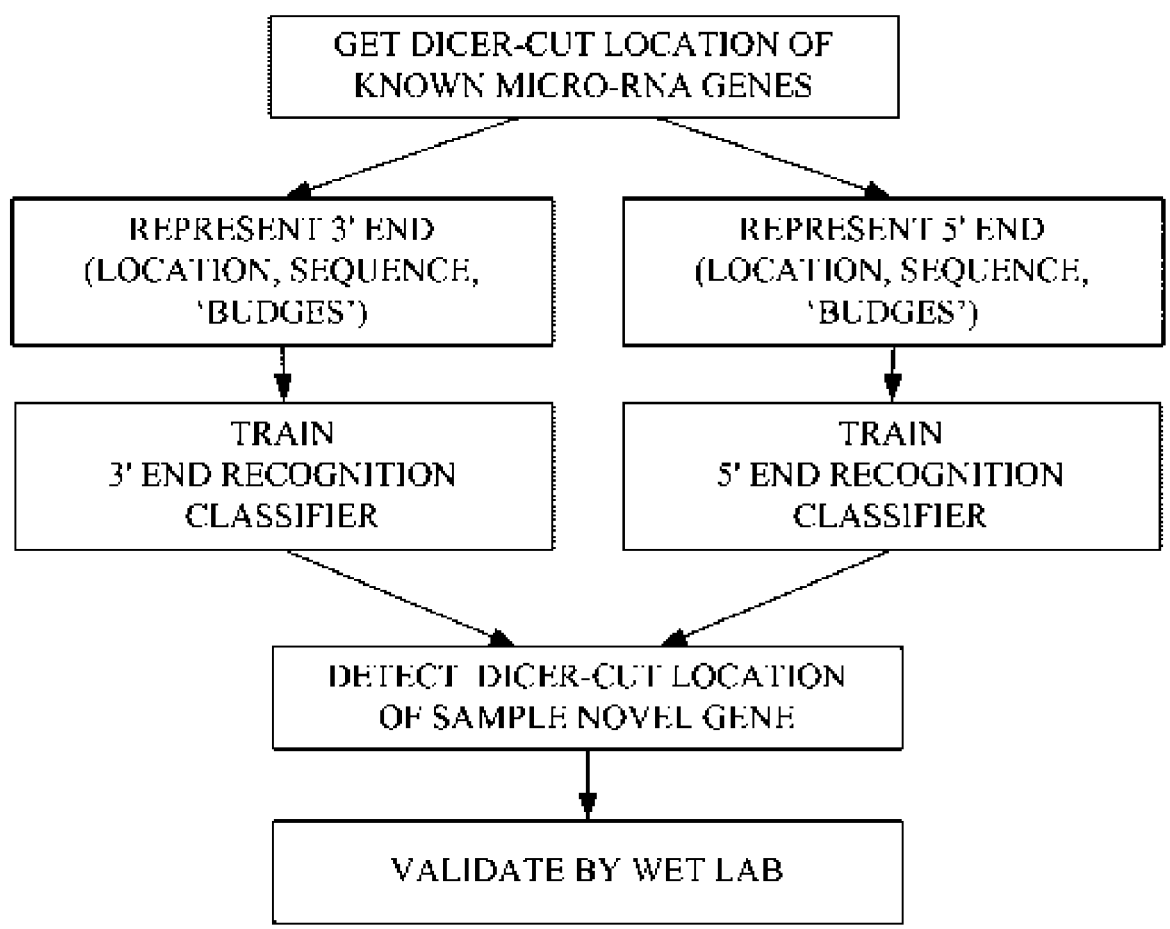
FIG. 6B is a simplified flowchart illustrating training of a dicer-cut location detector constructed and operative in accordance with a preferred embodiment of the present invention.
Figure 6C:
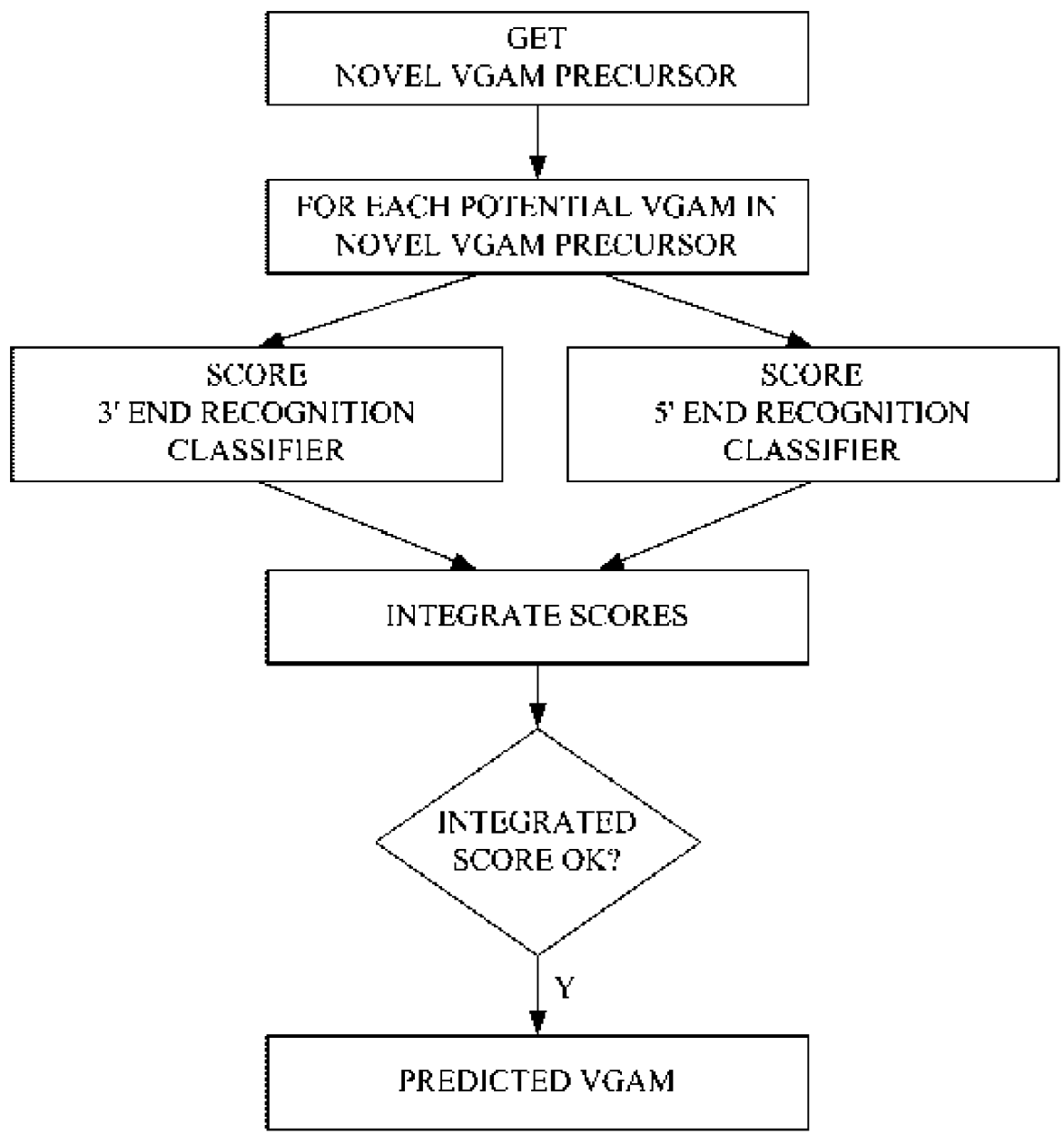

Reference is now made to FIG. 6B which is a simplified flowchart illustrating a preferred implementation of dicer-cut location detector training & validation 126 of FIG. 3. Dicer-cut location detector 116 first preprocesses known miRNA hairpins and their respective dicer-cut locations, so as to be able to properly analyze them and train the detection system accordingly:

The folding pattern is calculated for each known miRNA, preferably based on free-energy calculation, and the size of the hairpin, the size of the loop at the center of the hairpin, and "bulges" (i.e. mismatched base-pairs) in the folded hairpin are noted.

The dicer-cut location, which is known for known miRNA genes, is noted relative to the above, as well as to the nucleotides in each location along the hairpin. Frequency of identity of nucleotides, and nucleotide-pairing, relative to their location in the hairpin, and relative to the known dicer-cut location in the known miRNA genes is analyzed and modeled.

Different techniques are well known in the art for analysis of existing pattern from a given "training set" of species belonging to a genus, which techniques are then capable, to a certain degree, to detect similar patterns in other species not belonging to the training-set genus. Such techniques include, but are not limited to neural networks, Bayesian networks, Support Vector Machines (SVM), Genetic Algorithms, Markovian modeling, and others, as is well known in the art.

Using such techniques, preferably a combination of several of the above techniques, the known hairpins are represented as a several different networks (such as neural, Bayesian, or SVM) input and output layers. Both nucleotide, and "bulge" (i.e. nucleotide pairing or mismatch) are represented for each position in the hairpin, at the input layer, and a corresponding true/false flag at each position, indicating whether it was diced by dicer at the output layer. Multiple networks are preferably used concurrently, and the results therefrom are integrated and further optimized. Markovian modeling may also be used to validate the results and enhance their accuracy. Finally, the bioinformatic detection of dicer-cut location of a sample novel is confirmed by wet-lab experimentation.

Figure 7A:
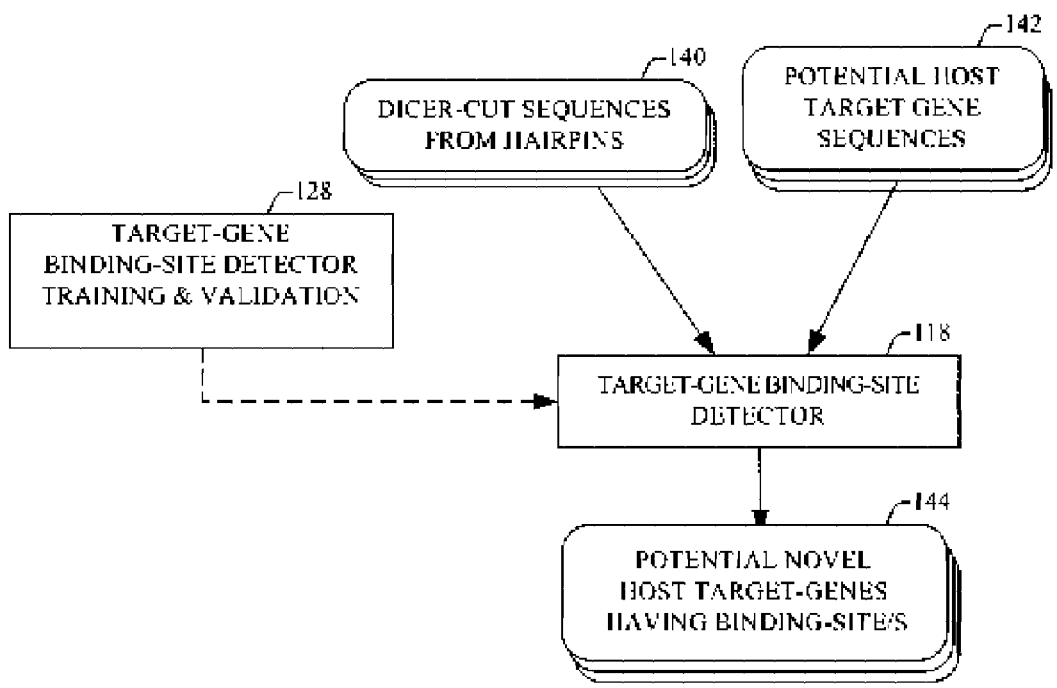
FIG. 7A is a simplified block diagram of a target-gene binding-site detector constructed and operative in accordance with a preferred embodiment of the present invention.

Reference is now made to FIG. 7A which is a simplified block diagram of a preferred implementation of the target-gene binding-site detector 118 described hereinabove with reference to FIG. 2. The goal of the target gene binding-site detector 118 is to detect a BINDING SITE of FIG. 1, located in an untranslated region of the RNA of a known gene, the nucleotide sequence of which BINDING SITE is at least partially complementary to that of a VGAM RNA of FIG. 1, thereby determining that the abovementioned known gene is a target gene of VGAM of FIG. 1.

The target-gene binding-site detector 118 of FIG. 2 therefore receives as input a plurality of dicer-cut sequences from hairpins 140 of FIG. 6A which were calculated by the previous step, and a plurality of potential target gene sequences 142 which derive sequence DNA data 104 of FIG. 2, and after a phase of target-gene binding-site detector training & validation 128 of FIG. 3, is operative to detect target-genes having binding site/s 144 the nucleotide sequence of which is at least partially complementary to that of each of the plurality of dicer-cut sequences from hairpins 140. Preferred operation of the target-gene binding-site detector is further described hereinbelow with reference to FIG. 7B.

Figure 7B:
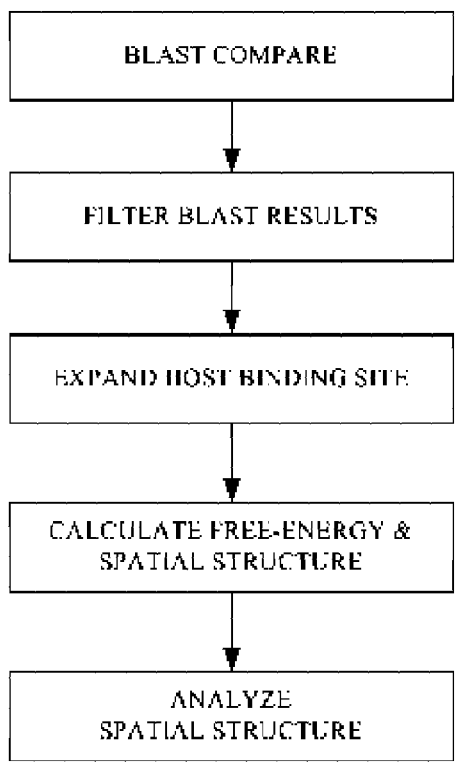
FIG. 7B is a simplified flowchart illustrating operation of a target-gene binding-site detector constructed and operative in accordance with a preferred embodiment of the present invention.

Reference is now made to FIG. 7B which is a simplified flowchart illustrating a preferred operation of the target-gene binding-site detector 118 of FIG. 2. In a preferred embodiment of the present invention, the target-gene binding-site detector 118 first performs a BLAST comparison of the nucleotide sequence of each of the plurality of dicer-cut sequences from hairpins 140, to the potential target gene sequences 142, in order to find crude potential matches. Blast results are then filtered to results which are similar to those of known binding sites (e.g. binding sites of miRNA genes Lin-4 and Let-7 to target genes Lin-14, Lin-41, Lin 28 etc.). Next the binding site is expanded, checking if nucleotide sequenced immediately adjacent to the binding site found by BLAST, may improve the match. Suitable binding sites, then are computed for free-energy and spatial structure. The results are analyzed, selecting only those binding sites, which have free-energy and spatial structure similar to that of known binding sites.

Reference is now made to FIG. 8 which is a simplified flowchart illustrating a preferred operation of the function & utility analyzer 120 described hereinabove with reference to FIG. 2. The goal of the function & utility analyzer 120 is to determine if a potential target gene is in fact a valid clinically useful target gene. Since a potential novel VGAM gene binding a binding site in the UTR of a target gene is understood to inhibit expression of that target gene, and if that target gene is shown to have a valid clinical utility, then in such a case it follows that the potential novel gene itself also has a valid useful function which is the opposite of that of the target gene.

The function & utility analyzer 120 preferably receives as input a plurality of potential novel target genes having binding-site/s 144, generated by the target-gene binding-site detector 118, both of FIG. 7A. Each potential gene, is evaluated as follows:

First the system first checks to see if the function of the potential target gene is scientifically well established. Preferably, this can be achieved bioinformatically by searching various published data sources presenting information on known function of proteins. Many such data sources exist and are published as is well known in the art.

Next, for those target genes the function of which is scientifically known and is well documented, the system then checks if scientific research data exists which links them to known diseases. For example, a preferred embodiment of the present invention utilizes the OMIM(TM) database published by NCBI, which summarizes research publications relating to genes which have been shown to be associated with diseases.

Finally, the specific possible utility of the target gene is evaluated. While this process too may be facilitated by bioinformatic means, it might require human evaluation of published scientific research regarding the target gene, in order to determine the utility of the target gene to the diagnosis and or treatment of specific disease. Only potential novel genes, the target-genes of which have passed all three examinations, are accepted as novel genes.

Figure 9:
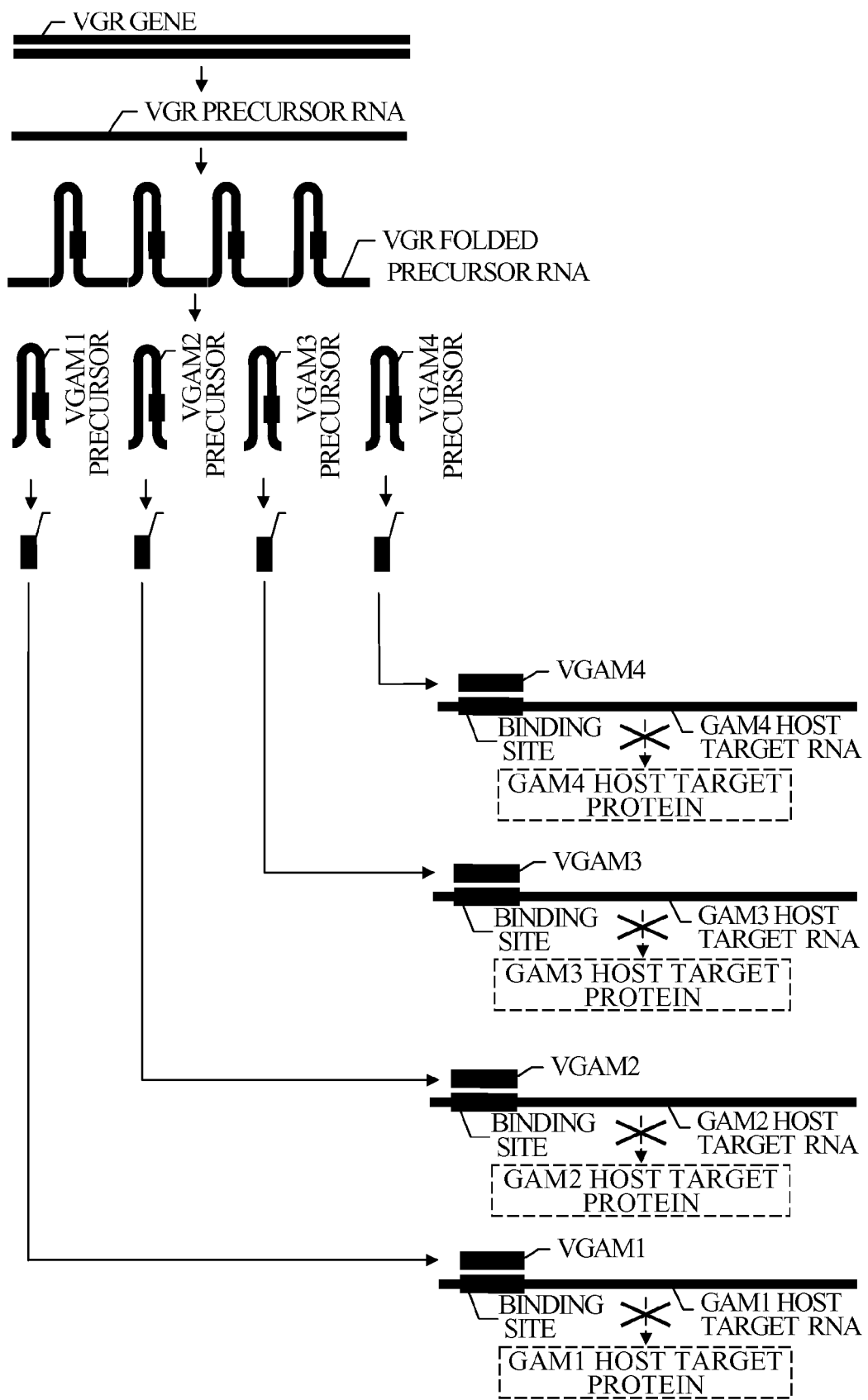
FIG. 9 is a simplified diagram describing a novel bioinformatically detected group of regulatory genes, referred to here as Genomic Record (GR) genes, each of which encodes an "operon-like" cluster of novel miRNA-like genes, which in turn modulates expression of a plurality of target genes.

Reference is now made to FIG. 9, which is a simplified diagram describing a novel bioinformatically detected group of regulatory genes, referred to here as Genomic Record (GR) genes, that encode an "operon-like" cluster of novel miRNA-like genes, each modulating expression of a plurality of host target, the function and utility of which target genes is known.

GR GENE (Genomic Record Gene) is gene of a novel, bioinformatically detected group of regulatory, non protein coding, RNA genes. The method by which GR is detected is described hereinabove with reference to FIGS. 6–15.

GR GENE encodes an RNA molecule, typically several hundred nucleotides long, designated GR PRECURSOR RNA.

GR PRECURSOR RNA folds spatially, as illustrated by GR FOLDED PRECURSOR RNA, into a plurality of what is known in the art as "hair-pin" structures. The nucleotide sequence of GR PRECURSOR RNA comprises a plurality of segments, the first half of each such segment having a nucleotide sequence which is at least a partial inversed-reversed sequence of the second half thereof, thereby causing formation of a plurality of "hairpin" structures, as is well known in the art.

GR FOLDED PRECURSOR RNA is naturally processed by cellular enzymatic activity, into 3 separate hairpin shaped RNA segments, each corresponding to VGAM PRECURSOR RNA of FIG. 1, designated VGAM1 PRECURSOR, VGAM2 PRECURSOR and VGAM3 PRECURSOR respectively.

The above mentioned VGAM precursors, are diced by Dicer of FIG. 1, yielding short RNA segments of about 22 nucleotides in length, each corresponding to VGAM RNA of FIG. 1, designated VGAM1, VGAM2 and VGAM3 respectively.

VGAM1, VGAM2 and VGAM3 each bind complementarily to binding sites located in untranslated regions of respective host target, designated VGAM1-TARGET RNA, VGAM2-TARGET RNA and VGAM3-TARGET RNA respectively. This binding inhibits translation of the respective target proteins designated VGAM1-TARGET PROTEIN, VGAM2-TARGET PROTEIN and VGAM3-TARGET PROTEIN respectively.

The structure of VGAM genes comprised in a GR GENE, and their mode of modulation of expression of their respective target genes is described hereinabove with reference to FIG. 1. The bioinformatic approach to detection of VGAM genes comprised in a GR GENE is described hereinabove with reference to FIGS. 9 through 14.

The present invention discloses 17 novel viral genes of the GR group of genes, which have been detected bioinformatically, as described hereinbelow with reference to FIGS. 15 through 31. Laboratory confirmation of 3 genes of the GR group of genes is described hereinbelow with reference to FIGS. 9A through 14.

In summary, the current invention discloses a very large number of novel viral GR genes, each of which encodes a plurality of VGAM genes, which in turn may modulate expression of a plurality of host target proteins.

Reference is now made to FIG. 10 which is a block diagram illustrating different utilities of genes of the novel group of genes of the present invention referred to here as VGAM genes and GR genes.

The present invention discloses a first plurality of novel genes referred to here as VGAM genes, and a second plurality of operon-like genes referred to here as GR genes, each of the GR genes encoding a plurality of VGAM genes. The present invention further discloses a very large number of known target-genes, which are bound by, and the expression of which is modulated by each of the novel genes of the present invention. Published scientific data referenced by the present invention provides specific, substantial, and credible evidence that the abovementioned target genes modulated by novel genes of the present invention, are associated with various diseases. Specific novel genes of the present invention, target genes thereof and diseases associated therewith, are described hereinbelow with reference to FIGS. 15 through 29 It is therefore appreciated that a function of VGAM genes and GR genes of the present invention is modulation of expression of target genes related to known diseases, and that therefore utilities of novel genes of the present invention include diagnosis and treatment of the above-mentioned diseases. FIG. 10 describes various types of diagnostic and therapeutic utilities of novel genes of the present invention.

A utility of novel genes of the present invention is detection of VGAM genes and of GR genes. It is appreciated that since VGAM genes and GR genes modulate expression of disease related target genes, that detection of expression of VGAM genes in clinical scenarios associated with said diseases is a specific, substantial and credible utility. Diagnosis of novel genes of the present invention may preferably be implemented by RNA expression detection techniques, including but not limited to biochips, as is well known in the art. Diagnosis of expression of genes of the present invention may be useful for research purposes, in order to further understand the connection between the novel genes of the present invention and the abovementioned related diseases, for disease diagnosis and prevention purposes, and for monitoring disease progress.

Another utility of novel genes of the present invention is anti-VGAM gene therapy, a mode of therapy which allows up regulation of a disease related target-gene of a novel VGAM gene of the present invention, by lowering levels of the novel VGAM gene which naturally inhibits expression of that target gene. This mode of therapy is particularly useful with respect to target genes which have been shown to be under-expressed in association with a specific disease. Anti-VGAM gene therapy is further discussed hereinbelow with reference to FIGS. 11A and 11B.

A further utility of novel genes of the present invention is VGAM replacement therapy, a mode of therapy which achieves down regulation of a disease related target-gene of a novel VGAM gene of the present invention, by raising levels of the VGAM gene which naturally inhibits expression of that target gene. This mode of therapy is particularly useful with respect to target genes which have been shown to be over-expressed in association with a specific disease. VGAM replacement therapy involves introduction of supplementary VGAM gene products into a cell, or stimulation of a cell to produce excess VGAM gene products. VGAM replacement therapy may preferably be achieved by transfecting cells with an artificial DNA molecule encoding a VGAM gene, which causes the cells to produce the VGAM gene product, as is well known in the art.

Yet a further utility of novel genes of the present invention is modified VGAM therapy. Disease conditions are likely to exist, in which a mutation in a binding site of a VGAM gene prevents natural VGAM gene to effectively bind inhibit a disease related target-gene, causing up regulation of that target gene, and thereby contributing to the disease pathology. In such conditions, a modified VGAM gene is designed which effectively binds the mutated VGAM binding site, i.e. is an effective anti-sense of the mutated VGAM binding site, and is introduced in disease effected cells. Modified VGAM therapy is preferably achieved by transfecting cells with an artificial DNA molecule encoding the modified VGAM gene, which causes the cells to produce the modified VGAM gene product, as is well known in the art.

An additional utility of novel genes of the present invention is induced cellular differentiation therapy. As aspect of the present invention is finding genes which determine cellular differentiation, as described hereinabove with reference to FIG. 11. Induced cellular differentiation therapy comprises transfection of cell with such VGAM genes thereby determining their differentiation as desired. It is appreciated that this approach may be widely applicable, inter alia as a means for auto transplantation harvesting cells of one cell-type from a patient, modifying their differentiation as desired, and then transplanting them back into the patient. It is further appreciated that this approach may also be utilized to modify cell differentiation in vivo, by transfecting cells in a genetically diseased tissue with a cell-differentiation determining VGAM gene, thus stimulating these cells to differentiate appropriately.

Reference is now made to FIGS. 11A and 11B, simplified diagrams which when taken together illustrate anti-VGAM gene therapy mentioned hereinabove with reference to FIG. 10. A utility of novel genes of the present invention is anti-VGAM gene therapy, a mode of therapy which allows up regulation of a disease related target-gene of a novel VGAM gene of the present invention, by lowering levels of the novel VGAM gene which naturally inhibits expression of that target gene. FIG. 11A shows a normal VGAM gene, inhibiting translation of a target gene of VGAM gene, by binding to a BINDING SITE found in an untranslated region of TARGET RNA, as described hereinabove with reference to FIG. 1.

FIG. 11B shows an example of anti-VGAM gene therapy. ANTI-VGAM RNA is short artificial RNA molecule the sequence of which is an anti-sense of VGAM RNA. Anti-VGAM treatment comprises transfecting diseased cells with ANTI-VGAM RNA, or with a DNA encoding thereof. The ANTI-VGAM RNA binds the natural VGAM RNA, thereby preventing binding of natural VGAM RNA to its BINDING SITE. This prevents natural translation inhibition of TARGET RNA by VGAM RNA, thereby up regulating expression of TARGET PROTEIN.

It is appreciated that anti-VGAM gene therapy is particularly useful with respect to target genes which have been shown to be under-expressed in association with a specific disease.

Reference is now made to FIG. 12A which is an annotated sequence of an EST comprising a novel gene detected by the gene detection system of the present invention. FIG. 12A shows the nucleotide sequence of a known human non-protein coding EST (Expressed Sequence Tag), identified as EST72223 (SEQ ID NO: 415). It is appreciated that the sequence of this EST comprises sequences of one known miRNA gene, identified as MIR98 (SEQ ID NO: 418), and of one novel GAM gene, referred to here as GAM24 (SEQ ID NO: 419), detected by the bioinformatic gene detection system of the present invention, described hereinabove with reference to FIG. 2.

Reference is now made to FIGS. 12B and 12C that are pictures of laboratory results, which when taken together demonstrate laboratory confirmation of expression of the bioinformatically detected novel gene of FIG. 12A. Reference is now made to FIG. 12B which is a Northern blot analysis of MIR-98 and EST72223 transcripts. MIR-98 and EST72223 were reacted with MIR-98 and GAM24 probes as indicated in the figure. It is appreciated that the probes of both MIR-98 and GAM24 reacted with EST72223, indicating that EST72223 contains the sequences of MIR-98 and of GAM24. It is further appreciated that the probe of GAM24 does not cross-react with MIR-98.

Reference is now made to FIG. 12C. A Northern blot analysis of EST72223 and MIR-98 transfections were performed, subsequently marking RNA by the MIR-98 and GAM24 probes. Left, Northern reacted with MIR-98, Right, Northern reacted with GAM24. The molecular Sizes of EST72223, MIR-98 and GAM24 are indicated by arrows. Hela are control cells that have not been introduced to exogenous RNA. EST and MIR-98 Transfections are RNA obtained from Hela transfected with EST72223 and MIR-98, respectively. MIR-98 and EST are the transcripts used for the transfection experiment. The results indicate that EST72223, when transfected into Hela cells, is cut yielding known miRNA gene MIR-98 and novel miRNA gene GAM24.

Reference is now made to FIG. 12D, which is a Northern blot of a lisate experiment with MIR-98 and GAM24. Northern blot analysis of hairpins in EST72223. Left, Northern reacted with predicted Mir-98 hairpin probe, Right, Northern reacted with predicted GAM24 hairpin probe. The molecular size of EST Is indicated by arrow. The molecular sizes of Mir-98 and GAM24 are 80 nt and 100 nt, respectively as indicated by arrows. The 22 nt molecular marker is indicated by arrow. 1-Hela lysate; 2-EST incubated 4h with Hela lysate; 3-EST without lysate; 4-Mir transcript incubated 4h with Hela lysate; 5-Mir transcript incubated overnight with Hela lysate; 6-Mir transcript without lysate; 7-RNA extracted from Hela cells following transfection with Mir transcript.

Technical methods used in experiments, the results of which are depicted in FIGS. 12B, 12C and 12D are as follows:

Transcript preparations. Digoxigenin (DIG) labeled transcripts were prepared from EST72223 (TIGER), MIR98 and predicted precursor hairpins by using a DIG RNA labeling kit (Roche Molecular Biochemicals) according to the manufacture's protocol. Briefly, PCR products with T7 promoter at the 5" end or T3 promoter at the 3" end were prepared from each DNA in order to use it as a template to prepare sense and antisense transcripts, respectively. MIR-98 was amplified using EST72223 as a template with T7miR98 forward primer: 5"-TAATACGACTCACTATAGGGTGAGGTAGTAAGTTGTATTGTT-3" (SEQ ID NO: 409) and T3miR98 reverse primer: 5"-AATTAACCCTCACTAAAGGGAAAGTAGTAAGTTGTATAGTT-3" (SEQ ID NO: 410). EST72223 was amplified with T7-EST 72223 forward primer: 5"-TAATACGAC TCACTATAGGCCCTTATTAGAGGATTCTGCT-3" (SEQ ID NO: 411) and T3-EST72223 reverse primer: 5"-AATTAACCCTCAC-TAAAGGTTTTTTTTTC CTGAGACAGAGT-3" (SEQ ID NO: 412). Bet-4 was amplified using EST72223 as a template with Bet-4 forward primer: 5"-GAGGCAGGA GAAT-TGCTTGA-3" (SEQ ID NO: 413) and T3-EST72223 reverse primer: 5"-AATTAACCCTCACTAAAGGCCT-GAGACAGAGTCTTGCTC-3" (SEQ ID NO: 414). The PCR products were cleaned and used for DIG-labeled or unlabeled transcription reactions with the appropriate polymerase. For transfection experiments, CAP reaction was performed by using a mMassage mMachine kit (Ambion).

Transfection procedure: Transfection of Hela cells was performed by using TransMessenger reagent (Qiagen) according to the manufacture's protocol. Briefly, Hela cells were seeded to 1–2×10^6 cells per plate a day before transfection. Two μg RNA transcripts were mixed with 8 μl Enhancer in a final volume of 100 μl, mixed and incubated at room temperature for 5 min. 16 μl TransMessenger reagent was added to the RNA-Enhancer, mixed and incubated for additional 10 min. Cell plates were washed with sterile PBS twice and then incubated with the transfection mix diluted with 2.5 ml DMEM medium without serum. Cells were incubated with transfection mix for three hours under their normal growth condition (370C and 5% $CO_2$) before the transfection mix was removed and a fresh DMEM medium containing serum was added to the cells. Cells were left to grow 48 hours before harvesting.

Target RNA cleavage assay: Cap-labeled target RNAs were generated using mMessage mMachine™ (Ambion). Caped RNA transcripts were preincubated at 30° C. for 15 min in supplemented Hela S100 obtained from Computer Cell Culture, Mos, Belgium. After addition of all components, final concentrations were 100 mM target RNA, 1 m M ATP, 0.2 mM GTP, 10 U/ml RNasin, 30 μg/ml creatine kinase, 25 mM creatine phosphate, and 50% S100 extract. Incubation was continued for 4 hours to overnight. Cleavage reaction was stopped by the addition of 8 volumes of proteinase K buffer (200 Mm Tris-Hcl, pH 7.5, 25 m M EDTA, 300 mM NaCl, and 2% SDS). Proteinase K, dissolved in 50 mM Tris-HCl, pH 8, 5 m M CaCl2, and 50% glycerol, was added to a final concentration of 0.6 mg/ml. Sample were subjected to phenol/chloroform extraction and kept frozen until analyzed by urea-TBE PAGE.

Northern analysis: RNAs were extracted from cells by using Tri-reagent according to the manufacture's protocol. The RNAs were dissolved in water and heated to 650 C to disrupt any association of the 25 nt RNA with larger RNA molecules. RNA were placed on ice and incubated for 30 min with PEG (MW=8000) in a final concentration of 5% and NaCl in a final concentration of 0.5 M to precipitate high molecular weight nucleic acid. The RNAs were centrifuged at 10,000×g for 10 min to pellet the high molecular weight nucleic acid. The supernatant containing the low molecular weight RNAs was collected and three volumes of ethanol was added. The RNAs were placed at −200 C for at least two hours and then centrifuged at 10,000×g for 10 min. The pellets were dissolved in Urea-TBE buffer (1×tbe, 7 M urea) for further analysis by a Northern blot.

RNA samples were boiled for 5 min before loading on 15%–8% polyacrylamide (19:1) gels containing 7M urea and 1×TBE. Gels were run in 1×TBE at a constant voltage of 300V and then transferred into a nylon membrane. The membrane was exposed to 3 min ultraviolet light to cross link the RNAs to the membrane. Hybridization was performed overnight with DIG-labeled probes at 420 C. Membranes were washed twice with SSC×2 and 0.2% SDS for 10 min. at 420 C and then washed twice with SSC×0.5 for 5 min at room temperature. The membrane was then developed by using a DIG luminescent detection kit (Roche) using anti DIG and CSPD reaction, according to the manufacture's protocol.

It is appreciated that the data presented in FIGS. 12A, 12B, 12C and 12D, when taken together validate the function of the bioinformatic gene detection engine 100 of FIG. 2. FIG. 12A shows a novel GAM gene bioinformatically detected by the bioinformatic gene detection engine 100, and FIGS. 12B, 12C and 12D show laboratory confirmation of the expression of this novel gene. This is in accord with the engine training and validation methodology described hereinabove with reference to FIG. 3.

Reference is now made to FIG. 13A which is an annotated sequence of an EST comprising a novel gene detected by the gene detection system of the present invention. FIG. 13A shows the nucleotide sequence of a known human non-protein coding EST (Expressed Sequence Tag), identified as EST 7929020 (SEQ ID NO: 416). It is appreciated that the sequence of this EST comprises sequences of two novel GAM genes, referred to here as GAM23 (SEQ ID NO: 420) and GAM25 (SEQ ID NO: 421), detected by the bioinformatic gene detection system of the present invention, described hereinabove with reference to FIG. 2.

Reference is now made to FIG. 13B which presents pictures of laboratory results, that demonstrate laboratory confirmation of expression of the bioinformatically detected novel gene of FIG. 13A. Northern blot analysis of hairpins in EST7929020. Left, Northern reacted with predicted GAM25 hairpin probe, Right, Northern reacted with predicted GAM23 hairpin probe. The molecular size of EST is indicated by arrow. The molecular sizes of GAM23 and GAM25 are 60 nt, as indicated by arrow. The 22 nt molecular marker is indicated by arrow. 1-Hela lysate; 2-EST incubated 4h with Hela lysate; 3-EST incubated overnight with Hela lysate; 4-EST without lysate; 5-GAM transcript; 6-GAM 22 nt marker; 7-GAM PCR probe; 8-RNA from control Hela cells; 9-RNA extracted from Hela cells following transfection with EST.

Figure 13C:
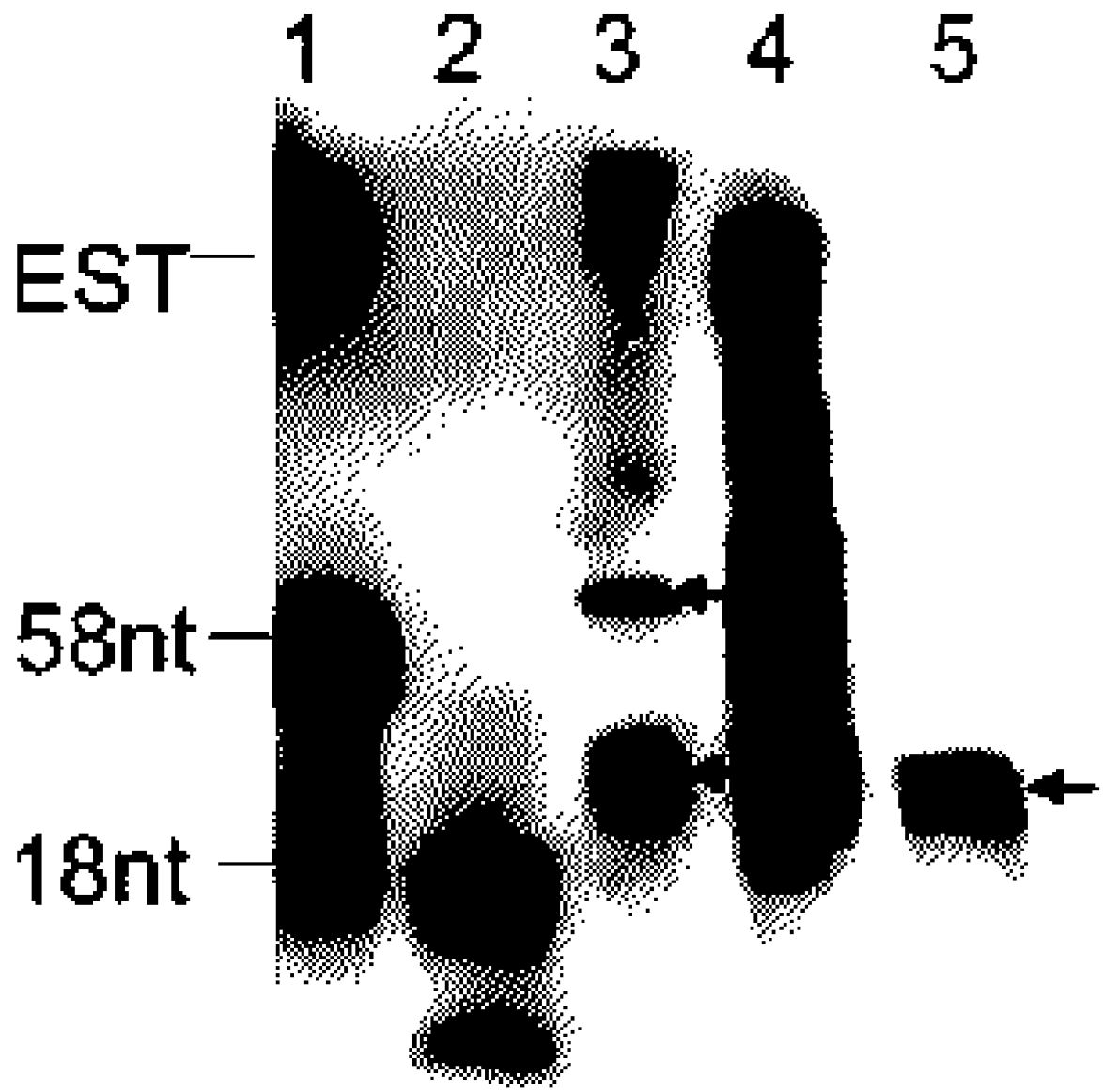
FIG. 13C is a picture of laboratory results, which confirm endogenous expression of bioinformatically detected novel gene GAM25 of FIG. 15A.

Reference is now made to FIG. 13C which is a picture of a Northern blot confirming Endogenous expression of bioinformatically detected gene GAM25 of FIG. 13A from in Hela cells. Northern was reacted with a predicted GAM25 hairpin probe. The molecular size of EST7929020 is indicated. The molecular sizes of GAM25 is 58 nt, as indicated. A 19 nt DNA oligo molecular marker is indicated. Endogenous expression of GAM25 in Hela total RNA fraction and in S-100 fraction is indicated by arrows. 1-GAM25 transcript; 2-GAM25 DNA oligo marker; 3-RNA from control Hela cells; 4-RNA extracted from Hela cells following transfection with EST; 5-RNA extracted from S-100 Hela lysate.

Reference is now made to FIG. 14A which is an annotated sequence of an EST comprising a novel gene detected by the gene detection system of the present invention. FIG. 14A shows the nucleotide sequence of a known human non-protein coding EST (Expressed Sequence Tag), identified as EST 1388749 (SEQ ID NO: 417). It is appreciated that the sequence of this EST comprises sequence of a novel GAM gene, referred to here as GAM26 (SEQ ID NO: 422), detected by the bioinformatic gene detection system of the present invention, described hereinabove with reference to FIG. 2.

Reference is now made to FIG. 14B which is a picture of Northern blot analysis, confirming expression of novel bioinformatically detected gene GAM26, and natural processing thereof from EST1388749. Northern reacted with predicted GAM26 hairpin probe. The molecular size of EST is indicated by arrow. The molecular sizes of GAM26 is 130 nt, as indicated by arrow. The 22 nt molecular marker is indicated by arrow. 1-Hela lysate; 2-EST incubated 4 h with Hela lysate; 3-EST incubated overnight with Hela lysate; 4-EST without lysate; 5-GAM transcript; 6-GAM 22 nt marker; 7-GAM PCR probe.

FIG. 1 further provides a conceptual description of a novel bioinformatically detected viral gene of the present invention, referred to here as Viral Genomic Address Messenger 15 (VGAM15) viral gene, which modulates expression of respective host target genes thereof, the function and utility of which host target genes is known in the art.

VGAM15 is a novel bioinformatically detected regulatory, non protein coding, viral micro RNA (miRNA) gene. The method by which VGAM15 was detected is described hereinabove with reference to FIGS. 2–8.

VGAM15 gene, herein designated VGAM GENE, is a viral gene contained in the genome of Human immunodeficiency virus 1. VGAM 15 host target gene, herein designated VGAM HOST TARGET GENE, is a human gene contained in the human genome.

VGAM15 gene, herein designated VGAM GENE, encodes a VGAM15 precursor RNA, herein designated VGAM PRECURSOR RNA. Similar to other miRNA genes, and unlike most ordinary genes, VGAM15 precursor RNA, herein designated VGAM PRECURSOR RNA, does not encode a protein. A nucleotide sequence identical or highly similar to the nucleotide sequence of VGAM15 precursor RNA is designated SEQ ID:1, and is provided hereinbelow with reference to the sequence listing part. Nucleotide sequence SEQ ID:1 is located at position 7156 relative to the genome of Human immunodeficiency virus 1.

VGAM15 precursor RNA, herein designated VGAM PRECURSOR RNA, folds onto itself, forming VGAM15 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM15 folded precursor RNA, herein designated VGAM FOLDED PRECURSOR RNA, into VGAM15 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7200%) nucleotide sequence of VGAM15 RNA is designated SEQ ID:16, and is provided hereinbelow with reference to the sequence listing part.

VGAM15 host target gene, herein designated VGAM HOST TARGET GENE, encodes a corresponding messenger RNA, VGAM15 host target RNA, herein designated VGAM HOST TARGET RNA. VGAM15 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM15 RNA, herein designated VGAM RNA, binds complementarily to one or more host target binding sites located in untranslated regions of VGAM15 host target RNA, herein designated VGAM HOST TARGET RNA. This complementary binding is due to the fact that the nucleotide sequence of VGAM15 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM15 RNA, herein designated VGAM RNA, may have a different number of host target binding sites in untranslated regions of a VGAM15 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM15 RNA, herein designated VGAM RNA, to host target binding sites on VGAM15 host target RNA, herein designated VGAM HOST TARGET RNA, such as BINDING SITE I, BINDING SITE II and BINDING SITE III, inhibits translation of VGAM15 host target RNA, herein designated VGAM HOST TARGET RNA, into VGAM15 host target protein, herein designated VGAM HOST TARGET PROTEIN. VGAM host target protein is therefore outlined by a broken line.

It is appreciated that VGAM15 host target gene, herein designated VGAM HOST TARGET GENE, in fact represents a plurality of VGAM15 host target genes. The mRNA of each one of this plurality of VGAM15 host target genes comprises one or more host target binding sites, each having a nucleotide sequence which is at least partly complementary to VGAM15 RNA, herein designated VGAM RNA, and which when bound by VGAM15 RNA, herein designated VGAM RNA, causes inhibition of translation of respective one or more VGAM15 host target proteins.

It is further appreciated by one skilled in the art that the mode of translational inhibition illustrated by FIG. 1 with specific reference to translational inhibition exerted by VGAM15 gene, herein designated VGAM GENE, on one or more VGAM15 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM15 is inhibition of expression of host target genes, as part of a novel viral mechanism of attacking a host. Accordingly, utilities of VGAM15 include diagnosis, prevention and treatment of viral infection by Human immunodeficiency virus 1. Specific functions, and accordingly utilities, of VGAM15 correlate with, and may be deduced from, the identity of the host target genes which VGAM15 binds and inhibits, and the function of these host target genes, as elaborated hereinbelow.

Nucleotide sequences of the VGAM15 precursor RNA, herein designated VGAM PRECURSOR RNA, and of the diced VGAM15 RNA, herein designated VGAM RNA, and a schematic representation of the secondary folding of VGAM15 folded precursor RNA, herein designated VGAM FOLDED PRECURSOR RNA, of VGAM15 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM15 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 16 (VGAM16) viral gene, which modulates expression of respective host target genes thereof, the function and utility of which host target genes is known in the art.

VGAM16 is a novel bioinformatically detected regulatory, non protein coding, viral micro RNA (miRNA) gene. The method by which VGAM16 was detected is described hereinabove with reference to FIGS. 2–8.

VGAM16 gene, herein designated VGAM GENE, is a viral gene contained in the genome of Human immunodeficiency virus 1. VGAM16 host target gene, herein designated VGAM HOST TARGET GENE, is a human gene contained in the human genome.

VGAM16 gene, herein designated VGAM GENE, encodes a VGAM16 precursor RNA, herein designated VGAM PRECURSOR RNA. Similar to other miRNA genes, and unlike most ordinary genes, VGAM16 precursor RNA, herein designated VGAM PRECURSOR RNA, does not encode a protein. A nucleotide sequence identical or highly similar to the nucleotide sequence of VGAM16 precursor RNA is designated SEQ ID:2, and is provided hereinbelow with reference to the sequence listing part. Nucleotide sequence SEQ ID:2 is located at position 4668 relative to the genome of Human immunodeficiency virus 1.

VGAM16 precursor RNA, herein designated VGAM PRECURSOR RNA, folds onto itself, forming VGAM16 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM16 folded precursor RNA, herein designated VGAM FOLDED PRECURSOR RNA, into VGAM16 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7900%) nucleotide sequence of VGAM16 RNA is designated SEQ ID:17, and is provided hereinbelow with reference to the sequence listing part.

VGAM16 host target gene, herein designated VGAM HOST TARGET GENE, encodes a corresponding messenger RNA, VGAM16 host target RNA, herein designated VGAM HOST TARGET RNA. VGAM16 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM16 RNA, herein designated VGAM RNA, binds complementarily to one or more host target binding sites located in untranslated regions of VGAM16 host target RNA, herein designated VGAM HOST TARGET RNA. This complementary binding is due to the fact that the nucleotide sequence of VGAM16 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM16 RNA, herein designated VGAM RNA, may have a different number of host target binding sites in untranslated regions of a VGAM16 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM16 RNA, herein designated VGAM RNA, to host target binding sites on VGAM16 host target RNA, herein designated VGAM HOST TARGET RNA, such as BINDING SITE I, BINDING SITE II and BINDING SITE III, inhibits translation of VGAM16 host target RNA, herein designated VGAM HOST TARGET RNA, into VGAM16 host target protein, herein designated VGAM HOST TARGET PROTEIN. VGAM host target protein is therefore outlined by a broken line.

It is appreciated that VGAM16 host target gene, herein designated VGAM HOST TARGET GENE, in fact represents a plurality of VGAM16 host target genes. The mRNA of each one of this plurality of VGAM16 host target genes comprises one or more host target binding sites, each having a nucleotide sequence which is at least partly complementary to VGAM 16 RNA, herein designated VGAM RNA, and which when bound by VGAM16 RNA, herein designated VGAM RNA, causes inhibition of translation of respective one or more VGAM16 host target proteins.

It is further appreciated by one skilled in the art that the mode of translational inhibition illustrated by FIG. 1 with specific reference to translational inhibition exerted by VGAM16 gene, herein designated VGAM GENE, on one or more VGAM16 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM16 is inhibition of expression of host target genes, as part of a novel viral mechanism of attacking a host. Accordingly, utilities of VGAM16 include diagnosis, prevention and treatment of viral infection by Human immunodeficiency virus 1. Specific functions, and accordingly utilities, of VGAM16 correlate with, and may be deduced from, the identity of the host target genes which VGAM16 binds and inhibits, and the function of these host target genes, as elaborated hereinbelow.

Nucleotide sequences of the VGAM16 precursor RNA, herein designated VGAM PRECURSOR RNA, and of the diced VGAM16 RNA, herein designated VGAM RNA, and a schematic representation of the secondary folding of VGAM16 folded precursor RNA, herein designated VGAM FOLDED PRECURSOR RNA, of VGAM16 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM16 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 17 (VGAM17) viral gene, which modulates expression of respective host target genes thereof, the function and utility of which host target genes is known in the art.

VGAM17 is a novel bioinformatically detected regulatory, non protein coding, viral micro RNA (miRNA) gene. The method by which VGAM 17 was detected is described hereinabove with reference to FIGS. 2–8.

VGAM17 gene, herein designated VGAM GENE, is a viral gene contained in the genome of Human immunodeficiency virus 1. VGAM17 host target gene, herein designated VGAM HOST TARGET GENE, is a human gene contained in the human genome.

VGAM17 gene, herein designated VGAM GENE, encodes a VGAM17 precursor RNA, herein designated VGAM PRECURSOR RNA. Similar to other miRNA genes, and unlike most ordinary genes, VGAM17 precursor RNA, herein designated VGAM PRECURSOR RNA, does not encode a protein. A nucleotide sequence identical or highly similar to the nucleotide sequence of VGAM17 precursor RNA is designated SEQ ID:3, and is provided hereinbelow with reference to the sequence listing part. Nucleotide sequence SEQ ID:3 is located at position 5919 relative to the genome of Human immunodeficiency virus 1.

VGAM17 precursor RNA, herein designated VGAM PRECURSOR RNA, folds onto itself, forming VGAM17 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM17 folded precursor RNA, herein designated VGAM FOLDED PRECURSOR RNA, into VGAM17 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 8400%) nucleotide sequence of VGAM17 RNA is designated SEQ ID:18, and is provided hereinbelow with reference to the sequence listing part.

VGAM17 host target gene, herein designated VGAM HOST TARGET GENE, encodes a corresponding messenger RNA, VGAM17 host target RNA, herein designated VGAM HOST TARGET RNA. VGAM17 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM17 RNA, herein designated VGAM RNA, binds complementarily to one or more host target binding sites located in untranslated regions of VGAM17 host target RNA, herein designated VGAM HOST TARGET RNA. This complementary binding is due to the fact that the nucleotide sequence of VGAM17 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM17 RNA, herein designated VGAM RNA, may have a different number of host target binding sites in untranslated regions of a VGAM17 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM17 RNA, herein designated VGAM RNA, to host target binding sites on VGAM17 host target RNA, herein designated VGAM HOST TARGET RNA, such as BINDING SITE I, BINDING SITE II and BINDING SITE III, inhibits translation of VGAM17 host target RNA, herein designated VGAM HOST TARGET RNA, into VGAM17 host target protein, herein designated VGAM HOST TARGET PROTEIN. VGAM host target protein is therefore outlined by a broken line.

It is appreciated that VGAM17 host target gene, herein designated VGAM HOST TARGET GENE, in fact represents a plurality of VGAM17 host target genes. The mRNA of each one of this plurality of VGAM17 host target genes comprises one or more host target binding sites, each having a nucleotide sequence which is at least partly complementary to VGAM 17 RNA, herein designated VGAM RNA, and which when bound by VGAM17 RNA, herein designated VGAM RNA, causes inhibition of translation of respective one or more VGAM17 host target proteins.

It is further appreciated by one skilled in the art that the mode of translational inhibition illustrated by FIG. 1 with specific reference to translational inhibition exerted by VGAM17 gene, herein designated VGAM GENE, on one or more VGAM17 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM17 is inhibition of expression of host target genes, as part of a novel viral mechanism of attacking a host. Accordingly, utilities of VGAM17 include diagnosis, prevention and treatment of viral infection by Human immunodeficiency virus 1. Specific functions, and accordingly utilities, of VGAM17 correlate with, and may be deduced from, the identity of the host target genes which VGAM17 binds and inhibits, and the function of these host target genes, as elaborated hereinbelow.

Nucleotide sequences of the VGAM17 precursor RNA, herein designated VGAM PRECURSOR RNA, and of the diced VGAM17 RNA, herein designated VGAM RNA, and a schematic representation of the secondary folding of VGAM17 folded precursor RNA, herein designated VGAM FOLDED PRECURSOR RNA, of VGAM17 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM17 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 18 (VGAM18) viral gene, which modulates expression of respective host target genes thereof, the function and utility of which host target genes is known in the art.

VGAM18 is a novel bioinformatically detected regulatory, non protein coding, viral micro RNA (miRNA) gene. The method by which VGAM 18 was detected is described hereinabove with reference to FIGS. 2–8.

VGAM18 gene, herein designated VGAM GENE, is a viral gene contained in the genome of Human immunodeficiency virus 1. VGAM18 host target gene, herein designated VGAM HOST TARGET GENE, is a human gene contained in the human genome.

VGAM18 gene, herein designated VGAM GENE, encodes a VGAM18 precursor RNA, herein designated VGAM PRECURSOR RNA. Similar to other miRNA genes, and unlike most ordinary genes, VGAM18 precursor RNA, herein designated VGAM PRECURSOR RNA, does not encode a protein. A nucleotide sequence identical or highly similar to the nucleotide sequence of VGAM18 precursor RNA is designated SEQ ID:4, and is provided hereinbelow with reference to the sequence listing part. Nucleotide sequence SEQ ID:4 is located at position 1459 relative to the genome of Human immunodeficiency virus 1.

VGAM18 precursor RNA, herein designated VGAM PRECURSOR RNA, folds onto itself, forming VGAM18 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM18 folded precursor RNA, herein designated VGAM FOLDED PRECURSOR RNA, into VGAM18 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7200%) nucleotide sequence of VGAM18 RNA is designated SEQ ID:19, and is provided hereinbelow with reference to the sequence listing part.

VGAM18 host target gene, herein designated VGAM HOST TARGET GENE, encodes a corresponding messenger RNA, VGAM18 host target RNA, herein designated VGAM HOST TARGET RNA. VGAM18 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM18 RNA, herein designated VGAM RNA, binds complementarily to one or more host target binding sites located in untranslated regions of VGAM18 host target RNA, herein designated VGAM HOST TARGET RNA. This complementary binding is due to the fact that the nucleotide sequence of VGAM18 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM18 RNA, herein designated VGAM RNA, may have a different number of host target binding sites in untranslated regions of a VGAM18 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM18 RNA, herein designated VGAM RNA, to host target binding sites on VGAM18 host target RNA, herein designated VGAM HOST TARGET RNA, such as BINDING SITE I, BINDING SITE II and BINDING SITE III, inhibits translation of VGAM18 host target RNA, herein designated VGAM HOST TARGET RNA, into VGAM18 host target protein, herein designated VGAM HOST TARGET PROTEIN. VGAM host target protein is therefore outlined by a broken line.

It is appreciated that VGAM18 host target gene, herein designated VGAM HOST TARGET GENE, in fact represents a plurality of VGAM18 host target genes. The mRNA of each one of this plurality of VGAM18 host target genes comprises one or more host target binding sites, each having a nucleotide sequence which is at least partly complementary to VGAM 18 RNA, herein designated VGAM RNA, and which when bound by VGAM18 RNA, herein designated VGAM RNA, causes inhibition of translation of respective one or more VGAM18 host target proteins.

It is further appreciated by one skilled in the art that the mode of translational inhibition illustrated by FIG. 1 with specific reference to translational inhibition exerted by VGAM18 gene, herein designated VGAM GENE, on one or more VGAM18 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM18 is inhibition of expression of host target genes, as part of a novel viral mechanism of attacking a host. Accordingly, utilities of VGAM18 include diagnosis, prevention and treatment of viral infection by Human immunodeficiency virus 1. Specific functions, and accordingly utilities, of VGAM18 correlate with, and may be deduced from, the identity of the host target genes which VGAM18 binds and inhibits, and the function of these host target genes, as elaborated hereinbelow.

Nucleotide sequences of the VGAM18 precursor RNA, herein designated VGAM PRECURSOR RNA, and of the diced VGAM18 RNA, herein designated VGAM RNA, and a schematic representation of the secondary folding of VGAM18 folded precursor RNA, herein designated VGAM FOLDED PRECURSOR RNA, of VGAM18 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM18 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 19 (VGAM19) viral gene, which modulates expression of respective host target genes thereof, the function and utility of which host target genes is known in the art.

VGAM19 is a novel bioinformatically detected regulatory, non protein coding, viral micro RNA (miRNA) gene. The method by which VGAM 19 was detected is described hereinabove with reference to FIGS. 2–8.

VGAM19 gene, herein designated VGAM GENE, is a viral gene contained in the genome of Human immunodeficiency virus 1. VGAM19 host target gene, herein designated VGAM HOST TARGET GENE, is a human gene contained in the human genome.

VGAM19 gene, herein designated VGAM GENE, encodes a VGAM19 precursor RNA, herein designated VGAM PRECURSOR RNA. Similar to other miRNA genes, and unlike most ordinary genes, VGAM19 precursor RNA, herein designated VGAM PRECURSOR RNA, does not encode a protein. A nucleotide sequence identical or highly similar to the nucleotide sequence of VGAM19 precursor RNA is designated SEQ ID:5, and is provided hereinbelow with reference to the sequence listing part. Nucleotide sequence SEQ ID:5 is located at position 2168 relative to the genome of Human immunodeficiency virus 1.

VGAM19 precursor RNA, herein designated VGAM PRECURSOR RNA, folds onto itself, forming VGAM19 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM19 folded precursor RNA, herein designated VGAM FOLDED PRECURSOR RNA, into VGAM19 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 6000%) nucleotide sequence of VGAM19 RNA is designated SEQ ID:20, and is provided hereinbelow with reference to the sequence listing part.

VGAM19 host target gene, herein designated VGAM HOST TARGET GENE, encodes a corresponding messenger RNA, VGAM19 host target RNA, herein designated VGAM HOST TARGET RNA. VGAM19 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM19 RNA, herein designated VGAM RNA, binds complementarily to one or more host target binding sites located in untranslated regions of VGAM19 host target RNA, herein designated VGAM HOST TARGET RNA. This complementary binding is due to the fact that the nucleotide sequence of VGAM19 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM19 RNA, herein designated VGAM RNA, may have a different number of host target binding sites in untranslated regions of a VGAM19 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM19 RNA, herein designated VGAM RNA, to host target binding sites on VGAM19 host target RNA, herein designated VGAM HOST TARGET RNA, such as BINDING SITE I, BINDING SITE II and BINDING SITE III, inhibits translation of VGAM19 host target RNA, herein designated VGAM HOST TARGET RNA, into VGAM19 host target protein, herein designated VGAM HOST TARGET PROTEIN. VGAM host target protein is therefore outlined by a broken line.

It is appreciated that VGAM19 host target gene, herein designated VGAM HOST TARGET GENE, in fact represents a plurality of VGAM19 host target genes. The mRNA of each one of this plurality of VGAM19 host target genes comprises one or more host target binding sites, each having a nucleotide sequence which is at least partly complementary to VGAM 19 RNA, herein designated VGAM RNA, and which when bound by VGAM19 RNA, herein designated VGAM RNA, causes inhibition of translation of respective one or more VGAM19 host target proteins.

It is further appreciated by one skilled in the art that the mode of translational inhibition illustrated by FIG. 1 with specific reference to translational inhibition exerted by VGAM19 gene, herein designated VGAM GENE, on one or more VGAM19 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM19 is inhibition of expression of host target genes, as part of a novel viral mechanism of attacking a host. Accordingly, utilities of VGAM19 include diagnosis, prevention and treatment of viral infection by Human immunodeficiency virus 1. Specific functions, and accordingly utilities, of VGAM19 correlate with, and may be deduced from, the identity of the host target genes which VGAM19 binds and inhibits, and the function of these host target genes, as elaborated hereinbelow.

Nucleotide sequences of the VGAM19 precursor RNA, herein designated VGAM PRECURSOR RNA, and of the diced VGAM19 RNA, herein designated VGAM RNA, and a schematic representation of the secondary folding of VGAM19 folded precursor RNA, herein designated VGAM FOLDED PRECURSOR RNA, of VGAM19 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM19 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 20 (VGAM20) viral gene, which modulates expression of respective host target genes thereof, the function and utility of which host target genes is known in the art.

VGAM20 is a novel bioinformatically detected regulatory, non protein coding, viral micro RNA (miRNA) gene. The method by which VGAM20 was detected is described hereinabove with reference to FIGS. 2–8.

VGAM20 gene, herein designated VGAM GENE, is a viral gene contained in the genome of Human immunodeficiency virus 1. VGAM20 host target gene, herein designated VGAM HOST TARGET GENE, is a human gene contained in the human genome.

VGAM20 gene, herein designated VGAM GENE, encodes a VGAM20 precursor RNA, herein designated VGAM PRECURSOR RNA. Similar to other miRNA genes, and unlike most ordinary genes, VGAM20 precursor RNA, herein designated VGAM PRECURSOR RNA, does not encode a protein. A nucleotide sequence identical or highly similar to the nucleotide sequence of VGAM20 precursor RNA is designated SEQ ID:6, and is provided hereinbelow with reference to the sequence listing part. Nucleotide sequence SEQ ID:6 is located at position 587 relative to the genome of Human immunodeficiency virus 1.

VGAM20 precursor RNA, herein designated VGAM PRECURSOR RNA, folds onto itself, forming VGAM20 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM20 folded precursor RNA, herein designated VGAM FOLDED PRECURSOR RNA, into VGAM20 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 8400%) nucleotide sequence of VGAM20 RNA is designated SEQ ID:21, and is provided hereinbelow with reference to the sequence listing part.

VGAM20 host target gene, herein designated VGAM HOST TARGET GENE, encodes a corresponding messenger RNA, VGAM20 host target RNA, herein designated VGAM HOST TARGET RNA. VGAM20 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM20 RNA, herein designated VGAM RNA, binds complementarily to one or more host target binding sites located in untranslated regions of VGAM20 host target RNA, herein designated VGAM HOST TARGET RNA. This complementary binding is due to the fact that the nucleotide sequence of VGAM20 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM20 RNA, herein designated VGAM RNA, may have a different number of host target binding sites in untranslated regions of a VGAM20 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM20 RNA, herein designated VGAM RNA, to host target binding sites on VGAM20 host target RNA, herein designated VGAM HOST TARGET RNA, such as BINDING SITE I, BINDING SITE II and BINDING SITE III, inhibits translation of VGAM20 host target RNA, herein designated VGAM HOST TARGET RNA, into VGAM20 host target protein, herein designated VGAM HOST TARGET PROTEIN. VGAM host target protein is therefore outlined by a broken line.

It is appreciated that VGAM20 host target gene, herein designated VGAM HOST TARGET GENE, in fact represents a plurality of VGAM20 host target genes. The mRNA of each one of this plurality of VGAM20 host target genes comprises one or more host target binding sites, each having a nucleotide sequence which is at least partly complementary to VGAM20 RNA, herein designated VGAM RNA, and which when bound by VGAM20 RNA, herein designated VGAM RNA, causes inhibition of translation of respective one or more VGAM20 host target proteins.

It is further appreciated by one skilled in the art that the mode of translational inhibition illustrated by FIG. 1 with specific reference to translational inhibition exerted by VGAM20 gene, herein designated VGAM GENE, on one or more VGAM20 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM20 is inhibition of expression of host target genes, as part of a novel viral mechanism of attacking a host. Accordingly, utilities of VGAM20 include diagnosis, prevention and treatment of viral infection by Human immunodeficiency virus 1. Specific functions, and accordingly utilities, of VGAM20 correlate with, and may be deduced from, the identity of the host target genes which VGAM20 binds and inhibits, and the function of these host target genes, as elaborated hereinbelow.

Nucleotide sequences of the VGAM20 precursor RNA, herein designated VGAM PRECURSOR RNA, and of the diced VGAM20 RNA, herein designated VGAM RNA, and a schematic representation of the secondary folding of VGAM20 folded precursor RNA, herein designated VGAM FOLDED PRECURSOR RNA, of VGAM20 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM20 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 21 (VGAM21) viral gene, which modulates expression of respective host target genes thereof, the function and utility of which host target genes is known in the art.

VGAM21 is a novel bioinformatically detected regulatory, non protein coding, viral micro RNA (miRNA) gene. The method by which VGAM21 was detected is described hereinabove with reference to FIGS. 2–8.

VGAM21 gene, herein designated VGAM GENE, is a viral gene contained in the genome of Human immunodeficiency virus 1. VGAM21 host target gene, herein designated VGAM HOST TARGET GENE, is a human gene contained in the human genome.

VGAM21 gene, herein designated VGAM GENE, encodes a VGAM21 precursor RNA, herein designated VGAM PRECURSOR RNA. Similar to other miRNA genes, and unlike most ordinary genes, VGAM21 precursor RNA, herein designated VGAM PRECURSOR RNA, does not encode a protein. A nucleotide sequence identical or highly similar to the nucleotide sequence of VGAM21 precursor RNA is designated SEQ ID:7, and is provided hereinbelow with reference to the sequence listing part. Nucleotide sequence SEQ ID:7 is located at position 7857 relative to the genome of Human immunodeficiency virus 1.

VGAM21 precursor RNA, herein designated VGAM PRECURSOR RNA, folds onto itself, forming VGAM21 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM21 folded precursor RNA, herein designated VGAM FOLDED PRECURSOR RNA, into VGAM21 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7700%) nucleotide sequence of VGAM21 RNA is designated SEQ ID:22, and is provided hereinbelow with reference to the sequence listing part.

VGAM21 host target gene, herein designated VGAM HOST TARGET GENE, encodes a corresponding messenger RNA, VGAM21 host target RNA, herein designated VGAM HOST TARGET RNA. VGAM21 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM21 RNA, herein designated VGAM RNA, binds complementarily to one or more host target binding sites located in untranslated regions of VGAM21 host target RNA, herein designated VGAM HOST TARGET RNA. This complementary binding is due to the fact that the nucleotide sequence of VGAM21 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM21 RNA, herein designated VGAM RNA, may have a different number of host target binding sites in untranslated regions of a VGAM21 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM21 RNA, herein designated VGAM RNA, to host target binding sites on VGAM21 host target RNA, herein designated VGAM HOST TARGET RNA, such as BINDING SITE I, BINDING SITE II and BINDING SITE III, inhibits translation of VGAM21 host target RNA, herein designated VGAM HOST TARGET RNA, into VGAM21 host target protein, herein designated VGAM HOST TARGET PROTEIN. VGAM host target protein is therefore outlined by a broken line.

It is appreciated that VGAM21 host target gene, herein designated VGAM HOST TARGET GENE, in fact represents a plurality of VGAM21 host target genes. The mRNA of each one of this plurality of VGAM21 host target genes comprises one or more host target binding sites, each having a nucleotide sequence which is at least partly complementary to VGAM21 RNA, herein designated VGAM RNA, and which when bound by VGAM21 RNA, herein designated VGAM RNA, causes inhibition of translation of respective one or more VGAM21 host target proteins.

It is further appreciated by one skilled in the art that the mode of translational inhibition illustrated by FIG. 1 with specific reference to translational inhibition exerted by VGAM21 gene, herein designated VGAM GENE, on one or more VGAM21 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM21 is inhibition of expression of host target genes, as part of a novel viral mechanism of attacking a host. Accordingly, utilities of VGAM21 include diagnosis, prevention and treatment of viral infection by Human immunodeficiency virus 1. Specific functions, and accordingly utilities, of VGAM21 correlate with, and may be deduced from, the identity of the host target genes which VGAM21 binds and inhibits, and the function of these host target genes, as elaborated hereinbelow.

Nucleotide sequences of the VGAM21 precursor RNA, herein designated VGAM PRECURSOR RNA, and of the diced VGAM21 RNA, herein designated VGAM RNA, and a schematic representation of the secondary folding of VGAM21 folded precursor RNA, herein designated VGAM FOLDED PRECURSOR RNA, of VGAM21 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM21 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 22 (VGAM22) viral gene, which modulates expression of respective host target genes thereof, the function and utility of which host target genes is known in the art.

VGAM22 is a novel bioinformatically detected regulatory, non protein coding, viral micro RNA (miRNA) gene. The method by which VGAM22 was detected is described hereinabove with reference to FIGS. 2–8.

VGAM22 gene, herein designated VGAM GENE, is a viral gene contained in the genome of Human immunodeficiency virus 1. VGAM22 host target gene, herein designated VGAM HOST TARGET GENE, is a human gene contained in the human genome.

VGAM22 gene, herein designated VGAM GENE, encodes a VGAM22 precursor RNA, herein designated VGAM PRECURSOR RNA. Similar to other miRNA genes, and unlike most ordinary genes, VGAM22 precursor RNA, herein designated VGAM PRECURSOR RNA, does not encode a protein. A nucleotide sequence identical or highly similar to the nucleotide sequence of VGAM22 precursor RNA is designated SEQ ID:8, and is provided hereinbelow with reference to the sequence listing part. Nucleotide sequence SEQ ID:8 is located at position 8292 relative to the genome of Human immunodeficiency virus 1.

VGAM22 precursor RNA, herein designated VGAM PRECURSOR RNA, folds onto itself, forming VGAM22 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM22 folded precursor RNA, herein designated VGAM FOLDED PRECURSOR RNA, into VGAM22 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7600%) nucleotide sequence of VGAM22 RNA is designated SEQ ID:23, and is provided hereinbelow with reference to the sequence listing part.

VGAM22 host target gene, herein designated VGAM HOST TARGET GENE, encodes a corresponding messenger RNA, VGAM22 host target RNA, herein designated VGAM HOST TARGET RNA. VGAM22 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM22 RNA, herein designated VGAM RNA, binds complementarily to one or more host target binding sites located in untranslated regions of VGAM22 host target RNA, herein designated VGAM HOST TARGET RNA. This complementary binding is due to the fact that the nucleotide sequence of VGAM22 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM22 RNA, herein designated VGAM RNA, may have a different number of host target binding sites in untranslated regions of a VGAM22 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM22 RNA, herein designated VGAM RNA, to host target binding sites on VGAM22 host target RNA, herein designated VGAM HOST TARGET RNA, such as BINDING SITE I, BINDING SITE II and BINDING SITE III, inhibits translation of VGAM22 host target RNA, herein designated VGAM HOST TARGET RNA, into VGAM22 host target protein, herein designated VGAM HOST TARGET PROTEIN. VGAM host target protein is therefore outlined by a broken line.

It is appreciated that VGAM22 host target gene, herein designated VGAM HOST TARGET GENE, in fact represents a plurality of VGAM22 host target genes. The mRNA of each one of this plurality of VGAM22 host target genes comprises one or more host target binding sites, each having a nucleotide sequence which is at least partly complementary to VGAM22 RNA, herein designated VGAM RNA, and which when bound by VGAM22 RNA, herein designated VGAM RNA, causes inhibition of translation of respective one or more VGAM22 host target proteins.

It is further appreciated by one skilled in the art that the mode of translational inhibition illustrated by FIG. 1 with specific reference to translational inhibition exerted by VGAM22 gene, herein designated VGAM GENE, on one or more VGAM22 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM22 is inhibition of expression of host target genes, as part of a novel viral mechanism of attacking a host. Accordingly, utilities of VGAM22 include diagnosis, prevention and treatment of viral infection by Human immunodeficiency virus 1. Specific functions, and accordingly utilities, of VGAM22 correlate with, and may be deduced from, the identity of the host target genes which VGAM22 binds and inhibits, and the function of these host target genes, as elaborated hereinbelow.

Nucleotide sequences of the VGAM22 precursor RNA, herein designated VGAM PRECURSOR RNA, and of the diced VGAM22 RNA, herein designated VGAM RNA, and a schematic representation of the secondary folding of VGAM22 folded precursor RNA, herein designated VGAM FOLDED PRECURSOR RNA, of VGAM22 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM22 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 23 (VGAM23) viral gene, which modulates expression of respective host target genes thereof, the function and utility of which host target genes is known in the art.

VGAM23 is a novel bioinformatically detected regulatory, non protein coding, viral micro RNA (miRNA) gene. The method by which VGAM23 was detected is described hereinabove with reference to FIGS. 2–8.

VGAM23 gene, herein designated VGAM GENE, is a viral gene contained in the genome of Human immunodeficiency virus 1. VGAM23 host target gene, herein designated VGAM HOST TARGET GENE, is a human gene contained in the human genome.

VGAM23 gene, herein designated VGAM GENE, encodes a VGAM23 precursor RNA, herein designated VGAM PRECURSOR RNA. Similar to other miRNA genes, and unlike most ordinary genes, VGAM23 precursor RNA, herein designated VGAM PRECURSOR RNA, does not encode a protein. A nucleotide sequence identical or highly similar to the nucleotide sequence of VGAM23 precursor RNA is designated SEQ ID:9, and is provided hereinbelow with reference to the sequence listing part. Nucleotide sequence SEQ ID:9 is located at position 5531 relative to the genome of Human immunodeficiency virus 1.

VGAM23 precursor RNA, herein designated VGAM PRECURSOR RNA, folds onto itself, forming VGAM23 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM23 folded precursor RNA, herein designated VGAM FOLDED PRECURSOR RNA, into VGAM23 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 6900%) nucleotide sequence of VGAM23 RNA is designated SEQ ID:24, and is provided hereinbelow with reference to the sequence listing part.

VGAM23 host target gene, herein designated VGAM HOST TARGET GENE, encodes a corresponding messenger RNA, VGAM23 host target RNA, herein designated VGAM HOST TARGET RNA. VGAM23 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM23 RNA, herein designated VGAM RNA, binds complementarily to one or more host target binding sites located in untranslated regions of VGAM23 host target RNA, herein designated VGAM HOST TARGET RNA. This complementary binding is due to the fact that the nucleotide sequence of VGAM23 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM23 RNA, herein designated VGAM RNA, may have a different number of host target binding sites in untranslated regions of a VGAM23 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM23 RNA, herein designated VGAM RNA, to host target binding sites on VGAM23 host target RNA, herein designated VGAM HOST TARGET RNA, such as BINDING SITE I, BINDING SITE II and BINDING SITE III, inhibits translation of VGAM23 host target RNA, herein designated VGAM HOST TARGET RNA, into VGAM23 host target protein, herein designated VGAM HOST TARGET PROTEIN. VGAM host target protein is therefore outlined by a broken line.

It is appreciated that VGAM23 host target gene, herein designated VGAM HOST TARGET GENE, in fact represents a plurality of VGAM23 host target genes. The mRNA of each one of this plurality of VGAM23 host target genes comprises one or more host target binding sites, each having a nucleotide sequence which is at least partly complementary to VGAM23 RNA, herein designated VGAM RNA, and which when bound by VGAM23 RNA, herein designated VGAM RNA, causes inhibition of translation of respective one or more VGAM23 host target proteins.

It is further appreciated by one skilled in the art that the mode of translational inhibition illustrated by FIG. 1 with specific reference to translational inhibition exerted by VGAM23 gene, herein designated VGAM GENE, on one or more VGAM23 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM23 is inhibition of expression of host target genes, as part of a novel viral mechanism of attacking a host. Accordingly, utilities of VGAM23 include diagnosis, prevention and treatment of viral infection by Human immunodeficiency virus 1. Specific functions, and accordingly utilities, of VGAM23 correlate with, and may be deduced from, the identity of the host target genes which VGAM23 binds and inhibits, and the function of these host target genes, as elaborated hereinbelow.

Nucleotide sequences of the VGAM23 precursor RNA, herein designated VGAM PRECURSOR RNA, and of the diced VGAM23 RNA, herein designated VGAM RNA, and a schematic representation of the secondary folding of VGAM23 folded precursor RNA, herein designated VGAM FOLDED PRECURSOR RNA, of VGAM23 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM23 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 24 (VGAM24) viral gene, which modulates expression of respective host target genes thereof, the function and utility of which host target genes is known in the art.

VGAM24 is a novel bioinformatically detected regulatory, non protein coding, viral micro RNA (miRNA) gene. The method by which VGAM24 was detected is described hereinabove with reference to FIGS. 2–8.

VGAM24 gene, herein designated VGAM GENE, is a viral gene contained in the genome of Human immunodeficiency virus 1. VGAM24 host target gene, herein designated VGAM HOST TARGET GENE, is a human gene contained in the human genome.

VGAM24 gene, herein designated VGAM GENE, encodes a VGAM24 precursor RNA, herein designated VGAM PRECURSOR RNA. Similar to other miRNA genes, and unlike most ordinary genes, VGAM24 precursor RNA, herein designated VGAM PRECURSOR RNA, does not encode a protein. A nucleotide sequence identical or highly similar to the nucleotide sequence of VGAM24 precursor RNA is designated SEQ ID:10, and is provided hereinbelow with reference to the sequence listing part.

Nucleotide sequence SEQ ID:10 is located at position 1301 relative to the genome of Human immunodeficiency virus 1.

VGAM24 precursor RNA, herein designated VGAM PRECURSOR RNA, folds onto itself, forming VGAM24 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM24 folded precursor RNA, herein designated VGAM FOLDED PRECURSOR RNA, into VGAM24 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 8700%) nucleotide sequence of VGAM24 RNA is designated SEQ ID:25, and is provided hereinbelow with reference to the sequence listing part.

VGAM24 host target gene, herein designated VGAM HOST TARGET GENE, encodes a corresponding messenger RNA, VGAM24 host target RNA, herein designated VGAM HOST TARGET RNA. VGAM24 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM24 RNA, herein designated VGAM RNA, binds complementarily to one or more host target binding sites located in untranslated regions of VGAM24 host target RNA, herein designated VGAM HOST TARGET RNA. This complementary binding is due to the fact that the nucleotide sequence of VGAM24 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM24 RNA, herein designated VGAM RNA, may have a different number of host target binding sites in untranslated regions of a VGAM24 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM24 RNA, herein designated VGAM RNA, to host target binding sites on VGAM24 host target RNA, herein designated VGAM HOST TARGET RNA, such as BINDING SITE I, BINDING SITE II and BINDING SITE III, inhibits translation of VGAM24 host target RNA, herein designated VGAM HOST TARGET RNA, into VGAM24 host target protein, herein designated VGAM HOST TARGET PROTEIN. VGAM host target protein is therefore outlined by a broken line.

It is appreciated that VGAM24 host target gene, herein designated VGAM HOST TARGET GENE, in fact represents a plurality of VGAM24 host target genes. The mRNA of each one of this plurality of VGAM24 host target genes comprises one or more host target binding sites, each having a nucleotide sequence which is at least partly complementary to VGAM24 RNA, herein designated VGAM RNA, and which when bound by VGAM24 RNA, herein designated VGAM RNA, causes inhibition of translation of respective one or more VGAM24 host target proteins.

It is further appreciated by one skilled in the art that the mode of translational inhibition illustrated by FIG. 1 with specific reference to translational inhibition exerted by VGAM24 gene, herein designated VGAM GENE, on one or more VGAM24 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM24 is inhibition of expression of host target genes, as part of a novel viral mechanism of attacking a host. Accordingly, utilities of VGAM24 include diagnosis, prevention and treatment of viral infection by Human immunodeficiency virus 1. Specific functions, and accordingly utilities, of VGAM24 correlate with, and may be deduced from, the identity of the host target genes which VGAM24 binds and inhibits, and the function of these host target genes, as elaborated hereinbelow.

Nucleotide sequences of the VGAM24 precursor RNA, herein designated VGAM PRECURSOR RNA, and of the diced VGAM24 RNA, herein designated VGAM RNA, and a schematic representation of the secondary folding of VGAM24 folded precursor RNA, herein designated VGAM FOLDED PRECURSOR RNA, of VGAM24 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM24 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 25 (VGAM25) viral gene, which modulates expression of respective host target genes thereof, the function and utility of which host target genes is known in the art.

VGAM25 is a novel bioinformatically detected regulatory, non protein coding, viral micro RNA (miRNA) gene. The method by which VGAM25 was detected is described hereinabove with reference to FIGS. 2–8.

VGAM25 gene, herein designated VGAM GENE, is a viral gene contained in the genome of Human immunodeficiency virus 1. VGAM25 host target gene, herein designated VGAM HOST TARGET GENE, is a human gene contained in the human genome.

VGAM25 gene, herein designated VGAM GENE, encodes a VGAM25 precursor RNA, herein designated VGAM PRECURSOR RNA. Similar to other miRNA genes, and unlike most ordinary genes, VGAM25 precursor RNA, herein designated VGAM PRECURSOR RNA, does not encode a protein. A nucleotide sequence identical or highly similar to the nucleotide sequence of VGAM25 precursor RNA is designated SEQ ID:11, and is provided hereinbelow with reference to the sequence listing part. Nucleotide sequence SEQ ID:11 is located at position 9080 relative to the genome of Human immunodeficiency virus 1.

VGAM25 precursor RNA, herein designated VGAM PRECURSOR RNA, folds onto itself, forming VGAM25 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM25 folded precursor RNA, herein designated VGAM FOLDED PRECURSOR RNA, into VGAM25 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 9000%) nucleotide sequence of VGAM25 RNA is designated SEQ ID:26, and is provided hereinbelow with reference to the sequence listing part.

VGAM25 host target gene, herein designated VGAM HOST TARGET GENE, encodes a corresponding messenger RNA, VGAM25 host target RNA, herein designated VGAM HOST TARGET RNA. VGAM25 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM25 RNA, herein designated VGAM RNA, binds complementarily to one or more host target binding sites located in untranslated regions of VGAM25 host target RNA, herein designated VGAM HOST TARGET RNA. This complementary binding is due to the fact that the nucleotide sequence of VGAM25 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM25 RNA, herein designated VGAM RNA, may have a different number of host target binding sites in untranslated regions of a VGAM25 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM25 RNA, herein designated VGAM RNA, to host target binding sites on VGAM25 host target RNA, herein designated VGAM HOST TARGET RNA, such as BINDING SITE I, BINDING SITE II and BINDING SITE III, inhibits translation of VGAM25 host target RNA, herein designated VGAM HOST TARGET RNA, into VGAM25 host target protein, herein designated VGAM HOST TARGET PROTEIN. VGAM host target protein is therefore outlined by a broken line.

It is appreciated that VGAM25 host target gene, herein designated VGAM HOST TARGET GENE, in fact represents a plurality of VGAM25 host target genes. The mRNA of each one of this plurality of VGAM25 host target genes comprises one or more host target binding sites, each having a nucleotide sequence which is at least partly complementary to VGAM25 RNA, herein designated VGAM RNA, and which when bound by VGAM25 RNA, herein designated VGAM RNA, causes inhibition of translation of respective one or more VGAM25 host target proteins.

It is further appreciated by one skilled in the art that the mode of translational inhibition illustrated by FIG. 1 with specific reference to translational inhibition exerted by VGAM25 gene, herein designated VGAM GENE, on one or more VGAM25 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM25 is inhibition of expression of host target genes, as part of a novel viral mechanism of attacking a host. Accordingly, utilities of VGAM25 include diagnosis, prevention and treatment of viral infection by Human immunodeficiency virus 1. Specific functions, and accordingly utilities, of VGAM25 correlate with, and may be deduced from, the identity of the host target genes which VGAM25 binds and inhibits, and the function of these host target genes, as elaborated hereinbelow.

Nucleotide sequences of the VGAM25 precursor RNA, herein designated VGAM PRECURSOR RNA, and of the diced VGAM25 RNA, herein designated VGAM RNA, and a schematic representation of the secondary folding of VGAM25 folded precursor RNA, herein designated VGAM FOLDED PRECURSOR RNA, of VGAM25 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM25 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 26 (VGAM26) viral gene, which modulates expression of respective host target genes thereof, the function and utility of which host target genes is known in the art.

VGAM26 is a novel bioinformatically detected regulatory, non protein coding, viral micro RNA (miRNA) gene. The method by which VGAM26 was detected is described hereinabove with reference to FIGS. 2–8.

VGAM26 gene, herein designated VGAM GENE, is a viral gene contained in the genome of Human immunodeficiency virus 1. VGAM26 host target gene, herein designated VGAM HOST TARGET GENE, is a human gene contained in the human genome.

VGAM26 gene, herein designated VGAM GENE, encodes a VGAM26 precursor RNA, herein designated VGAM PRECURSOR RNA. Similar to other miRNA genes, and unlike most ordinary genes, VGAM26 precursor RNA, herein designated VGAM PRECURSOR RNA, does not encode a protein. A nucleotide sequence identical or highly similar to the nucleotide sequence of VGAM26 precursor RNA is designated SEQ ID:12, and is provided hereinbelow with reference to the sequence listing part. Nucleotide sequence SEQ ID:12 is located at position 2049 relative to the genome of Human immunodeficiency virus 1.

VGAM26 precursor RNA, herein designated VGAM PRECURSOR RNA, folds onto itself, forming VGAM26 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM26 folded precursor RNA, herein designated VGAM FOLDED PRECURSOR RNA, into VGAM26 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7200%) nucleotide sequence of VGAM26 RNA is designated SEQ ID:27, and is provided hereinbelow with reference to the sequence listing part.

VGAM26 host target gene, herein designated VGAM HOST TARGET GENE, encodes a corresponding messenger RNA, VGAM26 host target RNA, herein designated VGAM HOST TARGET RNA. VGAM26 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM26 RNA, herein designated VGAM RNA, binds complementarily to one or more host target binding sites located in untranslated regions of VGAM26 host target RNA, herein designated VGAM HOST TARGET RNA. This complementary binding is due to the fact that the nucleotide sequence of VGAM26 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM26 RNA, herein designated VGAM RNA, may have a different number of host target binding sites in untranslated regions of a VGAM26 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM26 RNA, herein designated VGAM RNA, to host target binding sites on VGAM26 host target RNA, herein designated VGAM HOST TARGET RNA, such as BINDING SITE I, BINDING SITE II and BINDING SITE III, inhibits translation of VGAM26 host target RNA, herein designated VGAM HOST TARGET RNA, into VGAM26 host target protein, herein designated VGAM HOST TARGET PROTEIN. VGAM host target protein is therefore outlined by a broken line.

It is appreciated that VGAM26 host target gene, herein designated VGAM HOST TARGET GENE, in fact represents a plurality of VGAM26 host target genes. The mRNA of each one of this plurality of VGAM26 host target genes comprises one or more host target binding sites, each having a nucleotide sequence which is at least partly complementary to VGAM26 RNA, herein designated VGAM RNA, and which when bound by VGAM26 RNA, herein designated VGAM RNA, causes inhibition of translation of respective one or more VGAM26 host target proteins.

It is further appreciated by one skilled in the art that the mode of translational inhibition illustrated by FIG. 1 with specific reference to translational inhibition exerted by VGAM26 gene, herein designated VGAM GENE, on one or more VGAM26 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM26 is inhibition of expression of host target genes, as part of a novel viral mechanism of attacking a host. Accordingly, utilities of VGAM26 include diagnosis, prevention and treatment of viral infection by Human immunodeficiency virus 1. Specific functions, and accordingly utilities, of VGAM26 correlate with, and may be deduced from, the identity of the host target genes which VGAM26 binds and inhibits, and the function of these host target genes, as elaborated hereinbelow.

Nucleotide sequences of the VGAM26 precursor RNA, herein designated VGAM PRECURSOR RNA, and of the diced VGAM26 RNA, herein designated VGAM RNA, and a schematic representation of the secondary folding of VGAM26 folded precursor RNA, herein designated VGAM FOLDED PRECURSOR RNA, of VGAM26 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM26 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 27 (VGAM27) viral gene, which modulates expression of respective host target genes thereof, the function and utility of which host target genes is known in the art.

VGAM27 is a novel bioinformatically detected regulatory, non protein coding, viral micro RNA (miRNA) gene. The method by which VGAM27 was detected is described hereinabove with reference to FIGS. 2–8.

VGAM27 gene, herein designated VGAM GENE, is a viral gene contained in the genome of Human immunodeficiency virus 1. VGAM27 host target gene, herein designated VGAM HOST TARGET GENE, is a human gene contained in the human genome.

VGAM27 gene, herein designated VGAM GENE, encodes a VGAM27 precursor RNA, herein designated VGAM PRECURSOR RNA. Similar to other miRNA genes, and unlike most ordinary genes, VGAM27 precursor RNA, herein designated VGAM PRECURSOR RNA, does not encode a protein. A nucleotide sequence identical or highly similar to the nucleotide sequence of VGAM27 precursor RNA is designated SEQ ID:13, and is provided hereinbelow with reference to the sequence listing part. Nucleotide sequence SEQ ID:13 is located at position 1810 relative to the genome of Human immunodeficiency virus 1.

VGAM27 precursor RNA, herein designated VGAM PRECURSOR RNA, folds onto itself, forming VGAM27 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM27 folded precursor RNA, herein designated VGAM FOLDED PRECURSOR RNA, into VGAM27 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 6000%) nucleotide sequence of VGAM27 RNA is designated SEQ ID:28, and is provided hereinbelow with reference to the sequence listing part.

VGAM27 host target gene, herein designated VGAM HOST TARGET GENE, encodes a corresponding messenger RNA, VGAM27 host target RNA, herein designated VGAM HOST TARGET RNA. VGAM27 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM27 RNA, herein designated VGAM RNA, binds complementarily to one or more host target binding sites located in untranslated regions of VGAM27 host target RNA, herein designated VGAM HOST TARGET RNA. This complementary binding is due to the fact that the nucleotide sequence of VGAM27 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM27 RNA, herein designated VGAM RNA, may have a different number of host target binding sites in untranslated regions of a VGAM27 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM27 RNA, herein designated VGAM RNA, to host target binding sites on VGAM27 host target RNA, herein designated VGAM HOST TARGET RNA, such as BINDING SITE I, BINDING SITE II and BINDING SITE III, inhibits translation of VGAM27 host target RNA, herein designated VGAM HOST TARGET RNA, into VGAM27 host target protein, herein designated VGAM HOST TARGET PROTEIN. VGAM host target protein is therefore outlined by a broken line.

It is appreciated that VGAM27 host target gene, herein designated VGAM HOST TARGET GENE, in fact represents a plurality of VGAM27 host target genes. The mRNA of each one of this plurality of VGAM27 host target genes comprises one or more host target binding sites, each having a nucleotide sequence which is at least partly complementary to VGAM27 RNA, herein designated VGAM RNA, and which when bound by VGAM27 RNA, herein designated VGAM RNA, causes inhibition of translation of respective one or more VGAM27 host target proteins.

It is further appreciated by one skilled in the art that the mode of translational inhibition illustrated by FIG. 1 with specific reference to translational inhibition exerted by VGAM27 gene, herein designated VGAM GENE, on one or more VGAM27 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM27 is inhibition of expression of host target genes, as part of a novel viral mechanism of attacking a host. Accordingly, utilities of VGAM27 include diagnosis, prevention and treatment of viral infection by Human immunodeficiency virus 1. Specific functions, and accordingly utilities, of VGAM27 correlate with, and may be deduced from, the identity of the host target genes which VGAM27 binds and inhibits, and the function of these host target genes, as elaborated hereinbelow.

Nucleotide sequences of the VGAM27 precursor RNA, herein designated VGAM PRECURSOR RNA, and of the diced VGAM27 RNA, herein designated VGAM RNA, and a schematic representation of the secondary folding of VGAM27 folded precursor RNA, herein designated VGAM FOLDED PRECURSOR RNA, of VGAM27 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM27 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 28 (VGAM28) viral gene, which modulates expression of respective host target genes thereof, the function and utility of which host target genes is known in the art.

VGAM28 is a novel bioinformatically detected regulatory, non protein coding, viral micro RNA (miRNA) gene. The method by which VGAM28 was detected is described hereinabove with reference to FIGS. 2–8.

VGAM28 gene, herein designated VGAM GENE, is a viral gene contained in the genome of Human immunodeficiency virus 1. VGAM28 host target gene, herein designated VGAM HOST TARGET GENE, is a human gene contained in the human genome.

VGAM28 gene, herein designated VGAM GENE, encodes a VGAM28 precursor RNA, herein designated VGAM PRECURSOR RNA. Similar to other miRNA genes, and unlike most ordinary genes, VGAM28 precursor RNA, herein designated VGAM PRECURSOR RNA, does not encode a protein. A nucleotide sequence identical or highly similar to the nucleotide sequence of VGAM28 precursor RNA is designated SEQ ID:14, and is provided hereinbelow with reference to the sequence listing part. Nucleotide sequence SEQ ID:14 is located at position 728 relative to the genome of Human immunodeficiency virus 1.

VGAM28 precursor RNA, herein designated VGAM PRECURSOR RNA, folds onto itself, forming VGAM28 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM28 folded precursor RNA, herein designated VGAM FOLDED PRECURSOR RNA, into VGAM28 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7600%) nucleotide sequence of VGAM28 RNA is designated SEQ ID:29, and is provided hereinbelow with reference to the sequence listing part.

VGAM28 host target gene, herein designated VGAM HOST TARGET GENE, encodes a corresponding messenger RNA, VGAM28 host target RNA, herein designated VGAM HOST TARGET RNA. VGAM28 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM28 RNA, herein designated VGAM RNA, binds complementarily to one or more host target binding sites located in untranslated regions of VGAM28 host target RNA, herein designated VGAM HOST TARGET RNA. This complementary binding is due to the fact that the nucleotide sequence of VGAM28 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM28 RNA, herein designated VGAM RNA, may have a different number of host target binding sites in untranslated regions of a VGAM28 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM28 RNA, herein designated VGAM RNA, to host target binding sites on VGAM28 host target RNA, herein designated VGAM HOST TARGET RNA, such as BINDING SITE I, BINDING SITE II and BINDING SITE III, inhibits translation of VGAM28 host target RNA, herein designated VGAM HOST TARGET RNA, into VGAM28 host target protein, herein designated VGAM HOST TARGET PROTEIN. VGAM host target protein is therefore outlined by a broken line.

It is appreciated that VGAM28 host target gene, herein designated VGAM HOST TARGET GENE, in fact represents a plurality of VGAM28 host target genes. The mRNA of each one of this plurality of VGAM28 host target genes comprises one or more host target binding sites, each having a nucleotide sequence which is at least partly complementary to VGAM28 RNA, herein designated VGAM RNA, and which when bound by VGAM28 RNA, herein designated VGAM RNA, causes inhibition of translation of respective one or more VGAM28 host target proteins.

It is further appreciated by one skilled in the art that the mode of translational inhibition illustrated by FIG. 1 with specific reference to translational inhibition exerted by VGAM28 gene, herein designated VGAM GENE, on one or more VGAM28 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM28 is inhibition of expression of host target genes, as part of a novel viral mechanism of attacking a host. Accordingly, utilities of VGAM28 include diagnosis, prevention and treatment of viral infection by Human immunodeficiency virus 1. Specific functions, and accordingly utilities, of VGAM28 correlate with, and may be deduced from, the identity of the host target genes which VGAM28 binds and inhibits, and the function of these host target genes, as elaborated hereinbelow.

Nucleotide sequences of the VGAM28 precursor RNA, herein designated VGAM PRECURSOR RNA, and of the diced VGAM28 RNA, herein designated VGAM RNA, and a schematic representation of the secondary folding of VGAM28 folded precursor RNA, herein designated VGAM FOLDED PRECURSOR RNA, of VGAM28 are further described hereinbelow with reference to Table 1.

Nucleotide sequences of host target binding sites, such as BINDING SITE-I, BINDING SITE-II and BINDING SITE-III of FIG. 1, found on, and schematic representation of the complementarity of each of these host target binding sites to VGAM28 RNA, herein designated VGAM RNA, are described hereinbelow with reference to Table 2.

FIG. 1 further provides a conceptual description of another novel bioinformatically detected viral gene of the present invention, referred to here as Viral Genomic Address Messenger 29 (VGAM29) viral gene, which modulates expression of respective host target genes thereof, the function and utility of which host target genes is known in the art.

VGAM29 is a novel bioinformatically detected regulatory, non protein coding, viral micro RNA (miRNA) gene. The method by which VGAM29 was detected is described hereinabove with reference to FIGS. 2–8.

VGAM29 gene, herein designated VGAM GENE, is a viral gene contained in the genome of Human immunodeficiency virus 1. VGAM29 host target gene, herein designated VGAM HOST TARGET GENE, is a human gene contained in the human genome.

VGAM29 gene, herein designated VGAM GENE, encodes a VGAM29 precursor RNA, herein designated VGAM PRECURSOR RNA. Similar to other miRNA genes, and unlike most ordinary genes, VGAM29 precursor RNA, herein designated VGAM PRECURSOR RNA, does not encode a protein. A nucleotide sequence identical or highly similar to the nucleotide sequence of VGAM29 precursor RNA is designated SEQ ID:15, and is provided hereinbelow with reference to the sequence listing part. Nucleotide sequence SEQ ID:15 is located at position 5471 relative to the genome of Human immunodeficiency virus 1.

VGAM29 precursor RNA, herein designated VGAM PRECURSOR RNA, folds onto itself, forming VGAM29 folded precursor RNA, herein designated VGAM FOLDED PRECURSOR RNA, which has a two-dimensional hairpin structure. As is well known in the art, this hairpin structure, is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof.

An enzyme complex designated DICER COMPLEX, dices the VGAM29 folded precursor RNA, herein designated VGAM FOLDED PRECURSOR RNA, into VGAM29 RNA, herein designated VGAM RNA, a single stranded ~22 nt long RNA segment. As is known in the art, dicing of a hairpin structured RNA precursor product into a short ~22 nt RNA segment is catalyzed by an enzyme complex comprising an enzyme called Dicer together with other necessary proteins. A probable (over 7000%) nucleotide sequence of VGAM29 RNA is designated SEQ ID:30, and is provided hereinbelow with reference to the sequence listing part.

VGAM29 host target gene, herein designated VGAM HOST TARGET GENE, encodes a corresponding messenger RNA, VGAM29 host target RNA, herein designated VGAM HOST TARGET RNA. VGAM29 host target RNA, herein designated VGAM HOST TARGET RNA, comprises three regions, as is typical of mRNA of a protein coding gene: a 5 untranslated region, a protein coding region and a 3 untranslated region, designated 5UTR, PROTEIN CODING and 3UTR respectively.

VGAM29 RNA, herein designated VGAM RNA, binds complementarily to one or more host target binding sites located in untranslated regions of VGAM29 host target RNA, herein designated VGAM HOST TARGET RNA. This complementary binding is due to the fact that the nucleotide sequence of VGAM29 RNA, herein designated VGAM RNA, is an accurate or a partial inversed-reversed sequence of the nucleotide sequence of each of the host target binding sites. As an illustration, FIG. 1 shows 3 such host target binding sites, designated BINDING SITE I, BINDING SITE II and BINDING SITE III respectively. It is appreciated that the number of host target binding sites shown in FIG. 1 is meant as an illustration only, and is not meant to be limiting VGAM29 RNA, herein designated VGAM RNA, may have a different number of host target binding sites in untranslated regions of a VGAM29 host target RNA, herein designated VGAM HOST TARGET RNA. It is further appreciated that while FIG. 1 depicts host target binding sites in the 3UTR region, this is meant as an example only these host target binding sites may be located in the 3UTR region, the 5UTR region, or in both 3UTR and 5UTR regions.

The complementary binding of VGAM29 RNA, herein designated VGAM RNA, to host target binding sites on VGAM29 host target RNA, herein designated VGAM HOST TARGET RNA, such as BINDING SITE I, BINDING SITE II and BINDING SITE III, inhibits translation of VGAM29 host target RNA, herein designated VGAM HOST TARGET RNA, into VGAM29 host target protein, herein designated VGAM HOST TARGET PROTEIN. VGAM host target protein is therefore outlined by a broken line.

It is appreciated that VGAM29 host target gene, herein designated VGAM HOST TARGET GENE, in fact represents a plurality of VGAM29 host target genes. The mRNA of each one of this plurality of VGAM29 host target genes comprises one or more host target binding sites, each having a nucleotide sequence which is at least partly complementary to VGAM29 RNA, herein designated VGAM RNA, and which when bound by VGAM29 RNA, herein designated VGAM RNA, causes inhibition of translation of respective one or more VGAM29 host target proteins.

It is further appreciated by one skilled in the art that the mode of translational inhibition illustrated by FIG. 1 with specific reference to translational inhibition exerted by VGAM29 gene, herein designated VGAM GENE, on one or more VGAM29 host target gene, herein designated VGAM HOST TARGET GENE, is in fact common to other known non-viral miRNA genes. As mentioned hereinabove with reference to the background section, although a specific complementary binding site has been demonstrated only for some of the known miRNA genes (primarily Lin-4 and Let-7), all other recently discovered miRNA genes are also believed by those skilled in the art to modulate expression of other genes by complementary binding, although specific complementary binding sites of these other miRNA genes have not yet been found (Ruvkun G., Perspective: Glimpses of a tiny RNA world, Science 294, 779 (2001)).

It is yet further appreciated that a function of VGAM29 is inhibition of expression of host target genes, as part of a novel viral mechanism of attacking a host. Accordingly, utilities of VGAM29 include diagnosis, prevention and treatment of viral infection by Human immunodeficiency virus 1. Specific functions, and accordingly utilities, of VGAM29 correlate with, and may be deduced from, the identity of the host target genes which VGAM29 binds and inhibits, and the function of these host target genes, as elaborated hereinbelow.

Nucleotide sequences of the VGAM29 precursor RNA, herein designated VGAM PRECURSOR RNA, and of the diced VGAM29 RNA, herein designated VGAM RNA, and a schematic representation of the secondary folding of VGAM29 folded precursor RNA, herein designated VGAM FOLDED PRECURSOR RNA, of VGAM29 are further described hereinbelow with reference to Table 1.

Nucleotide sequences of host target binding sites, such as BINDING SITE-I, BINDING SITE-II and BINDING SITE- III of FIG. 1, found on, and schematic representation of the complementarity of each of these host target binding sites to VGAM29 RNA, herein designated VGAM RNA, are described hereinbelow with reference to Table 2.

FIG. 9 further provides a conceptual description of novel bioinformatically detected regulatory viral gene, referred to here as Viral Genomic Record 30(VGR30) viral gene, which encodes an operon-like cluster of novel viral micro RNA-like genes, each of which in turn modulates expression of at least one host target gene, the function and utility of which at least one host target gene is known in the art.

VGR30 gene, herein designated VGR GENE, is a novel bioinformatically detected regulatory, non protein coding, RNA viral gene. The method by which VGR30 gene was detected is described hereinabove with reference to FIGS. 6–15.

VGR30 gene encodes VGR30 precursor RNA, herein designated VGR PRECURSOR RNA, an RNA molecule, typically several hundred nucleotides long.

VGR30 precursor RNA folds spatially, forming VGR30 folded precursor RNA, herein designated VGR FOLDED PRECURSOR RNA. It is appreciated that VGR30 folded precursor RNA, herein designated VGR FOLDED PRECURSOR RNA, comprises a plurality of what is known in the art as hairpin structures. These hairpin structures are due to the fact that the nucleotide sequence of VGR30 precursor RNA comprises a plurality of segments, the first half of each such segment having a nucleotide sequence which is at least a partial inversed-reversed sequence of the second half thereof, as is well known in the art.

VGR30 folded precursor RNA, herein designated VGR FOLDED PRECURSOR RNA, is naturally processed by cellular enzymatic activity into at least 8 separate VGAM precursor RNAs, VGAM15 precursor RNA, VGAM16 precursor RNA, VGAM17 precursor RNA, VGAM18 precursor RNA, VGAM19 precursor RNA, VGAM20 precursor RNA, VGAM21 precursor RNA and VGAM22 precursor RNA, herein schematically represented by VGAM1 PRECURSOR, VGAM2 PRECURSOR, VGAM3 PRECURSOR, VGAM4 PRECURSOR, VGAM5 PRECURSOR, VGAM6 PRECURSOR, VGAM7 PRECURSOR and VGAM8 PRECURSOR respectively, each of which VGAM precursor RNAs being a hairpin shaped RNA segment, corresponding to VGAM PRECURSOR RNA of FIG. 8.

The above mentioned VGAM precursor RNAs are diced by DICER COMPLEX of FIG. 8, yielding respective short RNA segments of about 22 nucleotides in length, VGAM15 RNA, VGAM16 RNA, VGAM17 RNA, VGAM18 RNA, VGAM19 RNA, VGAM20 RNA, VGAM21 RNA and VGAM22 RNA respectively, herein schematically represented by VGAM1 RNA, VGAM2 RNA, VGAM3 RNA, VGAM4 RNA, VGAM5 RNA, VGAM6 RNA, VGAM7 RNA and VGAM8 RNA respectively, each of which VGAM RNAs corresponding to VGAM RNA of FIG. 8.

VGAM15 RNA, herein schematically represented by VGAM1 binds complimentarily to a host target binding site located in an untranslated region of VGAM15 host target RNA, herein schematically represented by VGAM1 HOST TARGET RNA, which host target binding site corresponds to a host target binding site such as BINDING SITE I, BINDING SITE II or BINDING SITE III of FIG. 1, thereby inhibiting translation of VGAM15 host target RNA, herein schematically represented by VGAM1 HOST TARGET RNA into VGAM15 host target protein, herein schematically represented by VGAM1 HOST TARGET PROTEIN, both of FIG. 1.

VGAM16 RNA, herein schematically represented by VGAM2 binds complimentarily to a host target binding site located in an untranslated region of VGAM16 host target RNA, herein schematically represented by VGAM2 HOST TARGET RNA, which host target binding site corresponds to a host target binding site such as BINDING SITE I, BINDING SITE II or BINDING SITE III of FIG. 1, thereby inhibiting translation of VGAM16 host target RNA, herein schematically represented by VGAM2 HOST TARGET RNA into VGAM16 host target protein, herein schematically represented by VGAM2 HOST TARGET PROTEIN, both of FIG. 1.

VGAM17 RNA, herein schematically represented by VGAM3 binds complimentarily to a host target binding site located in an untranslated region of VGAM17 host target RNA, herein schematically represented by VGAM3 HOST TARGET RNA, which host target binding site corresponds to a host target binding site such as BINDING SITE I, BINDING SITE II or BINDING SITE III of FIG. 1, thereby inhibiting translation of VGAM17 host target RNA, herein schematically represented by VGAM3 HOST TARGET RNA into VGAM17 host target protein, herein schematically represented by VGAM3 HOST TARGET PROTEIN, both of FIG. 1.

VGAM18 RNA, herein schematically represented by VGAM4 binds complimentarily to a host target binding site located in an untranslated region of VGAM18 host target RNA, herein schematically represented by VGAM4 HOST TARGET RNA, which host target binding site corresponds to a host target binding site such as BINDING SITE I, BINDING SITE II or BINDING SITE III of FIG. 1, thereby inhibiting translation of VGAM18 host target RNA, herein schematically represented by VGAM4 HOST TARGET RNA into VGAM18 host target protein, herein schematically represented by VGAM4 HOST TARGET PROTEIN, both of FIG. 1.

VGAM19 RNA, herein schematically represented by VGAM5 binds complimentarily to a host target binding site located in an untranslated region of VGAM19 host target RNA, herein schematically represented by VGAM5 HOST TARGET RNA, which host target binding site corresponds to a host target binding site such as BINDING SITE I, BINDING SITE II or BINDING SITE III of FIG. 1, thereby inhibiting translation of VGAM19 host target RNA, herein schematically represented by VGAM5 HOST TARGET RNA into VGAM19 host target protein, herein schematically represented by VGAM5 HOST TARGET PROTEIN, both of FIG. 1.

VGAM20 RNA, herein schematically represented by VGAM6 binds complimentarily to a host target binding site located in an untranslated region of VGAM20 host target RNA, herein schematically represented by VGAM6 HOST TARGET RNA, which host target binding site corresponds to a host target binding site such as BINDING SITE I, BINDING SITE II or BINDING SITE III of FIG. 1, thereby inhibiting translation of VGAM20 host target RNA, herein schematically represented by VGAM6 HOST TARGET RNA into VGAM20 host target protein, herein schematically represented by VGAM6 HOST TARGET PROTEIN, both of FIG. 1.

VGAM21 RNA, herein schematically represented by VGAM7 binds complimentarily to a host target binding site located in an untranslated region of VGAM21 host target RNA, herein schematically represented by VGAM7 HOST TARGET RNA, which host target binding site corresponds to a host target binding site such as BINDING SITE I, BINDING SITE II or BINDING SITE III of FIG. 1, thereby inhibiting translation of VGAM21 host target RNA, herein schematically represented by VGAM7 HOST TARGET RNA into VGAM21 host target protein, herein schematically represented by VGAM7 HOST TARGET PROTEIN, both of FIG. 1.

VGAM22 RNA, herein schematically represented by VGAM8 binds complimentarily to a host target binding site located in an untranslated region of VGAM22 host target RNA, herein schematically represented by VGAM8 HOST TARGET RNA, which host target binding site corresponds to a host target binding site such as BINDING SITE I, BINDING SITE II or BINDING SITE III of FIG. 1, thereby inhibiting translation of VGAM22 host target RNA, herein schematically represented by VGAM8 HOST TARGET RNA into VGAM22 host target protein, herein schematically represented by VGAM8 HOST TARGET PROTEIN, both of FIG. 1.

It is appreciated that a function of VGR30 gene, herein designated VGR GENE, is inhibition of expression of host target genes, as part of a novel viral mechanism of attacking a host. Accordingly, utilities of VGR30 gene include diagnosis, prevention and treatment of viral infection by. Specific functions, and accordingly utilities, of VGR30 gene, herein designated VGR GENE, correlate with, and may be deduced from, the identity of the host target genes, which are inhibited by VGAM RNAs comprised in the operon-like cluster of VGR30 gene: VGAM15 host target protein, VGAM16 host target protein, VGAM17 host target protein, VGAM18 host target protein, VGAM19 host target protein, VGAM20 host target protein, VGAM21 host target protein and VGAM22 host target protein, herein schematically represented by VGAM 1 HOST TARGET PROTEIN through VGAM HOST TARGET PROTEIN respectively. The function of these host target genes is elaborated hereinabove with reference to VGAM15, VGAM16, VGAM17, VGAM18, VGAM19, VGAM20, VGAM21 and VGAM22

FIG. 9 further provides a conceptual description of novel bioinformatically detected regulatory viral gene, referred to here as Viral Genomic Record 31(VGR31) viral gene, which encodes an operon-like cluster of novel viral micro RNA-like genes, each of which in turn modulates expression of at least one host target gene, the function and utility of which at least one host target gene is known in the art.

VGR31 gene, herein designated VGR GENE, is a novel bioinformatically detected regulatory, non protein coding, RNA viral gene. The method by which VGR31 gene was detected is described hereinabove with reference to FIGS. 6–15.

VGR31 gene encodes VGR31 precursor RNA, herein designated VGR PRECURSOR RNA, an RNA molecule, typically several hundred nucleotides long.

VGR31 precursor RNA folds spatially, forming VGR31 folded precursor RNA, herein designated VGR FOLDED PRECURSOR RNA. It is appreciated that VGR31 folded precursor RNA, herein designated VGR FOLDED PRECURSOR RNA, comprises a plurality of what is known in the art as hairpin structures. These hairpin structures are due to the fact that the nucleotide sequence of VGR31 precursor RNA comprises a plurality of segments, the first half of each such segment having a nucleotide sequence which is at least a partial inversed-reversed sequence of the second half thereof, as is well known in the art.

VGR31 folded precursor RNA, herein designated VGR FOLDED PRECURSOR RNA, is naturally processed by cellular enzymatic activity into at least 7 separate VGAM precursor RNAs, VGAM23 precursor RNA, VGAM24 precursor RNA, VGAM25 precursor RNA, VGAM26 precursor RNA, VGAM27 precursor RNA, VGAM28 precursor RNA and VGAM29 precursor RNA, herein schematically represented by VGAM1 PRECURSOR, VGAM2 PRECURSOR, VGAM3 PRECURSOR, VGAM4 PRECURSOR, VGAM5 PRECURSOR, VGAM6 PRECURSOR and VGAM7 PRECURSOR respectively, each of which VGAM precursor RNAs being a hairpin shaped RNA segment, corresponding to VGAM PRECURSOR RNA of FIG. 8.

The above mentioned VGAM precursor RNAs are diced by DICER COMPLEX of FIG. 8, yielding respective short RNA segments of about 22 nucleotides in length, VGAM23 RNA, VGAM24 RNA, VGAM25 RNA, VGAM26 RNA, VGAM27 RNA, VGAM28 RNA and VGAM29 RNA respectively, herein schematically represented by VGAM1 RNA, VGAM2 RNA, VGAM3 RNA, VGAM4 RNA, VGAM5 RNA, VGAM6 RNA and VGAM7 RNA respectively, each of which VGAM RNAs corresponding to VGAM RNA of FIG. 8.

VGAM23 RNA, herein schematically represented by VGAM1 binds complimentarily to a host target binding site located in an untranslated region of VGAM23 host target RNA, herein schematically represented by VGAM1 HOST TARGET RNA, which host target binding site corresponds to a host target binding site such as BINDING SITE I, BINDING SITE II or BINDING SITE III of FIG. 1, thereby inhibiting translation of VGAM23 host target RNA, herein schematically represented by VGAM 1 HOST TARGET RNA into VGAM23 host target protein, herein schematically represented by VGAM1 HOST TARGET PROTEIN, both of FIG. 1.

VGAM24 RNA, herein schematically represented by VGAM2 binds complimentarily to a host target binding site located in an untranslated region of VGAM24 host target RNA, herein schematically represented by VGAM2 HOST TARGET RNA, which host target binding site corresponds to a host target binding site such as BINDING SITE I, BINDING SITE II or BINDING SITE III of FIG. 1, thereby inhibiting translation of VGAM24 host target RNA, herein schematically represented by VGAM2 HOST TARGET RNA into VGAM24 host target protein, herein schematically represented by VGAM2 HOST TARGET PROTEIN, both of FIG. 1.

VGAM25 RNA, herein schematically represented by VGAM3 binds complimentarily to a host target binding site located in an untranslated region of VGAM25 host target RNA, herein schematically represented by VGAM3 HOST TARGET RNA, which host target binding site corresponds to a host target binding site such as BINDING SITE I, BINDING SITE II or BINDING SITE III of FIG. 1, thereby inhibiting translation of VGAM25 host target RNA, herein schematically represented by VGAM3 HOST TARGET RNA into VGAM25 host target protein, herein schematically represented by VGAM3 HOST TARGET PROTEIN, both of FIG. 1.

VGAM26 RNA, herein schematically represented by VGAM4 binds complimentarily to a host target binding site located in an untranslated region of VGAM26 host target RNA, herein schematically represented by VGAM4 HOST TARGET RNA, which host target binding site corresponds to a host target binding site such as BINDING SITE I, BINDING SITE II or BINDING SITE III of FIG. 1, thereby inhibiting translation of VGAM26 host target RNA, herein schematically represented by VGAM4 HOST TARGET RNA into VGAM26 host target protein, herein schematically represented by VGAM4 HOST TARGET PROTEIN, both of FIG. 1.

VGAM27 RNA, herein schematically represented by VGAM5 binds complimentarily to a host target binding site located in an untranslated region of VGAM27 host target RNA, herein schematically represented by VGAM5 HOST TARGET RNA, which host target binding site corresponds to a host target binding site such as BINDING SITE I, BINDING SITE II or BINDING SITE III of FIG. 1, thereby inhibiting translation of VGAM27 host target RNA, herein schematically represented by VGAM5 HOST TARGET RNA into VGAM27 host target protein, herein schematically represented by VGAM5 HOST TARGET PROTEIN, both of FIG. 1.

VGAM28 RNA, herein schematically represented by VGAM6 binds complimentarily to a host target binding site located in an untranslated region of VGAM28 host target RNA, herein schematically represented by VGAM6 HOST TARGET RNA, which host target binding site corresponds to a host target binding site such as BINDING SITE I, BINDING SITE II or BINDING SITE III of FIG. 1, thereby inhibiting translation of VGAM28 host target RNA, herein schematically represented by VGAM6 HOST TARGET RNA into VGAM28 host target protein, herein schematically represented by VGAM6 HOST TARGET PROTEIN, both of FIG. 1.

VGAM29 RNA, herein schematically represented by VGAM7 binds complimentarily to a host target binding site located in an untranslated region of VGAM29 host target RNA, herein schematically represented by VGAM7 HOST TARGET RNA, which host target binding site corresponds to a host target binding site such as BINDING SITE I, BINDING SITE II or BINDING SITE III of FIG. 1, thereby inhibiting translation of VGAM29 host target RNA, herein schematically represented by VGAM7 HOST TARGET RNA into VGAM29 host target protein, herein schematically represented by VGAM7 HOST TARGET PROTEIN, both of FIG. 1.

It is appreciated that a function of VGR31 gene, herein designated VGR GENE, is inhibition of expression of host target genes, as part of a novel viral mechanism of attacking a host. Accordingly, utilities of VGR31 gene include diagnosis, prevention and treatment of viral infection by Specific functions, and accordingly utilities, of VGR31 gene, herein designated VGR GENE, correlate with, and may be deduced from, the identity of the host target genes, which are inhibited by VGAM RNAs comprised in the operon-like cluster of VGR31 gene: VGAM23 host target protein, VGAM24 host target protein, VGAM25 host target protein, VGAM26 host target protein, VGAM27 host target protein, VGAM28 host target protein and VGAM29 host target protein, herein schematically represented by VGAM 1 HOST TARGET PROTEIN through VGAM HOST TARGET PROTEIN respectively. The function of these host target genes is elaborated hereinabove with reference to VGAM23, VGAM24, VGAM25, VGAM26, VGAM27, VGAM28 and VGAM29

BIBLIOGRAPHY

It is appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specifications and which are not in the prior art.

1. Simard, J.; Berube, D.; Sandberg, M.; Grzeschik, K.-H.; Gagne, R.; Hansson, V.; Jahnsen, T.: Assignment of the gene encoding the catalytic subunit C-beta of cAMP-dependent protein kinase to the p36 band on chromosome 1. Hum. Genet. 88: 653–657, 1992.
2. Elliott, K. J.; Ellis, S. B.; Berckhan, K. J.; Urrutia, A.; Chavez-Noriega, L. E.; Johnson, E. C.; Velicelebi, G.; Harpold, M. M.: Comparative structure of human neuronal alpha(2)-alpha(7) and beta(2)-beta(4)nicotinic acetylcholine receptor subunits and functional expression of the alpha(2), alpha(3), alpha(4), alpha(7), beta(2), and beta(4)subunits. J. Molec. Neurosci. 7: 217–228, 1996.
3. Seldin, M. F.: Personal Communication. Durham, N. C. Mar. 13, 1989.
4. Mattei, M.-G.; Pebusque, M.-J.; Birnbaum, D.: Chromosomal localizations of mouse Fgf2 and Fgf5 genes. Mammalian Genome 2: 135–137, 1992.
5. Avraham, K. B.; Givol, D.; Avivi, A.; Yayon, A.; Copeland, N. G.; Jenkins, N. A.: Mapping of murine fibroblast growth factor receptors refines regions of homology between mouse and human chromosomes. Genomics 21:656–658, 1994.
6. Keegan, K.; Johnson, D. E.; Williams, L. T.; Hayman, M. J.: Isolation of an additional member of the fibroblast growth factor receptor family, FGFR-3. Proc. Nat. Acad. Sci. 88: 1095–1099, 1991.
7. Mannick, J. B.; Hausladen, A.; Liu, L.; Hess, D. T.; Zeng, M.; Miao, Q. X.; Kane, L. S.; Gow, A. J.; Stamler, J. S.: Fasinducedcaspase denitrosylation. Science 284: 651–654, 1999.
8. Groot Kormelink, P. J.; Luyten, W. H. M. L.: Cloning and sequence of full-length cDNAs encoding the human neuronal nicotinic acetylcholine receptor (nAChR) subunits beta-3 and beta-4 and expression of seven nAChR subunits in the human neuroblastoma cell line SH-SY5Y and/or IMR-32. FEBS Lett. 400: 309–314, 1997.
9. Bauer, H.; Mayer, H.; Marchler-Bauer, A.; Salzer, U.; Prohaska, R.: Characterization of p40/GPR69A as a peripheral membrane protein related to the lantibiotic synthetase component C. Biochem. Biophys. Res. Commun. 275: 69–74, 2000.
10. Mayer, H.; Bauer, H.; Prohaska, R.: Organization and chromosomallocalization of the human and mouse genes coding for LanC-like protein 1 (LANCL1). Cytogenet. Cell Genet. 93: 100–104, 2001.
11. Mayer, H.; Salzer, U.; Breuss, J.; Ziegler, S.; Marchler-Bauer, A.; Prohaska, R.: Isolation, molecular characterization, and tissue-specific expression of a novel putative G protein-coupled receptor. Biochim. Biophys. Acta 1395: 301–308, 1998.
12. Li, S.-H.; Lam, S.; Cheng, A. L.; Li, X.-J.: Intra-nuclear huntingtin increases the expression of caspase-1 and induces apoptosis. Hum. Molec. Genet. 9: 2859–2867, 2000.
13. Duke-Cohan, J. S.; Gu, J.; McLaughlin, D. F.; Xu, Y.; Freeman, G. J.; Schlossman, S. F.: Attractin (DPPT-L), a member of the CUBfamily of cell adhesion and guidance proteins, is secreted by activated human T lymphocytes and modulates immune cell interactions. Proc. Nat. Acad. Sci. 95: 11336–11341, 1998.
14. Gunn, T. M.; Miller, K. A.; He, L.; Hyman, R. W.; Davis, R. W.; Azarani, A.; Schlessman, S. F.; Duke-Cohan, J. S.; Barsh, G. S.: The mouse mahogany locus encodes a transmembrane form of human attractin. Nature 398: 152–156, 1999.
15. He, L.; Gunn, T. M.; Bouley, D. M.; Lu, X.-Y.; Watson, S. J.; Schlossman, S. F.; Duke-Cohan, J. S.; Barsh, G. S.:

A biochemical function for attractin in agouti-induced pigmentation and obesity. Nature Genet. 27:40–47, 2001.

16. Tang, W.; Gunn, T. M.; McLaughlin, D. F.; Barsh, G. S.; Schlossman, S. F.; Duke-Cohan, J. S.: Secreted and membrane attractin result from alternative splicing of the human ATRN gene. Proc. Nat. Acad. Sci. 97: 6025–6030, 2000.

17. Dionne, C. A.; Kaplan, R.; Seuanez, H.; O'Brien, S. J.; Jaye, M.: Chromosome assignment by polymerase chain reaction techniques: assignment of the oncogene FGF-5 to human chromosome 4. Biotechniques 8: 190–194, 1990.

18. Hebert, J. M.; Rosenquist, T.; Gotz, J.; Martin, G. R.: FGF5 as a regulator of the hair growth cycle: evidence from targeted and spontaneous mutations. Cell 78: 1017–1025, 1994.

19. Nguyen, C.; Roux, D.; Mattei, M.-G.; de Lapeyriere, O.; Goldfarb, M.; Birnbaum, D.; Jordan, B. R.: The FGF-related oncogenes hst and int.2, and the bcl.1 locus are contained within one megabase in band q13 of chromosome 11, while the fgf.5 oncogene maps to 4q21. Oncogene 3:703–708, 1988.

20. Zhan, X.; Bates, B.; Hu, X.; Goldfarb, M.: The human FGF-5 oncogene encodes a novel protein related to fibroblast growth factors. Molec. Cell. Biol. 8: 3487–3495, 1988.

21. Douhan, J., III; Hauber, I.; Eibl, M. M.; Glimcher, L. H.: Genetic evidence for a new type of major histocompatibility complex class II combined immunodeficiency characterized by a dyscoordinate regulation of HLA-D alpha and beta chains. J. Exp. Med. 183: 1063–1069, 1996.

22. Pan, H.; Yin, C.; Dyson, N. J.; Harlow, E.; Yamasaki, L.; VanDyke, T.: Key roles for E2F1 in signaling p53-dependent apoptosis and in cell division within developing tumors. Molec. Cell 2: 283–292, 1998.

23. Phillips, A. C.; Ernst, M. K.; Bates, S.; Rice, N. R.; Vousden, K. H.: E2F-1 potentiates cell death by blocking anti-apoptotic signaling pathways. Molec. Cell 4: 771–781, 1999.

24. Saenz Robles, M. T.; Symonds, H.; Chen, J.; Van Dyke, T.: Induction versus progression of brain tumor development: differential functions for the pRB- and p53-targeting domains of simian virus 40 T antigen. Molec. Cell. Biol. 14: 2686–2698, 1994.

25. Sherr, C. J.: Tumor surveillance via the ARF-p53 pathway. Genes Dev. 12: 2984–2991, 1998.

26. Tsai, K. Y.; Hu, Y.; Macleod, K. F.; Crowley, D.; Yamasaki, L.; Jacks, T.: Mutation of E2f-1 suppresses apoptosis and inappropriateS phase entry and extends survival of Rb-deficient mouse embryos. Molec. Cell 2: 293–304, 1998.

27. Weinberg, R. A.: E2F and cell proliferation: a world turned upside down. Cell 85: 457–459, 1996.

28. Wu, L.; Timmers, C.; Maiti, B.; Saavedra, H. I.; Sang, L.; Chong, G. T.; Nuckolls, F.; Giangrande, P.; Wright, F. A.; Field, S. J.; Greenberg, M. E.; Orkin, S.; Nevins, J. R.; Robinson, M. L.; Leone, G.: The E2F1-3 transcription factors are essential for cellular proliferation. Nature 414:457–462, 2001.

29. Yamasaki, L.; Jacks, T.; Bronson, R.; Goillot, E.; Harlow, E.; Dyson, N. J.: Tumor induction and tissue atrophy in mice lacking E2F-1. Cell 85: 537–548, 1996.

30. Zhang, H. S.; Postigo, A. A.; Dean, D. C.: Active transcriptional repression by the Rb-E2F complex mediates G1 arrest triggered by p16(INK4a), TGF-beta, and contact inhibition. Cell 97: 53–61, 1999.

31. Zhang, Y.; Chellappan, S. P.: Cloning and characterization of human DP2, a novel dimerization partner of E2F. Oncogene 10: 2085–2093, 1995.

32. Nagase, T.; Ishikawa, K.; Nakajima, D.; Ohira, M.; Seki, N.; Miyajima, N.; Tanaka, A.; Kotani, H.; Nomura, N.; Ohara, O.: Prediction of the coding sequences of unidentified human genes. VII. The complete sequences of 100 new cDNA clones from brain which can code for large proteins in vitro. DNA Res. 4: 141–150, 1997.

33. Hu, X.; Ray, P. N.; Murphy, E. G.; Thompson, M. W.; Worton, R. G.: Duplicational mutation at the Duchenne muscular dystrophy locus: its frequency, distribution, origin, and phenotype-genotype correlation. Am. J. Hum. Genet. 46: 682–695, 1990.

34. Hu, X.; Ray, P. N.; Worton, R. G.: Mechanisms of tandem duplication in the Duchenne muscular dystrophy gene include both homologous and nonhomologous intrachromosomal recombination. EMBO J. 10: 2471–2477, 1991.

35. Hu, X.; Worton, R. G.: Partial gene duplication as a cause of human disease. Hum. Mutat. 1: 3–12, 1992.

36. Ingram, V. M.: Gene evolution and the haemoglobins. Nature 189:704–708, 1961.

37. Itagaki, Y.; Saida, K.; Iwamura, K.: Regenerative capacity of mdx mouse muscles after repeated applications of myo-necrotic bupivacaine. ActaNeuropath. 89: 380–384, 1995.

38. Kaplan, J.-C.; Kahn, A.; Chelly, J.: Illegitimate transcription: its use in the study of inherited disease. Hum. Mutat. 1: 357–360, 1992.

39. Kavaslar, G. N.; Telatar, M.; Serdaroglu, P.; Deymeer, F.; Ozdemir, C.; Tolun, A.: Identification of a one-base pair deletion in exon6 of the dystrophin gene. Hum. Mutat. 6: 85–86, 1995.

40. Kilimann, M. W.; Pizzuti, A.; Grompe, M.; Caskey, C. T.: Point mutations and polymorphisms in the human dystrophin gene identified in genomic DNA sequences amplified by multiplex PCR. Hum. Genet. 89:253–258, 1992.

41. Kim, T.-W.; Wu, K.; Black, I. B.: Deficiency of brain synaptic dystrophin in human Duchenne muscular dystrophy. Ann. Neurol. 38:446–449, 1995.

42. Kneppers, A. L. J.; Deutz-Terlouw, P. P.; van Ommen, G. J. B.; Bakker, E.: Point mutation screening for Duchenne muscular dystrophy(DMD) by SSCP-analysis of multiplex PCR products by use of the PhastSystem(™). Am. J. Hum. Genet. Suppl. 53: Abstract-1493, 1993.

43. Koenig, M.: Personal Communication. Boston, Mass. Oct. 8, 1987. 100. Koenig, M.; Beggs, A. H.; Moyer, M.; Scherpf, S.; Heindrich, K.; Bettecken, T.; Meng, G.; Muller, C. R.; Lindlof, M.; Kaariainen, H.; de la Chapelle, A.; Kiuru, A.; and 24 others: The molecular basis for Duchenne versus Becker muscular dystrophy: correlation of severity with type of deletion. Am. J. Hum. Genet. 45: 498–506,1989.101. Koenig, M.; Bertelson, C. J.; Monaco, A. P.; Hoffman, E.; Feener, C. C.; Kunkel, L. M.: Complete cloning of the Duchenne muscular dystrophycDNA and an analysis of the entire DMD locus. (Abstract) Am. J. Hum. Genet. 41: A222, 1987.102. Koenig, M.; Hoffman, E. P.; Bertelson, C. J.; Monaco, A. P.; Feener, C.; Kunkel, L. M.: Complete cloning of the Duchenne muscular dystrophy (DMD) cDNA and preliminary genomic organization of the DMD gene in normal and affected individuals. Cell 50: 509–517, 1987.103. Koenig, M.; Monaco, A. P.; Kunkel, L. M.: The complete sequence of dystrophin predicts a rod-shaped cytoskeletal protein. Cell 53:219–228, 1988.104. Koh, J.; Bartlett, R. J.; Pericak-Vance, M. A.; Speer, M. C.; Yamaoka, L. H.; Phillips, K.; Hung, W.-Y.; Ray, P. N.; Worton, R. G.; Gilbert, J. R.; Lee, J. E.; Siddique, T.; Kandt, R. S.; Roses, A. D.: Inherited deletion at Duchenne dystrophy locus in normal male. (Letter) Lancet II: 1154–1155, 1987.105. Kunkel, L. M.: Analysis of deletions in DNA from patients with Becker and Duchenne muscular dystrophy. Nature 322: 73–77, 1986.106. Kunkel, L. M.; Monaco, A. P.; Middlesworth, W.; Ochs, H. D.; Latt, S. A.: Specific cloning of DNA fragments absent from the DNA of a male patient with an X chromosome deletion. Proc. Nat. Acad. Sci. 82: 4778–4782, 1985.107. Laing, N. G.; Layton, M. G.; Johnsen, R. D.; Chandler, D. C.; Mears, M. E.; Goldblatt, J.; Kakulas, B. A.: Two distinct mutations in a single dystrophin gene: chance occurrence or premutation? Am. J. Med. Genet. 42: 688–692, 1992.108. Lederfein, D.; Levy, Z.; Augier, N.; Mornet, D.; Morris, G.; Fuchs, O.; Yaffe, D.; Nudel, U.: A 71-kilodalton protein is a major product of the Duchenne muscular dystrophy gene in brain and other nonmuscle tissues. Proc. Nat. Acad. Sci. 89: 5346–5350, 1992.109. Lederfein, D.; Yaffe, D.; Nudel, U.: A housekeeping type promoter, located in the 3-prime region of the Duchenne muscular dystrophy gene, controls the expression of Dp71, a major product of the gene. Hum. Molec. Genet. 2: 1883–1888, 1993.110. Lee, C. C.; Pearlman, J. A.; Chamberlain, J. S.; Caskey, C. T.: Expression of recombinant dystrophin and its localization to the cell membrane. Nature 349: 334–336, 1991.111. Lee, G.-H.; Badorff, C.; Knowlton, K. U.: Dissociation of sarcoglycans and the dystrophin carboxyl terminus from the sarcolemma in enteroviralcardiomyopathy. Circ. Res. 87: 489–495, 2000.112. Lenk, U.; Hanke, R.; Kraft, U.; Grade, K.; Grunewald, I.; Speer, A.: Non-isotopic analysis of single strand conformation polymorphism(SSCP) in the exon 13 region of the human dystrophin gene. J. Med. Genet. 30: 951–954, 1993.113. Lenk, U.; Hanke, R.; Speer, A.: Carrier detection in DMD families with point mutations, using PCR-SSCP and direct sequencing. Neuromusc. Disord. 4: 411–418, 1994.114. Lenk, U.; Hanke, R.; Thiele, H.; Speer, A.: Point mutations at the carboxy terminus of the human dystrophin gene: implications for an association with mental retardation in DMD patients. Hum. Molec. Genet. 2: 1877–1881, 1993.115. Lenk, U.; Oexle, K.; Voit, T.; Ancker, U.; Hellner, K.-A.; Speer, A.; Hubner, C.: A cysteine 3340 substitution in the dystroglycan-binding domain of dystrophin associated with Duchenne muscular dystrophy, mental retardation and absence of the ERG b-wave. Hum. Molec. Genet. 973–975, 1996.116. Liechti-Gallati, S.; Braga, S.; Hirsiger, H.; Moser, H.: Familial deletion in Becker type muscular dystrophy within the pXJ region. Hum. Genet. 77: 267–268, 1987.117. Lindlof, M.; Kaariainen, H.; van Ommen, G. J. B.; de la Chapelle, A.: Microdeletions in patients with X-linked muscular dystrophy: molecular-clinical correlations. Clin. Genet. 33: 131–139, 1988.118. Lindlof, M.; Kiuru, A.; Kaariainen, H.; Kalimo, H.; Lang, H.; Pihko, H.; Rapola, J.; Somer, H.; Somer, M.; Savontaus, M.-L.; dela Chapelle, A.: Gene deletions in X-linked muscular dystrophy. Am. J. Hum. Genet. 44: 496–503, 1989.119. Mankin, A. S.; Liebman, S. W.: Baby, don't stop! Nature Genet. 23:8–10, 1999.120. Mao, Y.; Cremer, M.: Detection of Duchenne muscular dystrophy carriers by dosage analysis using the DMD cDNA clone 8. Hum. Genet. 81:193–195, 1989.121. Matsuo, M.; Masumura, T.; Nakajima, T.; Kitoh, Y.; Takumi, T.; Nishio, H.; Koga, J.; Nakamura, H.: A very small frame-shifting deletion within exon 19 of the Duchenne muscular dystrophy gene. Biochem. Biophys. Res. Commun. 170: 963–967, 1990.122. Matsuo, M.; Masumura, T.; Nishio, H.; Nakajima, T.; Kitoh, Y.; Takumi, T.; Koga, J.; Nakamura, H.: Exon skipping during splicing of dystrophin mRNA precursor due to an intraexon deletion in the dystrophin gene of Duchenne muscular dystrophy. J. Clin. Invest. 87: 2127–2131, 1991.123. McArdle, A.; Edwards, R. H. T.; Jackson, M. J.: Time course of changes in plasma membrane permeability in the dystrophin-deficient mdx mouse. Muscle Nerve 17: 1378–1384, 1994.124. McCabe, E. R. B.; Towbin, J.; Chamberlain, J.; Baumbach, L.; Witkowski, J.; van Ommen, G. J. B.; Koenig, M.; Kunkel, L. M.; Seltzer, W. K.: Complementary DNA probes for the Duchenne muscular dystrophylocus demonstrate a previously undetectable deletion in a patient with dystrophic myopathy, glycerol kinase deficiency, and congenitaladrenal hypoplasia. J. Clin. Invest. 83: 95–99, 1989.125. Milasin, J.; Muntoni, F.; Severini, G. M.; Bartoloni, L.; Vatta, M.; Krajinovic, M.; Mateddu, A.; Angelini, C.; Camerini, F.; Falaschi, A.; Mestroni, L.; Giacca, M.; Heart Muscle Disease Study Group: A point mutation in the 5-prime splice site of the dystrophin gene first intron responsible for X-linked dilated cardiomyopathy. Hum. Molec. Genet. 5: 73–79, 1996.126. Minetti, C.; Bonilla, E.: Mosaic expression of dystrophin in carriers of Becker's muscular dystrophy and the X-linked syndrome of myalgia and cramps. (Letter) New Eng. J. Med. 327: 1100, 1992.127. Moizard, M.-P.; Toutain, A.; Fournier, D.; Berret, F.; Raynaud, M.; Billard, C.; Andres, C.; Moraine, C.: Severe cognitive impairment in DMD: obvious clinical indication for Dp71 isoform point mutation screening. Europ. J. Hum. Genet. 8: 552–556, 2000.128. Monaco, A. P.; Bertelson, C. J.; Liechti-Gallati, S.; Moser, H.; Kunkel, L. M.: An explanation for phenotypic differences between patients bearing partial deletions of DMD locus. Genomics 2: 90–95, 1988.129. Monaco, A. P.; Kunkel, L. M.: A giant locus for the Duchenne and Becker muscular dystrophy gene. Trends Genet. 3: 33–37, 1987.130. Monaco, A. P.; Neve, R. L.; Colletti-Feener, C.; Bertelson, C. J.; Kurnit, D. M.; Kunkel, L. M.: Isolation of candidate cDNAs for portions of the Duchenne muscular dystrophy gene. Nature 323: 646–650,1986.131. Muntoni, F.; Cau, M.; Ganau, A.; Congiu, R.; Arvedi, G.; Mateddu, A.; Marrosu, M. G.; Cianchetti, C.; Realdi, G.; Cao, A.; Melis, M. A.: Deletion of the dystrophin muscle-promoter region associated with X-linked dilated cardiomyopathy. New Eng. J. Med. 329: 921–925, 1993.132. Muntoni, F.; Melis, M. A.; Ganau, A.; Dubowitz, V.: Transcription of the dystrophin gene in normal tissues and in skeletal muscle of a family with X-linked dilated cardiomyopathy. Am. J. Hum. Genet. 56:151–157, 1995.133. Muntoni, F.; Wilson, L.; Marrosu, G.; Marrosu, M. G.; Cianchetti, C.; Mestroni, L.; Ganau, A.; Dubowitz, V.; Sewry, C.: A mutation in the dystrophin gene selectively affecting dystrophin expression in the heart. J. Clin. Invest. 96: 693–699, 1995.134. Nevin, N. C.; Hughes, A. E.; Calwell, M.; Lim, J. H. K.: Duchenne muscular dystrophy in a female with a translocation involving Xp21. J. Med. Genet. 23: 171–187, 1986.135. Nigro, V.; Politano, L.; Nigro, G.; Romano, S. C.; Molinari, A. M.; Puca, G. A.: Detection of a nonsense mutation in the dystrophin gene by multiple SSCP. Hum. Molec. Genet. 1: 517–520, 1992.136. Nobile, C.; Marchi, J.; Nigro, V.; Roberts, R. G.; Danieli, G. A.: Exon-intron organization of the human dystrophin gene. Genomics 45:421–424, 1997.137. Nobile, C.; Toffolatti, L.; Rizzi, F.; Simionati, B.; Nigro, V.; Cardazzo, B.; Patarnello, T.; Valle, G.; Danieli, G. A.: Analysis of 22 deletion breakpoints in dystrophin intron 49. Hum. Genet. 110:418–421, 2002.138. Norman, A.; Harper, P.: A survey of manifesting carriers of Duchenne and Becker muscular dystrophy in Wales. Clin. Genet. 36:31–37, 1989.139. Ohno, S.: Evolution by Gene Duplication. Berlin: Springer-Verlag (pub.) 1970.140. Ortiz Lopez, R.; Li, H.; Su, J.; Goytia, V.; Towbin, J. A.: Evidence for a dystrophin missense mutation as a cause of X-linked dilated cardiomyopathy. Circulation 95: 2434–2440, 1997.141. Palmucci, L.; Doriguzzi, C.; Mongini, T.; Restagno, G.; Chiado-Piat, L.; Maniscalco, M.: Unusual expression and very mild course of Xp21 muscular dystrophy (Becker type) in a 60-year-old man with 26 percent deletion of the dystrophin gene. Neurology 44: 541–543, 1994.142. Passos-Bueno, M. R.; Bakker, E.; Kneppers, A. L. J.; Takata, R. I.; Rapaport, D.; den Dunnen, J. T.; Zatz, M.; van Ommen, G. J. B.: Different mosaicism frequencies for proximal and distal Duchenne muscular dystrophy (DMD) mutations indicate difference in etiology and recurrence risk. Am. J. Hum. Genet. 51: 1150–1155, 1992.143. Paulson, K. E.; Deka, N.; Schmid, C. W.; Misra, R.; Schindler, C. W.; Rush, M. G.; Kadyk, L.; Leinwand, L.: A transposon-like element in human DNA. Nature 316: 359–361, 1985.144. Pernelle, J.-J.; Chafey, P.; Chelly, J.; Wahrmann, J. P.; Kaplanj.-C.; Tome, F.; Fardeau, M.: Nebulin seen in DMD males including one patient with a large DNA deletion encompassing the DMD gene. Hum. Genet. 78: 285, 1988.145. Pillers, D.-A. M.; Fitzgerald, K. M.; Duncan, N. M.; Rash, S. M.; White, R. A.; Dwinnell, S. J.; Powell, B. R.; Schnur, R. E.; Ray, P. N.; Cibis, G. W.; Weleber, R. G.: Duchenne/Becker muscular dystrophy: correlation of phenotype by electroretinography with sites of dystrophin mutations. Hum. Genet. 105: 2–9, 1999.146. Pizzuti, A.; Pieretti, M.; Fenwick, R. G.; Gibbs, R. A.; Caskey, C. T.: A transposon-like element in the deletion-prone region of the dystrophin gene. Genomics 13: 594–600, 1992.147. Porter, J. D.; Khanna, S.; Kaminski, H. J.; Rao, J. S.; Merriam, A. P.; Richmonds, C. R.; Leahy, P.; Li, J.; Guo, W.; Andrade, F. H.: A chronic inflammatory response dominates the skeletal muscle molecular signature in dystrophin-deficient mdx mice. Hum. Molec. Genet. 11:263–272, 2002.148. Prior, T. W.; Papp, A. C.; Snyder, P. J.; Burghes, A. H. M.; Bartolo, C.; Sedra, M. S.; Western, L. M.; Mendell, J. R.: A missense mutation in the dystrophin gene in a Duchenne muscular dystrophy patient. Nature Genet. 4: 357–360, 1993.149. Prior, T. W.; Papp, A. C.; Snyder, P. J.; Burghes, A. H. M.; Sedra, M. S.; Western, L. M.; Bartello, C.; Mendell, J. R.: Identification of two point mutations and a one base deletion in exon 19 of the dystrophin gene by heteroduplex formation. Hum. Molec. Genet. 2: 311–313, 1993.150. Prior, T. W.; Papp, A. C.; Snyder, P. J.; Burghes, A. H. M.; Sedra, M. S.; Western, L. M.; Bartolo, C.; Mendell, J. R.: Exon 44 nonsense mutation in two-Duchenne muscular dystrophy brothers detected by heteroduplex analysis. Hum. Mutat. 2: 192–195, 1993.151. Prior, T. W.; Papp, A. C.; Snyder, P. J.; Sedra, M. S.; Western, L. M.; Bartolo, C.; Moxley, R. T.; Mendell, J. R.: Heteroduplex analysis of the dystrophin gene: application to point mutation and carrier detection. Am. J. Med. Genet. 50: 68–73, 1994.152. Rafael, J. A.; Sunada, Y.; Cole, N. M.; Campbell, K. P.; Faulkner J. A.; Chamberlain, J. S.: Prevention of dystrophic pathology in mdx mice by a truncated dystrophin isoform. Hum. Molec. Genet. 3:1725–1733, 1994.153. Rafael, J. A.; Townsend, E. R.; Squire, S. E.; Potter, A. C.; Chamberlain, J. S.; Davies, K. E.: Dystrophin and utrophin influence fiber type composition and post-synaptic membrane structure. Hum. Molec. Genet. 9: 1357–1367, 2000.154. Ray, P. N.; Belfall, B.; Duff, C.; Logan, C.; Kean, V.; Thompson, M. W.; Sylvester, J. E.; Gorski, J. L.; Schmickel, R. D.; Worton, R. G.: Cloning of the breakpoint of an X; 21 translocation associated with Duchenne muscular dystrophy. Nature 318: 672–675, 1985.155. Read, A. P.; Mountford, R. C.; Forrest, S. M.; Kenwrick, S. J.; Davies, K. E.; Harris, R.: Patterns of exon deletions in Duchenne and Becker muscular dystrophy. Hum. Genet. 80: 152–156, 1988.156. Rininsland, F.; Hahn, A.; Niemann-Seyde, S.; Slomski, R.; Hanefeld, F.; Reiss, J.: Identification of a new DMD gene deletion by ectopic transcript analysis. J. Med. Genet. 29: 647–651, 1992.157. Roberts, R. G.; Bentley, D. R.; Bobrow, M.: Infidelity in the structure of ectopic transcripts: a novel exon in lymphocyte dystrophin transcripts. Hum. Mutat. 2: 293–299, 1993.158. Roberts, R. G.; Bobrow, M.; Bentley, D. R.: The spectrum of mild X-linked recessive muscular dystrophy. Arch. Neurol. 34: 408–416, 1992.159. Roberts, R. G.; Bobrow, M.; Bentley, D. R.: Point mutations in the dystrophin gene. Proc. Nat. Acad. Sci. 89: 2331–2335, 1992.160. Roberts, R. G.; Gardner, R. J.; Bobrow, M.: Searching for the 1 in 2,400,000: a review of dystrophin gene point mutations. Hum. Mutat. 4: 1–11, 1994.161. Roberts, R. G.; Passos-Bueno, M. R.; Bobrow, M.; Vainzof, M.; Zatz, M.: Point mutation in a Becker muscular dystrophy patient. Hum. Molec. Genet. 2: 75–77, 1992.162. Rowland, L. P.: Biochemistry of muscle membranes in Duchenne muscular dystrophy. Muscle Nerve 3: 3–20, 1980.163. Ryder-Cook, A. S.; Sicinski, P.; Thomas, K.; Davies, K. E.; Worton, R. G.; Barnard, E. A.; Darlison, M. G.; Barnard, P. J.: Localization of the mdx mutation within the mouse dystrophin gene. EMBO J. 7:3017–3021, 1988.164. Saad, F. A.; Vita, G.; Mora, M.; Morandi. L.; Vitiello, L.; Oliviero, S.; Danieli, G. A.: A novel nonsense mutation in the human dystrophin gene. Hum. Mutat. 2: 314–316, 1993.165. Saad, F. A.; Vita, G.; Toffolatti, L.; Danieli, G. A.: A possible missense mutation detected in the dystrophin gene by double strand conformation analysis (DSCA). Neuromusc. Disord. 4: 335–341, 1994.166. Sakamoto, M.; Yuasa, K.; Yoshimura, M.; Yokota, T.; Ikemoto, T.; Suzuki, M.; Dickson, G.; Miyagoe-Suzuki, Y.; Takeda, S.: Microdystrophinc DNA ameliorates dystrophic phenotypes when introduced into mdx mice as a transgene. Biochem. Biophys. Res. Commun. 293: 1265–1272, 2002.167. Sarig, R.; Mezger-Lallemand, V.; Gitelman, I.; Davis, C.; Fuchs, O.; Yaffe, D.; Nudel, U.: Targeted inactivation of Dp71, the major non-muscle product of the DMD gene: differential activity of the Dp71 promoter during development. Hum. Molec. Genet. 8: 1–10, 1999.168. Sarkar, G.; Sommer, S. S.: Access to a messenger RNA sequence or its protein product is not limited by tissue or species specificity. Science 244:331–334, 1989.169. Schwartz, L. S.; Tarleton, J.; Popovich, B.; Seltzer, W. K.; Hoffman, E. P.: Fluorescent multiplex linkage analysis and carrier detection for Duchenne/Becker muscular dystrophy. Am. J. Hum. Genet. 51:721–729, 1992.170. Scott, M. O.; Sylvester, J. E.; Heiman-Patterson, T.; Shi, Y.-J.; Fieles, W.; Stedman, H.; Burghes, A.; Ray, P.; Worton, R.; Fischbeck, K. H.: Duchenne muscular dystrophy gene expression in normal and diseased human muscle. Science 239: 1418–1420, 1988.171. Sharp, N. J. H.; Kornegay, J. N.; Van Camp, S. D.; Herbstreith, M. H.; Secore, S. L.; Kettle, S.; Hung, W.-Y.; Constantinou, C. D.; Dykstra, M. J.; Roses, A. D.; Bartlett, R. J.: An error in dystrophin miRNA processing in golden retriever muscular dystrophy, an animal homologue of Duchenne muscular dystrophy. Genomics 13: 115–121, 1992. 172. Shiga, N.; Takeshima, Y.; Sakamoto, H.; Inoue, K.; Yokota, Y.; Yokoyama, M.; Matsuo, M.: Disruption of the splicing enhancer sequence within exon 27 of the dystrophin gene by a nonsense mutation induces partial skipping of the exon and is responsible for Becker muscular dystrophy. J. Clin. Invest. 100: 2204–2210, 1997. 173. Sicinski, P.; Geng, Y.; Ryder-Cook, A. S.; Barnard, E. A.; Darlison, M. G.; Barnard, P. J.: The molecular basis of muscular dystrophyin the mdx mouse: a point mutation. Science 244: 1578–1580, 1989. 174. Smithies, O.; Connell, G. E.; Dixon, G. H.: Chromosomal rearrangements and the evolution of haptoglobin genes. Nature 196: 232–236, 1962. 175. Southern, E. M.: Detection of specific sequences among DNA fragments separated by gel electrophoresis. J. Molec. Biol. 98: 503–517, 1975. 176. Stratford-Perricaudet, L. D.; Makeh, I.; Perricaudet, M.; Briand, P.: Widespread long-term gene transfer to mouse skeletal muscles and heart. J. Clin. Invest. 90: 626–630, 1992. 177. Takeshima, Y.; Nishio, H.; Narita, N.; Wada, H.; Ishikawa, Y.; Ishikawa, Y.; Minami, R.; Nakamura, H.; Matsuo, M.: Amino-terminal deletion of 53% of dystrophin results in an intermediate Duchenne-Becker muscular dystrophy phenotype. Neurology 44: 1648–1651, 1994. 178. Tennyson, C. N.; Klamut, H. J.; Worton, R. G.: The human dystrophingene requires 16 hours to be transcribed and is cotranscriptionally spliced. Nature Genet. 9: 184–190, 1995. 179. Tinsley, J. M.; Blake, D. J.; Davies, K. E.: Apodystrophin-3: a 2.2 kb transcript from the DMD locus encoding the dystrophin glycoprotein binding site. Hum. Molec. Genet. 2: 521–524, 1993. 180. Tinsley, J. M.; Potter, A. C.; Phelps, S. R.; Fisher, R.; Trickett J. I.; Davies, K. E.: Amelioration of the dystrophic phenotype of mdx mice using a truncated utrophin transgene. Nature 384: 349–353, 1996. 181. Todorova, A.; Danieli, G. A.: Large majority of single-nucleotide mutations along the dystrophin gene can be explained by more than one mechanism of mutagenesis. Hum. Mutat. 9: 537–547, 1997. 182. Torelli, S.; Muntoni, F.: Alternative splicing of dystrophin exon 4 in normal human muscle. Hum. Genet. 97: 521–523, 1996. 183. Towbin, J. A.; Hejtmancik, J. F.; Brink, P.; Gelb, B.; Zhu, X. M.; Chamberlain, J. S.; McCabe, E. R. B.; Swift, M.: X-linked dilated cardiomyopathy: molecular genetic evidence of linkage to the Duchenne muscular dystrophy (dystrophin) gene at the Xp21 locus. Circulation 87:1854–1865, 1993. 184. Towbin, J. A.; Ortiz-Lopez, R.: X-linked dilated cardiomyopathy. (Letter) New Eng. J. Med. 330: 369–370, 1994. 185. Towbin, J. A.; Zhu, X. M.; Gelb, B.; Bies, R.; Chamberlain, J.; Maichele, A.; Ohlendieck, K.; Campbell, K.; McCabe, E. R. B.; Swift, M.: X-linked dilated cardiomyopathy (XLCM): molecular characterization. (Abstract) Am. J. Hum. Genet. 49 (suppl.): 421, 1991. 186. Tuffery, S.; Lenk, U.; Roberts, R. G.; Coubes, C.; Demaille, J.; Claustres, M.: Protein truncation test: analysis of two novel point mutations at the carboxy-terminus of the human dystrophin gene associated with mental retardation. Hum. Mutat. 6: 126–135, 1995. 187. Valentine, B. A.; Winand, N. J.; Pradhan, D.; Moise, N. S.; deLahunta, A.; Kornegay, J. N.; Cooper, B. J.: Canine X-linked muscular dystrophy as an animal model of Duchenne muscular dystrophy: a review. Am. J. Med. Genet. 42: 352–356, 1992. 188. Verellen-Dumoulin, C.; Freund, M.; De Meyer, R.; Laterre, C.; Frederic, J.; Thompson, M. W.; Markovic, V. D.; Worton, R. G.: Expression of an X-linked muscular dystrophy in a female due to translocation involving Xp21 and non-random inactivation of the normal X chromosome. Hum. Genet. 67: 115–119, 1984. 189. Wehling, M.; Spencer, M. J.; Tidball, J. G.: A nitric oxide synthase transgene ameliorates muscular dystrophy in mdx mice. J. Cell Biol. 155: 123–131, 2001. 190. Werner, W.; Spiegler, A. W. J.: Inherited deletion of subband Xp21.13 in a male with Duchenne muscular dystrophy. J. Med. Genet. 25:377–382, 1988. 191. Wilton, S. D.; Chandler, D. C.; Kakulas, B. A.; Laing, N. G.: Identification of a point mutation and germinal mosaicism in a Duchenne muscular dystrophy family. Hum. Mutat. 3: 133–140, 1994. 192. Wilton, S. D.; Johnsen, R. D.; Pedretti, J. R.; Laing, N. G.: Two distinct mutations in a single dystrophin gene: identification of an altered splice-site as the primary Becker muscular dystrophy mutation. Am. J. Med. Genet. 46: 563–569, 1993. 193. Winnard, A. V.; Jia-Hsu, Y.; Gibbs, R. A.; Mendell, J. R.; Burghes, A. H. M.: Identification of a 2 base pair nonsense mutation causing a cryptic splice site in a DMD patient. Hum. Molec. Genet. 1: 645–646, 1992. 194. Wood, D. S.; Zeviani, M.; Prelle, A.; Bonilla, E.; Salviati, G.; Miranda, A. F.; DiMauro, S.; Rowland, L. P.: Is nebulin the defective gene product in Duchenne muscular dystrophy? (Letter) New Eng. J. Med. 316: 107–108, 1987. 195. Worton, R. G.: Dystrophin: the long and short of it. (Editorial) J. Clin. Invest. 93: 4, 1994. 196. Worton, R. G.: Personal Communication. Toronto, Ontario, Canada Sep. 12, 1987. 197. Xiong, D.; Lee, G.-H.; Badorff, C.; Dorner, A.; Lee, S.; Wolf, P.; Knowlton, K. U.: Dystrophin deficiency markedly increases enterovirus-induced cardiomyopathy: a genetic predisposition to viral heart disease. Nature Med. 8: 872–877, 2002. 198. Yang, T. P.; Patel, P. I.; Chinault, A. C.; Stout, J. T.; Jackson, L. G.; Hildebrand, B. M.; Caskey, C. T.: Molecular evidence for new mutation at the HPRT locus in Lesch-Nyhan patients. Nature 310:412–414, 1984. 199. Yoshida, K.; Ikeda, S.; Nakamura, A.; Kagoshima, M.; Takeda, S.; Shoji, S.; Yanagisawa, N.: Molecular analysis of the Duchenne muscular dystrophy gene in patients with Becker muscular dystrophy presenting with dilated cardiomyopathy. Muscle Nerve 16: 1161–1166, 1993. 200. Yoshida, K.; Nakamura, A.; Yazaki, M.; Ikeda, S.; Takeda, S.: Insertional mutation by transposable element, L1, in the DMD gene results in X-linked dilated cardiomyopathy. Hum. Molec. Genet. 7:1129–1132, 1998. 201. Zubrzycka-Gaarn, E. E.; Bulman, D. E.; Karpati, G.; Burghes, A. H. M.; Belfall, B.; Klamut, H. J.; Talbot, J.; Hodges, R. S.; Ray, P. N.; Worton, R. G.: The Duchenne muscular dystrophy gene product is localized in sarcolemma of human skeletal muscle. Nature 333:466–469, 1988.

44. Alimova-Kost, M. V.; Imreh, S.; Buchman, V. L.; Ninkina, N. N.: Assignment of phosphotriesterase-related gene (PTER) to human chromosome band 10 p12 by in situ hybridization. Cytogenet. Cell Genet. 83:16–17, 1998.

45. Davies, J. A.; Buchman, V. L.; Krylova, O.; Ninkina, N. N.: Molecular cloning and expression pattern of rpr-1, a resiniferatoxin-binding, phosphotriesterase-related protein, expressed in rat kidney tubules. FEBS Lett. 410: 378–382, 1997.

46. Ishikawa, K.; Nagase, T.; Nakajima, D.; Seki, N.; Ohira, M.; Miyajima, N.; Tanaka, A.; Kotani, H.; Nomura, N.; Ohara, O.: Prediction of the coding sequences of unidentified human genes. VIII. 78 new cDNA clones from brain which code for large proteins in vitro. DNA Res. 4:307–313, 1997.

47. Duilio, A.; Faraonio, R.; Minopoli, G.; Zambrano, N.; Russo, T.: Fe65L2: a new member of the Fe65 protein family interacting with the intracellular domain of the Alzheimer's beta-amyloid precursor protein. Biochem. J. 330: 513–519, 1998.

48. Tanahashi, H.; Tabira, T.: Genome structure and chromosomal mapping of the gene for Fe65L2 interacting with Alzheimer's beta-amyloid precursor protein. Biochem. Biophys. Res. Commun. 258: 385–389, 1999.

49. Tanahashi, H.; Tabira, T.: Molecular cloning of human Fe65L2 and its interaction with the Alzheimer's beta-amyloid precursor protein. Neurosci. Lett. 261: 143–146, 1999.

50. Delon, J.; Kaibuchi, K.; Germain, R. N.: Exclusion of CD43 from the immunological synapse is mediated by phosphorylation-regulated relocation of the cytoskeletal adaptor moesin. Immunity 15: 691–701, 2001.

51. Nekrep, N.; Jabrane-Ferrat, N.; Wolf, H. M.; Eibl, M. M.; Geyer, M.; Peterlin, B. M.: Mutation in a winged-helix DNA binding motif causes a typical bare lymphocyte syndrome. Nature Immun. 30 Sept. 2002. Note: Advance Electronic Publication.

52. Gervais, F. G.; Xu, D.; Robertson, G. S.; Vaillancourt, J. P.; Zhu, Y.; Huang, J.; LeBlanc, A.; Smith, D.; Rigby, M.; Shearman, M. S.; Clarke, E. E.; Zheng, H.; Van Der Ploeg, L. H. T.; Ruffolo, S. C.; Thornberry, N. A.; Xanthoudakis, S.; Zamboni, R. J.; Roy, S.; Nicholson, D. W.: Involvement of caspases in proteolytic cleavage of Alzheimer's amyloid beta precursor protein and amyloidogenic A-betapeptide formation. Cell 97: 395–406, 1999.

53. Orstavik, S.; Solberg, R.; Tasken, K.; Nordahl, M.; Altherr, M. R.; Hansson, V.; Jahnsen, T.; Sandberg, M.: Molecular cloning, cDNA structure, and chromosomal localization of the human type II cGMP-dependent protein kinase. Biochem. Biophys. Res. Commun. 220: 759–765, 1996.

54. Pfeifer, A.; Aszodi, A.; Seidler, U.; Ruth, P.; Hofmann, F.; Fassler, R.: Intestinal secretory defects and dwarfism in mice lacking cGMP-dependent protein kinase II. Science 274: 2082–2084, 1996.

55. Liu, N.; Schild, D.; Thelen, M. P.; Thompson, L. H.: Involvement of Rad51C in two distinct protein complexes of Rad51 paralogs in human cells. Nucleic Acids Res. 30: 1009–1015, 2002.

56. Masson, J.-Y.; Tarsounas, M. C.; Stasiak, A. Z.; Stasiak, A.; Shah, R.; Mcllwraith, M. J.; Benson, F. E.; West, S. C.: Identification and purification of two distinct complexes containing the five RAD51 paralogs. Genes Dev. 15: 3296–3307, 2001.

57. Isnard, P.; Depetris, D.; Mattei, M.-G.; Ferrier, P.; Djabali, M.: cDNA cloning, expression and chromosomal localization of the murine AF-4 gene involved in human leukemia. Mammalian Genome 9:1065–1068, 1998.

58. Lovett, B. D.; Lo Nigro, L.; Rappaport, E. F.; Blair, I. A.; Osheroff, N.; Zheng, N.; Megonigal, M. D.; Williams, W. R.; Nowell, P. C.; Felix, C. A.: Near-precise interchromosomal recombination and functional DNA topoisomerase II cleavage sites at MLL and AF-4 genomic breakpoints in treatment-related acute lymphoblastic leukemia with t(4; 11) translocation. Proc. Nat. Acad. Sci. 98: 9802–9807, 2001.

59. Uckun, F. M.; Herman-Hatten, K.; Crotty, M.-L.; Sensel, M. G.; Sather, H. N.; Tuel-Ahlgren, L.; Sarquis, M. B.; Bostrom, B.; Nachmanj. B.; Steinherz, P. G.; Gaynon, P. S.; Heerema, N.: Clinical significance of MLL-AF4 fusion transcript expression in the absence of a cytogenetically detectable t(4;11)(q21;q23) chromosomal translocation. Blood 92:810–821, 1998.

60. Huh, G. S.; Boulanger, L. M.; Du, H.; Riquelme, P. A.; Brotz, T. M.; Shatz, C. J.: Functional requirement for class I MHC in CNS development and plasticity. Science 290: 2155–2159, 2000.

61. Qian, F.; Kruse, U.; Lichter, P.; Sippel, A. E.: Chromosomal localization of the four genes (NFIA, B, C, and X) for the human transcription factor nuclear factor I by FISH. Genomics 28: 66–73, 1995.

62. Engelender, S.; Kaminsky, Z.; Guo, X.; Sharp, A. H.; Amaravi, R. K.; Kleiderlein, J. J.; Margolis, R. L.; Troncoso, J. C.; Lanahan, A. A.; Worley, P. F.; Dawson, V. L.; Dawson, T. M.; Ross, C. A.: Synphilin-1 associates with alpha synuclein and promotes the formation of cytosolic inclusions. Nature Genet. 22: 110–114, 1999.

63. Amiel, J.; Salomon, R.; Attie, T.; Pelet, A.; Trang, H.; Mokhtari, M.; Gaultier, C.; Munnich, A.; Lyonnet, S.: Mutations of the RET-GDNF signaling pathway in Ondine's curse. (Letter) Am. J. Hum. Genet. 62:715–717, 1998.

64. Angrist, M.; Bolk, S.; Thiel, B.; Puffenberger, E. G.; Hofstra, R. M.; Buys, C. H. C. M.; Cass, D. T.; Chakravarti, A.: Mutation analysis of the RET receptor tyrosine kinase in Hirschsprung disease. Hum. Molec. Genet. 4: 821–830, 1995.

65. Antinolo, G.; Marcos, I.; Fernandez, R. M.; Romero, M.; Borrego, S.: A novel germline point mutation, c.2304G(T, in codon 768 of the RET proto-oncogene in a patient with medullary thyroid carcinoma. (Letter) Am. J. Med. Genet. 110: 85–87, 2002.

66. Attie, T.; Pelet, A.; Edery, P.; Eng, C.; Mulligan, L. M.; Amielj.; Boutrand, L.; Beldjord, C.; Nihoul-Fekete, C.; Munnich, A.; Ponder, B. A. J.; Lyonnet, S.: Diversity of RET proto-oncogene mutations in familial and sporadic Hirschsprung disease. Hum. Molec. Genet. 4:1381–1386, 1995.

67. Attie-Bitach, T.; Abitbol, M.; Gerard, M.; Delezoide, A.-L.; Augej.; Pelet, A.; Amiel, J.; Pachnis, V.; Munnich, A.; Lyonnet, S.; Vekemans, M.: Expression of the RET protooncogene in human embryos. Am. J. Med. Genet. 80: 481–486, 1998.

68. Auricchio, A.; Griseri, P.; Carpentieri, M. L.; Betsos, N.; Staiano, A.; Tozzi, A.; Priolo, M.; Thompson, H.; Bocciardi, R.; Romeo, G.; Ballabio, A.; Ceccherini, I.: Double heterozygosity for a RET substitution interfering with splicing and an EDNRB missense mutation in Hirschsprung disease. (Letter) Am. J. Hum. Genet. 64: 1216–1221, 1999.

69. Batourina, E.; Choi, C.; Paragas, N.; Bello, N.; Hensle, T.; Costantini, F. D.; Schuchardt, A.; Bacallao, R. L.; Mendelsohn, C. L.: Distalureter morphogenesis depends on epithelial cell remodeling mediated by vitamin A and Ret. Nature Genet. 32: 109–115, 2002. Note: Erratum: Nature Genet. 32: 331 only, 2002.

70. Batourina, E.; et al; et al: Vitamin A controls epithelial/mesenchymal interactions through Ret expression. Nature Genet. 27: 74–78, 2001.

71. Berndt, I.; Reuter, M.; Saller, B.; Frank-Raue, K.; Groth, P.; Grubendorf, M.; Raue, F.; Ritter, M. M.; Hoppner, W.: A new hot spot for mutations in the ret protooncogene causing familial medullary thyroid carcinoma and multiple endocrine neoplasia type 2A. J. Clin. Endocr. Metab. 83: 770–774, 1998.

72. Boccia, L. M.; Green, J. S.; Joyce, C.; Eng, C.; Taylor, S. A. M.; Mulligan, L. M.: Mutation of RET codon 768 is associated with the FMTC phenotype. Clin. Genet. 51: 81–85, 1997.

73. Bolino, A.; Schuffenecker, I.; Luo, Y.; Seri, M.; Silengo, M.; Tocco, T.; Chabrier, G.; Houdent, C.; Murat, A.; Schlumberger, M.; Tourniaire, J.; Lenoir, G. M.; Romeo, G.: RET mutations in exons 13 and 14 of FMTC patients. Oncogene 10: 2415–2419, 1995.

74. Bolk, S.; Angrist, M.; Schwartz, S.; Silvestri, J. M.; Weese-Mayer, D. E.; Chakravarti, A.: Congenital central hypoventilation syndrome: mutation analysis of the receptor tyrosine kinase RET. Am. J. Med. Genet. 63: 603–609, 1996.

75. Bolk Gabriel, S.; Salomon, R.; Pelet, A.; Angrist, M.; AmielJ.; Fornage, M.; Attie-Bitach, T.; Olson, J. M.; Hofstra, R.; Buys, C.; Steffann, J.; Munnich, A.; Lyonnet, S.; Chakravarti, A.: Segregationat three loci explains familial and population risk in Hirschsprung disease. Nature Genet. 31: 89–93, 2002.

76. Ceccherini, I.; Hofstra, R. M.; Luo, Y.; Stulp, R. P.; Barone, V.; Stelwagen, T.; Bocciardi, R.; Nijveen, H.; Bolino, A.; Seri, M.; Ronchetto, P.; Pasini, B.; Bozzano, M.; Buys, C. H. C. M.; Romeo, G.: DNA polymorphisms and conditions for SSCP analysis of the 20 exons of the Ret protooncogene. Oncogene 9: 3025–3029, 1994.

77. Puffenberger, E. G.; Hosoda, K.; Washington, S. S.; Nakao, K.; deWit, D.; Yanagisawa, M.; Chakravarti, A.: A missense mutation of the endothelin-B receptor gene in multigenic Hirschsprung's disease. Cell 79:1257–1266, 1994.

78. Svensson, P.-J.; Anvret, M.; Molander, M.-L.; Nordenskjold, A.: Phenotypic variation in a family with mutations in two Hirschsprung-relatedgenes (RET and endothelin receptor B). Hum. Genet. 103: 145–148, 1998.

79. Lipinski, M.; Virelizier, J. L.; Tursz, T.; Griscelli, C.: Natural killer and killer cell activities in patients with primary immunodeficiencies or defects in immune interferon production. Europ. J. Immun. 10:246–249, 1980.

80. Walder, K.; Norman, R. A.; Hanson, R. L.; Schrauwen, P.; Neverova, M.; Jenkinson, C. P.; Easlick, J.; Warden, C. H.; Pecqueur, C.; Raimbault, S.; Ricquier, D.; Harper, M.; Silver, K.; Shuldiner, A. R.; Solanes, G.; Lowell, B. B.; Chung, W. K.; Leibel, R. L.; Pratley, R.; Ravussin, E.: Association between uncoupling protein polymorphisms (UCP2–UCP3) and energy metabolism/obesity in Pima Indians. Hum. Molec. Genet. 7:1431–1435, 1998.

81. Hagiwara, T.; Tanaka, K.; Takai, S.; Maeno-Hikichi, Y.; Mukainaka, Y.; Wada, K.: Genomic organization, promoter analysis, and chromosomallocalization of the gene for the mouse glial high-affinity glutamate transporter Slc1a3. Genomics 33: 508–515, 1996.

82. Harada, T.; Harada, C.; Watanabe, M.; Inoue, Y.; Sakagawa, T.; Nakayama, N.; Sasaki, S.; Okuyama, S.; Watase, K.; Wada, K.; Tanaka, K.: Functions of the two glutamate transporters GLAST and GLT-1 in the retina. Proc. Nat. Acad. Sci. 95: 4663–4666, 1998.

83. Keppen, L. D.; Gollin, S. M.; Edwards, D.; Sawyer, J.; Wilson, W.; Overhauser, J.: Clinical phenotype and molecular analysis of a three-generation family with an interstitial deletion of the shortarm of chromosome 5. Am. J. Med. Genet. 44: 356–360, 1992.

84. Kirschner, M. A.; Arriza, J. L.; Copeland, N. G.; Gilbert, D. J.; Jenkins, N. A.; Magenis, E.; Amara, S. G.: The mouse and human excitatory amino acid transporter gene (EAAT1) maps to mouse chromosome 15 and a region of syntenic homology on human chromosome 5. Genomics 22:631–633, 1994.

85. Shashidharan, P.; Huntley, G. W.; Meyer, T.; Morrison, J. H.; Plaitakis, A.: Neuron-specific human glutamate transporter: molecular cloning, characterization and expression in human brain. Brain Res. 662:245–250, 1994.

86. Stoffel, W.; Sasse, J.; Duker, M.; Muller, R.; Hofmann, K.; Fink, T.; Lichter, P.: Human high affinity, Na(+)-dependent L-glutamate/L-aspartate transporter GLAST-1 (EAAT-1): gene structure and localization to chromosome 5p11–p12. FEBS Lett. 386: 189–193, 1996.

87. Takai, S.; Yamada, K.; Kawakami, H.; Tanaka, K.; Nakamura, S.: Localization of the gene (SLC1A3) encoding human glutamate transporter(GluT-1) to 5p13 by fluorescence in situ hybridization. Cytogenet. Cell Genet. 69: 209–210, 1995.

88. Hu, X.; Burghes, A. H. M.; Ray, P. N.; Thompson, M. W.; Murphy, E. G.; Worton, R. G.: Partial gene duplication in Duchenne and Becker muscular dystrophies. J. Med. Genet. 25: 369–376, 1988.

89. Bucan, M.; Gatalica, B.; Nolan, P.; Chung, A.; Leroux, A.; Grossman, M. H.; Nadeau, J. H.; Emanuel, B. S.; Budarf, M.: Comparative mapping of 9 human chromosome 22q loci in the laboratory mouse. Hum. Molec. Genet. 2: 1245–1252, 1993.

90. Cetta, F.; Chiappetta, G.; Melillo, R. M.; Petracci, M.; Montalto, G.; Santoro, M.; Fusco, A.: The ret/ptcl oncogene is activated in familial a denomatous polyposis-associated thyroid papillary carcinomas. J. Clin. Endocr. Metab. 83: 1003–1006, 1998.

91. Decker, R. A.; Peacock, M. L.; Watson, P.: Hirschsprung disease in MEN 2A: increased spectrum of RET exon 10 genotypes and strong genotype-phenotype correlation. Hum. Molec. Genet. 7: 129–134, 1998.

92. Donis-Keller, H.; Dou, S.; Chi, D.; Carlson, K. M.; Toshima, K.; Lairmore, T. C.; Howe, J. R.; Moley, J. F.; Goodfellow, P.; Wells, S. A., Jr.: Mutations in the RET protooncogene are associated with MEN 2A and FMTC. Hum. Molec. Genet. 2: 851–856, 1993.

93. Doray, B.; Salomon, R.; Amiel, J.; Pelet, A.; Touraine, R.; Billaud, M.; Attie, T.; Bachy, B.; Munnich, A.; Lyonnet, S.: Mutation of the RET ligand, neurturin, supports multigenic inheritance in Hirschsprung disease. Hum. Molec. Genet. 7: 1449–1452, 1998.

94. Edery, P.; Lyonnet, S.; Mulligan, L. M.; Pelet, A.; Dow, E.; Abel, L.; Holder, S.; Nihoul-Fekete, C.; Ponder, B. A. J.; Munnich, A.: Mutations of the RET proto-oncogene in Hirschsprung's disease. Nature 367:378–380, 1994.

95. Eng, C.: The RET proto-oncogene in multiple endocrine neoplasiatype 2 and Hirschsprung's disease. New Eng. J. Med. 335: 943–951, 1996.

96. Eng, C.; Crossey, P. A.; Mulligan, L. M.; Healey, C. S.; Houghton, C.; Prowse, A.; Chew, S. L.; Dahia, P. L. M.; O'Riordan, J. L. H.; Toledo, S. P. A.; Smith, D. P.; Maher, E. R.; Ponder, B. A. J.: Mutations in the RET protooncogene and the von Hippel-Lindau disease tumour suppressor gene in sporadic and syndromic phaeochromocytomas. J. Clin. Genet. 32: 934–937, 1995.

97. Eng, C.; Mulligan, L. M.: Mutations of the RET protooncogene in the multiple endocrine neoplasia type 2 syndromes, related sporadic tumours, and Hirschsprung disease. Hum. Mutat. 9: 97–109, 1997.

98. Eng, C.; Mulligan, L. M.; Smith, D. P.; Healey, C. S.; Frilling, A.; Raue, F.; Neumann, H. P. H.; Pfragner, R.; Behmel, A.; Lorenzo, M. J.; Stonehouse, T. J.; Ponder, M.

A.; Ponder, B. A. J.: Mutation of the RET proto-oncogene in sporadic medullary thyroid carcinoma. GenesChromosomes Cancer 12: 209–212, 1995.
99. Eng, C.; Smith, D. P.; Mulligan, L. M.; Healey, C. S.; Zvelebil, M. J.; Stonehouse, T. J.; Ponder, M. A.; Jackson, C. E.; Waterfield, M. D.; Ponder, B. A. J.: A novel point mutation in the tyrosine kinase domain of the RET proto-oncogene in sporadic medullary thyroid carcinoma and in a family with FMTC. Oncogene 10: 509–513, 1995.
100. Eng, C.; Smith, D. P.; Mulligan, L. M.; Nagai, M. A.; Healey, C. S.; Ponder, M. A.; Gardner, E.; Scheumann, G. F. W.; Jackson, C. E.; Tunnacliffe, A.; Ponder, B. A. J.: Point mutation within the tyrosine kinase domain of the RET proto-oncogene in multiple endocrineneoplasia type 2B and related sporadic tumors. Hum. Molec. Genet. 3:237–241, 1994.
101. Fearon, E. R.: Human cancer syndromes: clues to the origin and nature of cancer. Science 278: 1043–1050, 1997.
102. Fitze, G.; Schreiber, M.; Kuhlisch, E.; Schackert, H. K.; Roesner, D.: Association of RET proto-oncogene codon 45 polymorphism with Hirschsprung disease. (Letter) Am. J. Hum. Genet. 65: 1469–1473, 1999.
103. Gardner, E.; Mulligan, L. M.; Eng, C.; Healey, C. S.; Kwok, J. B. J.; Ponder, M. A.; Ponder, B. A. J.: Haplotype analysis of MEN2 mutations. Hum. Molec. Genet. 3: 1771–1774, 1994.
104. Grieco, M.; Santoro, M.; Berlingieri, M. T.; Melillo, R. M.; Donghi, R.; Bongarzone, I.; Pierotti, M. A.; Della Porta, G.; Fusco, A.; Vecchio, G.: PTC is a novel rearranged form of the ret proto-oncogene and is frequently detected in vivo in human thyroid papillary carcinomas. Cell 60:557–563, 1990.
105. Hofstra, R. M. W.; Landsvater, R. M.; Ceccherini, I.; Stulp, R. P.; Stelwagen, T.; Luo, Y.; Pasini, B.; Hoppener, J. W. M.; Ploosvan Amstel, H. K.; Romeo, G.; Lips, C. J. M.; Buys, C. H. C. M.: A mutation in the RET proto-oncogene associated with multiple endocrineneoplasia type 2B and sporadic medullary thyroid carcinoma. Nature 367:375–376, 1994.
106. Hoppener, J. W. M.; Lips, C. J. M.: RET receptor tyrosine kinase gene mutations: molecular biological, physiological and clinical aspects. Europ. J. Clin. Invest. 26: 613–624, 1996.
107. Hoppner, W.; Ritter, M. M.: A duplication of 12 bp in the critical cysteine rich domain of the RET proto-oncogene results in a distinct phenotype of multiple endocrine neoplasia type 2A. Hum. Molec. Genet. 6:587–590, 1997.
108. Ikeda, I.; Ishizaka, Y.; Tahira, T.; Suzuki, T.; Onda, M.; Sugimura, T.; Nagao, M.: Specific expression of the ret proto-oncogene in human neuroblastoma cell lines. Oncogene 5: 1291–1296, 1990.
109. Ishizaka, Y.; Itoh, F.; Tahira, T.; Ikeda, I.; Sugimura, T.; Tucker J.; Fertitta, A.; Carrano, A. V.; Nagao, M.: Human ret proto-oncogene mapped to chromosome 10q11.2. Oncogene 4: 1519–1521, 1989.
110. Japon, M. A.; Urbano, A. G.; Saez, C.; Segura, D. I.; Cerro, A. L.; Dieguez, C.; Alvarez, C. V.: Glial-derived neurotropic factor and RET gene expression in normal human anterior pituitary cell types and in pituitary tumors. J. Clin. Endocr. Metab. 87: 1879–1884, 2002.
111. Julies, M. G.; Moore, S. W.; Kotze, M. J.; du Plessis, L.: Novel RET mutations in Hirschsprung's disease patients from the diverse South African population. Europ. J. Hum. Genet. 9: 419–423, 2001.
112. Klugbauer, S.; Demidchik, E. P.; Lengfelder, E.; Rabes, H. M.: Detection of a novel type of RET rearrangement (PTC5) in thyroid carcinomas after Chernobyl and analysis of the involved RET-fused gene RFG5. Cancer Res. 58: 198–203, 1998.
113. Allikmets, R.; Seddon, J. M.; Bernstein, P. S.; Hutchinson, A.; Atkinson, A.; Sharma, S.; Gerrard, B.; Li, W.; Metzker, M. L.; Wadelius, C.; Caskey, C. T.; Dean, M.; Petrukhin, K.: Evaluation of the Best disease gene in patients with age-related macular degeneration and other maculopathies. Hum. Genet. 104: 449–453, 1999.
114. Bascom, R. A.; Liu, L.; Chen, J.; Duncan, A.; Kimberling, W. J.; Moller, C. G.; Humphries, P.; Nathans, J.; McInnes, R. R.: ROM1: a candidate gene for autosomal dominant retinitis pigmentosa (ADRP), Usher syndrome type 1, and Best vitelliform macular dystrophy. (Abstract) Am. J. Hum. Genet. 51 (suppl.): A6, 1992.
115. Best, F.: Ueber eine hereditaere Maculaaffektion. Z. Augenheilk. 13:199–212, 1905.
116. Braley, A. E.: Dystrophy of the macula. Am. J. Ophthal. 61:1–24, 1966.
117. Braley, A. E.; Spivey, B. E.: Hereditary vitelline macular degeneration: a clinical and functional evaluation of a new pedigree with variable expressivity and dominant inheritance. Arch. Ophthal. 72: 743–762,1964.
118. Brecher, R.; Bird, A. C.: Adult vitelliform macular dystrophy. Eye 4:210–215, 1990.
119. Davis, C. T.; Hollenhorst, R. W.: Hereditary degeneration of themacula: occurring in five generations. Am. J. Ophthal. 39: 637–643,1955.
120. Deutman, A. F.: Electro-oculography in families with vitelliform dystrophy of the fovea: detection of the carrier state. Arch. Ophthal. 81:305–316, 1969.
121. Falls, H. F.: Hereditary congenital macular degeneration. Am. J. Hum. Genet. 1: 96–104, 1949.
122. Forsman, K.; Graff, C.; Nordstrom, S.; Johansson, K.; Westermark, E.; Lundgren, E.; Gustavson, K.-H.; Wadelius, C.; Holmgren, G.: The gene for Best's macular dystrophy is located at 11q13 in a Swedish family. Clin. Genet. 42: 156–159, 1992.
123. Francois, J.: Vitelliform degeneration of the macula. Bull. N.Y. Acad. Med. 44: 18–27, 1968.
124. Friedenwald, J. S.; Maumenee, A. E.: Peculiar macular lesions with unaccountably good vision. Arch. Ophthal. 45: 567–570, 1951.
125. Goodstadt, L.; Ponting, C. P.: Sequence variation and disease in the wake of the draft human genome. Hum. Molec. Genet. 10: 2209–2214, 2001.
126. Graff, C.; Eriksson, A.; Forsman, K.; Sandgren, O.; Holmgren, G.; Wadelius, C.: Refined genetic localization of the Best disease gene in 11q13 and physical mapping of linked markers on radiation hybrids. Hum. Genet. 101: 263–270, 1997.
127. Graff, C.; Forsman, K.; Larsson, C.; Nordstrom, S.; Lind, L.; Johansson, K.; Sandgren, O.; Weissenbach, J.; Holmgren, G.; Gustavson, K.-H.; Wadelius, C.: Fine mapping of Best's macular dystrophy localizes the gene in close proximity to but distinct from the D11S480/ROM1loci. Genomics 24: 425–434, 1994.
128. Hagemeijer, A.; Hoovers, J.; Smit, E. M. E.; Bootsma, D.: Replication pattern of the X chromosomes in three X/autosomal translocations. Cytogenet. Cell Genet. 18: 333–348, 1977.
129. Hou, Y.-C.; Richards, J. E.; Bingham, E. L.; Pawar, H.; Scott, K.; Segal, M.; Lunetta, K. L.; Boehnke, M.; Sieving, P. A.: Linkage study of Best's vitelliform macular 129. dystrophy (VMD2) in a large North American family. Hum. Hered. 46: 211–220, 1996.
130. Jung, E. E.: Ueber eine Sippe mit angeborener Maculadegeneration. Giessen: Seibert (pub.) 1936.
131. Bandmann, O.; Davis, M. B.; Marsden, C. D.; Wood, N. W.: The human homologue of the weaver mouse gene in familial and sporadic Parkinson's disease. Neuroscience 72: 877–879, 1996.
132. Domer, P. H.; Fakharzadeh, S. S.; Chen, C.-S.; Jockel, J.; Johansen, L.; Silverman, G. A.; Kersey, J. H.; Korsmeyer, S. J.: Acute mixed-lineage leukemia t(4;11)(q21;q23) generates an MLL-AF4 fusion product. Proc. Nat. Acad. Sci. 90: 7884–7888, 1993.
133. Gu, Y.; Nakamura, T.; Alder, H.; Prasad, R.; Canaani, O.; Cimino, G.; Croce, C. M.; Canaani, E.: The t(4;11) chromosome translocation of human acute leukemias fuses the ALL-1 gene, related to Drosophilatrithorax, to the AF-4 gene. Cell 71: 701–708, 1992.
134. Nakamura, T.; Alder, H.; Gu, Y.; Prasad, R.; Canaani, O.; Kamada, N.; Gale, R. P.; Lange, B.; Crist, W. M.; Nowell, P. C.; Croce, C. M.; Canaani, E.: Genes on chromosomes 4, 9, and 19 involved in 11q23 abnormalities in acute leukemia share sequence homology and/or common motifs. Proc. Nat. Acad. Sci. 90: 4631–4635, 1993.
135. Adkison, L. R.; White, R. A.; Haney, D. M.; Lee, J. C.; Pusey, K. T.; Gardner, J.: The fibronectin receptor, alpha subunit (Itga5) maps to murine chromosome 15, distal to D15Mit16. Mammalian Genome 5:456–457, 1994.
136. Argraves, W. S.; Pytela, R.; Suzuki, S.; Millan, J. L.; Pierschbacher, M. D.; Ruoslahti, E.: cDNA sequences from the alpha subunit of the fibronectin receptor predict a transmembrane domain and a short cytoplasmic peptide. J. Biol. Chem. 261: 12922–12924, 1986.
137. Argraves, W. S.; Suzuki, S.; Arai, H.; Thompson, K.; Pierschbacher, M. D.; Ruoslahti, E.: Amino acid sequence of the human fibronectin receptor. J. Cell Biol. 105: 1183–1190, 1987.
138. Fitzgerald, L. A.; Poncz, M.; Steiner, B.; Rall, S. C., Jr.; Bennett, J. S.; Phillips, D. R.: Comparison of cDNA-derived protein sequences of the human fibronectin and vitronectin receptor alpha-subunits and platelet glycoprotein lib. Biochemistry 26: 8158–8165, 1987.
139. Krissansen, G. W.; Yuan, Q.; Jenkins, D.; Jiang, W.-M.; Rooke, L.; Spurr, N. K.; Eccles, M.; Leung, E.; Watson, J. D.: Chromosomal locations of the genes coding for the integrin beta-6 and beta-7 subunits. Immunogenetics 35:58–61, 1992.
140. Sosnoski, D.; Emanuel, B. S.; Hawkins, A. L.; van Tuinen, P.; Ledbetter, D. H.; Nussbaum, R. L.; Kaos, F.-T.; Schwartz, E.; Phillips, D.; Bennett, J. S.; Fitzgerald, L. A.; Poncz, M.: Chromosomal localization of the genes for the vitronectin and fibronectin receptors alpha-subunits and for platelet glycoproteins IIb and IIIa. J. Clin. Invest. 81:1993–1998, 1988.
141. Spurr, N. K.; Rooke, L.: Confirmation of the assignment of the vitronectin (VNRA) and fibronectin (FNRA) receptor alpha-subunits. Ann. Hum. Genet. 55: 217–223, 1991.
142. Klugbauer, S.; Rabes, H. M.: The transcription coactivator HTIF1 and a related protein are fused to the RET receptor tyrosine kinase in childhood papillary thyroid carcinomas. Oncogene 18: 4388–4393, 1999.
143. Lairmore, T. C.; Dou, S.; Howe, J. R.; Chi, D.; Carlson, K.; Veile, R.; Mishra, S. K.; Wells, S. A., Jr.; Donis-Keller, H.: A 1.5-megabase yeast artificial chromosome contig from human chromosome 10q11.2 connecting three genetic loci (RET, D10S94, and D10S102) closely linked to the MEN2A locus. Proc. Nat. Acad. Sci. 90: 492–496, 1993.
144. Lombardo, F.; Baudin, E.; Chiefari, E.; Arturi, F.; Bardet, S.; Caillou, B.; Conte, C.; Dallapiccola, B.; Giuffrida, D.; Bidart, J.-M.; Schlumberger, M.; Filetti, S.: Familial medullary thyroid carcinoma: clinical variability and low aggressiveness associated with RET mutation at codon 804. J. Clin. Endocr. Metab. 87: 1674–1680, 2002.
145. Lore, F.; Di Cairano, G.; Talidis, F.: Unilateral renal agenesisin a family with medullary thyroid carcinoma. (Letter) New Eng. J. Med. 342: 1218–1219, 2000.
146. Machens, A.; Gimm, O.; Hinze, R.; Hoppner, W.; Boehm, B. O.; Dralle, H.: Genotype-phenotype correlations in hereditary medullary thyroid carcinoma: oncological features and biochemical properties. J. Clin. Endocr. Metab. 86: 1104–1109, 2001.
147. Mendelsohn, C.; et al; et al: Function of the retinoic acid receptors(RARs) during development (II). Multiple abnormalities at various stages of organogenesis in RAR double mutants. Development 120:2749–2771, 1994.
148. Menko, F. H.; van der Luijt, R. B.; de Valk, I. A. J.; Toorians, A. W. F. T.; Sepers, J. M.; van Diest, P. J.; Lips, C. J. M.: A typical MEN type 2B associated with two germline RET mutations on the same allele not involving codon 918. J. Clin. Endocr. Metab. 87: 393–397, 2002.
149. Mulligan, L. M.; Kwok, J. B. J.; Healey, C. S.; Elsdon, M. J.; Eng, C.; Gardner, E.; Love, D. R.; Mole, S. E.; Moore, J. K.; Papi, L.; Ponder, M. A.; Telenius, H.; Tunnacliffe, A.; Ponder, B. A. J.: Germ-line mutations of the RET proto-oncogene in multiple endocrineneoplasia type 2A. Nature 363: 458–460, 1993.
150. Munnes, M.; Fanaei, S.; Schmitz, B.; Muiznieks, I.; Holschneider, A. M.; Doerfler, W.: Familial form of Hirschsprung disease: nucleotide sequence studies reveal point mutations in the RET proto-oncogene in two of six families but not in other candidate genes. Am. J. Med. Genet. 94: 19–27, 2000.
151. Nakata, T.; Kitamura, Y.; Shimizu, K.; Tanaka, S.; Fujimori, M.; Yokoyama, S.; Ito, K.; Emi, M.: Fusion of a novel gene, ELKS, to RET due to translocation t(10;12)(q11;p13) in a papillary thyroid carcinoma. Genes Chromosomes Cancer 25: 97–103, 1999.
152. Niccoli-Sire, P.; Murat, A.; Rohmer, V.; Franc, S.; Chabrier, G.; Baldet, L.; Maes, B.; Savagner, F.; Giraud, S.; Bezieau, S.; Kottler, M.-L.; Morange, S.; Conte-Devolx, B.: The French Calcitonin Tumors Study Group (GETC).: Familial medullary thyroid carcinoma with noncysteine RET mutations: phenotype-genotype relationship in a large series of patients. J. Clin. Endocr. Metab. 86: 3746–3753, 2001.
153. Pachnis, V.; Mankoo, B.; Costantini, F.: Expression of the c-retproto-oncogene during mouse embryogenesis. Development 119: 1005–1017, 1993.
154. Pasini, B.; Hofstra, R. M. W.; Yin, L.; Bocciardi, R.; Santamaria, G.; Grootscholten, P. M.; Ceccherini, I.; Patrone, G.; Priolo, M.; Buys, C. H. C. M.; Romeo, G.: The physical map of the human RET proto-oncogene. Oncogene 11:1737–1743, 1995.
155. Pelet, A.; Geneste, O.; Edery, P.; Pasini, A.; Chappuis, S.; Attie, T.; Munnich, A.; Lenoir, G.; Lyonnet, S.; Billaud, M.: Various mechanisms cause RET-mediated signaling defects in Hirschsprung's disease. J. Clin. Invest. 101: 1415–1423, 1998.
156. Pigny, P.; Bauters, C.; Wemeau, J.-L.; Houcke, M. L.; Crepin, M.; Caron, P.; Giraud, S.; Calender, A.; Buisine, M.-P.; Kerckaert, j.-P.; Porchet, N.: A novel 9-base pair duplication in RET exon 8 in familial medullary thyroid carcinoma. J. Clin. Endocr. Metab. 84:1700–1704, 1999.
157. Pierotti, M. A.; Santoro, M.; Jenkins, R. B.; Sozzi, G.; Bongarzone, I.; Grieco, M.; Monzini, N.; Miozzo, M.; Herrmann, M. A.; Fusco, A.; Hay, I. D.; Della Porta, G.; Vecchio, G.: Characterization of an inversion on the long arm of chromosome 10 juxtaposing D10S170 and RET and creating the oncogenic sequence RET/PTC. Proc. Nat. Acad. Sci. 89: 1616–1620, 1992.
158. Rodrigues, G. A.; Park, M.: Dimerization mediated through a leucine zipper activates the oncogenic potential of the met receptor tyrosine kinase. Molec. Cell. Biol. 13: 6711–6722, 1993.
159. Romeo, G.; Ronchetto, P.; Luo, Y.; Barone, V.; Seri, M.; Ceccherini, I.; Pasini, B.; Bocciardi, R.; Lerone, M.; Kaariainen, H.; Martucciello, G.: Point mutations affecting the tyrosine kinase domain of the RET proto-oncogene in Hirschsprung's disease. Nature 367: 377–378, 1994.
160. Salvatore, D.; Barone, M. V.; Salvatore, G.; Melillo, R. M.; Chiappetta, G.; Mineo, A.; Fenzi, G.; Vecchio, G.; Fusco, A.; Santoro, M.: Tyrosines1015 and 1062 are in vivo autophosphorylation sites in Ret and Ret derived oncoproteins. J. Clin. Endocr. Metab. 85: 3898–3907, 2000.
161. Robinson, M. F.; Cote, G. J.; Nunziata, V.; Brandi, M. L.; Ferrer, J. P.; Martins Bugalho, M. J. G.; Almeida Ruas, M. M.; Chik, C.; Colantuoni, V.; Gagel, R. F.: Mutation of a specific codon of the RET proto-oncogene in the multiple endocrine neoplasia type 2A/cutaneous lichen amyloidosis syndrome. (Abstract) Fifth International Workshop on Multiple Endocrine Neoplasia, Stockholm, Archipelago, 1994.
162. Ceccherini, I.; Romei, C.; Barone, V.; Pacini, F.; Martino, E.; Loviselli, A.; Pinchera, A.; Romeo, G.: Identification of the cys634-to-tyrmutation of the RET proto-oncogene in a pedigree with multiple endocrine neoplasia type 2A and localized cutaneous lichen amyloidosis. J. Endocr. Invest. 17: 201–204, 1994.
163. Echtay, K. S.; Roussel, D.; St-Pierre, J.; Jekabsons, M. B.; Cadenas, S.; Stuart, J. A.; Harper, J. A.; Roebuck, S. J.; Morrison, A.; Pickering, S.; Clapham, J. C.; Brand, M. D.: Superoxide activates mitochondrial uncoupling proteins. Nature 415: 96–99, 2002.
164. Enerback, S.; Jacobsson, A.; Simpson, E. M.; Guerra, C.; Yamashita, H.; Harper, M.-E.; Kozak, L. P.: Mice lacking mitochondrial uncoupling protein are cold-sensitive but not obese. Nature 387: 90–93, 1997.
165. Borrego, S.; Ruiz, A.; Saez, M. E.; Gimm, O.; Gao, X.; Lopez-Alonso, M.; Hernandez, A.; Wright, F. A.; Antinolo, G.; Eng, C.: RET genotypes comprising specific haplotypes of polymorphic variants predispose to isolated Hirschsprung disease. J. Med. Genet. 37: 572–578, 2000.
166. Borrego, S.; Saez, M. E.; Ruiz, A.; Gimm, O.; Lopez-Alonso, M.; Antinolo, G.; Eng, C.: Specific polymorphisms in the RET proto-oncogene are over-represented in patients with Hirschsprung disease and may represent loci modifying phenotypic expression. J. Med. Genet. 36:771–774, 1999.
167. Beranova, M.; Oliveira, L. M. B.; Bedecarrats, G. Y.; Schipani, E.; Vallejo, M.; Ammini, A. C.; Quintos, J. B.; Hall, J. E.; Martin, K. A.; Hayes, F. J.; Pitteloud, N.; Kaiser, U. B.; Crowley, W. F. Jr.; Seminara, S. B.: Prevalence, phenotypic spectrum, and modes of inheritance of gonadotropin-releasing hormone receptor mutations in idiopathic hypogonadotropic hypogonadism. J. Clin. Endocr. Metab. 86:1580–1588, 2001.
168. Caron, P.; Chauvin, S.; Christin-Maitre, S.; Bennet, A.; Lahlou, N.; Counis, R.; Bouchard, P.; Kottler, M.-L.: Resistance of hypogonadic patients with mutated GnRH receptor genes to pulsatile GnRH administration. J. Clin. Endocr. Metab. 84: 990–996, 1999.
169. Costa, E. M. F.; Bedecarrats, G. Y.; Mendonca, B. B.; Arnhold, I. J. P.; Kaiser, U. B.; Latronico, A. C.: Two novel mutations in the gonadotropin-releasing hormone receptor gene in Brazilian patients with hypogonadotropic hypogonadism and normal olfaction. J. Clin. Endocr. Metab. 86: 2680–2686, 2001.
170. de Roux, N.; Young, J.; Brailly-Tabard, S.; Misrahi, M.; Milgrom, E.; Schaison, G.: The same molecular defects of the gonadotropin-releasing hormone receptor determine a variable degree of hypogonadism in affected kindred. J. Clin. Endocr. Metab. 84: 567–572, 1999.
171. de Roux, N.; Young, J.; Misrahi, M.; Genet, R.; Chanson, P.; Schaison, G.; Milgrom, E.: A family with hypogonadotropic hypogonadism and mutations in the gonadotropin-releasing hormone receptor. New Eng. J. Med. 337: 1597–1602, 1997.
172. Fan, N. C.; Jeung, E.-B.; Peng, C.; Olofsson, J. I.; Krisinger, J.; Leung, P. C. K.: The human gonadotropin-releasing hormone (GnRH)receptor gene: cloning, genomic or ganization and chromosomal assignment. Molec. Cell. Endocr. 103: R1-R6, 1994.
173. Iwashita, T.; Murakami, H.; Asai, N.; Takahashi, M.: Mechanism of Ret dysfunction by Hirschsprung mutations affecting its extracellular domain. Hum. Molec. Genet. 5: 1577–1580, 1996.
174. Fan, N. C.; Peng, C.; Krisinger, J.; Leung, P. C. K.: The humangonadotropin-releasing hormone receptor gene: complete structure including multiple promoters, transcription initiation sites, and polyadenylation signals. Molec. Cell. Endocr. 107: R1–R8, 1995.
175. Grosse, R.; Schoneberg, T.; Schultz, G.; Gudermann, T.: Inhibition of gonadotropin-releasing hormone receptor signaling by expression of a splice variant of the human receptor. Molec. Endocr. 11: 1305–1318, 1997.
176. Kaiser, U. B.; Dushkin, H.; Altherr, M. R.; Beier, D. R.; Chin, W. W.: Chromosomal localization of the gonadotropin-releasing hormonereceptor gene to human chromosome 4q13.1–q21.1 and mouse chromosomes. Genomics 20: 506–508, 1994.
177. Kakar, S. S.; Musgrove, L. C.; Devor, D. C.; Sellers, J. C.; Neill, J. D.: Cloning, sequencing, and expression of human gonadotropin releasing hormone (GnRH) receptor. Biochem. Biophys. Res. Commun. 189:289–295, 1992.
178. Kakar, S. S.; Neill, J. D.: The human gonadotropin releasing hormone receptor gene (GNRHR) maps to chromosome band 4q13. Cytogenet. Cell Genet. 70: 211–214, 1995.
179. Kottler, M.-L.; Chauvin, S.; Lahlou, N.; Harris, C. E.; Johnston, C. J.; Lagarde, J.-P.; Bouchard, P.; Farid, N. R.; Counis, R.: Anew compound heterozygous mutation of the gonadotropin-releasing hormone receptor (L314X, Q106R) in a woman with complete hypogonadotropichypogonadism: chronic estrogen administration amplifies the gonadotropin defect. J. Clin. Endocr. Metab. 85: 3002–3008, 2000.
180. Kottler, M.-L.; Counis, R.; Bouchard, P.: Mutations of the GnRH receptor gene: a new cause of autosomal-recessive hypogonadotropichypogonadism. Arch. Med. Res. 30: 481–485, 1999.
181. Kottler, M. L.; Lorenzo, F.; Bergametti, F.; Commercon, P.; Souchier, C.; Counis, R.: Subregional mapping of the human gonadotropin-releasing hormone receptor 181. (GnRH-R) gene to 4q between the markers D4S392 and D4S409. Hum. Genet. 96: 477–480, 1995.

182. Layman, L. C.; Cohen, D. P.; Jin, M.; Xie, J.; Li, Z.; Reindollar, R. H.; Bolbolan, S.; Bick, D. P.; Sherins, R. R.; Duck, L. W.; Musgrove, L. C.; Sellers, J. C.; Neill, J. D.: Mutations in gonadotropin-releasing hormone receptor gene cause hypogonadotropic hypogonadism. (Letter) Nature-Genet. 18: 14–15, 1998.

183. Leung, P. C. K.; Squire, J.; Peng, C.; Fan, N.; Hayden, M. R.; Olofsson, J. I.: Mapping of the gonadotropin-releasing hormone (GnRH)receptor gene to human chromosome 4q21.2 by fluorescence in situ hybridization. Mammalian Genome 6: 309–310, 1995.

184. Mason, A. J.; Hayflick, J. S.; Zoeller, R. T.; Young, W. S., III; Phillips, H. S.; Nikolics, K.; Seeburg, P. H.: A deletion truncating the gonadotropin-releasing hormone gene is responsible for hypogonadism in the 'hpg' mouse. Science 234: 1366–1371, 1986.

185. Morrison, N.; Sellar, R. E.; Boyd, E.; Eidne, K. A.; Connor, J. M.: Assignment of the gene encoding the human gonadotropin-releasing hormone receptor to 4q13.2–13.3 by fluorescence in situ hybridization. Hum. Genet. 93: 714–715, 1994.

186. Pitteloud, N.; Boepple, P. A.; DeCruz, S.; Valkenburgh, S. B.; Crowley, W. F., Jr.; Hayes, F. J.: The fertile eunuch variant of idiopathic hypogonadotropic hypogonadism: spontaneous reversal associated with a homozygous mutation in the gonadotropin-releasing hormone receptor. J. Clin. Endocr. Metab. 86: 2470–2475, 2001.

187. Pralong, F. P.; Gomez, F.; Castillo, E.; Cotecchia, S.; Abuin, L.; Aubert, M. L.; Portmann, L.; Gaillard, R. C.: Complete hypogonadotropichypogonadism associated with a novel inactivating mutation of the gonadotropin-releasing hormone receptor. J. Clin. Endocr. Metab. 84:3811–3816, 1999.

188. Szende, B.; Srkalovic, G.; Timar, J.; Mulchahey, J. J.; Neill, J. D.; Lapis, K.; Csikos, A.; Szepeshazi, K.; Schally, A. V.: Localization of receptors for luteinizing hormone-releasing hormone in pancreatic and mammary cancer cells. Proc. Nat. Acad. Sci. 88: 4153–4156, 1991.

189. Carrasquillo, M. M.; McCallion, A. S.; Puffenberger, E. G.; Kashuk, C. S.; Nouri, N.; Chakravarti, A.: Genome-wide association study and mouse model identify interaction between RET and EDNRB pathways in Hirschsprung disease. Nature Genet. 32: 237–244, 2002.

190. Wolffe, A. P.: Transcriptional control: sinful repression. Nature 387:16–17, 1997.

191. Allenspach, E. J.; Cullinan, P.; Tong, J.; Tang, Q.; Tesciuba, A. G.; Cannon, J. L.; Takahashi, S. M.; Morgan, R.; Burkhardt, J. K.; Sperling, A. I.: ERM-dependent movement of CD43 defines a novel protein complex distal to the immunological synapse. Immunity 15:739–750, 2001.

192. Fenster, S. D.; Chung, W. J.; Zhai, R.; Cases-Langhoff, C.; Voss, B.; Garner, A. M.; Kaempf, U.; Kindler, S.; Gundelfinger, E. D.; Garner, C. C.: Piccolo, a presynaptic zinc finger protein structurally related to Bassoon. Neuron 25: 203–214, 2000.

193. Bak, M.; Hansen, C.; Henriksen, K. F.; Tommerup, N.: The human hedgehog-interacting protein gene: structure and chromosome mapping to 4q31.21–q31.3. Cytogenet. Cell Genet. 92: 300–303, 2001.

194. Chuang, P.-T.; McMahon, A. P.: Vertebrate hedgehog signalling modulated by induction of a hedgehog-binding protein. Nature 397:617–621, 1999.

195. Anand, R.; Lindstrom, J.: Chromosomal localization of seven neuronal nicotinic acetylcholine receptor subunit genes in humans. Genomics 13:962–967, 1992.

196. Armstrong, E.; Partanen, J.; Cannizzaro, L.; Huebner, K.; Alitalo, K.: Localization of the fibroblast growth factor receptor-4 gene to chromosome region 5q33-qter. Genes Chromosomes Cancer 4: 94–98, 1992.

197. Bange, J.; Prechtl, D.; Cheburkin, Y.; Specht, K.; Harbeck, N.; Schmitt, M.; Knyazeva, T.; Muller, S.; Gartner, S.; Sures, I.; Wang, H.; Imyanitov, E.; Haring, H.-U.; Knayzev, P.; lacobelli, S.; Hofler, H.; Ullrich, A.: Cancer progression and tumor cell motility are associated with the FGFR4 Arg388 allele. Cancer Res. 62: 840–847, 2002.

198. Holtrich, U.; Brauninger, A.; Strebhardt, K.; Rubsamen-Waigmann, H.: Two additional protein-tyrosine kinases expressed in human lung: fourth member of the fibroblast growth factor receptor family and an intracellular protein-tyrosine kinase. Proc. Nat. Acad. Sci. 88:10411–10415, 1991.

199. Kostrzewa, M.; Muller, U.: Genomic structure and complete sequence of the human FGFR4 gene. Mammalian Genome 9: 131–135, 1998.

200. Partanen, J.; Makela, T. P.; Eerola, E.; Korhonen, J.; Hirvonen, H.; Claesson-Welsh, L.; Alitalo, K.: FGFR-4, a novel acidic fibroblast growth factor receptor with a distinct expression pattern. EMBO J. 10:1347–1354, 1991.

201. Scott, A. F.: Personal Communication. Baltimore, Md. Oct. 12, 1999.

202. Vainikka, S.; Partanen, J.; Bellosta, P.; Coulier, F.; Basilico, C.; Jaye, M.; Alitalo, K.: Fibroblast growth factor receptor-4 shows novel features in genomic structure, ligand binding and signal transduction. EMBO J. 11: 4273–4280, 1992.

203. Warrington, J. A.; Bailey, S. K.; Armstrong, E.; Aprelikova, O.; Alitalo, K.; Dolganov, G. M.; Wilcox, A. S.; Sikela, J. M.; Wolfe, S. F.; Lovett, M.; Wasmuth, J. J.: A radiation hybrid map of 18 growth factor, growth factor receptor, hormone receptor, or neurotransmitter receptor genes on the distal region of the long arm of chromosomes. Genomics 13: 803–808, 1992.

204. Diaz, M. O.; Bohlander, S.: Nomenclature of the human interferon genes. J. Interferon Res. 13: 443–444, 1993.

205. Olopade, O. I.; Bohlander, S. K.; Pomykala, H.; Maltepe, E.; VanMelle, E.; Le Beau, M. M.; Diaz, M. O.: Mapping of the shortest region of overlap of deletions of the short arm of chromosome 9 associated with human neoplasia. Genomics 14: 437–443, 1992.

206. Habas, R.; Kato, Y.; He, X.: Wnt/Frizzled activation of Rho regulates vertebrate gastrulation and requires a novel Formin homology protein Daam1. Cell 107: 843–854, 2001.

207. Tollervey, D.; Kiss, T.: Function and synthesis of small nucleolar RNAs. Curr. Opin. Cell Biol. 9: 337–342, 1997.

208. Pogacic, V.; Dragon, F.; Filipowicz, W.: Human H/ACA small nucleolar RNPs and telomerase share evolutionarily conserved proteins NHP2 and NOP10. Molec. Cell. Biol. 20: 9028–9040, 2000.

209. Olavesen, M. G.; Bentley, E.; Mason, R. V. F.; Stephens, R. J.; Ragoussis, J.: Fine mapping of 39 ESTs on human chromosome 6p23–p25. Genomics 46:303–306, 1997.

210. Blake, D. J.; Love, D. R.; Tinsley, J.; Morris, G. E.; Turley, H.; Gatter, K.; Dickson, G.; Edwards, Y. H.; Davies, K. E.: Characterization of a 4.8 kb transcript from the Duchenne muscular dystrophy locus expressed in schwannoma cells. Hum. Molec. Genet. 1: 103–109, 1992.

211. Fuentes, J. J.; Genesca, L.; Kingsbury, T. J.; Cunningham, K. W.; Perez-Riba, M.; Estivill, X.; de la Luna, S.: DSCR1, overexpressed in Down syndrome, is an inhibitor of calcineurin-mediated signaling pathways. Hum. Molec. Genet. 9: 1681–1690, 2000.

212. Nagase, T.; Ishikawa, K.; Suyama, M.; Kikuno, R.; Hirosawa, M.; Miyajima, N.; Tanaka, A.; Kotani, H.; Nomura, N.; Ohara, O.: Prediction of the coding sequences of unidentified human genes. XII. The complete sequences of 100 new cDNA clones from brain which code for large proteins in vitro. DNA Res. 5: 355–364, 1998.

213. Belinsky, M. G.; Bain, L. J.; Balsara, B. B.; Testa, J. R.; Kruh, G. D.: Characterization of MOAT-C and MOAT-D, new members of the MRP/cMOAT subfamily of transporter proteins. J. Nat. Cancer Inst. 90:1735–1741, 1998.

214. Fromm, M. F.; Leake, B.; Roden, D. M.; Wilkinson, G. R.; Kim, R. B.: Human MRP3 transporter: identification of the 5-prime flanking region, genomic organization and alternative splice variants. Biochim. Biophys. Acta 1415: 369–374, 1999.

215. Kiuchi, Y.; Suzuki, H.; Hirohashi, T.; Tyson, C. A.; Sugiyama, Y.: cDNA cloning and inducible expression of human multidrug resistance associated protein 3 (MRP3). FEBS Lett. 433: 149–152, 1998.

216. Konig, J.; Rost, D.; Cui, Y.; Keppler, D.: Characterization of the human multidrug resistance protein isoform MRP3 localized to the basolateral hepatocyte membrane. Hepatology 29: 1156–1163, 1999.

217. Kool, M.; van der Linden, M.; de Haas, M.; Scheffer, G. L.; deVree, J. M. L.; Smith, A. J.; Jansen, G.; Peters, G. J.; Ponne, N.; Scheper, R. J.; Oude Elferink, R. P. J.; Baas, F.; Borst, P.: MRP3, an organic anion transporter able to transport anti-cancer drugs. Proc. Nat. Acad. Sci. 96: 6914–6919, 1999.

218. Ortiz, D. F.; Li, S.; Iyer, R.; Zhang, X.; Novikoff, P.; Arias, I. M.: MRP3, a new ATP-binding cassette protein localized to the canalicular domain of the hepatocyte. Am. J. Physiol. 276: G1493–G1500, 1999.

219. Santoro, M.; Carlomagno, F.; Hay, I. D.; Herrmann, M. A.; Grieco, M.; Melillo, R.; Pierotti, M. A.; Bongarzone, I.; Della Porta, G.; Berger, N.; Peix, J. L.; Paulin, C.; Fabien, N.; Vecchio, G.; Jenkins, R. B.; Fusco, A.: Ret oncogene activation in human thyroid neoplasmsis restricted to the papillary cancer subtype. J. Clin. Invest. 89:1517–1522, 1992.

220. Santoro, M.; Carlomagno, F.; Romano, A.; Bottaro, D. P.; Dathan, N. A.; Grieco, M.; Fusco, A.; Vecchio, G.; Matoskova, B.; Kraus, M. H.; Di Fiore, P. P.: Activation of RET as a dominant transforming gene by germline mutations of MEN2A and MEN2B. Science 267: 381–383, 1995.

221. Schuchardt, A.; D'Agati, V.; Larsson-Blomberg, L.; Costantini, F.; Pachnis, V.: Defects in the kidney and enteric nervous system of mice lacking the tyrosine kinase receptor Ret. Nature 367: 380–383, 1994.

222. Shirahama, S.; Ogura, K.; Takami, H.; Ito, K.; Tohsen, T.; Miyauchi, A.; Nakamura, Y.: Mutational analysis of the RET proto-oncogene in 71 Japanese patients with medullary thyroid carcinoma. J. Hum. Genet. 43:101–106, 1998.

223. Seri, M.; Yin, L.; Barone, A.; Bolino, A.; Celli, I.; Bocciardi, R.; Pasini, B.; Ceccherini, I.; Lerone, M.; Kristoffersson, U.; Larsson, L. T.; Casasa, J. M.; Cass, D. T.; Abramowicz, M. J.; Vanderwinden, J.-M.; Kravcenkiene, I.; Baric, I.; Silengo, M.; Martucciello, G.; Romeo, G.: Frequency of RET mutations in long- and short segment Hirschsprung disease. Hum. Mutat. 9: 243–249, 1997.

224. Takahashi, M.; Buma, Y.; Hiai, H.: Isolation of ret proto-oncogene cDNA with an amino-terminal signal sequence. Oncogene 4: 805–806,1989.

225. Takahashi, M.; Buma, Y.; Iwamoto, T.; Inaguma, Y.; Ikeda, H.; Hiai, H.: Cloning and expression of the ret proto-oncogene encoding a tyrosine kinase with two potential transmembrane domains. Oncogene 3:571–578, 1988.

226. Takahashi, M.; Ritz, J.; Cooper, G. M.: Activation of a novel human transforming gene, ret, by DNA rearrangement. Cell 42: 581–588,1985.

227. Tessitore, A.; Sinisi, A. A.; Pasquali, D.; Cardone, M.; Vitale, D.; Bellastella, A.; Colantuoni, V.: A novel case of multiple endocrine neoplasia type 2A associated with two de novo mutations of the RET protooncogene. J. Clin. Endocr. Metab. 84: 3522–3527, 1999.

228. van Heyningen, V.: One gene—four syndromes. Nature 367: 319–320, 1994.

229. Xue, F.; Yu, H.; Maurer, L. H.; Memoli, V. A.; Nutile-McMenemey, N.; Schuster, M. K.; Bowden, D. W.; Mao, J.; Noll, W. W.: Germline RET mutations in MEN 2A and FMTC and their detection by simple DNA diagnostic tests. Hum. Molec. Genet. 3: 635–638, 1994.

230. Yin, L.; Ceccherini, I.; Pasini, B.; Matera, I.; Bicocchi, M. P.; Barone, V.; Bocciardi, R.; Kaariainen, H.; Weber, D.; Devoto, M.; Romeo, G.: Close linkage with the RET protooncogene and boundaries of deletion mutations in autosomal dominant Hirschsprung disease. Hum. Molec. Genet. 2: 1803–1808, 1993.

231. Schuuring, E.; Verhoeven, E.; Mooi, W. J.; Michalides, R. J. A. M.: Identification and cloning of two overexpressed genes, U21B31/PRAD1 and EMS1, within the amplified chromosome 11q13 region in human carcinomas. Oncogene 7:355–361, 1992.

232. van Damme, H.; Brok, H.; Schuuring-Scholtes, E.; Schuuring, E.: The redistribution of cortactin into cell-matrix contact sites inhuman carcinoma cells with 11q13 amplification is associated with both overexpression and post-translational modification. J. Biol. Chem. 272: 7374–7380, 1997.

233. Yamashita, A.; Ohnishi, T.; Kashima, I.; Taya, Y.; Ohno, S.: Human SMG-1, a novel phosphatidylinositol 3-kinase-related protein kinase, associates with components of the mRNA surveillance complex and is involved in the regulation of nonsense-mediated mRNA decay. Genes Dev. 15: 2215–2228, 2001.

234. Nagle, D. L.; McGrail, S. H.; Vitale, J.; Woolf, E. A.; Dussault, B. J., Jr.; DiRocco, L.; Holmgren, L.; Montagno, J.; Bork, P.; Huszar, D.; Fairchild-Huntress, V.; Ge, P.; Keilty, J.; Ebelling, C.; Baldini, L.; Gilchrist, J.; Burr, P.; Carlson, G. A.; Moore, K. J.: The mahogany protein is a receptor involved in suppression of obesity. Nature 398:148–151, 1999.

235. Brown, C. W.; Houston-Hawkins, D. E.; Woodruff, T. K.; Matzuk, M. M.: Insertion of Inhbb into the Inhba locus rescues the Inhba-nullphenotype and reveals new activin functions. Nature Genet. 25: 453–457, 2000.

236. Ferguson, C. A.; Tucker, A. S.; Christensen, L.; Lau, A. L.; Matzuk, M. M.; Sharpe, P. T.: Activin is an essential early mesenchymal signal in tooth development that is required for patterning of the murinedentition. Genes Dev. 12: 2636–2649, 1998.

237. Burger, H. G.; Igarashi, M.; Baird, D.; Mason, T.; Bardin, W.; McLachlan, R.; Chappel, S.; Miyamoto, K.; de Jong, F.; Moudgal, A.; Demoulin, A.; Nieschlag, E.; de Kretser, D.; Robertson, D.; Findlay, J.; Sasamoto, S.; Forage, R.; Schwartz, N.; Fukuda, M.; Steinberger, A.; Hasegawa, Y.; Tanabe, K.; Ling, N.; Ying, S.-Y.: Inhibin: definition and nomenclature, including related substances. (Letter)J. Clin. Endocr. Metab. 66: 885–886, 1988.

238. Lumpkin, M. D.; Moltz, J. H.; Yu, W. H.; Samson, W. K.; McCann, S. M.: Purification of FSH-releasing factor: its dissimilarity from LHRH of mammalian, avian, and piscian origin. Brain Res. Bull. 18:175–178, 1987.

239. Matzuk, M. M.; Kumar, T. R.; Vassalli, A.; Bickenbach, J. R.; Roop, D. R.; Jaenisch, R.; Bradley, A.: Functional analysis of activins during mammalian development. Nature 374: 354–356, 1995.

240. Mellor, S. L.; Cranfield, M.; Ries, R.; Pedersen, J.; Cancilla, B.; de Kretser, D.; Groome, N. P.; Mason, A. J.; Ris-bridger, G. P.: Localization of activin beta(A)-, beta (B)-, and beta(C)-subunits in human prostate and evidence for formation of new activin heterodimers of beta (C)-subunit. J. Clin. Endocr. Metab. 85: 4851–4858, 2000.

241. Murata, M.; Eto, Y.; Shibai, H.; Sakai, M.; Muramatsu, M.: Erythroid differentiation factor is encoded by the same mRNA as that of the inhibin beta-A chain. Proc. Nat. Acad. Sci. 85: 2434–2438, 1988.

242. You, L.; Kruse, F. E.: Differential effect of activin A and BMP-7 on myofibroblast differentiation and the role of the Smad signaling pathway. Invest. Ophthal. Vis. Sci. 43: 72–81, 2002.

243. E I-Husseini, A. E.-D.; Schnell, E.; Chetkovich, D. M.; Nicoll, R. A.; Bredt, D. S.: PSD-95 involvement in maturation of excitatory synapses. Science 290: 1364–1368, 2000.

244. E I-Husseini, A. E.-D.; Schnell, E.; Dakoji, S.; Sweeney, N.; Zhou, Q.; Prange, O.; Gauthier-Campbell, C.; Aguilera-Moreno, A.; Nicoll, R. A.; Bredt, D. S.: Synaptic strength regulated by palmitate cycling on PSD-95. Cell 108: 849–863, 2002.

245. Kim, E.; Cho, K.-O.; Rothschild, A.; Sheng, M.: Heteromultimerization and NMDA receptor-clustering activity of Chapsyn-110, a member of the PSD-95 family of proteins. Neuron 17: 103–113, 1996.

246. Kim, E.; Niethammer, M.; Rothschild, A.; Jan, Y. N.; Sheng, M.: Clustering of Shaker-type K+ channels by interaction with a family of membrane-associated guanylate kinases. Nature 378: 85–88, 1995.

247. Kistner, U.; Wenzel, B. M.; Veh, R. W.; Cases-Langhoff, C.; Garner, A. M.; Appeltauer, U.; Voss, B.; Gundelfinger, E. D.; Garner, C. C.: SAP90, a rat presynaptic protein related to the product of the Drosophilatumor suppressor gene, dLg-A. J. Biol. Chem. 268: 4580–4583, 1993.

248. Migaud, M.; Charlesworth, P.; Dempster, M.; Webster, L. C.; Watabe, A. M.; Makhinson, M.; He, Y.; Ramsay, M. F.; Morris, R. G. M.; Morrison J. H.; O'Dell, T. J.; Grant, S. G. N.: Enhanced long-term potentiation and impaired learning in mice with mutant postsynaptic density-95 protein. Nature 396: 433–439, 1998.

249. Sattler, R.; Xiong, Z.; Lu, W.-Y.; Hafner, M.; MacDonald, J. F.; Tymianski, M.: Specific coupling of NMDA receptor activation to nitricoxide neurotoxicity by PSD-95 protein. Science 284: 1845–1848, 1999.

250. Stathakis, D. G.; Hoover, K. B.; You, Z.; Bryant, P. J.: Human postsynaptic density-95 (PSD95): location of the gene (DLG4) and possible function in normeural as well as in neural tissues. Genomics 44:71–82, 1997.

251. Strippoli, P.; Petrini, M.; Lenzi, L.; Carinci, P.; Zannotti, M.: The murine DSCR1-like (Down syndrome candidate region 1) gene family: conserved synteny with the human orthologous genes. Gene 257: 223–232, 2000.

252. Yang, J.; Rothermel, B.; Vega, R. B.; Frey, N.; McKinsey, T. A.; Olson, E. N.; Bassel-Duby, R.; Williams, R. S.: Independent signals control expression of the calcineurin inhibitory proteins MCIP1 and MCIP2 in striated muscles. Circ. Res. 87: 61e-68e, 2000.

253. Denning, G.; Jamieson, L.; Maquat, L. E.; Thompson, E. A.; Fields, A. P.: Cloning of a novel phosphatidylinositol kinase-related kinase: characterization of the human SMG-1 RNA surveillance protein. J. Biol. Chem. 276: 22709–22714, 2001.

254. Diaz-Meco, M. T.; Municio, M. M.; Sanchez, P.; Lozano, J.; Moscat, J.: Lambda-interacting protein, a novel protein that specifically interacts with the zinc finger domain of the atypical protein kinaseC isotype lambda/iota and stimulates its kinase activity in vitroand in vivo. Molec. Cell. Biol. 16: 105–114, 1996.

255. Alarcon, B.; Regueiro, J. R.; Arnaiz-Villena, A.; Terhorst, C.: Familial defect in the surface expression of the T-cell receptor-CD3 complex. New Eng. J. Med. 319: 1203–1208, 1988.

256. Caplan, S.; Zeliger, S.; Wang, L.; Baniyash, M.: Cell-surface-expressedT-cell antigen-receptor epsilon chain is associated with the cytoskeleton. Proc. Nat. Acad. Sci. 92: 4768–4772, 1995.

257. Clevers, H.; Alarcon, B.; Wileman, T.; Terhorst, C.: The T cell receptor/CD3 complex: a dynamic protein ensemble. Annu. Rev. Immun. 6:629–662, 1988.

258. Grakoui, A.; Bromley, S. K.; Sumen, C.; Davis, M. M.; Shaw, A. S.; Allen, P. M.; Dustin, M. L.: The immunological synapse: a molecular machine controlling T cell activation. Science 285: 221–227, 1999.

259. Krummel, M. F.; Sjaastad, M. D.; Wulfing, C.; Davis, M. M.: Differential clustering of CD4 and CD3-zeta during T cell recognition. Science 289:1349–1352, 2000.

260. Weissman, A. M.; Baniyash, M.; Hou, D.; Samelson, L. E.; Burgess, W. H.; Klausner, R. D.: Molecular cloning of the zeta chain of the T cell antigen receptor. Science 239: 1018–1021, 1988.

261. Weissman, A. M.; Hou, D.; Orloff, D. G.; Modi, W. S.; Seuanez, H.; O'Brien, S. J.; Klausner, R. D.: Molecular cloning and chromosomal localization of the human T-cell receptor zeta chain: distinction from the molecular CD3 complex. Proc. Nat. Acad. Sci. 85: 9709–9713,1988.

262. Weissman, A. M.; Samelson, L. E.; Klausner, R. D.: A new subunit of the human T-cell antigen receptor complex. Nature 324: 480–482,1986.

263. Patel, A.; Rochelle, J. M.; Jones, J. M.; Sumegi, J.; Uhl, G. R.; Seldin, M. F.; Meisler, M. H.; Gregor, P.: Mapping of the taurine transporter gene to mouse chromosome 6 and to the short arm of human chromosome 3. Genomics 25: 314–317, 1995.

264. Ramamoorthy, S.; Leibach, F. H.; Mahesh, V. B.; Han, H.; Yang-Feng, T.; Blakely, R. D.; Ganapathy, V.: Functional characterization and chromosomal localization of a cloned taurine transporter from human placenta. Biochem. J. 300: 893–900, 1994.

265. Uchida, S.; Kwon, H. M.; Yamauchi, A.; Preston, A. S.; Marumo, F.; Handler, J. S.: Molecular cloning of the cDNA for an MDCK cell Na(+)- and Cl(–)-dependent taurine transporter that is regulated by hypertonicity. Proc. Nat. Acad. Sci. 89: 8230–8234, 1992.

266. Durand, B.; Sperisen, P.; Emery, P.; Barras, E.; Zufferey, M.; Mach, B.; Reith, W.: RFXAP, a novel subunit of the RFX DNA bindingcomplex is mutated in MHC class II deficiency. EMBO J. 16: 1045–1055, 1997.

267. Nekrep, N.; Jabrane-Ferrat, N.; Peterlin, B. M.: Mutations in the bare lymphocyte syndrome define critical steps in the assembly of the regulatory factor X complex. Molec. Cell Biol. 20: 4455–4461, 2000.

268. Peijnenburg, A.; Van Eggermond, M. C. J. A.; Van den Berg, R.; Sanal, O.; Vossen, J. M. J. J.; Van den Elsen, P. J.: Molecular analysis of an MHC class II deficiency patient reveals a novel mutation in the RFX5 gene. Immunogenetics 49: 338–345, 1999.

269. Fuentes, J.-J.; Pritchard, M. A.; Planas, A. M.; Bosch, A.; Ferrer, I.; Estivill, X.: A new human gene from the Down syndrome critical region encodes a proline-rich protein highly expressed in fetal brain and heart. Hum. Molec. Genet. 4: 1935–1944, 1995.

270. Wolf, H. M.; Hauber, I.; Guile, H.; Thon, V.; Eggenbauer, H.; Fischer, M. B.; Fiala, S.; Eibl, M. M.: Brief report: Twin boys with major histocompatibility complex class II deficiency but inducible immune responses. New Eng. J. Med. 332: 86–90, 1995.

271. Doi, A.; Shiosaka, T.; Takaoka, Y.; Yanagisawa, K.; Fujita, S.: Molecular cloning of the cDNA encoding A+U-rich element RNA binding factor. Biochim. Biophys. Acta 1396: 51–56, 1998.

272. Kamei, D.; Tsuchiya, N.; Yamazaki, M.; Meguro, H.; Yamada, M.: Two forms of expression and genomic structure of the human heterogeneous nuclear ribonucleoprotein D-like JKTBP gene (HNRPDL). Gene 228: 13–22, 1999.

273. Tsuchiya, N.; Kamei, D.; Takano, A.; Matsui, T.; Yamada, M.: Cloning and characterization of a cDNA encoding a novel heterogeneous nuclearribonucleoprotein-like protein and its expression in myeloid leukemiacells. J. Biochem. 123: 499–507, 1998.

274. Fuentes, J. J.; Pritchard, M. A.; Estivill, X.: Genomic organization, alternative splicing, and expression patterns of the DSCR1 (Down syndrome candidate region 1) gene. Genomics 44: 358–361, 1997.

275. Kingsbury, T. J.; Cunningham, K. W.: A conserved family of calcineurin regulators. Genes Dev. 14: 1595–1604, 2000.

276. Rothermel, B.; Vega, R. B.; Yang, J.; Wu, H.; Bassel-Duby, R.; Williams, R. S.: A protein encoded within the Down syndrome critical region is enriched in striated muscles and inhibits calcineurin signaling. J. Biol. Chem. 275: 8719–8725, 2000.

277. Steimle, V.; Durand, B.; Barras, E.; Zuffrey, M.; Hadam, M. R.; Mach, B.; Reith, W.: A novel DNA binding regulatory factor is mutated in primary MHC class II deficiency (bare lymphocyte syndrome). GenesDev. 9: 1021–1032, 1995.

278. Villard, J.; Reith, W.; Barras, E.; Gos, A.; Morris, M. A.; Antonarakis, S. E.; Van den Elsen, P. J.; Mach, B.: Analysis of mutations and chromosomal localisation of the gene encoding RFX5, a novel transcription factor affected in major histocompatibility complex class II deficiency. Hum. Mutat. 10: 430–435, 1997.

279. Scott, A. F.: Personal Communication. Baltimore, Md. Jul. 20, 2001.

280. Arsenijevic, D.; Onuma, H.; Pecqueur, C.; Raimbault, S.; Manning, B. S.; Miroux, B.; Couplan, E.; Alves-Guerra, M.-C.; Goubern, M.; Surwit, R.; Bouillard, F.; Richard, D.; Collins, S.; Ricquier, D.: Disruption of the uncoupling protein-2 gene in mice reveals a rolein immunity and reactive oxygen species production. Nature Genet. 26:435–439, 2000.

281. Bouchard, C.; Perusse, L.; Chagnon, Y. C.; Warden, C.; Ricquier, D.: Linkage between markers in the vicinity of the uncoupling protein2 gene and resting metabolic rate in humans. Hum. Molec. Genet. 6:1887–1889, 1997.

282. Brauner, P.; Nibbelink, M.; Flachs, P.; Vitkova, I.; Kopecky, P.; Mertelikova, I.; Janderova, L.; Penicaud, L.; Casteilla, L.; Plavka, R.; Kopecky, J.: Fast decline of hematopoiesis and uncoupling protein2 content in human liver after birth: location of the protein in Kupffer cells. Pediat. Res. 49: 440–447, 2001.

283. Esterbauer, H.; Schneitler, C.; Oberkofler, H.; Ebenbichler, C.; Paulweber, B.; Sandhofer, F.; Ladurner, G.; Hell, E.; Strosberg, A. D.; Patsch, J. R.; Krempler, F.; Patsch, W.: A common polymorphism in the promoter of UCP2 is associated with decreased risk of obesity in middle-aged humans. Nature Genet. 28: 178–183, 2001.

284. Fleury, C.; Neverova, M.; Collins, S.; Raimbault, S.; Champigny, O.; Levi-Meyrueis, C.; Bouillaud, F.; Seldin, M. F.; Surwit, R. S.; Ricquier, D.; Warden, C. H.: Uncoupling protein-2: a novel gene linked to obesity and hyperinsulinemia. Nature Genet. 15: 269–272, 1997.

285. Flier, J. S.; Lowell, B. B.: Obesity research springs a proton leak. Nature Genet. 15: 223–224, 1997.

286. Millet, L.; Vidal, H.; Andreelli, F.; Larrouy, D.; Riou, J.-P.; Ricquier, D.; Laville, M.; Langin, D.: Increased uncoupling protein-2 and -3 mRNA expression during fasting in obese and lean humans. J. Clin. Invest. 100: 2665–2670, 1997.

287. Suetsugu, S.; Miki, H.; Takenawa, T.: Identification of two human WAVE/SCAR homologues as general actin regulatory molecules which associate with the Arp2/3 complex. Biochem. Biophys. Res. Commun. 260: 296–302, 1999.

288. Wang, A. H.; Bertos, N. R.; Vezmar, M.; Pelletier, N.; Crosato, M.; Heng, H. H.; Th'ng, J.; Han, J.; Yang, X.-J.: HDAC4, a human histone deacetylase related to yeast HDA1, is a transcriptional core pressor. Molec. Cell. Biol. 19: 7816–7827, 1999.

289. Hirsch, D. S.; Pirone, D. M.; Burbelo, P. D.: A new family of Cdc42 effector proteins, CEPs, function in fibroblast and epithelial cell shape changes. J. Biol. Chem. 276: 875–883, 2001.

290. Joberty, G.; Perlungher, R. R.; Macara, I. G.: The Borgs, a new family of Cdc42 and TC10 GTPase-interacting proteins. Molec. Cell. Biol. 19: 6585–6597, 1999.

291. McCright, B.; Brothman, A. R.; Virshup, D. M.: Assignment of human protein phosphatase 2A regulatory subunit genes B56-alpha, B56-beta, B56-gamma, B56-delta, and B56-epsilon (PPP2R5A-PPP2R5E), highly expressed in muscle and brain, to chromosome regions 1q41, 11q12, 3p21, 6p21.1, and 7p11.2-to-p12. Genomics 36: 168–170, 1996.

292. McCright, B.; Virshup, D. M.: Identification of a new family of protein phosphatase 2A regulatory subunits. J. Biol. Chem. 270:26123–26128, 1995.

293. Zhang, C.-Y.; Baffy, G.; Perret, P.; Krauss, S.; Peroni, O.; Grujic, D.; Hagen, T.; Vidal-Puig, A.; Boss, O.; Kim, Y.-B.; Zheng, X. X.; Wheeler, M. B.; Shulman, G. I.; Chan, C. B.; Lowell, B. B.: Uncoupling protein-2 negatively regulates insulin secretion and is a major link between obesity, beta cell dysfunction, and type 2 diabetes. Cell 105:745–755, 2001.

294. Park, W. S.; Lee, J. H.; Shin, M. S.; Park, J. Y.; Kim, H. S.; Lee, J. H.; Kim, Y. S.; Lee, S. N.; Xiao, W.; Park, C. H.; Lee, S. H.; Yoo, N. J.; Lee, J. Y.: In activating mutations of the caspase-10 gene in gastric cancer. Oncogene 21: 2919–2925, 2002.
295. Shin, M. S.; Kim, H. S.; Kang, C. S.; Park, W. S.; Kim, S. Y.; Lee, S. N.; Lee, J. H.; Park, J. Y.; Jang, J. J.; Kim, C. W.; Kim, S. H.; Lee, J. Y.; Yoo, N. J.; Lee, S. H.: In activating mutations of CASP10 gene in non-Hodgkin lymphomas. Blood 99: 4094–4099, 2002.
296. Vincenz, C.; Dixit, V. M.: Fas-associated death domain protein interleukin-1-beta-converting enzyme 2 (FLICE2), an ICE/Ced-3 homologue, is proximally involved in CD95- and p55-mediated death signaling. J. Biol. Chem. 272: 6578–6583, 1997.
297. Wang, J.; Chun, H. J.; Wong, W.; Spencer, D. M.; Lenardo, M. J.: Caspase-10 is an initiator caspase in death receptor signaling. Proc. Nat. Acad. Sci. 98: 13884–13888, 2001.
298. Wang, J.; Zheng, L.; Lobito, A.; Chan, F. K.; Dale, J.; Sneller, M.; Yao, X.; Puck, J. M.; Straus, S. E.; Lenardo, M. J.: Inherited human caspase 10 mutations underlie defective lymphocyte and dendritic cell apoptosis in autoimmune lymphoproliferative syndrome type II. Cell 98:47–58, 1999.
299. Nagase, T.; Ishikawa, K.; Miyajima, N.; Tanaka, A.; Kotani, H.; Nomura, N.; Ohara, O.: Prediction of the coding sequences of unidentified human genes. IX. The complete sequences of 100 new cDNA clones from brain which can code for large proteins in vitro. DNA Res. 5: 31–39, 1998.
300. den Dunnen, J. T.; Grootscholten, P. M.; Bakker, E.; Blonden, L. A. J.; Ginjaar, H. B.; Wapenaar, M. C.; van Paassen, H. M. B.; van Broeckhoven, C.; Pearson, P. L.; van Ommen, G. J. B.: Topography of the Duchenne muscular dystrophy (DMD) gene: FIGE and cDNA analysis of 194 cases reveals 115 deletions and 13 duplications. Am. J. Hum. Genet. 45: 835–847, 1989.
301. Vanhalst, K.; Kools, P.; Eynde, E. V.; van Roy, F.: The human and murine protocadherin-beta one-exon gene families show high evolutionary conservation, despite the difference in gene number. FEBS Lett. 495:120–125, 2001.
302. Goldowitz, D.; Smeyne, R. J.: Tune into the weaver channel. Nature Genet. 11: 107–109, 1995.
303. Hess, E. J.: Identification of the weaver mouse mutation: the end of the beginning. Neuron 16: 1073–1076, 1996.
304. Lane, P. W.: New mutation: Weaver, wv. Mouse News Letter 32–33,1964.
305. Lesage, F.; Duprat, F.; Fink, M.; Guillemare, E.; Coppola, T.; Lazdunski, M.; Hugnot, J.-P.: Cloning provides evidence for a family of inward rectifier and G-protein coupled K(+) channels in the brain. FEBS Lett. 353: 37–42, 1994.
306. Rakic, P.; Sidman, R. L.: Sequence of developmental abnormalities leading to granule cell deficit in cerebellar cortex of weaver mutant mice. J. Comp. Neurol. 152: 103–132, 1973.
307. Sakura, H.; Bond, C.; Warren-Perry, M.; Horsley, S.; Kearney, L.; Tucker, S.; Adelman, J.; Turner, R.; Ashcroft, F. M.: Characterization and variation of a human inwardly rectifying K-channel gene (KCNJ6): a putative ATP sensitive K-channel subunit. FEBS Lett. 367: 193–197, 1995.
308. Tsaur, M.-L.; Menzel, S.; Lai, F.-P.; Espinosa, R., III; Concannon, P.; Spielman, R. S.; Hanis, C. L.; Cox, N. J.; Le Beau, M. M.; German, M. S.; Jan, L. Y.; Bell, G. I.; Stoffel, M.: Isolation of a cDNA clone encoding a K(ATP) channel-like protein expressed in insulin-secreting cells, localization of the human gene to chromosome band 21q22.1 and linkage studies with NIDDM. Diabetes 44: 592–596, 1995.
309. Yasuda, K.; Sakura, H.; Mori, Y.; Iwamoto, K.; Shimokawa, K.; Kadowaki, H.; Hagura, R.; Akanuma, Y.; Adelman, J. P.; Yazaki, Y.; Ashcroft, F. M.; Kadowaki, T.: No evidence for mutations in a putative subunit of the beta-cell ATP-sensitive potassium channel (K-ATP channel) in Japanese NIDDM patients. Biochem. Biophys. Res. Commun. 211:1036–1040, 1995.
310. Gospe, S. M., Jr.; Lazaro, R. P.; Lava, N. S.; Grootscholten, P. M.; Scott, M. O.; Fischbeck, K. H.: Familial X-linked myalgia and cramps: a nonprogressive myopathy associated with a deletion in the dystrophin gene. Neurology 39: 1277–1280, 1989.
311. Kingston, H. M.; Sarfarazi, M.; Thomas, N. S. T.; Harper, P. S.: Localisation of the Becker muscular dystrophy gene on the shortarm of the X chromosome by linkage to cloned DNA sequences. Hum. Genet. 67: 6–17, 1984.
312. Kingston, H. M.; Thomas, N. S. T.; Pearson, P. L.; Sarfarazi, M.; Harper, P. S.: Genetic linkage between Becker muscular dystrophy and a polymorphic DNA sequence on the short arm of the X chromosome. J. Med. Genet. 20: 255–258, 1983.
313. Acampora, D.; Postiglione, M. P.; Avantaggiato, V.; Di Bonito, M.; Vaccarino, F. M.; Michaud, J.; Simeone, A.: Progressive impairment of developing neuroendocrine cell lineages in the hypothalamus of mice lacking the Orthopedia gene. Genes Dev. 13: 2787–2800, 1999.
314. Lin, X.; State, M. W.; Vaccarino, F. M.; Greally, J.; Hass, M.; Leckman, J. F.: Identification, chromosomal assignment, and expression analysis of the human homeodomain-containing gene Orthopedia (OTP). Genomics 60:96–104, 1999.
315. Fernandes-Alnemri, T.; Armstrong, R. C.; Krebs, J.; Srinivasula, S. M.; Wang, L.; Bullrich, F.; Fritz, L. C.; Trapani, J. A.; Tomaselli, K. J.; Litwack, G.; Alnemri, E. S.: In vitro activation of CPP32 and Mch3 by Mch4, a novel human apoptotic cysteine protease containing two FADD-like domains. Proc. Nat. Acad. Sci. 93: 7464–7469, 1996.
316. Fernandes-Alnemri, T.; Litwack, G.; Alnemri, E. S.: CPP32, a novel human apoptotic protein with homology to *Caenorhabditis elegans* cell death protein Ced-3 and mammalian interleukin-1 beta-converting enzyme. J. Biol. Chem. 269: 30761–30764, 1994.
317. Fernando, P.; Kelly, J. F.; Balazsi, K.; Slack, R. S.; Megeney, L. A.: Caspase 3 activity is required for skeletal muscle differentiation. Proc. Nat. Acad. Sci. 99: 11025–11030, 2002.
318. Huang, Y.; Shin, N.-H.; Sun, Y.; Wang, K. K. W.: Molecular cloning and characterization of a novel caspase-3 variant that attenuates apoptosis induced by proteasome inhibition. Biochem. Biophys. Res. Commun. 283: 762–769, 2001.
319. Kuida, K.; Zheng, T. S.; Na, S.; Kuan, C.; Yang, D.; Karasuyama, H.; Rakio, P.; Flavell, R. A.: Decreased apoptosis in the brain and premature lethality in CPP32-deficient mice. Nature 384: 368–372, 1996.
320. Levkau, B.; Koyama, H.; Raines, E. W.; Clurman, B. E.; Herren, B.; Orth, K.; Roberts, J. M.; Ross, R.: Cleavage of p21(Cip1/Waf1) and p27(Kip1) mediates apoptosis in endothelial cells through activation of Cdk2: role of a caspase cascade. Molec. Cell 1: 553–563, 1998.
321. Nasir, J.; Theilmann, J. L.; Chopra, V.; Jones, A. M.; Walker, D.; Rasper, D. M.; Vaillancourt, J. P.; Hewitt, J.

E.; Nicholson, D. W.; Hayden, M. R.: Localization of the cell death genes CPP32 and Mch-2 to human chromosome 4q. Mammalian Genome 8: 56–59, 1997.
322. Tiso, N.; Pallavicini, A.; Muraro, T.; Zimbello, R.; Apolloni, E.; Valle, G.; Lanfranchi, G.; Danieli, G. A.: Chromosomal localization of the human genes, CPP32, Mch2, Mch3, and Ich-1, involved in cellular apoptosis. Biochem. Biophys. Res. Commun. 225: 983–989, 1996.
323. Woo, M.; Hakem, R.; Soengas, M. S.; Duncan, G. S.; Shahinian, A.; Kagi, K.; Hakem, A.; McCurrach, M.; Khoo, W.; Kaufman, S. A.; Senaldi, G.; Howard, T.; Lowe, S. W.; Mak, T. W.: Essential contribution of caspase 3/CPP32 to apoptosis and its associated nuclear changes. Genes Dev. 12: 806–819, 1998.
324. Nicholson, D. W.; Ali, A.; Thornberry, N. A.; Vaillancourt, J. P.; Ding, C. K.; Gallant, M.; Gareau, Y.; Griffin, P. R.; Labelle, M.; Lazebnik, Y. A.; Munday, N. A.; Raju, S. M.; Smulson, M. E.; Yamin, T.-T.; Yu, V. L.; Miller, D. K.: Identification and inhibition of the ICE/CED-3 protease necessary for mammalian apoptosis. Nature 376: 37–43, 1995. MEDLINE UID: 95319529
325. Geurts, J. M. W.; Schoenmakers, E. F. P. M.; Roijer, E.; Astrom, A.-K.; Stenman, G.; van de Ven, W. J. M.: Identification of NFIB as recurrent translocation partner gene of HMGIC in pleomorphic adenomas. Oncogene 16:865–872, 1998.
326. Becker, P. E.: Two new families of benign sex-linked recessive muscular dystrophy. Rev. Canad. Biol. 21: 551–566, 1962.
327. Becker, P. E.: Eine neue X-chromosomale Muskeldystrophie. ActaPsychiat. Neurol. Scand. 193: 427, 1955.
328. Becker, P. E.: Neue Ergebnisse der Genetik der Muskeldystrophien. ActaGenet. Statist. Med. 7: 303–310, 1957.
329. Bushby, K. M. D.; Cleghorn, N. J.; Curtis, A.; Haggerty, I. D.; Nicholson, L. V. B.; Johnson, M. A.; Harris, J. B.; Bhattacharya, S. S.: Identification of a mutation in the promoter region of the dystrophin gene in a patient with a typical Becker muscular dystrophy. Hum. Genet. 88: 195–199, 1991.
330. Doriguzzi, C.; Palmucci, L.; Mongini, T.; Chiado-Piat, L.; Restagno, G.; Ferrone, M.: Exercise intolerance and recurrent myoglobinuria as the only expression of Xp21 Becker type muscular dystrophy. J. Neurol. 240: 269–271, 1993.
331. England, S. B.; Nicholson, L. V. B.; Johnson, M. A.; Forrest, S. M.; Love, D. R.; Zubrzycka-Gaarn, E. E.; Bulman, D. E.; Harris, J. B.; Davies, K. E.: Very mild muscular dystrophy associated with the deletion of 46% dystrophin. Nature 343: 180–182, 1990.
332. Bodrug, S. E.; Ray, P. N.; Gonzalez, I. L.; Schmickel, R. D.; Sylvester, J. E.; Worton, R. G.: Molecular analysis of a constitutional X-autosome translocation in a female with muscular dystrophy. Science 237:1620–1624, 1987.
333. Boyce, F. M.; Beggs, A. H.; Feener, C.; Kunkel, L. M.: Dystrophin is transcribed in brain from a distant upstream promoter. Proc. Nat. Acad. Sci. 88: 1276–1280, 1991.
334. Boyd, Y.; Buckle, V. J.: Cytogenetic heterogeneity of translocations associated with Duchenne muscular dystrophy. Clin. Genet. 29: 108–115,1986.
335. Bulman, D. E.; Gangopadhyay, S. B.; Bebchuck, K. G.; Worton, R. G.; Ray, P. N.: Point mutation in the human dystrophin gene: identification through Western blot analysis. Genomics 10: 457–460, 1991.
336. Burke, J. F.; Mogg, A. E.: Suppression of a nonsense mutation in mammalian cells in vivo by the aminoglycoside antibiotics G-418 and paromomycin. Nucleic Acids Res. 13: 6265–6272, 1985.
337. Burnette, W. N.: 'Western blotting': electrophoretic transfer of proteins from sodium dodecyl sulfate polyacrylamide gels to unmodified nitrocellulose and radiographic detection with antibody and radioiodinated protein A. Anal. Biochem. 112: 195–203, 1981.
338. Chamberlain, J. S.; Pearlman, J. A.; Muzny, D. M.; Gibbs, R. A.; Ranier, J. E.; Reeves, A. A.; Caskey, C. T.: Expression of the murine Duchenne muscular dystrophy gene in muscle and brain. Science 239:1416–1418, 1988.
339. Chelly, J.; Concordet, J.-P.; Kaplan, J.-C.; Kahn, A.: Illegitimate transcription: transcription of any gene in any cell type. Proc. Nat. Acad. Sci. 86: 2617–2621, 1989.
340. Chelly, J.; Gilgenkrantz, H.; Hugnot, J. P.; Hamard, G.; Lambert, M.; Recan, D.; Akli, S.; Cometto, M.; Kahn, A.; Kaplan, J. C.: Illegitimate transcription: application to the analysis of truncated transcripts of the dystrophin gene in nonmuscle cultured cells from Duchenne and Becker patients. J. Clin. Invest. 88: 1161–1166, 1991.
341. Chelly, J.; Hamard, G.; Koulakoff, A.; Kaplan, J.-C.; Kahn, A.; Berwald-Netter, Y.: Dystrophin gene transcribed from different promoters in neuronal and glial cells. Nature 344: 64–65, 1990.
342. Chelly, J.; Kaplan, J.-C.; Maire, P.; Gautron, S.; Kahn, A.: Transcription of the dystrophin gene in human muscle and non-muscle tissues. Nature 333: 858–860, 1988.
343. Clemens, P. R.; Ward, P. A.; Caskey, C. T.; Bulman, D. E.; Fenwick, R. G.: Premature chain termination mutation causing Duchenne muscular dystrophy. Neurology 42: 1775–1782, 1992.
344. Cooper, B. J.; Valentine, B. A.; Wilson, S.; Patterson, D. F.; Concannon, P. W.: Canine muscular dystrophy: confirmation of X-linked inheritance. J. Hered. 79: 405–408, 1988.
345. Covone, A. E.; Lerone, M.; Romeo, G.: Genotype phenotype correlation and germline mosaicism in DMD/BMD patients with deletions of the dystrophin gene. Hum. Genet. 87: 353–360, 1991.
346. Cox, G. A.; Cole, N. M.; Matsumura, K.; Phelps, S. F.; Hauschka, S. D.; Campbell, K. P.; Faulkner, J. A.; Chamberlain, J. S.: Overexpression of dystrophin in transgenic mdx mice eliminates dystrophic symptoms without toxicity. Nature 364: 725–729, 1993.
347. Cox, G. A.; Sunada, Y.; Campbell, K. P.; Chamberlain, J. S.: Dp71 can restore the dystrophin-associated glycoprotein complex in muscle but fails to prevent dystrophy. Nature Genet. 8: 333–339, 1994.
348. Comi, G. P.; Ciafaloni, E.; de Silva, H. A. R.; Prelle, A.; Bardoni, A.; Rigoletto, C.; Robotti, M.; Bresolin, N.; Moggio, M.; Fortunato, F.; Ciscato, P.; Turconi, A.; Rose, A. D.; Scarlato, G.: A G(+1)-to-A transversion at the 5-prime splice site of intron 69 of the dystrophin gene causing the absence of peripheral nerve Dp116 and severe clinical involvement in a DMD patient. Hum. Molec. Genet. 4: 2171–2174, 1995.
349. Crawford, G. E.; Lu, Q. L.; Partridge, T. A.; Chamberlain, J. S.: Suppression of revertant fibers in mdx mice by expression of a functional dystrophin. Hum. Molec. Genet. 10: 2745–2750, 2001.
350. Darras, B. T.; Blattner, P.; Harper, J. F.; Spiro, A. J.; Alter, S.; Francke, U.: Intragenic deletions in 21 Duchenne muscular dystrophy(DMD)/Becker muscular dystrophy (BMD) families studied with the dystrophin cDNA: location of breakpoints on HindIII and BglII exon-containing fragment maps, meiotic and mitotic origin of the mutations. Am. J. Hum. Genet. 43: 620–629, 1988.
351. Darras, B. T.; Francke, U.: Normal human genomic restriction-fragment patterns and polymorphisms 351. revealed by hybridization with the entire dystrophin cDNA. Am. J. Hum. Genet. 43: 612–619, 1988.

352. Darras, B. T.; Francke, U.: A partial deletion of the muscular dystrophy gene transmitted twice by an unaffected male. Nature 329:556–558, 1987.

353. Davies, K. E.; Smith, T. J.; Bundey, S.; Read, A. P.; Flint, T.; Bell, M.; Speer, A.: Mild and severe muscular dystrophy associated with deletions in Xp21 of the human X chromosome. J. Med. Genet. 25:9–13, 1988.

354. De Angelis, F. G.; Sthandier, O.; Berarducci, B.; Toso, S.; Galluzzi, G.; Ricci, E.; Cossu, G.; Bozzoni, I.: Chimeric snRNA molecules carrying antisense sequences against the splice junctions of exon 51 of the dystrophin pre-mRNA induce exon skipping and restoration of a dystrophin synthesis in delta-48–50 DMD cells. Proc Nat. Acad. Sci. 99: 9456–9461, 2002.

355. den Dunnen, J. T.; Bakker, E.; Klein Breteler, E. G.; Pearson, P. L.; van Ommen, G. J. B.: Direct mutation of more than 50% of the Duchenne muscular dystrophy mutations by field inversion gels. Nature 329:640–642, 1987.

356. Dickson, G.; Pizzey, J. A.; Elsom, V. E.; Love, D.; Davies, K. E.; Walsh, F. S.: Distinct dystrophin mRNA species are expressed in embryonic and adult mouse skeletal muscle. FEBS Lett. 242: 47–52,1988.

357. Dominguez-Steglich, M.; Meng, G.; Bettecken, T.; Muller, C. R.; Schmid, M.: The dystrophin gene is autosomally located on a microchromosome in chicken. Genomics 8: 536–540, 1990.

358. Doolittle, R. F.: Similar amino acid sequences: chance or commonancestry? Science 214: 149–159, 1981.

359. Dubrovsky, A. L.; Taratuto, A. L.; Sevlever, G.; Schultz, M.; Pegoraro, E.; Hoop, R. C.; Hoffman, E. P.: Duchenne muscular dystrophy and myotonic dystrophy in the same patient. Am. J. Med. Genet. 55:342–348, 1995.

360. Emery, A. E. H.: Duchenne Muscular Dystrophy. Oxford, UK: Oxford University Press (pub.) (2nd ed.): 1993.

361. Fabb, S. A.; Wells, D. J.; Serpente, P.; Dickson, G.: Adeno-associated virus vector gene transfer and sarcolemmal expression of a 144 kDa micro-dystrophin effectively restores the dystrophin-associated protein complex and inhibits myofibre degeneration in nude/mdx mice. Hum. Molec. Genet. 11: 733–741, 2002.

362. Feener, C. A.; Boyce, F. M.; Kunkel, L. M.: Rapid detection of CA polymorphisms in cloned DNA: application to the 5-prime region of the dystrophin gene. Am. J. Hum. Genet. 48: 621–627, 1991.

363. Ferlini, A.; Galie, N.; Merlini, L.; Sewry, C.; Branzi, A.; Muntoni, F.: A novel Alu-like element rearranged in the dystrophin gene causes a splicing mutation in a family with X-linked dilated cardiomyopathy. Am. J. Hum. Genet. 63: 436–446, 1998.

364. Finnegan, D. J.: Eukaryotic transposable elements and genome evolution. Trends Genet. 5: 103–107, 1989.

365. Forrest, S. M.; Cross, G. S.; Speer, A.; Gardner-Medwin, D.; Burn, J.; Davies, K. E.: Preferential deletion of exons in Duchenne and Becker muscular dystrophies. Nature 329: 638–640, 1987.

366. Francke, U.; Ochs, H. D.; de Martinville, B.; Giacalone, J.; Lindgren, V.; Disteche, C.; Pagon, R. A.; Hofker, M. H.; van Ommen, G.-J. B.; Pearson, P. L.; Wedgwood, R. J.: Minor Xp21 chromosome deletion in a male associated with expression of Duchenne muscular dystrophy, chronic granulomatous disease, retinitis pigmentosa, and McLeod syndrome. Am. J. Hum. Genet. 37: 250–267, 1985.

367. Furst, D.; Nave, R.; Osborn, M.; Weber, K.; Bardosi, A.; Archidiacono, N.; Ferro, M.; Romano, V.; Romeo, G.: Nebulin and titin expression in Duchenne muscular dystrophy appears normal. FEBS Lett. 224: 49–53,1987.

368. Giacalone, J. P.; Francke, U.: Common sequence motifs at there arrangement sites of a constitutional X/autosome translocation and associated deletion. Am. J. Hum. Genet. 50: 725–741, 1992.

369. Gillard, E. F.; Chamberlain, J. S.; Murphy, E. G.; Duff, C. L.; Smith, B.; Burghes, A. H. M.; Thompson, M. W.; Sutherland, J.; Oss, I.; Bodrug, S. E.; Klamut, H. J.; Ray, P. N.; Worton, R. G.: Molecular and phenotypic analysis of patients with deletions within the deletion-rich region of the Duchenne muscular dystrophy (DMD) gene. Am. J. Hum. Genet. 45: 507–520, 1989.

370. Ginjaar, I. B.; Kneppers, A. L. J.; Meulen, J.-D. M.; Anderson, L. V. B.; Bremmer-Bout, M.; van Deutekom, J. C. T.; Weegenaar, J.; den Dunnen, J. T.; Bakker, E.: Dystrophin nonsense mutation induces different levels of exon 29 skipping and leads to variable phenotypes within one BMD family. Europ. J. Hum. Genet. 8: 793–796, 2000.

371. Greenberg, D. S.; Sunada, Y.; Campbell, K. P.; Yaffe, D.; Nudel, U.: Exogenous Dp71 restores the levels of dystrophin associated proteins but does not alleviate muscle damage in mdx mice. Nature Genet. 8:340–344, 1994.

372. Gussoni, E.; Soneoka, Y.; Strickland, C. D.; Buzney, E. A.; Khan, M. K.; Flint, A. F.; Kunkel, L. M.; Mulligan, R. C.: Dystrophin expression in the mdx mouse restored by stem cell transplantation. Nature 401:390–394, 1999.

373. Hagiwara, Y.; Mizuno, Y.; Takemitsu, M.; Matsuzaki, T.; Nonaka, I.; Ozawa, E.: Dystrophin-positive muscle fibers following C2 myoblast transplantation into mdx nude mice. Acta Neuropath. 90: 592–600, 1995.

374. Hagiwara, Y.; Nishio, H.; Kitoh, Y.; Takeshima, Y.; Narita, N.; Wada, H.; Yokoyama, M.; Nakamura, H.; Matsuo, M.: A novel point mutation(G(−1) to T) in a 5-prime splice donor site of intron 13 of the dystrophin gene results in exon skipping and is responsible for Becker muscular dystrophy. Am. J. Hum. Genet. 54: 53–61, 1994.

375. Hammonds, R. G., Jr.: Protein sequence of DMD gene is related to actin-binding domain of alpha-actinin. (Letter) Cell 51: 1, 1987.

376. Harper, S. Q.; Hauser, M. A.; DelloRusso, C.; Duan, D.; Crawford, R. W.; Phelps, S. F.; Harper, H. A.; Robinson, A. S.; Engelhardt, J. F.; Brooks, S. V.; Chamberlain, J. S.: Modular flexibility of dystrophin: implications for gene therapy of Duchenne muscular dystrophy. Nature Med. 8: 253–261, 2002.

377. Hart, K. A.; Hodgson, S.; Walker, A.; Cole, C. G.; Johnson, L.; Dubowitz, V.; Bobrow, M.: DNA deletions in mild and severe Becker muscular dystrophy. Hum. Genet. 75: 281–285, 1987.

378. Hodgson, S. V.; Abbs, S.; Clark, S.; Manzur, A.; Heckmatt, J. Z. H.; Dubowitz, V.; Bobrow, M.: Correlation of clinical and deletion data in Duchenne and Becker muscular dystrophy, with special reference to mental ability. Neuromusc. Disord. 2: 269–276, 1992.

379. Hoffman, E. P.; Brown, R. H., Jr.; Kunkel, L. M.: The protein product of the Duchenne muscular dystrophy locus. Cell 51: 919–928,1987.

380. Hoffman, E. P.; Knudson, C. M.; Campbell, K. P.; Kunkel, L. M.: Subcellular fractionation of dystrophin to the triads of skeletal muscle. Nature 330: 754–758, 1987.

381. Hoffman, E. P.; Monaco, A. P.; Feener, C. C.; Kunkel, L. M.: Conservation of the Duchenne muscular dystrophy gene in mice and humans. Science 238:347–350, 1987.

382. Hoop, R. C.; Russo, L. S.; Riconda, D. L.; Schwartz, L. S.; Hoffman, E. P.: Restoration of half the normal dystrophin sequence in a double-deletion Duchenne muscular dystrophy family. Am. J. Med. Genet. 49: 323–327, 1994.

383. Hoffman, E. P.; Fischbeck, K. H.; Brown, R. H.; Johnson, M.; Medori, R.; Loike, J. D.; Harris, J. B.; Waterston, R.; Brooke, M.; Specht, L.; Kupsky, W.; Chamberlain, J.; Caskey, C. T.; Shapiro, F.; Kunkel, L. M.: Characterization of dystrophin in muscle-biopsy specimens from patients with Duchenne's or Becker's muscular dystrophy. New Eng. J. Med. 318: 1363–1368, 1988.

384. Howard, P. L.; Dally, G. Y.; Wong, M. H.; Ho, A.; Weleber, R. G.; Pillers, D.-A. M.; Ray, P. N.: Localization of dystrophin isoform Dp71 to the inner limiting membrane of the retina suggests a unique functional contribution of Dp71 in the retina. Hum. Molec. Genet. 7:1385–1391, 1998.

385. Hu, X.; Burghes, A. H. M.; Bulman, D. E.; Ray, P. N.; Worton, R. G.: Evidence for mutation by unequal sister chromatid exchange in the Duchenne muscular dystrophy gene. Am. J. Hum. Genet. 44:855–863, 1989.

386. Kedra, D.; Pan, H.-Q.; Seroussi, E.; Fransson, I.; Guilbaud, C.; Collins, J. E.; Dunham, I.; Blennow, E.; Roe, B. A.; Piehl, F.; Dumanski, J. P.: Characterization of the human synaptogyrin gene family. Hum. Genet. 103: 131–141, 1998.

387. Fischle, W.; Emiliani, S.; Hendzel, M. J.; Nagase, T.; Nomura, N.; Voelter, W.; Verdin, E.: A new family of human histone deacetylases related to Saccharomyces cerevisiae HDA1p. J. Biol. Chem. 274: 11713–11720, 1999.

388. Pazin, M. J.; Kadonaga, J. T.: What's up and down with histonedeacetylation and transcription? Cell 89: 325–328, 1997.

389. Uchiumi, T.; Hinoshita, E.; Haga, S.; Nakamura, T.; Tanaka, T.; Toh, S.; Furukawa, M.; Kawabe, T.; Wada, M.; Kagotani, K.; Okumura, K.; Kohno, K.; Akiyama, S.; Kuwano, M.: Isolation of a novel human canalicular multi-specific organic anion transporter, cMOAT2/MRP3, and its expression in cisplatin-resistant cancer cells with decreased ATP-dependent drug transport. Biochem. Biophys. Res. Commun. 252:103–110, 1998.

390. Arriza, J. L.; Kavanaugh, M. P.; Fairman, W. A.; Wu, Y.-N.; Murdoch, G. H.; North, R. A.; Amara, S. G.: Cloning and expression of a human neutral amino acid transporter with structural similarity to the glutamate transporter gene family. J. Biol. Chem. 268: 15329–15332, 1993.

391. Hofmann, K.; Duker, M.; Fink, T.; Lichter, P.; Stoffel, W.: Human neutral amino acid transporter ASCT1: structure of the gene (SLC1A4) and localization to chromosome 2 p13–p15. Genomics 24: 20–26, 1994.

392. Shafqat, S.; Tamarappoo, B. K.; Kilberg, M. S.; Puranam, R. S.; McNamara, J. O.; Guadano-Ferraz, A.; Fremeau, R. T., Jr.: Cloning and expression of a novel Na(+)-dependent neutral amino acid transporter structurally related to mammalian Na(+)/glutamate cotransporters. J. Biol. Chem. 268: 15351–15355, 1993.

393. Zerangue, N.; Kavanaugh, M. P.: ASCT-1 is a neutral amino acid exchanger with chloride channel activity. J. Biol. Chem. 271: 27991–27994, 1996.

394. Schwientek, T.; Nomoto, M.; Levery, S. B.; et al: Control of O-glycanbranch formation. J. Biol. Chem. 274: 4504–4512, 1999.

395. Nonaka, S.; Tanaka, Y.; Okada, Y.; Takeda, S.; Harada, A.; Kanai, Y.; Kido, M.; Hirokawa, N.: Randomization of left-right a symmetry due to loss of nodal cilia generating leftward flow of extra embryonic fluid in mice lacking KIF3B motor protein. Cell 95: 829–837, 1998.

396. Yamazaki, H.; Nakata, T.; Okada, Y.; Hirokawa, N.: KIF3A/B: a heterodimeric kinesin superfamily protein that works as a microtubule plus end-directed motor for membrane organelle transport. J. CellBiol. 130: 1387–1399, 1995.

397. Akao, Y.; Matsuda, Y.: Identification and chromosome mapping of the mouse homologue of the human gene (DDX6) that encodes a putative RNA helicase of the DEAD box protein family. Cytogenet. Cell Genet. 75:38–44, 1996.

398. Akao, Y.; Seto, M.; Takahashi, T.; Kubonishi, I.; Miyoshi, I.; Nakazawa, S.; Tsujimoti, Y.; Croce, C. M.; Ueda, R.: Molecular cloning of the chromosomal breakpoint of a B-cell lymphoma with the t(11; 14)(q23;q32) chromosome translocation. Cancer Res. 51: 1574–1576, 1991.

399. Akao, Y.; Seto, M.; Yamamoto, K.; Iida, S.; Nakazawa, S.; Inazawaj.; Abe, T.; Takahashi, T.; Ueda, R.: The RCK gene associated with t(11;14) translocation is distinct from the MLL/ALL-1 gene with t(4;11) and t(11; 19) translocations. Cancer Res. 52: 6083–6087, 1992.

400. Akao, Y.; Tsujimoto, Y.; Finan, J.; Nowell, P. C.; Croce, C. M.: Molecular characterization of a t(11;14)(q23;q32) chromosome translocation in a B-cell lymphoma. Cancer Res. 50: 4856–4859, 1990.

401. Lu, D.; Yunis, J. J.: Cloning, expression and localization of an RNA helicase gene from a human lymphoid cell line with chromosomal breakpoint 11q23.3. Nucleic Acids Res. 20: 1967–1972, 1992.

402. Seto, M.; Yamamoto, K.; Takahashi, T.; Ueda, R.: Cloning and expression of a murine cDNA homologous to the human RCK/P54, a lymphoma-linked chromosomal translocation junction gene on 11q23. Gene 166: 293–296, 1995.

403. Tunnacliffe, A.; Perry, H.; Radice, P.; Budarf, M. L.; Emanuel, B. S.: A panel of sequence tagged sites for chromosome band 11q23. Genomics 17:744–747, 1993.

404. Abbs, S.; Roberts, R. G.; Mathew, C. G.; Bentley, D. R.; Bobrow, M.: Accurate assessment of intragenic recombination frequency within the Duchenne muscular dystrophy gene. Genomics 7: 602–606, 1990.

405. Ahn, A. H.; Kunkel, L. M.: The structural and functional diversity of dystrophin. Nature Genet. 3: 283–291, 1993.

406. Alwine, J. C.; Kemp, D. J.; Stark, G. R.: Method for detection of specific RNAs in agarose gels by transfer to diazobenzyloxymethyl-paper and by hybridization with DNA probes. Proc. Nat. Acad. Sci. 74:5350–5354, 1977.

407. Angelini, C.; Beggs, A. H.; Hoffman, E. P.; Fanin, M.; Kunkel, L. M.: Enormous dystrophin in a patient with Becker muscular dystrophy. Neurology 40:808–812, 1990.

408. Badorff, C.; Berkely, N.; Mehrotra, S.; Talhouk, J. W.; Rhoads, R. E.; Knowlton, K. U.: Enteroviral protease 2A directly cleaves dystrophin and is inhibited by a dystrophin based substrate analogue. J. Biol. Chem. 275: 11191–11197, 2000.

409. Badorff, C.; Lee, G.-H.; Lamphear, B. J.; Martone, M. E.; Campbell, K. P.; Rhoads, R. E.; Knowlton, K. U.:

Enteroviral protease 2A cleaves dystrophin: evidence of cytoskeletal disruption in an acquired cardiomyopathy. NatureMed. 5: 320–326, 1999.

410. Bakker, E.; Pearson, P. L.: Mutation of the Duchenne muscular dystrophy gene associated with meiotic recombination. (Letter) Clin. Genet. 30: 347–349, 1986.

411. Bakker, E.; Hofker, M. H.; Goor, N.; Mandel, J. L.; Wrogemann, K.; Davies, K. E.; Kunkel, L. M.; Willard, H. F.; Fenton, W. A.; Sandkuyl, L.; Majoor-Krakauer, D.; van Essen, A. J.; Jahoda, M. G. J.; Sachs, E. S.; van Ommen, G. J. B.; Pearson, P. L.: Prenatal diagnosis and carrier detection of Duchenne muscular dystrophy with closely linked RFLPs. Lancet I: 655–658, 1985.

412. Bakker, E.; Van Broeckhoven, C.; Bonten, E. J.; van de Vooren, M. J.; Veenema, H.; Van Hul, W.; Van Ommen, G. J. B.; Vandenberghe, A.; Pearson, P. L.: Germline mosaicism and Duchenne muscular dystrophy mutations. Nature 329: 554–556, 1987.

413. Bar, S.; Barnea, E.; Levy, Z.; Neuman, S.; Yaffe, D.; Nudel, U.: A novel product of the Duchenne muscular dystrophy gene which greatly differs from the known isoforms in its structure and tissue distribution. Biochem. J. 272: 557–560, 1990.

414. Barbieri, A. M.; Soriani, N.; Tubiello, G. M.; Ferrari, M.; Carrera, P.: A nonsense mutation (gln-673-term) in exon 17 of the human dystrophin gene detected by heteroduplex analysis. Hum. Genet. 96: 343–344, 1995.

415. Bartlett, R. J.; Pericak-Vance, M. A.; Koh, J.; Yamaoka, L. H.; Chen, J. C.; Hung, W.-Y.; Speer, M. C.; Wapenaar, M. C.; Van Ommen, G. J. B.; Bakker, E.; Pearson, P. L.; Kandt, R. S.; Siddique, T.; Gilbert, J. R.; Lee, J. E.; Sirotkin-Roses, M. J.; Roses, A. D.: Duchenne muscular dystrophy: high frequency of deletions. Neurology 38:1–4, 1988.

416. Barton-Davis, E. R.; Cordier, L.; Shoturma, D. I.; Leland, S. E.; Sweeney, H. L.: Aminoglycoside antibiotics restore dystrophin function to skeletal muscles of mdx mice. J. Clin. Invest. 104:375–381, 1999.

417. Bastianutto, C.; Bestard, J. A.; Lahnakoski, K.; Broere, D.; DeVisser, M.; Zaccolo, M.; Pozzan, T.; Ferlini, A.; Muntoni, F.; Patarnello, T.; Klamut, H. J.: Dystrophin muscle enhancer 1 is implicated in the activation of nonmuscle isoforms in the skeletal muscle of patients with X-linked dilated cardiomyopathy. Hum. Molec. Genet. 10: 2627–2635, 2001.

418. Baumbach, L. L.; Chamberlain, J. S.; Ward, P. A.; Farwell, N. J.; Caskey, C. T.: Molecular and clinical correlation of deletion leading to Duchenne and Becker muscular dystrophies. Neurology 39:465–474, 1989.

419. Baumbach, L. L.; Ward, P. A.; Fenwick, R.; Caskey, C. T.: Analysis of mutations at the Duchenne muscular dystrophy locus provides no evidence for illegitimate recombination in deletion formation. (Abstract) Am. J. Hum. Genet. 45 (suppl.): A173, 1989.

420. Beggs, A. H.; Koenig, M.; Boyce, F. M.; Kunkel, L. M.: Detection of 98% of DMD/BMD gene deletions by polymerase chain reaction. Hum. Genet. 86: 45–48, 1990.

421. Berko, B. A.; Swift, M.: X-linked dilated cardiomyopathy. New Eng. J. Med. 316: 1186–1191, 1987.

422. Bettecken, T.; Muller, C. R.: Identification of a 220-kb insertion into the Duchenne gene in a family with an atypical course of muscular dystrophy. Genomics 4: 592–596, 1989.

423. Bies, R. D.: X-linked dilated cardiomyopathy. (Letter) New Eng. J. Med. 330: 368–369, 1994.

424. Bies, R. D.; Caskey, C. T.; Fenwick, R.: An intact cysteine-rich domain is required for dystrophin function. J. Clin. Invest. 90:666–672, 1992.

425. Bittner, R. E.; Streubel, B.; Shorny, S.; Schaden, G.; Voit, T.; Hoger, H.: Coisogenic all-plus-one immunization: a model for identifying missing proteins in null-mutant conditions. Antibodies to dystrophin in mdx mouse after transplantation of muscle from normal coisogenic donor. Neuropediatrics 25: 176–182, 1994.

426. Abuladze, N.; Lee, I.; Newman, D.; Hwang, J.; Boorer, K.; Pushkin, A.; Kurtz, I.: Molecular cloning, chromosomal localization, tissue distribution, and functional expression of the human pancreatic sodium bicarbonate cotransporter. J. Biol. Chem. 273: 17689–17695, 1998.

427. Burnham, C. E.; Amlal, H.; Wang, Z.; Shull, G. E.; Soleimani, M.: Cloning and functional expression of a human kidney Na+: HCO3− cotransporter. J. Biol. Chem. 272: 19111–19114, 1997.

428. Choi, I.; Romero, M. F.; Khandoudi, N.; Bril, A.; Boron, W. F.: Cloning and characterization of a human electrogenic Na(+)-HCO(3−)cotransporter isoform (hh-NBC). Am. J. Physiol. 276: C576–C584, 1999.

429. Igarashi, T.; Inatomi, J.; Sekine, T.; Cha, S. H.; Kanai, Y.; Kunimi, M.; Tsukamoto, K.; Satoh, H.; Shimadzu, M.; Tozawa, F.; Mori, T.; Shiobara, M.; Seki, G.; Endou, H.: Mutations in SLC4A4 cause permanent isolated proximal renal tubular acidosis with ocular abnormalities. (Letter) Nature Genet. 23: 264–265, 1999.

430. Romero, M. F.; Boron, W. F.: Electrogenic Na(+)/HCO (3−) cotransporters: cloning and physiology. Annu. Rev. Physiol. 61: 699–723, 1999.

431. Soleimani, M.; Burnham, C. E.: Physiologic and molecular aspects of the Na(+):HCO(3−) cotransporter in health and disease processes. Kidney int. 57: 371–384, 2000.

432. Usui, T.; et al.; et al.: Pflugers Arch. 438: 458–462, 1999.

433. Hirohata, S.; Seldin, M. F.; Apte, S. S.: Chromosomal assignment of two ADAM genes, TACE (ADAM17) and MLTNB (ADAM19), to human chromosomes2 and 5, respectively, and of Mltnb to mouse chromosome 11. Genomics 54:178–179, 1998.

434. Inoue, D.; Reid, M.; Lum, L.; Kratzschmar, J.; Weskamp, G.; Myung, Y. M.; Baron, R.; Blobel, C. P.: Cloning and initial characterization of mouse meltrin beta and analysis of the expression of four metalloprotease-disintegrins in bone cells. J. Biol. Chem. 273: 4180–4187, 1998.

435. Kools, P.; Van Imschoot, G.; van Roy, F.: Characterization of three novel human cadherin genes (CDH7, CDH19, and CDH$_2$O) clustered on chromosome 18q22-q23 and with high homology to chicken cadherin-7. Genomics 68:283–295, 2000.

436. Janz, R.; Sudhof, T. C.; Hammer, R. E.; Unni, V.; Siegelbaum, S. A.; Bolshakov, V. Y.: Essential roles in synaptic plasticity for synaptogyrin I and synaptophysin I. Neuron 24: 687–700, 1999.

437. McMahon, H. T.; Bolshakov, V. Y.; Janz, R.; Hammer, R. E.; Siegelbaum, S. A.; Sudhof, T. C.: Synaptophysin, a major synaptic vesicle protein, is not essential for neurotransmitter release. Proc. Nat. Acad. Sci. 93:4760–4764, 1996.

438. Engelender, S.; Wanner, T.; Kleiderlein, J. J.; Wakabayashi, K.; Tsuji, S.; Takahashi, H.; Ashworth, R.; Margolis, R. L.; Ross, C. A.: Organization of the human synphilin-1 gene, a candidate for Parkinson's disease. Mammalian Genome 11: 763–766, 2000.

439. Mach, B.; Steimle, V.; Martinez-Soria, E.; Reith, W.: Regulation of MHC class II genes: lessons from a disease. Annu. Rev. Immun. 14:301–331, 1996.
440. Scholl, T.; Mahanta, S. K.; Strominger, J. L.: Specific complex formation between the type II bare lymphocyte syndrome-associated transactivators CIITA and RFX5. Proc. Nat. Acad. Sci. 94: 6330–6334, 1997.
441. Emery, P.; Durand, B.; Mach, B.; Reith, W.: RFX proteins, a novel family of DNA binding proteins conserved in the eukaryotic kingdom. Nucleic Acids Res. 24: 803–807, 1996.
442. Braverman, N.; Lin, P.; Moebius, F. F.; Obie, C.; Moser, A.; Glossmann, H.; Wilcox, W. R.; Rimoin, D. L.; Smith, M.; Kratz, L.; Kelley, R. I.; Valle, D.: Mutations in the gene encoding 3-beta-hydroxysteroid-delta(8), delta(7)-isomerase cause X-linked dominant Conradi-Hunermann syndrome. Nature Genet. 22:291–294, 1999.
443. Cho, S. Y.; Kim, J. H.; Paik, Y. K.: Cholesterol biosynthesis from lanosterol: differential inhibition of sterol delta 8-isomerase and other lanosterol-converting enzymes by tamoxifen. Molec. Cells 8:233–239, 1998.
444. Clayton, P. T.; Kalter, D. C.; Atherton, D. J.; Besley, G. T.; Broadhead, D. M.: Peroxisomal enzyme deficiency in X-linked dominant Conradi-Hunermann syndrome. J. Inherit. Metab. Dis. 12: 358–360,1989.
445. Derry, J. M. J.; Gormally, E.; Means, G. D.; Zhao, W.; Meindl, A.; Kelley, R. I.; Boyd, Y.; Herman, G. E.: Mutations in a delta(8)-delta(7)sterol isomerase in the tattered mouse and X-linked dominant chondrodysplasiapunctata. Nature Genet. 22: 286–290, 1999.
446. Grange, D. K.; Kratz, L. E.; Braverman, N. E.; Kelley, R. I.: CHILD syndrome caused by deficiency of 3-beta-hydroxysteroid-delta-8, delta-7-isomerase. Am. J. Med. Genet. 90: 328–335, 2000.
447. Hanner, M.; Moebius, F. F.; Weber, F.; Grabner, M.; Striessnig, J.; Glossmann, H.: Phenylalkylamine Ca(2+) antagonist binding protein: molecular cloning, tissue distribution, and heterologous expression. J. Biol. Chem. 270: 7551–7557, 1995.
448. Has, C.; Bruckner-Tuderman, L.; Muller, D.; Floeth, M.; Folkers, E.; Donnai, D.; Traupe, H.: The Conradi-Hunermann-Happle syndrome(CDPX2) and emopamil binding protein: novel mutations, and somatic and gonadal mosaicism. Hum. Molec. Genet. 9: 1951–1955, 2000.
449. Holmes, R. D.; Wilson, G. N.; Hajra, A. K.: Peroxisomal enzyme deficiency in the Conradi-Hunerman (sic) form of chondrodysplasiapunctata. New Eng. J. Med. (Letter) 316: 1608 only, 1987.
450. Ikegawa, S.; Ohashi, H.; Ogata, T.; Honda, A.; Tsukahara, M.; Kubo, T.; Kimizuka, M.; Shimode, M.; Hasegawa, T.; Nishimura, G.; Nakamura, Y.: Novel and recurrent EBP mutations in X-linked dominant chondrodysplasiapunctata. Am. J. Med. Genet. 94: 300–305, 2000.
451. Kelley, R. I.; Wilcox, W. G.; Smith, M.; Kratz, L. E.; Moser, A.; Rimoin, D. S.: Abnormal sterol metabolism in patients with Conradi-Hunermann-Happle syndrome and sporadic lethal chondrodysplasia punctata. Am. J. Med. Genet. 83: 213–219, 1999.
452. Eudy, J. D.; Yao, S.; Weston, M. D.; Ma-Edmonds, M.; Talmadge, C. B.; Cheng, J. J.; Kimberling, W. J.; Sumegi, J.: Isolation of a gene encoding a novel member of the nuclear receptor superfamily from the critical region of Usher syndrome type IIa at 1q41. Genomics 50:382–384, 1998.
453. Greschik, H.; Wurtz, J.-M.; Sanglier, S.; Bourguet, W.; van Dorsselaer, A.; Moras, D.; Renaud, J.-P.: Structural and functional evidence for ligand-independent transcriptional activation by the estrogen-related receptor 3. Molec. Cell 9: 303–313, 2002.
454. Ding, H.; Descheemaeker, K.; Marynen, P.; Nelles, L.; Carvalho, T.; Carmo-Fonseca, M.; Collen, D.; Belayew, A.: Characterization of a helicase-like transcription factor involved in the expression of the human plasminogen activator inhibitor-1 gene. DNA Cell Biol. 15:429–442, 1996.
455. Lin, Y.; Sheridan, P. L.; Jones, K. A.; Evans, G. A.: The HIP116SNF2/SWI2-related transcription factor gene (SNF2L3) is located on human chromosome 3q25.1-q26.1 Genomics 27: 381–382, 1995.
456. Moinova, H. R.; Chen, W.-D.; Shen, L.; Smiraglia, D.; Olechnowicz, J.; Ravi, L.; Kasturi, L.; Myeroff, L.; Plass, C.; Parsons, R.; Minna, J.; Willson, J. K. V.; Green, S. B.; Issa, J.-P.; Markowitz, S. D.: HLTF gene silencing in human colon cancer. Proc. Nat. Acad. Sci. 99:4562–4567, 2002.
457. Sheridan, P. L.; Schorpp, M.; Voz, M. L.; Jones, K. A.: Cloning of an SNF2/SWI2-related protein that binds specifically to the SPH motifs of the SV40 enhancer and to the HIV-1 promoter. J. Biol. Chem. 270:4575–4587, 1995.
458. Heard, D. J.; Norby, P. L.; Holloway, J.; Vissing, H.: Human ERR-gamma, a third member of the estrogen receptor-related receptor (ERR) subfamily of orphan nuclear receptors: tissue-specific isoforms are expressed during development in the adult. Molec. Endocr. 14: 382–392, 2000.
459. Hong, H.; Yang, L.; Stallcup, M. R.: Hormone-independent transcriptional activation and coactivator binding by novel orphan nuclear receptor ERR3. J. Biol. Chem. 274: 22618–22626, 1999.
460. Schiebel, K.; Winkelmann, M.; Mertz, A.; Xu, X.; Page, D. C.; Weil, D.; Petit, C.; Rappold, G. A.: Abnormal XY interchange between a novel isolated protein kinase gene, PRKY, and its homologue, PRKX, accounts for one third of all (Y+)XX males and (Y–)XY females. Hum. Molec. Genet. 6: 1985–1989, 1997.
461. Bejjani, B. A.; Lewis, R. A.; Tomey, K. F.; Anderson, K. L.; Dueker, D. K.; Jabak, M.; Astle, W. F.; Otterud, B.; Leppert, M.; Lupski, J. R.: Mutations in CYP1B1, the gene for cytochrome P4501B1, are the predominant cause of primary congenital glaucoma in Saudi Arabia. Am. J. Hum. Genet. 62: 325–333, 1998.
462. Bejjani, B. A.; Stockton, D. W.; Lewis, R. A.; Tomey, K. F.; Dueker, D. K.; Jabak, M.; Astle, W. F.; Lupski, J. R.: Multiple CYP1B1 mutations and incomplete penetrance in an inbred population segregating primary congenital glaucoma suggest frequent de novo events and a dominant modifier locus. Hum. Molec. Genet. 9: 367–374, 2000.
463. Konig, A.; Happle, R.; Fink-Puches, R.; Soyer, H. P.; Bornholdt, D.; Engel, H.; Grzeschik, K.-H.: A novel missense mutation of NSDHL in an unusual case of CHILD syndrome showing bilateral, almost symmetric involvement. J. Am. Acad. Derm. 46: 594–596, 2002.
464. Labit-Le Bouteiller, C.; Jamme, M. F.; David, M.; Silve, S.; Lanau, C.; Dhers, C.; Picard, C.; Rahier, A.; Taton, M.; Loison, G.; Caput, D.; Ferrara, P.; Lupker, J.: Antiproliferative effects of SR31747A in animal cell lines are mediated by inhibition of cholesterol biosynthesis at the sterol isomerase step. Europ. J. Biochem. 256: 342–349, 1998.

465. Liu, X. Y.; Dangel, A. W.; Kelley, R. I.; Zhao, W.; Denny, P.; Botcherby, M.; Cattanach, B.; Peters, J.; Hunsicker, P. R.; Mallon, A.-M.; Strivens, M. A.; Bate, R.; Miller, W.; Rhodes, M.; Brown, S. D. M.; Herman, G. E.: The gene mutated in bare patches and striated mice encodes a novel 3-beta-hydroxysteroid dehydrogenase. Nature Genet. 22: 182–187, 1999.

466. Schindelhauer, D.; Hellebrand, H.; Grimm, L.; Bader, I.; Meitinger, T.; Wehnert, M.; Ross, M.; Meindl, A.: Long-range map of a 3.5-Mb region in Xp11.23-22 with a sequence-ready map from a 1.1-Mb gene-rich interval. Genome Res. 6: 1056–1069, 1996.

467. Silve, S.; Dupuy, P. H.; Labit-Lebouteiller, C.; Kaghad, M.; Chalon, P.; Rahier, A.; Taton, M.; Lupker, J.; Shire, D.; Loison, G.: Emopamil-binding protein, a mammalian protein that binds a series of structurally diverse neuroprotective agents, exhibits delta(8)-delta(7) sterol isomerase activity in yeast. J. Biol. Chem. 271: 22434–22440, 1996.

468. Traupe, H.; Muller, D.; Atherton, D.; Kalter, D. C.; Cremers, F. P. M.; van Oost, B. A.; Ropers, H.-H.: Exclusion mapping of the X-linked dominant chondrodysplasia punctata/ichthyosis/cataract/shortstature (Happle) syndrome: possible involvement of an unstable pre-mutation. Hum. Genet. 89: 659–665, 1992.

469. Lankes, W.; Griesmacher, A.; Grunwald, J.; Schwartz-Albiez, R.; Keller, R.: A heparin-binding protein involved in inhibition of smooth-muscle cell proliferation. Biochem. J. 251: 831–842, 1988.

470. Lankes, W. T.; Furthmayr, H.: Moesin: a member of the protein4.1-talin-ezrin family of proteins. Proc. Nat. Acad. Sci. 88: 8297–8301, 1991.

471. Shcherbina, A.; Bretscher, A.; Rosen, F. S.; Kenney, D. M.; Remold-O'Donnell, E.: The cytoskeletal linker protein moesin: decreased levels in Wiskott-Aldrich syndrome platelets and identification of a cleavage pathway in normal platelets. Brit. J. Haemat. 106: 216–223, 1999.

472. Wilgenbus, K. K.; Hsieh, C.-L.; Lankes, W. T.; Milatovich, A.; Francke, U.; Furthmayr, H.: Structure and localization on the X chromosome of the gene coding for the human filopodial protein moesin (MSN). Genomics 19:326–333, 1994.

473. Hanna, I. H.; Dawling, S.; Roodi, N.; Guengerich, F. P.; Parl, F. F.: Cytochrome P450 1B1 (CYP1B1) pharmacogenetics: association of polymorphisms with functional differences in estrogen hydroxylation activity. Cancer Res. 60: 3440–3444, 2000.

474. Plasilova, M.; Stoilov, I.; Sarfarazi, M.; Kadasi, L.; Ferakova, E.; Ferak, V.: Identification of a single ancestral CYP1B1 mutation in Slovak Gypsies (Roms) affected with primary congenital glaucoma. J. Med. Genet. 36: 290–294, 1999.

475. Schwartzman, M. L.; Balazy, M.; Masferrer, J.; Abraham, N. G.; McGiff, J. C.; Murphy, R. C.: 12(R)-hydroxyicosatetraenoic acid: a cytochrome P450-dependent arachidonate metabolite that inhibits NA+, K+-ATPase in the cornea. Proc. Nat. Acad. Sci. 84: 8125–8129,1987.

476. Stoilov, I.; Akarsu, A. N.; Alozie, I.; Child, A.; Barsoum-Homsy, M.; Turacli, M. E.; Or, M.; Lewis, R. A.; Ozdemir, N.; Brice, G.; Aktan, S. G.; Chevrette, L.; CocaPrados, M.; Sarfarazi, M.: Sequence analysis and homology modeling suggest that primary congenital glaucomaon 2p21 results from mutations disrupting either the hinge region or the conserved core structures of cytochrome P4501B1. Am. J. Hum. Genet. 62: 573–584, 1998.

477. Stoilov, I.; Akarsu, A. N.; Sarfarazi, M.: Identification of three different truncating mutations in cytochrome P4501B1 (CYP1B1) as the principal cause of primary congenital glaucoma (buphthalmos) in families linked to the GLC3A locus on chromosome 2p21. Hum. Molec. Genet. 6:641–647, 1997.

478. Sutter, T. R.; Tang, Y. M.; Hayes, C. L.; Wo, Y.-Y. P.; Jabs, E. W.; Li, X.; Yin, H.; Cody, C. W.; Greenlee, W. F.: Complete cDNA sequence of a human dioxin-inducible mRNA identifies a new gene subfamily of cytochrome P450 that maps to chromosome 2. J. Biol. Chem. 269: 13092–13099, 1994.

479. Tang, Y. M.; Wo, Y.-Y. P.; Stewart, J.; Hawkins, A. L.; Griffin, C. A.; Sutter, T. R.; Greenlee, W. F.: Isolation and characterization of the human cytochrome P450 CYP1B1 gene. J. Biol. Chem. 271: 28324–28330, 1996.

480. Vincent, A.; Billingsley, G.; Priston, M.; Williams-Lyn, D.; Sutherland, J.; Glaser, T.; Oliver, E.; Walter, M. A.; Heathcote, G.; Levin, A.; Heon, E.: Phenotypic heterogeneity of CYP1B1: mutations in a patient with Peters' anomaly. J. Med. Genet. 38: 324–326, 2001.

481. Wu, Q.; Zhang, T.; Cheng, J.-F.; Kim, Y.; Grimwood, J.; Schmutz, J.; Dickson, M.; Noonan, J. P.; Zhang, M. Q.; Myers, R. M.; Maniatis, T.: Comparative DNA sequence analysis of mouse and human protocadheringene clusters. Genome Res. 11: 389–404, 2001.

482. Field, S. J.; Tsai, F.-Y.; Kuo, F.; Zubiaga, A. M.; Kaelin, W. G., Jr.; Livingston, D. M.; Orkin, S. H.; Greenberg, M. E.: E2F-1 functions in mice to promote apoptosis and suppress proliferation. Cell 85:549–561, 1996.

483. Helin, K.; Lees, J. A.; Vidal, M.; Dyson, N.; Harlow, E.; Fattaey, A.: A cDNA encoding a pRB-binding protein with properties of the transcription factor E2F. Cell 70: 337–350, 1992.

484. Irwin, M.; Marin, M. C.; Phillips, A. C.; Seelan, R. S.; Smith, D. I.; Liu, W.; Flores, E. R.; Tsai, K. Y.; Jacks, T.; Vousden, K. H.; Kaelin, W. G., Jr.: Role for the p53 homologue p73 in E2F-1-induced apoptosis. Nature 407: 645–648, 2000.

485. Jacks, T.; Fazeli, A.; Schmitt, E. M.; Bronson, R. T.; Goodell, M. A.; Weinberg, R. A.: Effects of an Rb mutation in the mouse. Nature 359:295–300, 1992.

486. Lees, J. A.; Saito, M.; Valentine, M.; Look, T.; Harlow, E.; Dyson, N.; Helin, K.: The retinoblastoma protein binds to a family of E2F transcription factors. Molec. Cell. Biol. 13: 7813–7825, 1993.

487. Leone, G.; Sears, R.; Huang, E.; Rempel, R.; Nuckolls, F.; Park, C.-H.; Giangrande, P.; Wu, L.; Saavedra, H. I.; Field, S. J.; Thompson, M. A.; Yang, H.; Fujiwara, Y.; Greenberg, M. E.; Orkin, S.; Smith, C.; Nevins, J. R.: Myc requires distinct E2F activities to induceS phase and apoptosis. Molec. Cell 8: 105–113, 2001.

488. Lissy, N. A.; Davis, P. K.; Irwin, M.; Kaelin, W. G.; Dowdy, S. F.: A common E2F-1 and p73 pathway mediates cell death induced by TCR activation. Nature 407: 642–645, 2000.

489. Neuman, E.; Sellers, W. R.; McNeil, J. A.; Lawrence, J. B.; Kaelin, W. G., Jr.: Structure and partial genomic sequence of the human E2F1 gene. Gene 173: 163–169, 1996.

490. Nevins, J. R.: The Rb/E2F pathway and cancer. Hum. Molec. Genet. 10:699–703, 2001.

491. Nevins, J. R.: E2F: a link between the Rb tumor suppressor protein and viral oncoproteins. Science 258: 424–429, 1992.

492. Ohtani, K.; DeGregori, J.; Nevins, J. R.: Regulation of the cyclinE gene by transcription factor E2F1. Proc. Nat. Acad. Sci. 92: 12146–12150, 1995.

493. Arden, K. C.; Boutin, J.-M.; Djiane, J.; Kelly, P. A.; Cavenee, W. K.: The receptors for prolactin and growth hormone are localized in the same region of human chromosome 5. Cytogenet. Cell Genet. 53:161–165, 1990.

494. Arden, K. C.; Cavenee, W. K.; Boutin, J.-M.; Kelly, P. A.: The genes encoding the receptors for prolactin and growth hormone map to human chromosome 5. (Abstract) Am. J. Hum. Genet. 45 (suppl.): A129 only, 1989.

495. Boutin, J.-M.; Edery, M.; Shirota, M.; Jolicoeur, C.; Lesueur, L.; Ali, S.; Gould, D.; Djiane, J.; Kelly, P. A.: Identification of a cDNA encoding a long form of prolactin receptor in human hepatoma and breast cancer cells. Molec. Endocr. 3: 1455–1461, 1989.

496. Cunningham, B. C.; Bass, S.; Fuh, G.; Wells, J. A.: Zinc mediation of the binding of human growth hormone to the human prolactin receptor. Science 250:1709–1712, 1990.

497. Glasow, A.; Horn, L.-C.; Taymans, S. E.; Stratakis, C. A.; Kelly, P. A.; Kohler, U.; Gillespie, J.; Vonderhaar, B. K.; Bornstein, S. R.: Mutational analysis of the PRL receptor gene in human breast tumors with differential PRL receptor protein expression. J. Clin. Endocr. Metab. 86: 3826–3832, 2001.

498. Hu, Z.-Z.; Zhuang, L.; Meng, J.; Leondires, M.; Dufau, M. L.: The human prolactin receptor gene structure and alternative promoter utilization: the generic promoter hPIII and a novel human promoter hP(N). J. Clin. Endocr. Metab. 84: 1153–1156, 1999.

499. Ormandy, C. J.; Camus, A.; Barra, J.; Damotte, D.; Lucas, B.; Buteau, H.; Edery, M.; Brousse, N.; Babinet, C.; Binart, N.; Kelly, P. A.: Null mutation of the prolactin receptor gene produces multiple reproductive defects in the mouse. Genes Dev. 11: 167–178, 1997.

500. Perrot-Applanat, M.; Gualillo, O.; Pezet, A.; Vincent, V.; Edery, M.; Kelly, P. A.: Dominant negative and cooperative effects of mutant forms of prolactin receptor. Molec. Endocr. 11: 1020–1032, 1997.

501. Brenneman, M. A.; Wagener, B. M.; Miller, C. A.; Allen, C.; Nickoloff, J. A.: XRCC3 controls the fidelity of homologous recombination: roles for XRCC3 in late stages of recombination. Molec. Cell 10: 387–395, 2002.

502. Liu, N.; Lamerdin, J. E.; Tebbs, R. S.; Schild, D.; Tucker, J. D.; Shen, M. R.; Brookman, K. W.; Siciliano, M. J.; Walter, C. A.; Fan, W.; Narayana, L. S.; Zhou, Z.-Q.; Adamson, A. W.; Sorensen, K. J.; Chen, D. J.; Jones, N. J.; Thompson, L. H.: XRCC2 and XRCC3, new human Rad51-family members, promote chromosome stability and protect against DNA cross-links and other damages. Molec. Cell 1: 783–793, 1998.

503. Tebbs, R. S.; Zhao, Y.; Tucker, J. D.; Scheerer, J. B.; Siciliano, M. J.; Hwang, M.; Liu, N.; Legerski, R. J.; Thompson, L. H.: Correction of chromosomal instability and sensitivity to diverse mutagens by a cloned cDNA of the XRCC3 DNA repair gene. Proc. Nat. Acad. Sci. 92:6354–6358, 1995.

504. Winsey, S. L.; Haldar, N. A.; Marsh, H. P.; Bunce, M.; Marshall, S. E.; Harris, A. L.; Wojnarowska, F.; Welsh, K. I.: A variant within the DNA repair gene XRCC3 is associated with the development of melanomaskin cancer. Cancer Res. 60: 5612–5616, 2000.

505. Fischle, W.; Dequiedt, F.; Hendzel, M. J.; Guenther, M. G.; Lazar, M. A.; Voelter, W.; Verdin, E.: Enzymatic activity associated with class II HDACs is dependent on a multiprotein complex containing HDAC3 and SMRT/N-CoR. Molec. Cell 9: 45–57, 2002.

506. Patil, N.; Cox, D. R.; Bhat, D.; Faham, M.; Myers, R. M.; Peterson, A. S.: A potassium channel mutation in weaver mice implicates membrane excitability in granule cell differentiation. Nature Genet. 11:126–129, 1995.

507. Al-Chalabi, A.; Andersen, P. M.; Nilsson, P.; Chioza, B.; Andersson, J. L.; Russ, C.; Shaw, C. E.; Powell, J. F.; Leigh, P. N.: Deletions of the heavy neurofilament subunit tail in amyotrophic lateral sclerosis. Hum. Molec. Genet. 8: 157–164, 1999.

508. Collard, J.-F.; Cote, F.; Julien, J.-P.: Defective axonal transport in a transgenic mouse model of amyotrophic lateral sclerosis. Nature 375:61–64, 1995.

509. Figlewicz, D. A.; Krizus, A.; Martinoli, M. G.; Meininger, V.; Dib, M.; Rouleau, G. A.; Julien, J.-P.: Variants of the heavy neurofilament subunit are associated with the development of amyotrophic lateral sclerosis. Hum. Molec. Genet. 3: 1757–1761, 1994.

510. Lees, J. F.; Shneidman, P. S.; Skuntz, S. F.; Carden, M. J.; Lazzarini, R. A.: The structure and organization of the human heavy neurofilament subunit (NF-H) and the gene encoding it. EMBO J. 7: 1947–1955, 1988.

511. Mattei, M.-G.; Dautigny, A.; Pham-Dinh, D.; Passage, E.; Mattei, J.-F.; Jolles, P.: The gene encoding the large human neurofilament subunit (NF-H) maps to the q121–q131 region on human chromosome 22. Hum. Genet. 80: 293–295, 1988.

512. Rooke, K.; Figlewicz, D. A.; Han, F.; Rouleau, G. A.: Analysis of the KSP repeat of the neurofilament heavy subunit in familial amyotrophic lateral sclerosis. Neurology 46: 789–790, 1996.

513. Rouleau, G. A.; Merel, P.; Lutchman, M.; Sanson, M.; Zucman, J.; Marineau, C.; Hoang-Xuan, K.; Demczuk, S.; Desmaze, C.; Plougastel, B.; Pulst, S. M.; Lenoir, G.; Biilsma, E.; Fashold, R.; Dumanski, J.; dejong, P.; Parry, D.; Eldrige, R.; Aurias, A.; Delattre, O.; Thomas, G.: Alteration in a new gene encoding a putative membrane-organizing protein causes neuro-fibromatosis type 2. Nature 363: 515–521, 1993.

514. Tomkins, J.; Usher, P.; Slade, J. Y.; Ince, P. G.; Curtis, A.; Bushby, K.; Shaw, P. J.: Novel insertion in the KSP region of the neurofilament heavy gene in amyotrophic lateral sclerosis. Neuroreport 9:3967–3970, 1998.

515. Vechio, J. D.; Bruijn, L. I.; Xu, Z.; Brown, R. H., Jr.; Cleveland, D. W.: Sequence variants in human neurofilament proteins: absence of linkage to familial amyotrophic lateral sclerosis. Ann. Neurol. 40:603–610, 1996.

516. Watson, C. J.; Gaunt, L.; Evans, G.; Patel, K.; Harris, R.; Strachan, T.: A disease-associated germline deletion maps the type 2 neurofibromatosis(NF2) gene between the Ewing sarcoma region and the leukaemia inhibitory factor locus. Hum. Molec. Genet. 2: 701–704, 1993.

517. Bongarzone, I.; Vigano, E.; Alberti, L.; Borrello, M. G.; Pasini, B.; Greco, A.; Mondellini, P.; Smith, D. P.; Ponder, B. A. J.; Romeo, G.; Pierotti, M. A.: Full activation of MEN2B mutant RET by an additional MEN2A mutation or by ligand GDNF stimulation. Oncogene 16: 2295–2301, 1998.

518. Carlson, K. M.; Bracamontes, J.; Jackson, C. E.; Clark, R.; Lacroix, A.; Wells, S. A., Jr.; Goodfellow, P. J.: Parent of-origin effects in multiple endocrine neoplasia type 2B. Am. J. Hum. Genet. 55:1076–1082, 1994.

519. Carlson, K. M.; Dou, S.; Chi, D.; Scavarda, N.; Toshima, K.; Jackson, C. E.; Wells, S. A., Jr.; Goodfellow, P. J.; Donis-Keller, H.: Single missense mutation in the tyrosine kinase catalytic domain of the RET protooncogene is associated with multiple endocrine neoplasia type2B. Proc. Nat. Acad. Sci. 91: 1579–1583, 1994.

520. Mulligan, L. M.; Eng, C.; Healey, C. S.; Clayton, D.; Kwok, J. B. J.; Gardner, E.; Ponder, M. A.; Frilling, A.; Jackson, C. E.; Lehnert, H.; Neumann, H. P. H.; Thibodeau, S. N.; Ponder, B. A. J.: Specific mutations of the RET protooncogene are related to disease phenotype in MEN 2A and FMTC. Nature Genet. 6: 70–74, 1994.

521. Grozinger, C. M.; Hassig, C. A.; Schreiber, S. L.: Three proteins define a class of human histone deacetylases related to yeast Hda1p. Proc. Nat. Acad. Sci. 96: 4868–4873, 1999.

522. Sturm, R. A.; Eyre, H. J.; Baker, E.; Sutherland, G. R.: The human OTF1 locus which overlaps the CD3Z gene is located at lq22–q23. Cytogenet. Cell Genet. 68: 231–232, 1995.

523. Klink, A.; Schiebel, K.; Winkelmann, M.; Rao, E.; Horsthemke, B.; Ludecke, H.-J.; Claussen, U.; Scherer, G.; Rappold, G.: The human protein kinase gene PKX1 on Xp22.3 displays Xp/Yp homology and is a site of chromosomal instability. Hum. Molec. Genet. 4: 869–878, 1995.

524. Schiebel, K.; Mertz, A.; Winkelmann, B.; Glaser, B.; Schempp, W.; Rappold, G.: FISH localization of the human Y-homolog of protein kinase PRKX (PRKY) to Yp11.2 and two pseudogenes to 15q26 and Xq12–q13. Cytogenet. Cell Genet. 76: 49–52, 1997.

525. Lee, S. M. Y.; Tsui, S. K. W.; Chan, K. K.; Garcia-Barcelo, M.; Waye, M. M. Y.; Fung, K. P.; Liew, C. C.; Lee, C. Y.: Chromosomal mapping, tissue distribution and cDNA sequence of four-and-a-halfLIM domain protein 1 (FHL1). Gene 216: 163–170, 1998.

526. Morgan, M. J.; Madgwick, A. J.; Charleston, B.; Pell, J. M.; Loughna, P. T.: The developmental regulation of a novel muscle LIM-protein. Biochem. Biophys. Res. Commun. 212: 840–846, 1995.

527. Morgan, M. J.; Madgwick, A. J. A.: Slim defines a novel family of LIM-proteins expressed in skeletal muscle. Biochem. Biophys. Res. Commun. 225: 632–638, 1996.

528. Bowcock, A. M.; Kidd, J. R.; Lathrop, G. M.; Daneshvar, L.; May, L. T.; Ray, A.; Sehgal, P. B.; Kidd, K. K.; Cavalli-Sforza, L. L.: The human 'interferon-beta-2/hepatocyte stimulating factor/interleukin-6'gene: DNA polymorphism studies and localization to chromosome 7p21. Genomics 3:8–16, 1988.

529. Chen, Y.; Ferguson-Smith, A. C.; Newman, M. S.; May, L. T.; Sehgal, P. B.; Ruddle, F. H.: Regional localization of the human beta 2-interferon gene. (Abstract) Am. J. Hum. Genet. 41: A161, 1987.

530. Chow, D.; He, X.; Snow, A. L.; Rose-John, S.; Garcia, K. C.: Structure of an extracellular gp130 cytokine receptor signaling complex. Science 291:2150–2155, 2001.

531. Chung, U.; Tanaka, Y.; Fujita, T.: Association of interleukin-6 and hypoaldosteronism in patients with cancer. (Letter) New Eng. J. Med. 334: 473, 1996.

532. Cressman, D. E.; Greenbaum, L. E.; DeAngelis, R. A.; Ciliberto, G.; Furth, E. E.; Poli, V.; Taub, R.: Liver failure and defective hepatocyte regeneration in interleukin-6-deficient mice. Science 274:1379–1382, 1996.

533. De Benedetti, F.; Alonzi, T.; Moretta, A.; Lazzaro, D.; Costa, P.; Poli, V.; Martini, A.; Ciliberto, G.; Fattori, E.: Interleukin6 causes growth impairment in transgenic mice through a decrease in insulin-like growth factor-1. J. Clin. Invest. 99: 643–650, 1997.

534. Ferguson-Smith, A. C.; Chen, Y.-F.; Newman, M. S.; May, L. T.; Sehgal, P. B.; Ruddle, F. H.: Regional localization of the interferon beta-2/B-cell stimulatory factor 2/hepatocyte stimulating factor gene to human chromosome 7 p15–p21. Genomics 2: 203–208, 1988.

535. Fernandez-Real, J.-M.; Broch, M.; Vendrell, J.; Richart, C.; Ricart, W.: Interleukin-6 gene polymorphism and lipid abnormalities in healthy subjects. J. Clin. Endocr. Metab. 85: 1334–1339, 2000.

536. Fishman, D.; Faulds, G.; Jeffery, R.; Mohamed-Ali, V.; Yudkin, J. S.; Humphries, S.; Woo, P.: The effect of novel polymorphisms in the interleukin-6 (IL-6) gene on IL-6 transcription and plasma IL-6 levels, and an association with systemic-onset juvenile chronicarthritis. J. Clin. Invest. 102: 1369–1376, 1998.

537. Foster, C. B.; Lehrnbecher, T.; Samuels, S.; Stein, S.; Mol, F.; Metcalf, J. A.; Wyvill, K.; Steinberg, S. M.; Kovacs, J.; Blauvelt, A.; Yarchoan, R.; Chanock, S. J.: An IL6 promoter polymorphism is associated with a lifetime risk of development of Kaposi sarcoma in men infected with human immunodeficiency virus. Blood 96: 2562–2567, 2000.

538. Funatsu, H.; Yamashita, H.; Noma, H.; Mimura, T.; Yamashita, T.; Hori, S.: Increased levels of vascular endothelial growth factor and interleukin-6 in the aqueous humor of diabetics with macular edema. Am. J. Ophthal. 133: 70–77, 2002.

539. Hirano, T.; Yasukawa, K.; Harada, H.; Taga, T.; Watanabe, Y.; Matsuda, T.; Kashiwamura, S.; Nakajima, K.; Koyama, K.; Iwamatsu, A.; Tsunasawa, S.; Sakiyama, F.; Matsui, H.; Takahara, Y.; Taniguchi, T.; Kishimoto, T.: Complementary DNA for a novel human interleukin (BSF-2) that induces B lymphocytes to produce immunoglobulin. Nature 324:73–76, 1986.

540. Kawano, M.; Hirano, T.; Matsuda, T.; Taga, T.; Horii, Y.; Iwato, K.; Asaoku, H.; Tang, B.; Tanabe, O.; Tanaka, H.; Kuramoto, A.; Kishimoto, T.: Autocrine generation and requirement of BSF-2/IL-6 for human multiple myelomas. Nature 332: 83–85, 1988.

541. Kovalchuk, A. L.; Kim, J. S.; Park, S. S.; Coleman, A. E.; Ward, J. M.; Morse, H. C, III; Kishimoto, T.; Potter, M.; Janz, S.: IL-6 transgenic mouse model for extraosseous plasmacytoma. Proc. Nat. Acad. Sci. 99: 1509–1514, 2002.

542. May, L. T.; Ghrayeb, J.; Santhanam, U.; Tatter, S. B.; Sthoeger, Z.; Helfgott, D. C.; Chiorazzi, N.; Grieninger, G.; Sehgal, P. B.: Synthesis and secretion of multiple forms of beta-2-interferon/B-cell differentiation factor 2/hepatocyte-stimulating factor by human fibroblasts and monocytes. J. Biol. Chem. 263: 7760–7766, 1988.

543. Ota, N.; Hunt, S. C.; Nakajima, T.; Suzuki, T.; Hosoi, T.; Orimo, H.; Shirai, Y.; Emi, M.: Linkage of interleukin 6 locus to human osteopenia by sibling pair analysis. Hum. Genet. 105: 253–257, 1999.

544. Ota, N.; Nakajima, T.; Nakazawa, I.; Suzuki, T.; Hosoi, T.; Orimo, H.; Inoue, S.; Shirai, Y.; Emi, M.: A nucleotide variant in the promoter region of the interleukin-6 gene associated with decreased bone mineral density. J. Hum. Genet. 46: 267–272, 2001.

545. Redwine, L.; Hauger, R. L.; Gillin, J. C.; Irwin, M.: Effects of sleep and sleep deprivation on interleukin-6, growth hormone, cortisol, and melatonin levels in humans. J. Clin. Endocr. Metab. 85: 3597–3603, 2000.

546. Roodman, G. D.; Kurihara, N.; Ohsaki, Y.; Kukita, A.; Hosking, D.; Demulder, A.; Smith, J. F.; Singer, F. R.: Interleukin 6: a potential autocrine/paracrine factor in Paget's disease of bone. J. Clin. Invest. 89:46–52, 1992.

547. Rooney, M.; David, J.; Symons, J.; Di Giovine, F.; Varsani, H.; Woo, P.: Inflammatory cytokine responses in juvenile chronic arthritis. Brit. J. Rheum. 34: 454–460, 1995.

548. Santhanam, U.; Ray, A.; Sehgal, P. B.: Repression of the interleukin6 gene promoter by p53 and the retinoblastoma susceptibility gene product. Proc. Nat. Acad. Sci. 88: 7605–7609, 1991.

549. Scheidt-Nave, C.; Bismar, H.; Leidig-Bruckner, G.; Woitge, H.; Seibel, M. J.; Ziegler, R.; Pfeilschifter, J.: Serum interleukin6 is a major predictor of bone loss in women specific to the first decade past menopause. J. Clin. Endocr. Metab. 86: 2032–2042, 2001.

550. Sehgal, P. B.; May, L. T.; Tamm, I.; Vilcek, J.: Human beta-2interferon and B-cell differentiation factor BSF-2 are identical. Science 235:731–732, 1987.

551. Sehgal, P. B.; Walther, Z.; Tamm, I.: Rapid enhancement of beta(2)-interferon/B-cell differentiation factor BSF-2 gene expression in human fibroblasts by diacylglycerols and the calcium ionophore A23187. Proc. Nat. Acad. Sci. 84: 3663–3667, 1987.

552. Sehgal, P. B.; Zilberstein, A.; Ruggieri, R.-M.; May, L. T.; Ferguson-Smith, A.; Slate, D. L.; Revel, M.; Ruddle, F. H.: Human chromosome 7 carries the beta-2 interferon gene. Proc. Nat. Acad. Sci. 83: 5219–5222, 1986.

553. Berube, D.; Simard, J.; Sandberg, M.; Grzeschik, K.-H.; Gagne, R.; Hansson, V.; Jahnsen, T.: Assignment of the gene encoding the catalytic subunit C(beta) of cAMP dependent protein kinase to the p36 band on chromosome 1. (Abstract) Cytogenet. Cell Genet. 58:1850 only, 1991.

554. Sutherland, G. R.; Baker, E.; Callen, D. F.; Hyland, V. J.; Wong, G.; Clark, S.; Jones, S. S.; Eglinton, L. K.; Shannon, M. F.; Lopez, A. F.; Vadas, M. A.: Interleukin 4 is at 5q31 and interleukin 6 is at 7p15. Hum. Genet. 79: 335–337, 1988.

555. Symmons, D. P.; Jones, M.; Osborne, J.; Sills, J.; Southwood, T. R.; Woo, P.: Pediatric rheumatology in the United Kingdom: data from the British Pediatric Rheumatology Group National Diagnostic Register. J. Rheum. 23: 1975–1980, 1996.

556. Tosato, G.; Seamon, K. B.; Goldman, N. D.; Sehgal, P. B.; May, L. T.; Washington, G. C.; Jones, K. D.; Pike, S. E.: Monocyte-derived human B-cell growth factor identified as interferon-beta-2 (BSF-2,IL-6). Science 239: 502–504, 1988.

557. Villuendas, G.; San Millan, J. L.; Sancho, J. and Escobar-Morreale, H. F.: The −597 G-A and -174 G-C polymorphisms in the promoter of the IL-6 gene are associated with hyper and rogenism. J. Clin. Endocr. Metab. 87: 1134–1141, 2002.

558. Zilberstein, A.; Ruggieri, R.; Korn, J. H.; Revel, M.: Structure and expression of cDNA and genes for human interferon-beta-2, a distinct species inducible by growth stimulatory cytokines. EMBO J. 5: 2529–2537,1986.

559. Diaz, M. O.; Le Beau, M. M.; Pitha, P.; Rowley, J. D.: Interferon and c-ets-1 genes in the translocation (9;11) (p22;q23) in human acute monocytic leukemia. Science 231: 265–267, 1986.

560. Ohlsson, M.; Feder, J.; Cavalli-Sforza, L. L.; von Gabain, A.: Close linkage of alpha and beta interferons and infrequent duplication of beta interferon in humans. Proc. Nat. Acad. Sci. 82: 4473–4476,1985.

561. Owerbach, D.; Rutter, W. J.; Shows, T. B.; Gray, P.; Goeddel, D. V.; Lawn, R. M.: Leukocyte and fibroblast interferon genes are located on human chromosome 9. Proc. Nat. Acad. Sci. 78: 3123–3127,1981.

562. Siegal, F. P.; Kadowaki, N.; Shodell, M.; Fitzgerald-Bocarsly, P. A.; Shah, K.; Ho, S.; Antonenko, S.; Liu, Y.-J.: The nature of the principal type 1 interferon-producing cells in human blood. Science 284:1835–1837, 1999.

563. Kramer, F.; White, K.; Pauleikhoff, D.; Gehrig, A.; Passmore, L.; Rivera, A.; Rudolph, G.; Kellner, U.; Andrassi, M.; Lorenz, B.; Rohrschneider, K.; Blankenagel, A.; Jurklies, B.; Schilling, H.; Schutt, F.; Holz, F. G.; Weber, B. H. F.: Mutations in the VMD2 gene are associated with juvenile-onset vitelli form macular dystrophy (Bestdisease) and adult vitelli form macular dystrophy but not age-related macular degeneration. Europ. J. Hum. Genet. 8: 286–292, 2000.

564. Krill, A. E.; Morse, P. A.; Potts, A. M.; Klien, B. A.: Hereditary vitelliruptive macular degeneration. Am. J. Ophthal. 61: 1405–1415, 1966.

565. Maloney, W. F.; Robertson, D. M.; Miller, S. A.: Hereditary vitelli form macular degeneration—variable fundus findings within a single pedigree. Arch. Ophthal. 95: 979–983, 1977.

566. Mansergh, F. C.; Kenna, P. F.; Rudolph, G.; Meitinger, T.; Farrar, G. J.; Kumar-Singh, R.; Scorer, J.; Hally, A. M.; Mynett-Johnson, L.; Humphries, M. M.; Kiang, S.; Humphries, P.: Evidence for genetic heterogeneity in Best's vitelli form macular dystrophy. J. Med. Genet. 32:855–858, 1995.

567. Marmorstein, A. D.; Marmorstein, L. Y.; Rayborn, M.; Wang, X.; Hollyfield, J. G.; Petrukhin, K.: Bestrophin, the product of the Best vitelli form macular dystrophy gene (VMD2), localizes to the basolateral plasma membrane of the retinal pigment epithelium. Proc. Nat. Acad. Sci. 97: 12758–12763, 2000.

568. Marquardt, A.; Stohr, H.; Passmore, L. A.; Kramer, F.; Rivera, A.; Weber, B. H. F.: Mutations in a novel gene, VMD2, encoding a protein of unknown properties cause juvenile-onset vitelli form macular dystrophy (Best's disease). Hum. Molec. Genet. 7: 1517–1525, 1998.

569. Nichols, B. E.; Bascom, R.; Litt, M.; McInnes, R.; Sheffield, V. C.; Stone, E. M.: Refining the locus for Best vitelli form macular dystrophy and mutation analysis of the candidate gene ROM 1. Am. J. Hum. Genet. 54: 95–103, 1994.

570. Nordstrom, S.: Epidemiological studies of hereditary macular degeneration (Best's disease) in Swedish and Swedish-American populations. In: Eriksson, A. W.; Forsius, H. R.; Nevanlinna, H. R.; Workman, P. L.; Norio, R. K.: Population Structure and Genetic Disorders. New York: Academic Press (pub.) 1980. Pp. 431–443.

571. Nordstrom, S.: Personal Communication. Umea, Sweden 1978.

572. Nordstrom, S.; Thorburn, W.: Dominantly inherited macular degeneration(Best's disease) in a homozygous father with 11 children. Clin. Genet. 18:211–216, 1980.

573. O'Gorman, S.; Flaherty, W. A.; Fishman, G. A.; Berson, E. L.: Histopathologic findings in Best's vitelli form macular dystrophy. Arch. Ophthal. 106: 1261–1268, 1988.

574. Petrukhin, K.; Koisti, M. J.; Bakall, B.; Li, W.; Xie, G.; Marknell, T.; Sandgren, O.; Forsman, K.; Holmgren, G.; Andreasson, S.; Vujic, M.; Bergen, A. A. B.; McGarty-Dugan, V.; Figueroa, D.; Austin, C. P.; Metzker, M. L.; Caskey, C. T.; Wadelius, C.: Identification of the gene responsible for Best macular dystrophy. Nature Genet. 19:241–247, 1998.

575. Rivas, F.; Ruiz, C.; Rivera, H.; Moller, M.; Serrano-Lucas, J. L.; Cantu, J. M.: De novo del(6)(q25) associated with macular degeneration. Ann. Genet. 29: 42–44, 1986.
576. Rosas, F. E.: Maculopatia hereditaria viteliforme de Best. Ann. Soc. Mex. Oft. 50: 157–171, 1976.
577. Sorsby, A.; Savory, M.; Davey, J. B.; Fraser, R. J. L.: Macularcysts: a dominantly inherited affection with a progressive course. Brit. J. Ophthal. 40: 144–158, 1956.
578. Stohr, H.; Marquardt, A.; Rivera, A.; Cooper, P. R.; Nowak, N. J.; Shows, T. B.; Gerhard, D. S.; Weber, B. H. F.: A gene map of the Best's vitelli form macular dystrophy region in chromosome 11q12–q13.1. Genome Res. 8: 48–56, 1998.
579. Stone, E. M.; Nichols, B. E.; Streb, L. M.; Kimura, A. E.; Sheffield, V. C.: Genetic linkage of vitelli form macular degeneration (Best's disease) to chromosome 11q13. Nature Genet. 1: 246–250, 1992.
580. Sun, H.; Tsunenari, T.; Yau, K.-W.; Nathans, J.: The vitelli form macular dystrophy protein defines a new family of chloride channels. Proc. Nat. Acad. Sci. 99: 4008–4013, 2002.
581. Vail, D.; Shoch, D.: Hereditary degeneration of the macula. II. Follow-up report and histopathologic study. Trans. Am. Ophthal. Soc. 63:51–63, 1965.
582. Vossius, A.: Ueber die Bestsche familiaere Maculadegeneration. Arch. Ophthal. 105: 1050–1059, 1921.
583. Weber, B. H. F.; Walker, D.; Muller, B.: Molecular evidence for non-penetrance in Best's disease. J. Med. Genet. 31: 388–392, 1994.
584. Weber, B. H. F.; Walker, D.; Muller, B.; Mar, L.: Best's vitelli form dystrophy (VMD2) maps between D11S903 and PYGM: no evidence for locus heterogeneity. Genomics 20: 267–274, 1994.
585. White, K.; Marquardt, A.; Weber, B. H. F.: VMD2 mutations in vitelli form macular dystrophy (Best disease) and other maculopathies. Hum. Mutat. 15: 301–308, 2000.
586. Yoder, F. E.; Cross, H. E.; Chase, G. A.; Fine, S. L.; Freidhoff, L.; Machan, C. H.; Bias, W. B.: Linkage studies of Best's macular dystrophy. Clin. Genet. 34: 26–30, 1988.
587. Farndon, J. R.; Leight, G. S.; Dilley, W. G.; Baylin, S. B.; Smallridge, R. C.; Harrison, T. S.; Wells, S. A., Jr.: Familial medullary thyroid carcinoma without associated endocrinopathies: a distinct clinical entity. Brit. J. Surg. 73: 278–281, 1986.
588. Allen, G.; Fantes, K. H.: A family of structural genes for human lymphoblastoid (leucocyte-type) interferon. Nature 287: 408–411,1980.
589. Diaz, M. O.; Bohlander, S.; Allen, G.: Nomenclature of the human interferon genes. J. Interferon Cytokine Res. 16: 179–180, 1996.
590. Diaz, M. O.; Pomykala, H. M.; Bohlander, S. K.; Maltepe, E.; Malik, K.; Brownstein, B.; Olopade, O. I.: Structure of the human type-I interferon gene cluster determined from a YAC clone contig. Genomics 22:540–552, 1994.
591. Douglas, R. M.; Moore, B. W.; Miles, H. B.; Davies, L. M.; Graham, N. M. H.; Ryan, P.; Worswick, D. A.; Albrecht, J. K.: Prophylactic efficacy of intranasal alpha-2-interferon against rhinovirus infections in the family setting. New Eng. J. Med. 314: 65–70, 1986.
592. Edge, M. D.; Green, A. R.; Heathcliffe, G. R.; Meacock, P. A.; Schuch, W.; Scanlon, D. B.; Atkinson, T. C.; Newton, C. R.; Markham, A. F.: Total synthesis of a human leukocyte interferon gene. Nature 292:756–762, 1981.
593. Fountain, J. W.; Karayiorgou, M.; Taruscio, D.; Graw, S. L.; Buckler, A. J.; Ward, D. C.; Dracopoli, N. C.; Housman, D. E.: Genetic and physical map of the interferon region on chromosome 9p. Genomics 14:105–112, 1992.
594. Gillespie, D.; Carter, W.: Concerted evolution of human interferon alpha genes. J. Interferon Res. 3: 83–88, 1983.
595. Hayden, F. G.; Albrecht, J. K.; Kaiser, D. L.; Gwaltney, J. M., Jr.: Prevention of natural colds by contact prophylaxis with intranasal alpha-2-interferon. New Eng. J. Med. 314: 71–75, 1986.
596. Hitzeman, R. A.; Hagie, F. E.; Levine, H. L.; Goeddel, D. V.; Ammerer, G.; Hall, B. D.: Expression of a human gene for interferon in yeast. Nature 293: 717–722, 1981.
597. Imai, M.; Sano, T.; Yanase, Y.; Miyamoto, K.; Yonehara, S.; Mori, H.; Honda, T.; Fukuda, S.; Nakamura, T.; Miyakawa, Y.; Mayumi, M.: Demonstration of two subtypes of human leukocyte interferon (IFN-alpha)by monoclonal antibodies. J. Immun. 128: 2824–2825, 1982.
598. Isaacs, D.; Clarke, J. R.; Tyrrell, D. A. J.; Webster, A. D. B.; Valman, H. B.: Deficient production of leucocyte interferon (interferon-alpha) in vitro and in vivo in children with recurrent respiratory tract infections. Lancet II: 950–952, 1981.
599. Lawn, R. M.; Adelman, J.; Dull, T. J.; Gross, M.; Goeddel, D.; Ullrich, A.: DNA sequence of two closely linked human leukocyte interferon genes. Science 212: 1159–1162, 1981.
600. Lawn, R. M.; Goeddel, D. V.; Ullrich, A.: The human interferongene family. (Abstract) Sixth Int. Cong. Hum. Genet., Jerusalem 55 only, 1981.
601. Miyata, T.; Hayashida, H.: Recent divergence from a common ancestor of human IFN-alpha genes. Nature 295: 165–168, 1982.
602. Mory, Y.; Chernajovsky, Y.; Feinstein, S. I.; Chen, L.; Weissenbach, J.; Revel, M.: Expression of the cloned human interferon beta-1 gene in *E. coli*. (Abstract) Sixth Int. Cong. Hum. Genet., Jerusalem 56 only, 1981.
603. Huang, Y. Z.; Won, S.; Ali, D. W.; Wang, Q.; Tanowitz, M.; Du, Q. S.; Pelkey, K. A.; Yang, D. J.; Xiong, W. C.; Salter, M. W.; Mei, L.: Regulation of neuregulin signaling by PSD-95 interacting with ErbB4 at CNS synapses. Neuron 26: 443–455, 2000.
604. Kremmidiotis, G.; Baker, E.; Crawford, J.; Eyre, H. J.; Nahmias, J.; Callen, D. F.: Localization of human cadherin genes to chromosome regions exhibiting cancer-related loss of heterozygosity. Genomics 49:467–471, 1998.
605. Pestka, S.: The human interferons—from protein purification and sequence to cloning and expression in bacteria: before, between, and beyond. Arch. Biochem. Biophys. 221: 1–37, 1983.
606. Sehgal, P. B.; Sagar, A. D.; Braude, I. A.: Further heterogeneity of human alpha-interferon mRNA species. Science 214: 803–805, 1981.
607. Shows, T. B.; Sakaguchi, A. Y.; Naylor, S. L.; Goeddel, D. V.; Lawn, R. M.: Clustering of leukocyte and fibroblast interferon genes on human chromosome 9. Science 218: 373–374, 1982.
608. Slate, D. L.; D'Eustachio, P.; Pravtcheva, D.; Cunningham, A. C.; Nagata, S.; Weissmann, C.; Ruddle, F. H.: Chromosomal location of a human alpha interferon gene family. J. Exp. Med. 155: 1019–1024,1982.
609. Trent, J. M.; Olson, S.; Lawn, R. M.: Chromosomal localization of human leukocyte, fibroblast and immune interferon genes by means of in situ hybridization. Proc. Nat. Acad. Sci. 79: 7809–7813, 1982.

610. Ullrich, A.; Gray, A.; Goeddel, D. V.; Dull, T. J.: Nucleotide sequence of a portion of human chromosome 9 containing a leukocyte interferon gene cluster. J. Molec. Biol. 156: 467–486, 1982.
611. Virelizier, J. L.; Griscelli, C.: Defaut selectif de secretiond'interferon associe a un deficit d'activite cytotoxique naturelle. Arch. Franc. Pediat. 38: 77–81, 1981.
612. Virelizier, J. L.; Lenoir, G.; Griscelli, C.: Persistent Epstein-Barrvirus infection in a child with hypergammaglobulinaemia and immunoblastic proliferation associated with a selective defect in interferon secretion. Lancet II:231–234, 1978.
613. Jung, J.; Zheng, M.; Goldfarb, M.; Zaret, K. S.: Initiation of mammalian liver development from endoderm by fibroblast growth factors. Science 284:1998–2003, 1999.
614. Wijnen, J. T.; Oldenburg, M.; Bloemendal, H.; Meera Khan, P.: GS(gamma-S)-crystallin (CRYGS) assignment to chromosome 3. (Abstract) Cytogenet. Cell Genet. 51: 1108 only, 1989.
615. den Dunnen, J. T.; Jongbloed, R. J. E.; Geurts van Kessel, A. H. M.; Schoenmakers, J. G. G.: Human lens gamma-crystallin sequences are located in the p12-qter region of chromosome 2. Hum. Genet. 70:217–221, 1985.
616. Bierhuizen, M. F. A.; Mattei, M.-G.; Fukuda, M.: Expression of the developmental I antigen by a cloned human cDNA encoding a member of a beta-1,6-N-acetylglucosaminyltransferase gene family. Genes Dev. 7: 468–478, 1993.
617. Lin-Chu, M.; Broadberry, R. E.; Okubo, Y.; Tanaka, M.: The i phenotype and congenital cataracts among Chinese in Taiwan (Letter) Transfusion 31:676–677, 1991.
618. Ogata, H.; Okubo, Y.; Akabane, T.: Phenotype i associated with congenital cataract in Japanese. Transfusion 19: 166–168, 1979.
619. Yeh, J.-C.; Ong, E.; Fukuda, M.: Molecular cloning and expression of a novel beta-1,6-N-acetylglucosaminyltransferase that forms core 2, core 4, and I branches. J. Biol. Chem. 274: 3215–3221, 1999.
620. Yu, L.-C.; Twu, Y.-C.; Chang, C.-Y.; Lin, M.: Molecular basis of the adult i phenotype and the gene responsible for the expression of the human blood group I antigen. Blood 98: 3840–3845, 2001.
621. Seri, M.; Celli, I.; Betsos, N.; Claudiani, F.; Camera, G.; Romeo, G.: A cys634gly substitution of the RET protooncogene in a family with recurrence of multiple endocrine neoplasia type 2A and cutaneouslichen amyloidosis. Clin. Genet. 51: 86–90, 1997.
622. Hofstra, R. M. W.; Sijmons, R. H.; Stelwagen, T.; Stulp, R. P.; Kousseff, B. G.; Lips, C. J. M.; Steijlen, P. M.; Van Voorst Vader, P. C.; Buys, C. H. C. M.: RET mutation screening in familial cutaneouslichen amyloidosis and in skin amyloidosis associated with multiple endocrine neoplasia. J. Invest. Derm. 107: 215–218, 1996.
623. van Leeuwen, F. W.; de Kleijn, D. P. V.; van den Hurk, H. H.; Neubauer, A.; Sonnemans, M. A. F.; Sluijs, J. A.; Koycu, S.; Ramdjielal, R. D. J.; Salehi, A.; Martens, G. J. M.; Grosveld, F. G.; Burbach, J. P. H.; Hol, E. M.: Frameshift mutants of beta-amyloid precursor protein and ubiquitin B in Alzheimer's and Down patients. Science 279: 242–247, 1998.
624. Webb, G. C.; Baker, R. T.; Fagan, K.; Board, P. G.: Localization of the human UbB polyubiquitin gene to chromosome band 17p11.1–17 p12. Am. J. Hum. Genet. 46: 308–315, 1990.
625. Greco, A.; Ittmann, M.; Barletta, C.; Basilico, C.; Croce, C. M.; Cannizzaro, L. A.; Huebner, K.: Chromosomal localization of human genes required for G(1) progression in mammalian cells. Genomics 4:240–245, 1989.
626. Ittmann, M.; Greco, A.; Basilico, C.: Isolation of the human gene that complements a temperature-sensitive cell cycle mutation in BHK cells. Molec. Cell. Biol. 7: 3386–3393, 1987.
627. Zhong, G.; Fan, P.; Ji, H.; Dong, F.; Huang, Y.: Identification of a chlamydial protease-like activity factor responsible for the degradation of host transcription factors. J. Exp. Med. 193: 935–942, 2001.
628. Koyama, K.; Sudo, K.; Nakamura, Y.: Mapping of the human nicotinicacetylcholine receptor beta-3 gene (CHRNB3) within chromosome 8p11.2. Genomics 21:460–461, 1994.
629. Willoughby, J. J.; Ninkina, N. N.; Beech, M. M.; Latchman, D. S.; Wood, J. N.: Molecular cloning of a human neuronal nicotinic acetylcholine receptor beta-3-like subunit. Neurosci. Lett. 155: 136–139, 1993.

| GENE | PRECURSOR-SEQUENCE | P-SEQ-ID | GENE-SEQ | G-SEQID | FOLDED PRECURSOR |
|---|---|---|---|---|---|
| GAM15 | CAATGAGTCCGAGATCTTCA GACCTGGAGGAGGAGATATG AGGGACAATTG | 1 | TGAGTCCGAG ATCTTCAGAC CTGG | 16 | ```
     GA    GAG--       AGA  T
   CAAT  GTCC    ATCTTC   CC G
   ||||  ||||    ||||||   ||
   GTTA  CAGG    TAGAGG   GG G
     A-    GAGTA       A--  A
``` |
| GAM16 | CATATGTATGTTTCAGGGAA AGCTAGGGGATGGTTTTATA GACATCACTATG | 2 | TTTTATAGAC ATCACTATG | 17 | ```
     -  T        CAGGG        GG
   CATA TG ATGTTT       AAAGCTA G
   |||| || ||||||       |||||||
   GTAT AC TACAGA       TTTTGGT /
     C  -    TA---         AG
``` |
| GAM17 | CCACTCTATTTTGTGCATCA GATGCTAAAGCATATGATAC AGAGGTACATAATGTTTGG | 3 | TATGATACAG AGGTACATAA TGTT | 18 | ```
     CTC    T    ------    G   T
   CCA  TATT TGTGC    ATCA ATGC A
   |||  |||| |||||    |||| ||||
   GGT  GTAA ACATG    TAGT TACG A
    TT-    T    GAGACA    A   A
``` |

-continued

| GENE | PRECURSOR-SEQUENCE | P-SEQ-ID | GENE-SEQ | G-SEQID | FOLDED PRECURSOR |
|---|---|---|---|---|---|
| GAM18 | CCATAATGATGCAGAGAGGC AATTTTAGGAACCAAAGAAA GATTGTTAAGTGTTTCAATT GTGG | 4 | TTAAGTGTTT CAATTGTGG | 19 | ```
          -  T   GAGA          AGGAA
    CCATAAT GA GCA      GGCAATTTT     C
    ||||||| || |||      |||||||||     
    GGTGTTA CT TGT      TTGTTAGAA     C
          A  T   GAA-          AGAAA
``` |
| GAM19 | CCATTGACAGAAGAAAAAAT AAAAGCATTAGTAGAAATTT GTACAGAGATGG | 5 | TGACAGAAGA AAAAATAAAA GCAT | 20 | ```
    ---    -    AGAAAAAA   AA
    CCAT  TG ACAGA      TAA   G
    ||||  || ||||||     |||   
    GGTA  AC TGTTT      ATT  /
     GAG   A    AAAGATG-  AC
``` |
| GAM20 | CCTCTATTGTGTGCATCAAA GGATAGAGATAAAAGACACC AAGGAAGCTTTAGACAAGAT AGAGG | 6 | TATTGTGTGC ATCAAAGGAT AGAG | 21 | ```
               G  -----  A  AAA  ATAGAGA
    CCTCTATT TGT    GC TC   GG         T
    |||||||| |||    || ||   ||         
    GGAGATAG ACA    CG AG   CC         A
             A  GATTT  A  GAA  ACAGAAA
``` |
| GAM21 | GAATAGTTTTTGCTGTACTT TCTATAGTGAATAGAGTTAG GCAGGGATATTC | 7 | TAGTTTTTGC TGTACTTTCT ATAG | 22 | ```
              G       GTACT       AG
    GAATA TTTTTGCT      TTCTAT  T
    ||||| ||||||||      ||||||  
    CTTAT AGGGACGG      GAGATA  /
              -        ATT--      AG
``` |
| GAM22 | GCCACATACCTAGAAGAATA AGACAGGGCTTGGAAAGGAT TTTGCTATAAGATGGGTGGC AAGTGGT | 8 | TAAGATGGGT GGCAAGTGGT | 23 | ```
      A---       GAAGAATA  A    -   G
    GCCAC   TACCTA      AG CAGGG CTT G
    |||||   ||||||      || ||||| ||| 
    TGGTG   GTGGGT      TC GTTTT GGA A
            AACG     AGAATA--  -   A  A
``` |
| GAM23 | GGAGACAGCGACGAAGAGCT CATCAGAACAGTCAGACTCA TCAAGCTTCTCT | 9 | CAGACTCATC AAGCTTCTCT | 24 | ```
        C   GAC  A   -  C CAG
    GGAGA AGC    GA GAG CT AT    A
    ||||| |||    || ||| || ||    
    TCTCT TCG    CT CTC GA TG    /
        -   AA-  A   A  C ACA
``` |
| GAM24 | GGTCCAAAATGCGAACCCAG ATTGTAAGACTATTTTAAAA GCATTGGGACC | 10 | TCCAAAATGC GAACCCAGAT TGTA | 25 | ```
         AA       GAACCC    T  TA
    GGTCC   AATGC     AGAT  G  A
    |||||   |||||     ||||  |  
    CCAGG   TTAGG     TTTA  C  /
         G-       AAAAT-    T  AG
``` |
| GAM25 | GTACTGGGTCTCTCTGGTTA GACCAGATCTGAGCCTGGGA GCTCTCTGGCTAACTAGGGA ACCCACTGC | 11 | TCTCTGGTTA GACCAGATCT GAGC | 26 | ```
         C   C          A     TCT    CT
    GTA TGGGT TCTCTGGTTAG CCAGA   GAGC  G
    ||| ||||| |||||||||||| |||||   ||||  
    CGT ACCCA AGGGATCAATC  GGTCT   CTCG  G
         C   -          -     ---   AG
``` |
| GAM26 | TAATTGGAAGAAATCTGTTG ACTCAGATTGGTTGCACTTT AAATTTTCCCATTA | 12 | TTGGTTGCAC TTTAAATTTT CCCA | 27 | ```
      T    --------------       TT
    TAAT GGAAGA          AATCTG  G
    |||| ||||||          ||||||  
    ATTA CCTTTT          TTAGAC  A
      A     AAATTTCACGTTGG      TC
``` |
| GAM27 | TCTTTGGCAACGACCCCTCG TCACAATAAAGATAGGGGGG CAACTAAAGG | 13 | TGGCAACGAC CCCTCGTCAC AATA | 28 | ```
            CAACGA    CG  ACA
    TCTTTGG       CCCCT TC  A
    |||||||       ||||| ||  
    GGAAATC       GGGGG AG  T
            AACG--   AT  AAA
``` |
| GAM28 | TTACCCTATAGTGCAGAACA TCCAGGGGCAAATGGTACAT CAGGCCATATCACCTAGAAC TTTAAATGCATGGGTAA | 14 | TATAGTGCAG AACATCCAGG GGCA | 29 | ```
        TATA    GAACA--- C  GGCAA     ACA
    TTACCC   GTGCA      TC AGG    ATGGT  T
    ||||||   |||||      || |||    |||||  
    AATGGG   TACGT      AG TCC    TACCG  /
        ----    AAATTTCA  A  ACTA-    GAC
``` |
| GTM29 | TTCATTGCCAAGTTTGTTTC ATAACAAAAGCCTTAGGCAT CTCCTATGGCAGGAA | 15 | AGCCTTAGGC ATCTCCTATG GCAG | 30 | ```
      A   AG---------------         T
    TTC TTGCCA                  TTTGTT C
    ||| ||||||                  |||||| 
    AAG GACGGT                  AAACAA A
      -   ATCCTCTACGGATTCCGA         T
``` |

| GENE | G-SEQID | TARGET | UTR | SEQUENCE | T-SEQID | BINDING SITE |
|---|---|---|---|---|---|---|
| GAM15 | 423 | PRIM2A | 3' | CAGGCAGATCTCAGACTC | 50 | ```
        C         TCAGA
GAGTC GAGATCT      CCTG
||||| |||||||      ||||
CTCAG CTCTAGA      GGAC
        A       C
``` |
| GAM15 | 424 | RAP1B | 3' | CCAGGTCTGAAGAACTGTTGCCCA | 142 | ```
   A  CCG  A
TG GT  AG  TCTTCAGACCTGG
|| ||  ||  |||||||||||||
AC CG  TC  AGAAGTCTGGACC
   C  TTG  A
``` |
| GAM15 | 424 | RET | 3' | CCAGGTCTAAACAGCTGACCCA | 173 | ```
   A  CG  ATCTTC
TG GTC AG       AGACCTGG
|| ||| ||       ||||||||
AC CAG TC       TCTGGACC
   C  __  GACAAA
``` |
| GAM15 | 424 | RET | 3' | CCAGGTCTAAACAGCTGACCCA | 174 | ```
   A  CG  ATCTTC
TG GTC AG       AGACCTGG
|| ||| ||       ||||||||
AC CAG TC       TCTGGACC
   C  __  GACAAA
``` |
| GAM15 | 424 | RET | 3' | CCAGGTCTAAACAGCTGACCCA | 179 | ```
   A  CG  ATCTTC
TG GTC AG       AGACCTGG
|| ||| ||       ||||||||
AC CAG TC       TCTGGACC
   C  __  GACAAA
``` |
| GAM15 | 424 | RET | 3' | CCAGGTCTAAACAGCTGACCCA | 37 | ```
   A  CG  ATCTTC
TG GTC AG       AGACCTGG
|| ||| ||       ||||||||
AC CAG TC       TCTGGACC
   C  __  GACAAA
``` |
| GAM15 | 425 | AMOTL1 | 3' | CTGATAAAGATTTCAGACTCA | 304 | ```
        C
TGAGTC GAGATCT   TCAG
|||||| |||||||   ||||
ACTCAG CTTTAGA   AGTC
        A       AAT
``` |
| GAM15 | 424 | DGKZ | 3' | CCAGACCTAGGGCTGGACTCA | 70 | ```
              G  A    C  AC
TGAGTCC AG TCTT AG  CTGG
||||||| || |||| ||  ||||
ACTCAGG TC GGGA TC  GACC
  _     _    _      CA
``` |
| GAM15 | 426 | DKFZP586G1122 | 3' | CAGGTCTAGCCGGGCCCA | 265 | ```
   A   AGAT TC
TG GTCCG    CT AGACCTG
|| |||||    || |||||||
AC CGGGC    GA TCTGGAC
   C   C___  _
``` |
| GAM15 | 424 | FLJ22127 | 3' | CCAGGCCTGAATGGATGGACTCA | 192 | ```
         GAG      A
TGAGTCC     ATCT TCAG CCTGG
|||||||     |||| |||| |||||
ACTCAGG     TAGG AGTC GGACC
                 TA   C
``` |
| GAM15 | 423 | LOC126248 | 3' | CAGCCCTGGCTGGACTC | 308 | ```
         G ATCT   AC   _
GAGTCC AG      TCAG CT G
|||||| ||      |||| || |
CTCAGG TC      GGTC GA C
               CC   A
``` |
| GAM15 | 424 | LOC146640 | 5' | CCAGGTGACCTACCCGGACTCA | 323 | ```
          AGATCT  AG
TGAGTCCG      TC   ACCTGG
||||||||      ||   ||||||
ACTCAGGC      AG   TGGACC
          CCATCC   __
``` |
| GAM15 | 424 | LOC153416 | 3' | CCAGGTCTGAAGAACTGTTGCCCA | 263 | ```
   A  CCG  A
TG GT  AG  TCTTCAGACCTGG
|| ||  ||  |||||||||||||
AC CG  TC  AGAAGTCTGGACC
   C  TTG  A
``` |

-continued

| GENE | G-SEQID | TARGET | UTR | SEQUENCE | T-SEQID | BINDING SITE |
|---|---|---|---|---|---|---|
| GAM15 | 424 | LOC220790 | 3' | CCAGGTCTGAAGAACTGTTGCCCA | 378 | ```
  A   CCG  A
TG GT    AG  TCTTCAGACCTGG
|| ||    ||  |||||||||||||
AC CG    TC  AGAAGTCTGGACC
  C   TTG  A
``` |
| GAM16 | 427 | PRKG2 | 3' | CATGGTGGTATCTTAAAA | 103 | ```
      T   C
TTTTA AGA ATCACTATG
||||| ||| |||||||||
AAAAT TCT TGGTGGTAC
        A
``` |
| GAM16 | 427 | AFAP | 3' | CATAGCAGGGCGTCTGTAAAA | 183 | ```
          A_  A_
TTTTATAGAC TC  CTATG
|||||||||| ||  |||||
AAAATGTCTG GG  GATAC
          CG  AC
``` |
| GAM16 | 427 | C3AR1 | 3' | CATAGTGAAAGTTTATAAGA | 76 | ```
          A_
TTTTATAGAC TCACTATG
||||||||||  ||||||||
AGAATATTTG AGTGATAC
         AA
``` |
| GAM16 | 427 | FLJ22029 | 3' | CATGAAAATGTCTATAGAA | 203 | ```
            CAC
TTTTATAGACAT    TATG
||||||||||||    ||||
AAGATATCTGTA    GTAC
            AAA
``` |
| GAM16 | 427 | SEMA5A | 3' | CATAGTGACGTCCTGAAGA | 72 | ```
     ATA  A
TTTT    GAC TCACTATG
||||    ||| |||||||||
AGAA    CTG AGTGATAC
     GTC  C
``` |
| GAM16 | 427 | UNC5D | 3' | CATAGGATTTCTATAGAA | 234 | ```
          C   A
TTTTATAGA ATC CTATG
||||||||| ||| |||||
AAGATATCT TAG GATAC
          T   _
``` |
| GAM16 | 428 | LOC129446 | 3' | CATAGAATGTGTCTATAAA | 315 | ```
            CA_
TTTATAGACAT    CTATG
|||||||||||    |||||
AAATATCTGTG    GATAC
            TAA
``` |
| GAM16 | 427 | LOC153396 | 3' | CATAGTGGCTGCCTATAGAA | 338 | ```
         A
TTTTATAG CA TCACTATG
|||||||| || |||||||||
AAGATATC GT GGTGATAC
         C  C
``` |
| GAM16 | 427 | LOC50999 | 3' | CATAATGGTGTCTTAAAA | 145 | ```
      T        C
TTTTA AGACATCA TATG
||||| |||||||| ||||
AAAAT TCTGTGGT ATAC
      _        A
``` |
| GAM17 | 429 | KIAA0830 | 3' | AACATTATGCTTACTGCATC | 290 | ```
  A           TA
GAT CAG AGG   CATAATGTT
||| ||| |||   |||||||||
CTA GTC TTC   GTATTACAA
  C   A    __
``` |
| GAM17 | 430 | PREI3 | 3' | AACATTATGTACTGTATATCAT | 275 | ```
       CAGA_
ATGATA      GGTACATAATGTT
||||||      |||||||||||||
TACTAT      TCATGTATTACAA
       ATATG
``` |
| GAM17 | 431 | SEC15L | 3' | ACATATGCCTCTACTCATA | 297 | ```
     TAC         CATA
TATGA    AGAGGTA    ATGT
|||||    |||||||    ||||
ATACT    TCTCCGT    TACA
     CA_         A___
``` |

-continued

| GENE | G-SEQID | TARGET | UTR | SEQUENCE | T-SEQID | BINDING SITE |
|---|---|---|---|---|---|---|
| GAM17 | 432 | LOC152317 | 3' | AACATCAATGGACTCTGTATCA | 352 | ```
           GTA   A_
TGATACAGAG    CAT  ATGTT
||||||||||    |||  |||||
ACTATGTCTC    GTA  TACAA
           AG_   AC
``` |
| GAM18 | 433 | DSCR1 | 3' | CATTTTGAAATACTTAA | 81 | ```
                TT
TTAAGTGTTTCAA  GTC
|||||||||||||  |||
AATTCATAAAGTT  TAC
                T_
``` |
| GAM18 | 434 | ELMO2 | 3' | CCAGGAGAAACACTTA | 235 | ```
           AA   G
TAAGTGTTTC  TT TGG
||||||||||  || |||
ATTCACAAAG  AG ACC
           __   G
``` |
| GAM18 | 434 | ELMO2 | 3' | CCAGGAGAAACACTTA | 186 | ```
           AA   G
TAAGTGTTTC  TT TGG
||||||||||  || |||
ATTCACAAAG  AG ACC
           __   G
``` |
| GAM18 | 435 | FGF5 | 3' | CCACAGGGAGCAAACACTTAG | 227 | ```
           CAA__
TTAAGTGTTT     TTGTGG
||||||||||     ||||||
GATTCACAAA     GACACC
           CGAGG
``` |
| GAM18 | 435 | FGF5 | 3' | CCACAGGGAGCAAACACTTAG | 83 | ```
           CAA__
TTAAGTGTTT     TTGTGG
||||||||||     ||||||
GATTCACAAA     GACACC
           CGAGG
``` |
| GAM18 | 435 | NEFH | 3' | CCACACGTAAACACTTGA | 180 | ```
           CAAT
TTAAGTGTTT   TGTGG
||||||||||   |||||
AGTTCACAAA   ACACC
           TGC_
``` |
| GAM18 | 435 | NFIB | 3' | CCACAAAAGAAACACTTAA | 93 | ```
           AA
TTAAGTGTTTC  TTGTGG
|||||||||||  ||||||
AATTCACAAAG  AACACC
           AA
``` |
| GAM18 | 435 | PRKY | 3' | CCATAAATGAAACACTTGA | 62 | ```
            A
TTAAGTGTTTCA TTGTGG
|||||||||||| ||||||
AGTTCACAAAGT AATACC
            A
``` |
| GAM18 | 434 | RNF18 | 5' | CCACAATTGGGTTCTTA | 172 | ```
      TGT
TAAG    TTCAATTGTGG
||||    |||||||||||
ATTC    GGGTTAACACC
      TT_
``` |
| GAM18 | 435 | SLC1A3 | 3' | CCACAATTGAAATTTTAA | 77 | ```
         T
TTAAG GTTTCAATTGGGG
||||| |||||||||||||
AATTT TAAAGTTAACACC
         T
``` |
| GAM18 | 435 | VMD2 | 3' | CCATTGGAAACATTTAA | 78 | ```
            AATT
TTAAGTGTTTC    GTGG
|||||||||||    ||||
AATTACAAAG     TACC
            GT__
``` |
| GAM18 | 435 | XRCC3 | 5' | CCAGGGAGACACTTAA | 91 | ```
           AAT G
TTAAGTGTTTC   T TGG
|||||||||||   | |||
AATTCACAGAG   G ACC
           ___ G
``` |

-continued

| GENE | G-SEQID | TARGET | UTR | SEQUENCE | T-SEQID | BINDING SITE |
|------|---------|--------|-----|----------|---------|--------------|
| GAM18 | 435 | ARHGAP5 | 3' | CTATATGAAACATTTAA | 321 | ``` AT<br>TTAAGTGTTTCA   TGTGG<br>\|\|\|\|\|\|\|\|\|\|\|\|   \|\|\|\|\|<br>AATTTACAAAGT   ATATC<br>                    ─ ``` |
| GAM18 | 435 | EFA6R | 3' | CCATTGTGAAACACTTAA | 140 | ``` AATT<br>TTAAGTGTTTCA    GTGG<br>\|\|\|\|\|\|\|\|\|\|\|\|    \|\|\|\|<br>AATTCACAAAGT    TACC<br>           GT── ``` |
| GAM18 | 434 | KIAA0903 | 3' | CCACATGTAACACTTA | 294 | ``` T  AT<br>TAAGTGTT CA  TGTGG<br>\|\|\|\|\|\|\|\| \|\|  \|\|\|\|\|<br>ATTCACAA GT  ACACC<br>  T      ─ ``` |
| GAM18 | 436 | KIAA1244 | 3' | CCACAATTGTCTGAACAT | 295 | ``` GTGTTT── CAATTGTGG<br>\|\|\|\|\|\|   \|\|\|\|\|\|\|\|\|<br>TACAAG   GTTAACACC<br>     TCT ``` |
| GAM18 | 435 | Rpol-2 | 3' | CTGTGGTAAGAACACTTAA | 214 | ``` CA  TG<br>TTAAGTGTTT AT  TGG<br>\|\|\|\|\|\|\|\|\|\| \|\|  \|\|\|<br>AATTCACAAG TG  GTC<br>           AA  GT ``` |
| GAM18 | 435 | LOC115574 | 3' | CCACAACTGGAAACACTTGA | 303 | ``` AA─<br>TTAAGTGTTTC   TTGTGG<br>\|\|\|\|\|\|\|\|\|\|\|   \|\|\|\|\|\|<br>AGTTCACAAAG   AACACC<br>            GTC ``` |
| GAM18 | 434 | LOC144144 | 5' | CCACAATTGGGTTCTTA | 260 | ``` TGT<br>TAAG    TTCAATTGTGG<br>\|\|\|\|    \|\|\|\|\|\|\|\|\|\|\|<br>ATTC    GGGTTAACACC<br>  TT─ ``` |
| GAM18 | 435 | LOC148254 | 3' | CCATCAAAAGAAACACTTAA | 329 | ``` AA    ─<br>TTAAGTGTTTC   TTG TGG<br>\|\|\|\|\|\|\|\|\|\|\|   \|\|\| \|\|\|<br>AATTCACAAAG   AAC ACC<br>            AA    T ``` |
| GAM18 | 435 | LOC157624 | 5' | CCACTGAAACATTTAA | 359 | ``` ATT<br>TTAAGTGTTTCA    GTGG<br>\|\|\|\|\|\|\|\|\|\|\|\|    \|\|\|\|<br>AATTTACAAAGT    CACC<br>             ── ``` |
| GAM18 | 434 | LOC220486 | 5' | CCACAATTGGGTTCTTA | 374 | ``` TGT<br>TAAG    TTCAATTGTGG<br>\|\|\|\|    \|\|\|\|\|\|\|\|\|\|\|<br>ATTC    GGGTTAACACC<br>  TT─ ``` |
| GAM19 | 437 | AGL | 3' | ATGCTTTCATTTTTTCACTG | 31 | ``` AA       A<br>CAG  GAAAAAAT AAAGCAT<br>\|\|\|  \|\|\|\|\|\|\|\| \|\|\|\|\|\|\|<br>GTC  CTTTTTTA TTTCGTA<br>A─            C ``` |
| GAM19 | 437 | AGL | 3' | ATGCTTTCATTTTTTCACTG | 43 | ``` AA       A<br>CAG  GAAAAAAT AAAGCAT<br>\|\|\|  \|\|\|\|\|\|\|\| \|\|\|\|\|\|\|<br>GTC  CTTTTTTA TTTCGTA<br>A─            C ``` |
| GAM19 | 437 | AGL | 3' | ATGCTTTCATTTTTTCACTG | 44 | ``` AA       A<br>CAG  GAAAAAAT AAAGCAT<br>\|\|\|  \|\|\|\|\|\|\|\| \|\|\|\|\|\|\|<br>GTC  CTTTTTTA TTTCGTA<br>A─            C ``` |

| GENE | G-SEQID | TARGET | UTR | SEQUENCE | T-SEQID | BINDING SITE |
|---|---|---|---|---|---|---|
| GAM19 | 437 | AGL | 3' | ATGCTTTCATTTTTTCACTG | 45 | ```
    AA       A
CAG GAAAAAAT AAAGCAT
||| |||||||| |||||||
GTC CTTTTTTA TTTCGTA
 A_         C
``` |
| GAM19 | 437 | AGL | 3' | ATGCTTTCATTTTTTCACTG | 46 | ```
    AA       A
CAG GAAAAAAT AAAGCAT
||| |||||||| |||||||
GTC CTTTTTTA TTTCGTA
 A_         C
``` |
| GAM19 | 437 | AGL | 3' | ATGCTTTCATTTTTTCACTG | 47 | ```
    AA       A
CAG GAAAAAAT AAAGCAT
||| |||||||| |||||||
GTC CTTTTTTA TTTCGTA
 A_         C
``` |
| GAM19 | 438 | ALB | 5' | GCTTTCTCTTCTGTCA | 40 | ```
          AAAAAT
TGACAGAAGA      AAAAGC
||||||||||      ||||||
ACTGTCTTCT      TTTTCG
         C_____
``` |
| GAM19 | 439 | CKN1 | 3' | TTTTATTCTTTCTTCTTCA | 32 | ```
    C         A
TGA AGAAGAAA AATAAAA
||| |||||||| |||||||
ACT TCTTCTTT TTATTTT
 _            C
``` |
| GAM19 | 440 | HHIP | 3' | TTTATTTTTTATCCTGTCA | 189 | ```
       AAG
TGACAG    AAAAAATAAA
||||||    |||||||||
ACTGTC    TTTTTTATTT
       CTA
``` |
| GAM19 | 438 | IFNA1 | 3' | GCTTTCATGAATTCTGTCA | 194 | ```
        GAAAAA  A
TGACAGAA      AT AAAGC
||||||||      || |||||
ACTGTCTT      TA TTTCG
        AAG___  C
``` |
| GAM19 | 439 | KCNJ6 | 5' | TTTTTTTTTTTCTTCTGCCA | 60 | ```
   A           T
TG CAGAAGAAAAAA AAAA
|| |||||||||||| ||||
AC GTCTTCTTTTTT TTTT
 C             T
``` |
| GAM19 | 441 | OTP | 3' | GCTTTATTTTTATTTTATC | 212 | ```
   C  GA
GA AGAA    AAAAATAAAGC
|| ||||    |||||||||||
CT TTTT    TTTTTATTTCG
 A  A_
``` |
| GAM19 | 442 | RHEB2 | 3' | ATGCTTCTTTTTTCTTCTGTTA | 94 | ```
              TAA
TGACAGAAGAAAAAA   AAGCAT
||||||||||||||    ||||||
ATTGTCTTCTTTTTT   TTCGTA
             C__
``` |
| GAM19 | 442 | ANKRD6 | 3' | ATGCTTTTATTCCCTTTGTTA | 137 | ```
       AGAAAA
TGACAGA      AATAAAAGCAT
|||||||      |||||||||||
ATTGTTT      TTATTTTCGTA
       CCC___
``` |
| GAM19 | 443 | EVI5 | 3' | TGCAGGTTTTCTTCTTCA | 95 | ```
    C          ATAAAA
TGA AGAAGAAAA        GCA
||| |||||||||        |||
ACT TCTTCTTTT        CGT
 _            GGA___
``` |
| GAM19 | 442 | FLJ00026 | 3' | ATGCTTTGCTTTTTTCTTATGTCA | 270 | ```
     G          TA_
TGACA AAGAAAAAA    AAAGCAT
||||| |||||||||    |||||||
ACTGT TTCTTTTTT    TTTCGTA
     A          TCG
``` |

-continued

| GENE | G-SEQID | TARGET | UTR | SEQUENCE | T-SEQID | BINDING SITE |
|------|---------|--------|-----|----------|---------|--------------|
| GAM19 | 442 | GP5 | 3' | ATGCTCATATCATTTTTCTTCTTCA | 84 | ```
     C            __      AA
TGA AGAAGAAAAA   ATA   AGCAT
||| ||||||||||   |||   |||||
ACT TCTTCTTTTT   TAT   TCGTA
                  AC    AC
``` |
| GAM19 | 444 | KHDRBS3 | 3' | ATGCTAGTTTTTTTTCTCTT | 107 | ```
   C               AAA
GA AGAAGAAAAAT        AGCAT
|| |||||||||||        |||||
TT TCTTTTTTTTG        TCGTA
 C                 A__
``` |
| GAM19 | 443 | KIAA0254 | 3' | TGCTGTGTTCTTCTGTCA | 132 | ```
          _     AAAATAAA
TGACAGAA GAA             AGCA
|||||||| |||             ||||
ACTGTCTT CTT             TCGT
          T     GTG_____
``` |
| GAM19 | 445 | KIAA1165 | 3' | ATGCTTTATAACCTCTTCTGT | 281 | ```
            AAAAATA
ACAGAAGA           AAAGCAT
||||||||           |||||||
TGTCTTCT           TTTCGTA
       CCAATA_
``` |
| GAM19 | 438 | KIAA1240 | 3' | GTGGCCATTTTTTCTTCTGTCA | 277 | ```
               AAAA
TGACAGAAGAAAAAT        GC
|||||||||||||||        ||
ACTGTCTTCTTTTTA        TG
              CCG
``` |
| GAM19 | 445 | NYD-SP15 | 3' | ATGCCATTTTTTTCTTCTGT | 209 | ```
            TAAAA
ACAGAAGAAAAA       GCAT
||||||||||||       ||||
TGTCTTCTTTTT       CGTA
             TTAC_
``` |
| GAM19 | 441 | PELI1 | 5' | GCTTTACTCTTTCTTCTGTC | 175 | ```
            AAAATA
GACAGAAGAAA        AAAGC
|||||||||||        |||||
CTGTCTTCTTT        TTTCG
         CTCA__
``` |
| GAM19 | 446 | PRO0159 | 5' | TTATTTTTTCCTTGTCA | 125 | ```
        AA
TGACAG    GAAAAATAA
||||||    |||||||||
ACTGTT    CTTTTTTATT
     C_
``` |
| GAM19 | 442 | RACGAP1 | 3' | ATGTGAGCTTTTTCTTCTGTTA | 121 | ```
             ATAAAA
TGACAGAAGAAAA       GCAT
||||||||||||        ||||
ATTGTCTTCTTTTT      TGTA
             CGAG__
``` |
| GAM19 | 446 | SDFR1 | 3' | TTATCTTTTCTTCTGTTA | 118 | ```
             A
TGACAGAAGAAAA ATAA
||||||||||||| ||||
ATTGTCTTCTTTT TATT
              C
``` |
| GAM19 | 446 | SDFR1 | 3' | TTATCTTTTCTTCTGTTA | 151 | ```
             A
TGACAGAAGAAAA ATAA
||||||||||||| ||||
ATTGTCTTCTTTT TATT
              C
``` |
| GAM19 | 446 | SS18L1 | 3' | TTATTCTATCTTCTGTCA | 272 | ```
           AAA
TGACAGAAGA     AATAA
||||||||||     |||||
ACTGTCTTCT     TTATT
          ATC
``` |
| GAM19 | 442 | SV2B | 3' | ATGTTACTCTCCTTCTGTCA | 136 | ```
            AAAAAATAA
TGACAGAAG              AAGCAT
|||||||||              ||||||
ACTGTCTTC              TTTGTA
         CTCTCA___
``` |

-continued

| GENE | G-SEQID | TARGET | UTR | SEQUENCE | T-SEQID | BINDING SITE |
|------|---------|--------|-----|----------|---------|--------------|
| GAM19 | 443 | LOC130589 | 3' | TGCTTTTATTCCTCCTCCTTCA | 244 | ```
    CA  A   AA
TGA   GA  GA   AAATAAAAGCA
|||   ||  ||   |||||||||||
ACT   CT  CT   TTTATTTTCGT
    TC  C   CC
``` |
| GAM19 | 447 | LOC200107 | 3' | ATGCTTTTACTTTTCTTTT | 364 | ```
           A
AGAAGAAAAA TAAAAGCAT
|||||||||| |||||||||
TTTTCTTTTT ATTTTCGTA
           C
``` |
| GAM19 | 448 | LOC203340 | 3' | TGCTTTTATTTTCCTTC | 368 | ```
     AA
GAAG    AAAATAAAAGCA
||||    ||||||||||||
CTTC    TTTTATTTTCGT
     C_
``` |
| GAM19 | 443 | LOC221271 | 3' | TGCCTTTTTTTTCTGTCA | 380 | ```
              ATAAAA
TGACAGAAGAAAAA      GCA
||||||||||||||      |||
ACTGTCTTTTTTTT      CGT
              C_____
``` |
| GAM19 | 442 | LOC254778 | 3' | ATGCTTTTCTTCTATCA | 400 | ```
     C   AAATAAA
TGA AGAAGAAA       AGCAT
||| |||||||||      |||||
ACT TCTTCTTT       TCGTA
  A                _____
``` |
| GAM19 | 449 | LOC51312 | 5' | GCTTTTATTTTCTCCTCT | 164 | ```
      A  A
AGA GA   AAAATAAAAGC
||| ||   |||||||||||
TCT CT   TTTTATTTTCG
  C  C
``` |
| GAM19 | 450 | LOC91286 | 5' | TTTTATTTCTTTTCTGTCA | 273 | ```
           A
TGACAGAAGAA AAATAAAAG
||||||||||| |||||||||
ACTGTCTTTTT TTTATTTTT
           C
``` |
| GAM19 | 451 | LOC92223 | 3' | ATGCTTTTATTGTACCTTC | 286 | ```
     AAAA
GAAG      AATAAAAGCAT
||||      |||||||||||
CTTC      TTATTTTCGTA
 CATG
``` |
| GAM19 | 452 | LOC92482 | 5' | TGCATCTTTTCTTCTGT | 288 | ```
            A  AAAA
ACAGAAGAAAA AT     GCA
||||||||||| ||     |||
TGTCTTCTTTT TA     CGT
            C      ___
``` |
| GAM20 | 453 | ATRN | 3' | CTATCTGATGCACAGAA | 248 | ```
   G            AAG
TT  TGTGCATCA      GATAG
||  ||||||||||     |||||
AA  ACACGTAGT      CTATC
   G               _____
``` |
| GAM20 | 453 | ATRN | 3' | CTATCTGATGCACAGAA | 248 | ```
   G            AAG
TT  TGTGCATCA      GATAG
||  ||||||||||     |||||
AA  ACACGTAGT      CTATC
   G               _____
``` |
| GAM20 | 454 | DKFZP56O0463 | 3' | CTTTTTCTTAATGCATACAATA | 127 | ```
              CAA     T
TATTGTGTGCAT     AGGA   AGAG
||||||||||||     ||||   ||||
ATAACATACGTA     TTCT   TTTC
              A___    T
``` |
| GAM20 | 454 | DKFZP564O0463 | 3' | CTTTTTCTTAATGCATACAATA | 127 | ```
              CAA     T
TATTGTGTGCAT     AGGA   AGAG
||||||||||||     ||||   ||||
ATAACATACGTA     TTCT   TTTC
              A___    T
``` |

-continued

| GENE | G-SEQID | TARGET | UTR | SEQUENCE | T-SEQID | BINDING SITE |
|---|---|---|---|---|---|---|
| GAM20 | 454 | FLJ13102 | 3' | CTCTACCCTCTCCCACCACACAGTA | 202 | ```
        CATCAA_    A
TATTGTGTG      AGG TAGAG
|||||||||      ||| |||||
ATGACACAC      TCC ATCTC
        CACCCTC  C
``` |
| GAM20 | 454 | FLJ13102 | 3' | CTCTACCCTCTCCCACCACACAGTA | 202 | ```
        CATCAA_    A
TATTGTGTG      AGG TAGAG
|||||||||      ||| |||||
ATGACACAC      TCC ATCTC
        CACCCTC  C
``` |
| GAM20 | 453 | HSPC014 | 3' | CTGTAATTTGATGTACACAA | 144 | ```
              GG
TTGTGTGCATCAAA    ATAG
||||||||||||||    ||||
AACACATGTAGTTT    TGTC
              AA
``` |
| GAM20 | 454 | HSPC014 | 3' | CTGTAATTTGATGTACACAA | 144 | ```
              GG
TTGTGTGCATCAAA    ATAG
||||||||||||||    ||||
AACACATGTAGTTT    TGTC
              AA
``` |
| GAM20 | 455 | KIAA0040 | 3' | TCTATCCCCTTGTCACATA | 129 | ```
       _TCAAA
TGTGTG CA     GGATAGA
|||||| ||     |||||||
ATACAC GT     CCTATCT
     T  TCC__
``` |
| GAM20 | 455 | KIAA0040 | 3' | TCTATCCCCTTGTCACATA | 129 | ```
       _TCAAA
TGTGTG CA     GGATAGA
|||||| ||     |||||||
ATACAC GT     CCTATCT
     T  TCC__
``` |
| GAM20 | 456 | KIAA0470 | 3' | CCACTTGATGCACAAATA | 134 | ```
       G          A_
TATT TGTGCATCAA    GG
|||| ||||||||||    ||
ATAA ACACGTAGTT    CC
     _            CA
``` |
| GAM20 | 456 | KIAA0470 | 3' | CCACTTGATGCACAAATA | 134 | ```
       G          A_
TATT TGTGCATCAA    GG
|||| ||||||||||    ||
ATAA ACACGTAGTT    CC
     _            CA
``` |
| GAM20 | 457 | KIAA1908 | 5' | CTCTCGGGCGATGCACACAA | 302 | ```
              AAAGGAT
TTGTGTGCATC           AGAG
|||||||||||           ||||
AACACACGTAG           TCTC
              CGGGC__
``` |
| GAM20 | 457 | KIAA1908 | 5' | CTCTCGGGCGATGCACACAA | 302 | ```
              AAAGGAT
TTGTGTGCATC           AGAG
|||||||||||           ||||
AACACACGTAG           TCTC
              CGGGC__
``` |
| GAM20 | 454 | MGC22014 | 3' | CTCTATCCTTGTATATCACAATA | 269 | ```
       TGCATCA
TATTGTG         AAGGATAGAG
|||||||         ||||||||||
ATAACAC         TTCCTATCTC
       TATATG_
``` |
| GAM20 | 454 | MGC22014 | 3' | CTCTATCCTTGTATATCACAATA | 269 | ```
       TGCATCA
TATTGTG         AAGGATAGAG
|||||||         ||||||||||
ATAACAC         TTCCTATCTC
       TATATG_
``` |
| GAM20 | 453 | TNRC9 | 3' | CTGTATTTTGATGCAACAA | 293 | ```
     G         G
TTGT TGCATCAAAG ATAG
|||| |||||||||| ||||
AACA ACGTAGTTTT TGTC
     _          A
``` |

-continued

| GENE | G-SEQID | TARGET | UTR | SEQUENCE | T-SEQID | BINDING SITE |
|---|---|---|---|---|---|---|
| GAM20 | 453 | TNRC9 | 3' | CTGTATTTTGATGCAACAA | 293 | ```
       G            G
  TTGT TGCATCAAAG ATAG
  |||| |||||||||| ||||
  AACA ACGTAGTTTT TGTC
                    A
``` |
| GAM20 | 454 | LOC116123 | 3' | CTTTGGTTTGATGCATACAATA | 243 | ```
                   GGA
  TATTGTGTGCATCAAA  TAGAG
  ||||||||||||||||  |||||
  ATAACATACGTAGTTT  GTTTC
                  G__
``` |
| GAM20 | 454 | LOC116123 | 3' | CTTTGGTTTGATGCATACAATA | 243 | ```
                   GGA
  TATTGTGTGCATCAAA  TAGAG
  ||||||||||||||||  |||||
  ATAACATACGTAGTTT  GTTTC
                  G__
``` |
| GAM20 | 458 | LOC149721 | 3' | CTATCATGTGGATGCACACA | 334 | ```
            AAAG_
  TGTGTGCATC     GATAG
  ||||||||||     |||||
  ACACACGTAG     CTATC
            GTGTA
``` |
| GAM20 | 458 | LOC149721 | 3' | CTATCATGTGGATGCACACA | 334 | ```
            AAAG_
  TGTGTGCATC     GATAG
  ||||||||||     |||||
  ACACACGTAG     CTATC
            GTGTA
``` |
| GAM20 | 454 | LOC153338 | 5' | CTCTATCCCTCTGTGGCCAATA | 354 | ```
       T  G   CAAA
  TATTG GT CAT    GGATAGAG
  ||||| || |||    ||||||||
  ATAAC CG GTG    CCTATCTC
                TCTC
``` |
| GAM20 | 454 | LOC153338 | 5' | CTCTATCCCTCTGTGGCCAATA | 354 | ```
       T  G   CAAA
  TATTG GT CAT    GGATAGAG
  ||||| || |||    ||||||||
  ATAAC CG GTG    CCTATCTC
       _  _     TCTC
``` |
| GAM20 | 456 | LOC220766 | 3' | CCACTTGATGCACAAATA | 375 | ```
       G          A_
  TATT TGTGCATCAA  GG
  |||| ||||||||||  ||
  ATAA ACACGTAGTT  CC
                CA
``` |
| GAM20 | 456 | LOC220766 | 3' | CCACTTGATGCACAAATA | 375 | ```
       G          A_
  TATT TGTGCATCAA  GG
  |||| ||||||||||  ||
  ATAA ACACGTAGTT  CC
       _          CA
``` |
| GAM20 | 453 | LOC253351 | 5' | CTGGCACCTGATGCACACAA | 402 | ```
                AAGGA
  TTGTGTGCATCA     TAG
  ||||||||||||     |||
  AACACACGTAGT     GTC
                CCACG
``` |
| GAM20 | 453 | LOC253351 | 5' | CTGGCACCTGATGCACACAA | 402 | ```
                AAGGA
  TTGTGTGCATCA     TAG
  ||||||||||||     |||
  AACACACGTAGT     GTC
                CCACG
``` |
| GAM20 | 454 | LOC257484 | 3' | CTCTATCCTTGTATATCACAATA | 366 | ```
           TGCATCA
  TATTGTG         AAGGATAGAG
  |||||||         ||||||||||
  ATAACAC         TTCCTATCTC
           TATATG_
``` |
| GAM20 | 454 | LOC257484 | 3' | CTCTATCCTTGTATATCACAATA | 366 | ```
           TGCATCA
  TATTGTG         AAGGATAGAG
  |||||||         ||||||||||
  ATAACAC         TTCCTATCTC
           TATATG_
``` |

-continued

| GENE | G-SEQID | TARGET | UTR | SEQUENCE | T-SEQID | BINDING SITE |
|---|---|---|---|---|---|---|
| GAM21 | 459 | KIAA1843 | 3' | ATAGAAAGTAGCCAAAAA | 267 | ```
       CTG
TTTTTG    TACTTTCTAT
||||||    ||||||||||
AAAAAC    ATGAAAGATA
       CG
``` |
| GAM21 | 460 | SDFR1 | 3' | AAAGTACAGCAAAACCTA | 117 | ```
     T
TAG  TTTTGCTGTACTTT
|||  ||||||||||||||
ATC  AAAACGACATGAAA
     C
``` |
| GAM21 | 460 | SDFR1 | 3' | AAAGTACAGCAAAACCTA | 150 | ```
     T
TAG  TTTTGCTGTACTTT
|||  ||||||||||||||
ATC  AAAACGACATGAAA
     C
``` |
| GAM21 | 461 | LOC132617 | 3' | CTACAGACCATAGCAAAAAC | 314 | ```
          ACTT    A
GTTTTTGCTGT    TCT TAG
||||||||||     ||| |||
CAAAAACGATA    AGA ATC
          CC     C
``` |
| GAM21 | 461 | LOC145622 | 3' | CTATAGAACAATGCAAAAAC | 322 | ```
         TGTACT
GTTTTTGC       TTCTATAG
||||||||       ||||||||
CAAAAACG       AAGATACT
        TAAC
``` |
| GAM21 | 462 | LOC222681 | 3' | CTACAGAACATGGAGCAAAAAC TA | 386 | ```
           G  CT    A
TAGTTTTTGCT TA TTCT TAG
||||||||||| || |||| |||
ATCAAAAACGA GT AAGA ATC
           G  AC    C
``` |
| GAM21 | 462 | LOC257507 | 3' | CTACAGAACATGGAGCAAAAAC TA | 405 | ```
           G  CT    A
TAGTTTTTGCT TA TTCT TAG
||||||||||| || |||| |||
ATCAAAAACGA GT AAGA ATC
           G  AC    C
``` |
| GAM21 | 462 | LOC257625 | 3' | CTACAGAACATGGAGCAAAAAC TA | 406 | ```
           G  CT    A
TAGTTTTTGCT TA TTCT TAG
||||||||||| || |||| |||
ATCAAAAACGA GT AAGA ATC
           G  AC    C
``` |
| GAM22 | 463 | BTEB1 | 3' | ACCACTACATCCATCT | 53 | ```
         GCA
AGATGGGTG    AGTGGT
|||||||||    ||||||
TCTACCTAC    TCACCA
         A
``` |
| GAM22 | 464 | CEP2 | 3' | ACCACCTCCTTCATCTT | 112 | ```
        T  CAA
AAGATGGG GG    GTGGT
|||||||| ||    |||||
TTCTACTT CC    CACCA
           TC
``` |
| GAM22 | 463 | ECM1 | 3' | ACCCTGCCCCACCCATCT | 82 | ```
          CA_ T
AGATGGGTGG    AG GGT
||||||||||    || |||
TCTACCCACC    TC CCA
          CCG
``` |
| GAM22 | 465 | ENG | 3' | ACCACTTGCCACGCTGTT | 34 | ```
GATGG GTGGCAAGTGGT
||||| ||||||||||||
TTGTC CACCGTTCACCA
     G
``` |
| GAM22 | 463 | ESRRG | 3' | ACCACTTTTCAGCCATTT | 276 | ```
        G  C
AGATGG TGG AAGTGGT
|||||| ||| |||||||
TTTACC ACT TTCACCA
        G  T
``` |

-continued

| GENE | G-SEQID | TARGET | UTR | SEQUENCE | T-SEQID | BINDING SITE |
|---|---|---|---|---|---|---|
| GAM22 | 466 | HDAC4 | 3' | ACCACTCGACTCATCTTG | 98 | ```
      GGCA
TAAGATGGGT     AGTGGT
||||||||||     ||||||
GTTCTACTCA     TCACCA
      GC__
``` |
| GAM22 | 466 | IL6 | 3' | ACCACTTGAAACATTTTA | 41 | ```
     GGTGG
TAAGATG     CAAGTGGT
|||||||     ||||||||
ATTTTAC     GTTCACCA
     AAA__
``` |
| GAM22 | 466 | LRAT | 3' | ACCACTTAAAATTATCTTA | 259 | ```
      GTGGC
TAAGATGG     AAGTGGT
||||||||     |||||||
ATTCTATT     TTCACCA
      AAAA_
``` |
| GAM22 | 466 | MYLK2 | 3' | ACCACTCGGGGCCCCCATCTTG | 226 | ```
         T   A___
TAAGATGGG GGC    AGTGGT
||||||||| |||    ||||||
GTTCTACCC CCG    TCACCA
        _ GGGC
``` |
| GAM22 | 463 | PRKACB | 3' | ACCACTTCTTTTCATCT | 61 | ```
       T  C
AGATGGG GG AAGTGGT
||||||| || ||||||||
TCTACTT TC TTCACCA
       T  _
``` |
| GAM22 | 463 | PRLR | 3' | ACCACTTGCCTCTTTCT | 51 | ```
    T   T
AGA GGG GGCAAGTGGT
||| ||| ||||||||||
TCT TCT CCGTTCACCA
    T   _
``` |
| GAM22 | 464 | SLC6A6 | 3' | ACCACTTGAATTGATCTT | 65 | ```
     G    GG
AAGAT GGT  CAAGTGGT
||||| |||  ||||||||
TTCTA TTA  GTTCACCA
     G    A_
``` |
| GAM22 | 466 | WASF3 | 3' | ACCACTTGGTCAGAATTTA | 109 | ```
      GGG    _
TAAGAT    TGGC AAGTGGT
||||||    |||| |||||||
ATTTTA    ACTG TTCACCA
      AG_    G
``` |
| GAM22 | 466 | XK | 3' | ACCACTTGCACTATTCTTA | 181 | ```
     TG   G
TAAGA  GGTG CAAGTGGT
|||||  |||| ||||||||
ATTCT  TCAC GTTCACCA
     TA   _
``` |
| GAM22 | 463 | ZYX | 3' | ACCACCTGCCCCCACCT | 69 | ```
   A    T    A
AG TGGG GGCA GTGGT
|| |||| |||| |||||
TC ACCC CCGT CACCA
   C    _    C
``` |
| GAM22 | 463 | ARHF | 3' | ACCCTGGACCACCCATCT | 167 | ```
          CA_  T
AGATGGGTGG   AG GGT
||||||||||   || |||
TCTACCCACC   TC CCA
          AGG  _
``` |
| GAM22 | 467 | DDR1 | 5' | CGCACCACCCATTTTA | 57 | ```
           CAA
TAAGATGGTGG    GTG
|||||||||||    |||
ATTTTACCCACC   CGC
            A__
``` |
| GAM22 | 467 | DDR1 | 5' | CGCACCACCCATTTTA | 122 | ```
           CAA
TAAGATGGTGG    GTG
|||||||||||    |||
ATTTTACCCACC   CGC
            A__
``` |

-continued

| GENE | G-SEQID | TARGET | UTR | SEQUENCE | T-SEQID | BINDING SITE |
|---|---|---|---|---|---|---|
| GAM22 | 467 | DDR1 | 5' | CGCACCACCCATTTTA | 123 | ```
              CAA          
TAAGATGGGTGG    GT          
||||||||||||    ||          
ATTTTACCCACC    CG          
              A__           
``` |
| GAM22 | 466 | DKFZP547E1010 | 5' | ACCACCTCCCTATCTTA | 141 | ```
           TG CAA           
TAAGATGGG  G   GTGGT        
|||||||||  |   |||||        
ATTCTATCC  C   CACCA        
           CT __            
``` |
| GAM22 | 466 | DKFZP547E1010 | 5' | ACCACCTCCCTATCTTA | 280 | ```
           TG CAA           
TAAGATGGG  G   GTGGT        
|||||||||  |   |||||        
ATTCTATCC  C   CACCA        
           CT __            
``` |
| GAM22 | 463 | FLJ11715 | 3' | ACCGCGCCCAGCCCATCT | 197 | ```
            __ AA           
AGATGGGT  GGC   GTGGT       
||||||||  |||   |||||       
TCTACCCG  CCG   CGCCA       
            AC __           
``` |
| GAM22 | 463 | FLJ12587 | 3' | ACCAGGGCCGCATCCATCT | 190 | ```
         __    AAG          
AGATGG  GTGGC    TGGT       
||||||  |||||    ||||       
TCTACC  CGCCG    ACCA       
         TA    GG_          
``` |
| GAM22 | 465 | FLJ12650 | 3' | ACCACTTGCCAATGCCTCTC | 196 | ```
   T  ___                   
GA GGGT    GGCAAGTGGT       
|| ||||    ||||||||||       
CT TCCG    CCGTTCACCA       
   C  TAA                   
``` |
| GAM22 | 468 | FLJ13265 | 3' | ACCACTTGCCCTGCCTCA | 201 | ```
TG GGT__   GGCAAGTGGT       
|| |||     ||||||||||       
AC CCG     CCGTTCACCA       
 T  TC                      
``` |
| GAM22 | 463 | FLJ20546 | 3' | ACCTCTGCCACCCATCT | 155 | ```
             A T            
AGATGGGTGGCA G GGT          
|||||||||||| | |||          
TCTACCCACCGT C CCA          
             _ T            
``` |
| GAM22 | 466 | FLJ32865 | 3' | ACCACCACGCCCAGCTTA | 251 | ```
       A      GCAA          
TAAG TGGGTG     GTGGT       
|||| ||||||     |||||       
TAAC ACCCGC     CACCA       
       G      AC__          
``` |
| GAM22 | 463 | GPR88 | 3' | ACCACTTGTTGTACATCT | 185 | ```
       G TG                 
AGATG G  GCAAGTGGT          
||||| |  |||||||||          
TCTAC T  TGTTCACCA          
       A GT                 
``` |
| GAM22 | 463 | HSPC216 | 3' | ACCTGACCACCCATTT | 149 | ```
              AGT           
AGATGGGTGG CA   GGT         
|||||||||| ||   |||         
TTTACCCACC GT   CCA         
              A ___         
``` |
| GAM22 | 466 | JIK | 3' | ACCACATTCCCCATTTTA | 148 | ```
           T  CAA           
TAAGATGGG GG   GTGGT        
||||||||| ||   |||||        
ATTTTACCC CT   CACCA        
           _  TA_           
``` |
| GAM22 | 466 | KIAA0153 | 3' | ACCACCCAGCAAGCCCGCCTTA | 139 | ```
       A    G_ AA_          
TAAG TGGGT  GC   GTGGT      
|||| |||||  ||   |||||      
ATTC GCCCG  CG   CACCA      
       C    AA ACC          
``` |

| GENE | G-SEQID | TARGET | UTR | SEQUENCE | T-SEQID | BINDING SITE |
|---|---|---|---|---|---|---|
| GAM22 | 466 | KIAA0215 | 3' | ACCAGGAGACCACCATCTTA | 130 | ``` G    CAAG TAAGATGG TGG    TGGT ‖‖‖‖‖‖‖‖ ‖‖‖    ‖‖‖‖ ATTCTACC ACC    ACCA  _        AGAGG ``` |
| GAM22 | 468 | KIAA0461 | 3' | ACCACTTGTTGAAATCCA | 291 | ``` TGGGT___GGCAAGTGGT ‖‖‖‖‖   ‖‖‖‖‖‖‖‖‖‖ ACCTA   TTGTTCACCA    AAG ``` |
| GAM22 | 466 | MEGF10 | 3' | ACCACAGACTCATCTTA | 216 | ``` GGCAA TAAGATGGGT    GTGGT ‖‖‖‖‖‖‖‖‖‖    ‖‖‖‖‖ ATTCTACTCA    CACCA      GA___ ``` |
| GAM22 | 468 | MGC2452 | 5' | ACCACTAATTGCCACTCA | 218 | ``` TGGGTGGCA___AGTGGT ‖‖‖‖‖‖‖‖‖   ‖‖‖‖‖‖ ACTCACCGT   TCACCA     TAA ``` |
| GAM22 | 466 | MGC4796 | 3' | ACCTTCACCTCATCTTA | 266 | ``` _       CAAGT TAAGATG GGTGG    GGT ‖‖‖‖‖‖‖ ‖‖‖‖‖    ‖‖‖ ATTCTAC CCACT    CCA     T     T___ ``` |
| GAM22 | 463 | MRPL10 | 3' | ACCACATTGTACCCATTT | 256 | ```       G    _ AGATGGGTG CAA GTGT ‖‖‖‖‖‖‖‖‖ ‖‖‖ ‖‖‖‖‖ TTTACCCAT GTT CACCA  _             A ``` |
| GAM22 | 466 | MRPL42 | 5' | ACCACTTGATAAGCATCTTG | 299 | ``` GG  G TAAGATG  TG CAAGTGGT ‖‖‖‖‖‖‖  ‖‖ ‖‖‖‖‖‖‖‖ GTTCTAC  AT GTTCACCA    GA  A ``` |
| GAM22 | 464 | POLYDOM | 3' | ACCACTGCTATCCATCTT | 195 | ```              A AAGATGGGTGGCA GTGGT ‖‖‖‖‖‖‖‖‖‖‖‖‖ ‖‖‖‖‖ TTCTACCTATCGT CACCA              _ ``` |
| GAM22 | 463 | PRO0246 | 5' | ACCACTTGCTATGGTCT | 126 | ```     GG AGAT  GTGGCAAGTGGT ‖‖‖‖  ‖‖‖‖‖‖‖‖‖‖‖‖ TCTG  TATCGTTCACCA    G_ ``` |
| GAM22 | 466 | SMCR7 | 3' | ATGACTTGCCACCCACCT | 247 | ```   A          G AG TGGGTGGCAAGT GT ‖‖ ‖‖‖‖‖‖‖‖‖‖‖‖ ‖‖ TC ACCCACCGTTCA TA    C            G ``` |
| GAM22 | 466 | TPD52 | 3' | ACCACTTATATCAACTTA | 88 | ```     ATG   GC TAAG GGTG AAGTGGT ‖‖‖‖ ‖‖‖‖ ‖‖‖‖‖‖‖ ATTC CTAT TTCACCA     AA_   A_ ``` |
| GAM22 | 464 | ZNF384 | 3' | ACCACTCATCACGGCCATCTT | 239 | ```             CA AAGATGG GTGG AGTGGT ‖‖‖‖‖‖‖ ‖‖‖‖ ‖‖‖‖‖‖ TTCTACC CACT TCACCA       GG   AC ``` |
| GAM22 | 466 | LOC124216 | 3' | ACCTCTCCTCACCCATCTTA | 307 | ```              CA T TAAGATGGGTGG  AG GGT ‖‖‖‖‖‖‖‖‖‖‖‖  ‖‖ ‖‖‖ ATTCTACCCACT  TC CCA              CC  T ``` |

-continued

| GENE | G-SEQID | TARGET | UTR | SEQUENCE | T-SEQID | BINDING SITE |
|------|---------|--------|-----|----------|---------|--------------|
| GAM22 | 463 | LOC144509 | 5' | ACCACCAGCTGCACCCATCT | 320 | ``` 
            AA
AGATGGGTG  GC  GTGGT
|||||||||  ||  |||||
TCTACCCAC  CG  CACCA
            GT  AC
``` |
| GAM22 | 463 | LOC146822 | 3' | ACCACCTGCCCTACCATTT | 324 | ```
        GT   A
AGATGG   GGCA GTGGT
||||||   |||| |||||
TTTACC   CCGT CACCA
        ATC   C
``` |
| GAM22 | 463 | LOC148371 | 5' | ACCACTTCTGGCCATCT | 330 | ```
       G   C
AGATGG TGG AAGTGGT
|||||| ||| |||||||
TCTACC GTC TTCACCA
       G   _
``` |
| GAM22 | 464 | LOC149373 | 3' | ACCTGCCGGCCACCCATTCA | 333 | ```
A           AA
A GATGGGTGGC GT GGT
| |||||||||| || |||
A TTACCCACCG CG CCA
C           GC T
``` |
| GAM22 | 466 | LOC151146 | 5' | ACCCCCCAGCCCATCTTA | 336 | ```
           CAAGT
TAAGATGGG TGG    GGT
||||||||| |||    |||
ATTCTACCC ACC    CCA
         G   CC___
``` |
| GAM22 | 466 | LOC157562 | 5' | ACCACCCAGTCATTTTA | 357 | ```
          G  CAA
TAAGATGG TGG    GTGGT
|||||||| |||    |||||
ATTTTACT ACC    CACCA
         G      ___
``` |
| GAM22 | 466 | LOC160897 | 3' | ACCACTTATAATGCCTCATCTTA | 341 | ```
          _    GC__
TAAGATG GGTG    AAGTGGT
||||||| ||||    |||||||
ATTCTAC CCGT    TTCACCA
        T    AATA
``` |
| GAM22 | 463 | LOC161589 | 5' | ACCACTGCTGGCCATCT | 343 | ```
       G    A
AGATGG TGGCA GTGGT
|||||| ||||| |||||
TCTACC GTCGT CACCA
       G     _
``` |
| GAM22 | 468 | LOC163682 | 5' | ACCACTTGCCGAGCTCCTA | 361 | ```
TGGG___    TGGCAAGTGGT
||||       |||||||||||
ATCC       GCCGTTCACCA
   TCCA
``` |
| GAM22 | 466 | LOC199692 | 3' | ACCAGTAACCTATCTTA | 257 | ```
            G  AAG
TAAGATGGGT GC    TGGT
|||||||||| ||    ||||
ATTCTATCCA TG    ACCA
            A    ___
``` |
| GAM22 | 463 | LOC202108 | 5' | ACCACTACTGGCCATCT | 367 | ```
       G   CA
AGATGG TGG AGTGGT
|||||| ||| ||||||
TCTACC GTC TCACCA
       G   A_
``` |
| GAM22 | 464 | LOC221468 | 3' | ACCACCCAGTTCTTCATCTT | 258 | ```
         TG  AA_
AAGATGGG  GC  GTGGT
||||||||  ||  |||||
TTCTACTT  TG  CACCA
         CT  ACC
``` |
| GAM22 | 463 | LOC221838 | 5' | ACCACTACTGGCCATCT | 385 | ```
       G   CA
AGATGG TTG AGTGGT
|||||| ||| ||||||
TCTACC GTC TCACCA
       G   A_
``` |

-continued

| GENE | G-SEQID | TARGET | UTR | SEQUENCE | T-SEQID | BINDING SITE |
|---|---|---|---|---|---|---|
| GAM22 | 463 | LOC221839 | 5' | ACCACTACTGGCCATCT | 384 | <pre>         G   CA
AGATGG TTG  AGTGGT
|||||| |||  ||||||
TCTACC GTC  TCACCA
         G   A_</pre> |
| GAM22 | 465 | LOC90313 | 5' | ACCACCCCTGTGCCCATC | 268 | <pre>          G  A__
GATGGGTG CA  GTGGT
|||||||| ||  |||||
CTACCCGT GT  CACCA
         _  CCC</pre> |
| GAM22 | 466 | LOC92399 | 3' | ACCACCTGCTCCTCATCTTA | 242 | <pre>            TG  A
TAAGATGGG  GCA GTGGT
|||||||||  ||| |||||
ATTCTACTC  CGT CACCA
            CT  C</pre> |
| GAM23 | 469 | ADAM8 | 3' | AGAGAAGCCATGCGTTCC | 52 | <pre>  A   T   CAA
C GAC CAT   GCTTCTCT
| ||| |||   ||||||||
C TTG GTA   CGAAGAGA
  C   C   C__</pre> |
| GAM23 | 469 | BN51T | 3' | AGAGAGCAAGGATTGAGTCTG | 363 | <pre>           AA_  T
CAGACTCA TC   GCT CTCT
|||||||| ||   ||| ||||
GTCTGAGT AG   CGA GAGA
         T  GAA  _</pre> |
| GAM23 | 469 | CD3Z | 3' | AGACTGACCTTGATGAGCTG | 48 | <pre>    A       C  C_
CAG CTCATCAAG TT  TCT
||| ||||||||| ||  |||
GTC GAGTAGTTC AG  AGA
    _         C  TC</pre> |
| GAM23 | 470 | DAAM2 | 3' | AGGTGCTTGATGAATCTG | 381 | <pre>     C          T
CAGA TCATCAAGC TCT
|||| ||||||||| |||
GTCT AGTAGTTCG GGA
     A          T</pre> |
| GAM23 | 471 | DLG4 | 3' | AGGGAGGGATGGGTCT | 54 | <pre>         AAG
AGACTCATC   CTTCTCT
|||||||||   |||||||
TCTGGGTAG   GGAGGGA
         ___</pre> |
| GAM23 | 472 | DMD | 5' | AGAAAAGCTTGAGCAAGTC | 73 | <pre>    CA_       C
GACT   TCAAGCTT TCT
||||   |||||||| |||
CTGA   AGTTCGAA AGA
    ACG       A</pre> |
| GAM23 | 472 | DMD | 5' | AGAAAAGCTTGAGCAAGTC | 74 | <pre>    CA_       C
GACT   TCAAGCTT TCT
||||   |||||||| |||
CTGA   AGTTCGAA AGA
    ACG       A</pre> |
| GAM23 | 472 | DMD | 5' | AGAAAAGCTTGAGCAAGTC | 75 | <pre>    CA_       C
GACT   TCAAGCTT TCT
||||   |||||||| |||
CTGA   AGTTCGAA AGA
    ACG       A</pre> |
| GAM23 | 473 | E2F1 | 3' | AGGCCTCTTTGGTGAGCCTG | 348 | <pre>    A       ____
CAG CTCATCAA    GCTT
||| ||||||||    ||||
GTC GAGTGGTT    CGGA
    C       TCTC</pre> |
| GAM23 | 471 | EBP | 3' | AGAGAAGCCAGGAGGTCT | 108 | <pre>      CA AA_
AGACT TC   GCTTCTCT
||||| ||   ||||||||
TCTGG AG   CGAAGAGA
      __ GAC</pre> |

| GENE | G-SEQID | TARGET | UTR | SEQUENCE | T-SEQID | BINDING SITE |
|---|---|---|---|---|---|---|
| GAM23 | 472 | FANCG | 5' | AGAGAAGCAGGGGAGCTC | 85 | ```
        A    AA
GA CTC TC   GCTTCTCT
|| ||| ||   ||||||||
CT GAG GG   CGAAGAGA
   C    GA
``` |
| GAM23 | 470 | FE65L2 | 5' | AGGCGCCTGATGAGTTCA | 99 | ```
  A         A  T
C GACTCATCA GC TCT
| |||||||||| || |||
A TTGAGTAGT CG GGA
  C         C  C
``` |
| GAM23 | 470 | FE65L2 | 5' | AGGCGCCTGATGAGTTCA | 236 | ```
  A         A  T
C GACTCATCA GC TCT
| |||||||||| || |||
A TTGAGTAGT CG GGA
  C         C  C
``` |
| GAM23 | 470 | FE65L2 | 5' | AGGCGCCTGATGAGTTCA | 237 | ```
  A         A  T
C GACTCATCA GC TC
| |||||||||| || ||
A TTGAGTAGT CG GG
  C         C  C
``` |
| GAM23 | 470 | FE65L2 | 5' | AGGCGCCTGATGAGTTCA | 238 | ```
  A         A  T
C GACTCATCA GC TCT
| |||||||||| || |||
A TTGAGTAGT CG GGA
  C         C  C
``` |
| GAM23 | 469 | FGFR4 | 3' | AGAGAAGCTGGAAGCCTG | 193 | ```
    A CA  A
CAG CT TC AGCTTCTCT
||| || || |||||||||
GTC GA AG TCGAAGAGA
    C     G
``` |
| GAM23 | 469 | FGFR4 | 3' | AGAGAAGCTGGAAGCCTG | 58 | ```
    A CA  A
CAG CT TC AGCTTCTCT
||| || || |||||||||
GTC GA AG TCGAAGAGA
    C     G
``` |
| GAM23 | 472 | FHL1 | 3' | AGAGAAGCTGATGCCTC | 55 | ```
   CT    A
GA   CATCA GCTTCTCT
||   ||||| ||||||||
CT   GTAGT CGAAGAGA
   CC
``` |
| GAM23 | 469 | GCNT2 | 5' | AGAGAAACGAGTGAGTTTG | 56 | ```
           CAAGC
CAGACTCAT      TTCTCT
|||||||||      ||||||
GTTTGAGTG      AAGAGA
           AGCA
``` |
| GAM23 | 469 | GNRHR | 5' | AGAGAAGCTGGTAATTCTG | 38 | ```
     CTC    A
CAGA    ATCA GCTTCTCT
||||    |||| ||||||||
GTCT    TGGT CGAAGAGA
        TAA
``` |
| GAM23 | 470 | HIS1 | 5' | AGGGGAGATGAGTTTG | 105 | ```
           AAG
CAGACTCATC    CTTCT
||||||||||    |||||
GTTTGAGTAG    GGGGA
          A
``` |
| GAM23 | 469 | HNRPDL | 3' | AGAAAGGTATGAGTTTG | 92 | ```
          CAA   C
CAGACTCAT   GCTT TCT
|||||||||   |||| |||
GTTTGAGTA   TGGA AGA
                A
``` |
| GAM23 | 469 | INHBA | 3' | AGAAAGCCATGAGTTTG | 59 | ```
          CAA   C
CAGACTCAT   GCTT TCT
|||||||||   |||| |||
GTTTGAGTA   CGAA AGA
           C
``` |

-continued

| GENE | G-SEQID | TARGET | UTR | SEQUENCE | T-SEQID | BINDING SITE |
|------|---------|--------|-----|----------|---------|--------------|
| GAM23 | 469 | KIF3B | 3' | AGAGAAGCTCATAAGTGTG | 87 | ```
   G   C  CA
CA ACT AT   AGCTTCTCT
|| ||| ||   |||||||||
GT TGA TA   TCGAAGAGA
   A   A  C_
``` |
| GAM23 | 469 | MSN | 3' | AGAGAAGCCTGTGCCCTG | 262 | ```
    ACT  T  A
CAG   CA CA GCTTCTCT
|||   || || |||||||||
GTC   GT GT CGAAGAGA
 CC_  _  C
``` |
| GAM23 | 469 | MTR | 3' | AGAGAAGTGTGACCCTG | 36 | ```
    AC   CAA
CAG  TCAT    GCTTCTCT
|||  ||||    |||||||||
GTC  AGTG    TGAAGAGA
 CC         ___
``` |
| GAM23 | 469 | PCDHB9 | 3' | AGAGAAGTTAGATCCTG | 169 | ```
    ACTC    A
CAG     ATC AGCTTCTCT
|||     ||| |||||||||
GTC     TAG TTGAAGAGA
  C___    A
``` |
| GAM23 | 469 | SMARCA3 | 3' | AGAGAAGCTTCATGTTTG | 246 | ```
     TCATC
CAGAC      AAGCTTCTCT
|||||      ||||||||||
GTTTG      TTCGAAGAGA
     TAC__
``` |
| GAM23 | 469 | SMARCA3 | 3' | AGAGAAGCTTCATGTTTG | 66 | ```
     TCATC
CAGAC      AAGCTTCTCT
|||||      ||||||||||
GTTTG      TTCGAAGAGA
     TAC__
``` |
| GAM23 | 470 | SMG1 | 3' | AGACAGTAGATGAGTCTG | 138 | ```
          AA   _
CAGACTCATC   GCT TCT
||||||||||   ||| |||
GTCTGAGTAG   TGA AGA
          A_   C
``` |
| GAM23 | 469 | SNCAIP | 5' | AGAAAGGGGGTGAGTCTG | 399 | ```
          AAG  C
CAGACTCATC   CTT TGT
||||||||||   ||| |||
GTCTGAGTGG   GAA AGA
          GG_  _
``` |
| GAM23 | 469 | SYNGR1 | 3' | AGGGGAGCGATGAGCTG | 86 | ```
   A     AA
CAG CTCATC  GCTTCTCT
||| ||||||  |||||||||
CAG CTCATC  GCTTCTCT
 _          __
``` |
| GAM23 | 474 | UCP2 | 5' | AGAGAAGCTTGATCTTGGAG | 68 | ```
CTC____ATCAAGCTTCTCT
|||     |||||||||||||
GAC     TAGTTCGAAGAGA
   GTTC
``` |
| GAM23 | 470 | BMF | 3' | AGAGGCTGATGTGTCTG | 229 | ```
       T    A
CAGAC   CATCA GCTTCT
|||||   ||||| ||||||
GTCTG   GTAGT CGGAGA
       T     _
``` |
| GAM23 | 472 | BNIP2 | 3' | AGAGAATGTGATGAGTT | 278 | ```
         AGC
GACTCATCA   TTCTCT
|||||||||   ||||||
TTGAGTAGT   AAGAGA
         GT_
``` |
| GAM23 | 472 | DDX33 | 3' | AGAGAAGCCTTGGAATC | 171 | ```
   C  AT
GA TC  CAAG_CTTCTCT
|| ||  |||| |||||||||
CT AG  GTTC GAAGAGA
 A  ___    C
``` |

| GENE | G-SEQID | TARGET | UTR | SEQUENCE | T-SEQID | BINDING SITE |
|---|---|---|---|---|---|---|
| GAM23 | 475 | EML4 | 3' | AGAAACTTTGGATGAGTT | 168 | ``` C<br>GACTCATC AAG TTCT<br>|||||||| ||| ||||<br>TTGAGTAG TTC AAGA<br>         GT  A ``` |
| GAM23 | 471 | EPB41L4 | 3' | AGAGAAGAAATGGGTCT | 187 | ``` CAAG<br>AGACTCAT    CTTCTCT<br>||||||||    |||||||<br>TCTGGGTA    GAAGAGA<br>        AA__ ``` |
| GAM23 | 469 | FLJ11588 | 5' | AGAGAAGCAGAACGGCCTG | 199 | ``` A  CA AA<br>CAG CT TC  GCTTCTCT<br>||| || ||  |||||||<br>GTC GG AG  CGAAGAGA<br>  C CA A_ ``` |
| GAM23 | 471 | FLJ20150 | 3' | AGAGAAGCCTGTGGCT | 153 | ``` A T  T  A<br>AG C CA CA GCTTCTCT<br>|| | || || |||||||<br>TC G GT GT CGAAGAGA<br>  _  _  _  C ``` |
| GAM23 | 470 | FLJ20507 | 3' | AGTGTTGATGAGGCTG | 154 | ``` A         G T<br>CAG CTCATCAA C TCT<br>||| |||||||| | |||<br>GTC GAGTAGTT G AGA<br>  G         _ T ``` |
| GAM23 | 470 | FLJ20507 | 3' | AGATGTTGATGAGGCTG | 261 | ``` A         G T<br>CAG CTCATCAA C TCT<br>||| |||||||| | |||<br>GTC GAGTAGTT G AGA<br>  G         _ T ``` |
| GAM23 | 469 | FLJ20972 | 3' | AGAGAAGCAGTTGGCATCTG | 205 | ``` C_   TCAA<br>CAGA TCA    GCTTCTCT<br>||||  |||    |||||||<br>GTCT GGT    CGAAGAGA<br>    AC TGA_ ``` |
| GAM23 | 472 | FLJ22233 | 3' | AGAGAAGCTAGAAGTC | 204 | ``` CA  A<br>GACT TC AGCTTCTCT<br>|||| || |||||||||<br>CTGA AG TCGAAGAGA<br>   __  A ``` |
| GAM23 | 469 | FLJ23191 | 3' | AGAGAAGTTGTGACCTG | 198 | ``` AC   CA<br>CAG  TCAT AGCTTCTCT<br>|||  |||| |||||||||<br>GTC  AGTG TTGAAGAGA<br>  C_     __ ``` |
| GAM23 | 469 | FLJ23468 | 5' | AGAGAAACCAGCTGAGTCTG | 200 | ``` TCAA<br>CAGACTCA    GCT    TCTCT<br>||||||||    |||    |||||<br>GTCTGAGT    CGA    AGAGA<br>        ____   CCAA ``` |
| GAM23 | 471 | GIT2 | 3' | AGAGAAGCATCAGTCT | 133 | ``` C  CAA<br>AGACT AT  GCTTCTCT<br>||||| ||  |||||||<br>TCTGA TA  CGAAGAGA<br>     C  ___ ``` |
| GAM23 | 471 | GIT2 | 3' | AGAGAAGCATCAGTCT | 231 | ``` C  CAA<br>AGACT AT  GCTTCTCT<br>||||| ||  |||||||<br>TCTGA TA  CGAAGAGA<br>     C  ___ ``` |
| GAM23 | 471 | GIT2 | 3' | AGAGAAGCATCAGTCT | 232 | ``` C  CAA<br>AGACT AT  GCTTCTCT<br>||||| ||  |||||||<br>TCTGA TA  CGAAGAGA<br>     C  ___ ``` |

| GENE | G-SEQID | TARGET | UTR | SEQUENCE | T-SEQID | BINDING SITE |
|---|---|---|---|---|---|---|
| GAM23 | 471 | GRID1 | 3' | AGAGAAGCCTAGGTGGGCT | 285 | `    A       AA`<br>`AG CTCATC   GCTTCTCT`<br>`|| ||||||   ||||||||`<br>`TC GGGTGG   CGAAGAGA`<br>`      ATC` |
| GAM23 | 473 | GT650 | 3' | AAGCTTTCTATGAGTTTG | 230 | `         C`<br>`CAGACTCAT  AAGCTT`<br>`|||||||||  ||||||`<br>`GTTTGAGTA  TTCGAA`<br>`     TCT` |
| GAM23 | 470 | IKKE | 3' | AGGACTGTGAGTCTG | 124 | `         CA  C`<br>`CAGACTCAT AG TTCT`<br>`||||||||| || ||||`<br>`GTCTGAGTG TC AGGA` |
| GAM23 | 472 | KIAA0254 | 5' | AGAGGACCGCGATGAGTC | 131 | `        AA`<br>`GACTCATC  GC  TTCTCT`<br>`||||||||  ||  ||||||`<br>`CTGAGTAG  CG  AGGAGA`<br>`              CC` |
| GAM23 | 469 | KIAA1026 | 3' | AGAGAAGCTGCCTCAGTCTG | 292 | `      CATCA`<br>`CAGACT     AGCTTCTCT`<br>`||||||     |||||||||`<br>`GTCTGA     TCGAAGAGA`<br>`      CTCCG` |
| GAM23 | 472 | KIAA1163 | 3' | AGAGAAGCATGTCTGAGTT | 331 | `      T  A`<br>`GACTCA  CA GCTTCTCT`<br>`||||||  || |||||||||`<br>`TTGAGT  GT CGAAGAGA`<br>`      CT  A` |
| GAM23 | 470 | KIAA1598 | 3' | AGAAGCTTCTGTTTTGGGTCTG | 161 | `         TC`<br>`CAGACTCA    AAGCTTCT`<br>`||||||||    ||||||||`<br>`GTCTGGGT    TTCGAAGA`<br>`     TTTGTC` |
| GAM23 | 470 | KIAA1853 | 3' | AGAAGCAATGGGTCTG | 287 | `         CAA`<br>`CAGACTCAT    GCTTCT`<br>`|||||||||    ||||||`<br>`GTCTGGGTA    CGAAGA`<br>`         A` |
| GAM23 | 472 | LOXL4 | 3' | AGAGAAGCTGGTGGATC | 213 | `   CT    A`<br>`GA  CATCA GCTTCTCT`<br>`||  ||||| |||||||||`<br>`CT  GTGGT CGAAGAGA`<br>`AG` |
| GAM23 | 469 | METAP1 | 3' | AGAGAAGCGTGAAGTTTG | 298 | `      CA  A`<br>`CAGACT  TCA GCTTCTCT`<br>`||||||  ||| |||||||||`<br>`GTTTGA  AGT CGAAGAGA`<br>`            G` |
| GAM23 | 472 | MGC11034 | 3' | AGAGAAGCTCTTTGAAGTT | 211 | `      TCA`<br>`GACT CA   AGCTTCTCT`<br>`|||| ||   |||||||||`<br>`TTGA GT   TCGAAGAGA`<br>`   A TTC` |
| GAM23 | 470 | MGC14128 | 3' | AGAAGCTTTGAGAGCCTG | 222 | `    A   A`<br>`CAG CTC TCAA GCTTCT`<br>`||| ||| |||| ||||||`<br>`GTC GAG AGTT CGAAGA`<br>`  C        T` |
| GAM23 | 470 | MGC16175 | 5' | AGAGGCTGTGAGTCTG | 219 | `         CA`<br>`CAGACTCAT  AGCTTCT`<br>`|||||||||  |||||||`<br>`GTCTGAGTG  TCGGAGA` |

-continued

| GENE | G-SEQID | TARGET | UTR | SEQUENCE | T-SEQID | BINDING SITE |
|---|---|---|---|---|---|---|
| GAM23 | 472 | MGC2752 | 5' | AGAGAAGCTCAGTAGAATC | 327 | ```
    C   CA
GA TC AT   AGCTTCTCT
|| || ||   |||||||||
CT AG TG   TCGAAGAGA
   A  A  AC
``` |
| GAM23 | 469 | MGC34923 | 3' | AGAGAAGTAGGAAGAGCCTG | 254 | ```
    A   A  AA
CAG CTC TC   GCTTCTCT
||| ||| ||   ||||||||
GTC GAG AG   TGAAGAGA
 C   A  GA
``` |
| GAM23 | 469 | NR1I3 | 5' | AGAGAAGCAGGAGTCTG | 89 | ```
          ATCAA
CAGACTC        GCTTCTCT
|||||||        ||||||||
GTCTGAG        CGAAGAGA
          GA___
``` |
| GAM23 | 469 | NYD-SP15 | 3' | AGAGAAGAAATATTTGAGTCTG | 208 | ```
         TCAAG__
CAGACTCA        CTTCTCT
||||||||        |||||||
GTCTGAGT        GAAGAGA
         TTATAAA
``` |
| GAM23 | 369 | OSBPL8 | 5' | AGAGAAGTTGGGGTCTG | 177 | ```
          ATCAA
CAGACTC        GCTTCTCT
|||||||        ||||||||
GTCTGGG        TGAAGAGA
          GT___
``` |
| GAM23 | 469 | PLEKHA4 | 5' | AGAGACCCTGTGAGTCTG | 178 | ```
          CA  CT
CAGACTCAT  AG   TCTCT
|||||||||  ||   |||||
GTCTGAGTG  TC   AGAGA
          __  CC
``` |
| GAM23 | 469 | PRKWNK2 | 3' | AGAGATGATTGAGTCTG | 372 | ```
         __  AGCT
CAGACTCA TCA   TCTCT
|||||||| |||   |||||
GTCTGAGT AGT   AGAGA
         T    ____
``` |
| GAM23 | 469 | PSMD4 | 3' | AGGGTAGCTGAGTCTG | 63 | ```
         TCAA  T
CAGACTCA    GCT CTCT
||||||||    ||| ||||
GTCTGAGT    CGA GGGA
         ____  T
``` |
| GAM23 | 469 | RIS1 | 3' | AGAGAAGCTCTTTGTATCTG | 337 | ```
     CT  TCA
CAGA   CA   AGCTTCTCT
||||   ||   |||||||||
GTCT   GT   TCGAAGAGA
     AT  TTC
``` |
| GAM23 | 469 | RNF24 | 3' | AGAGGAGTGGATGAGCCTG | 114 | ```
    A      AA
CAG CTCATC   GCTTCTCT
||| ||||||   ||||||||
GTC GAGTAG   TGAGGAGA
 C       G_
``` |
| GAM23 | 469 | SNURF | 3' | AGAAAAGCGGGTTTTGGGTCTG | 96 | ```
        TCAA__   C
CAGACTCA       GCTT TCT
||||||||       |||| |||
GTCTGGGT       CGAA AGA
        TTTGGG   A
``` |
| GAM23 | 469 | SULT4A1 | 3' | AGAGAAGCTTGTGTTTTG | 284 | ```
     CT  T
CAGA   CA CAAGCTTCTCT
||||   || |||||||||||
GTTT   GT GTTCGAAGAGA
     TT   _
``` |
| GAM23 | 469 | SV2B | 3' | AGAGAATTGTGTGAGTCTG | 135 | ```
         __  GC
CAGACTCAT CAA  TTCTCT
||||||||| |||  ||||||
GTCTGAGTG GTT  AAGAGA
         T   __
``` |

-continued

| GENE | G-SEQID | TARGET | UTR | SEQUENCE | T-SEQID | BINDING SITE |
|------|---------|--------|-----|----------|---------|--------------|
| GAM23 | 469 | SZF1 | 5' | AGAGAAGCCTAGATATCTG | 147 | ```
     CTC    AA_
CAGA    ATC    GCTTCTCT
||||    |||    ||||||||
GTCT    TAG    CGAAGAGA
   A__    ATC
``` |
| GAM23 | 469 | TLR10 | 5' | AGAGAGGGTATTGAGTCTG | 210 | ```
           TCAAG
CAGACTCA         CTTCTCT
||||||||         |||||||
GTCTGAGT         GGAGAGA
           TATG_
``` |
| GAM23 | 472 | ZNF185 | 3' | AGAGGAGCTTGTGAATC | 111 | ```
   C   T
GA TCA CAAGCTTCTCT
|| ||| |||||||||||
CT AGT GTTCGAGGAGA
   A   _
``` |
| GAM23 | 470 | LOC113612 | 3' | AGAAGGATGAGTTTG | 300 | ```
           AAG
CAGACTCATC    CTTCT
||||||||||    |||||
GTTTGAGTAG    GAAGA
           ___
``` |
| GAM23 | 472 | LOC133539 | 3' | AGAGAAGCCCAGGATGGTC | 312 | ```
    T    AA__
GAC CATC    GCTTCTCT
||| ||||    ||||||||
CTG GTAG    CGAAGAGA
    _    GACC
``` |
| GAM23 | 469 | LOC139221 | 5' | AGAGAAGCACATGACCTG | 313 | ```
    AC   CAA
CAG   TCAT   GCTTCTCT
|||   ||||   ||||||||
GTC   AGTA   CGAAGAGA
    C_   CA_
``` |
| GAM23 | 473 | LOC142941 | 3' | AAGTTTATTGTAATGAGTCTG | 345 | ```
CAGACTCAT   CAA    GCTT
|||||||||   |||    ||||
GTCTGAGTA   GTT    TGAA
          AT    ATT
``` |
| GAM23 | 469 | LOC145717 | 5' | AGAGAGTGGGGGTGAGTCTG | 279 | ```
           AA_   T
CAGACTCATC    GCT CTCT
||||||||||    ||| ||||
GTCTGAGTGG    TGA GAGA
           GGG   _
``` |
| GAM23 | 469 | LOC147229 | 3' | AGAGAAGCTGGCAAGAGCTG | 325 | ```
    A   ATCA_
CAG CTC       AGCTTCTCT
||| |||       |||||||||
GTC GAG       TCGAAGAGA
    _   AACGG
``` |
| GAM23 | 472 | LOC147658 | 3' | AGAAAAGTTTGAAGTC | 326 | ```
     CA         C
GACT   TCAAGCTT TCT
||||   |||||||| |||
CTGA   AGTTTGAA AGA
     __         A
``` |
| GAM23 | 471 | LOC147920 | 3' | AGAGAAGCCTGAGGAATTT | 328 | ```
   C  A  A
AGA TC TCA GCTTCTCT
||| || ||| ||||||||
TTT AG AGT CGAAGAGA
   A  G  C
``` |
| GAM23 | 469 | LOC148894 | 5' | AGAGAAGCTCCGTGGGCCTG | 347 | ```
    A    CA
CAG CTCAT   AGCTTCTCT
||| |||||   |||||||||
GTC GGGTG   TCGAAGAGA
    C    CC
``` |
| GAM23 | 469 | LOC150606 | 3' | AGAGAAGCTGGGTGATCTG | 349 | ```
     C     C
CAGA TCATC AGCTTCTCT
|||| ||||| |||||||||
GTCT AGTGG TCGAAGAGA
     _     G
``` |

| GENE | G-SEQID | TARGET | UTR | SEQUENCE | T-SEQID | BINDING SITE |
|------|---------|--------|-----|----------|---------|--------------|
| GAM23 | 472 | LOC150606 | 3' | AGAGAAGCTTGTGGTC | 350 | <pre>    T  T            
GAC CA CAAGCTTCTCT
||| || |||||||||||
CTG GT GTTCGAAGAGA
 -   -           </pre> |
| GAM23 | 471 | LOC152220 | 3' | AGAGTATTTCTTGATGAATTT | 351 | <pre>    C          CTT__    
AGA TCATCAAG    CTCT
||| ||||||||    ||||
TTT AGTAGTTC    GAGA
 A            TTTAT </pre> |
| GAM23 | 469 | LOC155382 | 3' | AGAGAAGCTGCAGGAGCTG | 356 | <pre>  A     ATCA           
CAG CTC     AGCTTCTCT
||| |||     |||||||||
GTC GAG     TCGAAGAGA
  _     GACG         </pre> |
| GAM23 | 471 | LOC157621 | 3' | AGAGGGCGAAATGAGTCT | 358 | <pre>         CAA   T      
AGACTCAT    GCT CTCT
||||||||    ||| ||||
TCTGAGTA    CGG GAGA
         AAG    _    </pre> |
| GAM23 | 469 | LOC161528 | 5' | AGAGAGTGGGGGTGAGTCTG | 342 | <pre>            AA_  T    
CAGACTCATC   GCT CTCT
||||||||||   ||| ||||
GTCTGAGTGG   TGA GAGA
            GGG   _   </pre> |
| GAM23 | 469 | LOC197114 | 5' | AGAGAAGCCCGAGGGGGCTG | 369 | <pre>  A   A  AA          
CAG CTC TC GCTTCTCT
||| ||| || |||||||||
GTC GGG AG CGAAGAGA
  G   G  CC          </pre> |
| GAM23 | 472 | LOC199883 | 3' | AGAAAGGCGGTGAGTC | 370 | <pre>        AA     C    
GACTCATC  GCTT TCT
||||||||  |||| |||
CTGAGTGG  CGGA AGA
  __            A    </pre> |
| GAM23 | 472 | LOC200020 | 3' | AGAAAGGCGGTGAGTC | 371 | <pre>        AA     C    
GACTCATC  GCTT TCT
||||||||  |||| |||
CTGAGTGG  CGGA AGA
  __            A    </pre> |
| GAM23 | 472 | LOC200226 | 3' | AGAGAAGCTCGTGAATGTT | 365 | <pre>     __  CA          
GAC  TCAT AGCTTCTCT
|||  |||| |||||||||
TTG  AGTG TCGAAGAGA
      TA  C_         </pre> |
| GAM23 | 469 | LOC204820 | 5' | AGAGAAGCCAGGCCAGCTG | 373 | <pre>  A  CA AA          
CAG CT TC  GCTTCTCT
||| || ||  |||||||||
GTC GA GG  CGAAGAGA
 _    CC AC          </pre> |
| GAM23 | 472 | LOC219392 | 5' | AGAGAAATCCTAGATGAGTC | 377 | <pre>        A   C__     
GACTCATC AG   TTCTCT
|||||||| ||   ||||||
CTGAGTAG TC   AAGAGA
          A  CTA     </pre> |
| GAM23 | 471 | LOC219800 | 3' | AGAGAAGCTTGGGAGCCT | 389 | <pre>   A  A               
AG CTC TCAAGCTTCTCT
|| ||| ||||||||||||
TC GAG GGTTCGAAGAGA
    C     _          </pre> |
| GAM23 | 469 | LOC220753 | 5' | AGAGAAGCCAGAGGTGTG | 388 | <pre>   G  CA AA          
CA ACT TC  GCTTCTCT
|| ||| ||  |||||||||
GT TGG AG  CGAAGAGA
   G   __  AC        </pre> |

| GENE | G-SEQID | TARGET | UTR | SEQUENCE | T-SEQID | BINDING SITE |
|---|---|---|---|---|---|---|
| GAM23 | 469 | LOC220776 | 3' | AGAGGGGTGATGATAAACTG | 283 | ``` AC      AA<br>CAG  TCATC  GCTTCTCT<br>|||  |||||  ||||||||<br>GTC  AGTAG  TGGGGAGA<br>    AAAT ``` |
| GAM23 | 469 | LOC221454 | 5' | AGAGAAGATGAAAGTTTG | 382 | ``` CA     AG<br>CAGACT  TCA  CTTCTCT<br>||||||  |||  |||||||<br>GTTTGA  AGT  GAAGAGA<br>  A     A ``` |
| GAM23 | 472 | LOC222444 | 3' | AGAGAAGCCCAGGATGGTC | 392 | ``` T    AA<br>GAC CATC   GCTTCTCT<br>||| ||||   ||||||||<br>CTG GTAG   CGAAGAGA<br>  _  GACC ``` |
| GAM23 | 469 | LOC222962 | 3' | AGAGGGGAGGTAAGTCTG | 387 | ``` C      AAG<br>CAGACT ATC   CTTCTCT<br>|||||| |||   |||||||<br>GTCTGA TGG   GGGGAGA<br>  A     AA ``` |
| GAM23 | 469 | LOC245727 | 5' | AGAGAGTGGGGGTGAGTCTG | 376 | ``` AA    T<br>CAGACTCATC   GCT CTCT<br>||||||||||   ||| ||||<br>GTCTGAGTGG   TGA GAGA<br>      GGG ``` |
| GAM23 | 469 | LOC253525 | 5' | AGAGAAGCTGCAGGTTTG | 401 | ``` CATCA<br>CAGACT    AGCTTCTCT<br>||||||    |||||||||<br>GTTTGG    TCGAAGAGA<br>  ACG ``` |
| GAM23 | 469 | LOC254249 | 5' | AGAGAAGTTTGTAAATTTG | 397 | ``` CTCAT<br>CAGA   CAAGCTTCTCT<br>||||   |||||||||||<br>GTTT   GTTTGAAGAGA<br>  AAAT ``` |
| GAM23 | 469 | LOC255475 | 5' | AGAGAAGCCGAGCTCTG | 403 | ```      ATCAA<br>CAGA CTC   GCTTCTCT<br>|||| |||   ||||||||<br>GTCT GAG   CGAAGAGA<br>  C   C ``` |
| GAM23 | 476 | LOC51026 | 3' | AGAACCCTTGATGAGACT | 146 | ``` A          C<br>AG CTCATCAAG  TTCT<br>|| |||||||||  ||||<br>TC GAGTAGTTC  AAGA<br>  A          CC ``` |
| GAM23 | 470 | LOC91308 | 5' | AGAAGAGATGAGTTTG | 274 | ``` AAG<br>CAGACTCATC   CTTCT<br>||||||||||   |||||<br>GTTTGAGTAG   GAAGA<br>     A ``` |
| GAM24 | 523 | CASP10 | 3' | ATACAACCTGATGTCATATTCCATTTTGGA | 223, 524 | ``` C       C   A      III<br>TG GA   AC  CAG TTGTA  T<br>|| ||   ||  ||| |||||  |<br>AC CT   TG  GTC AACAT  A<br>     TATAC  TA   C    III ``` |
| GAM24 | 523 | CASP10 | 3' | ATACAACCTGATGTCATATTCCATTTTGGA | 223, 524 | ``` C       C   A      III<br>TG GA   AC  CAG TTGTA  T<br>|| ||   ||  ||| |||||  |<br>AC CT   TG  GTC AACAT  A<br>     TATAC  TA   C    III ``` |
| GAM24 | 477 | CHRNB3 | 5' | TTGGGTTCCACTTCGGA | 49 | ``` A  A  C<br>TCC AA TG GAACCCAG<br>||| || || ||||||||<br>AGG TT AC CTTGGGTT<br>  C  C ``` |

-continued

| GENE | G-SEQID | TARGET | UTR | SEQUENCE | T-SEQID | BINDING SITE |
|------|---------|--------|-----|----------|---------|--------------|
| GAM24 | 478 | LANCL1 | 3' | TACAATCTGGACTTGGTA | 100 | ```
    G  C_
TGC AA   CCAGATTGTA
||| ||   ||||||||||
ATG TT   GGTCTAACAT
    G  CA
``` |
| GAM24 | 479 | MS4A3 | 3' | ACATCTGGGTTCAAATTCTG | 101 | ```
     A  GC         T
CA AAT  GAACCCAGAT GT
|| |||  |||||||||| ||
GT TTA  CTTGGGTCTA CA
    C  AA            _
``` |
| GAM24 | 480 | SLC1A4 | 3' | TACAATTGTCCCAGTTCGCAT | 64 | ```
         CCA___
ATGCGAAC    GATTGTA
||||||||    |||||||
TACGCTTG    TTAACAT
         ACCCTG
``` |
| GAM24 | 25 | ALLC | 5' | TACAAGGATTTCGCATTCTGGG | 162 | ```
    A       C_ AGA
TCCA AATGCGAA CC   TTGTA
|||| ||||||||| ||   |||||
GGGT TTACGCTT  GG   AACAT
    C         TA ___
``` |
| GAM24 | 477 | APOL6 | 3' | CTGGGTTCACATTTTGGA | 206 | ```
         C
TCCAAAATG GAACCCAG
||||||||| ||||||||
AGGTTTTAC CTTGGGTC
         A
``` |
| GAM24 | 477 | CBX6 | 3' | TTGGGCTCCATTCTGGA | 128 | ```
    A    C  A
TCCA AATG GA CCCAG
|||| |||| || |||||
AGGT TTAC CT GGGTT
    C  _  C
``` |
| GAM24 | 477 | FLJ10055 | 3' | TTGGGAGTCCCATTTTGGA | 156 | ```
         C  A_
TCCAAAATG GA   CCCAG
||||||||| ||   |||||
AGGTTTTAC CT   GGGTT
         C  GA
``` |
| GAM24 | 481 | FLJ22059 | 5' | CAGTCTGGACCAGCACCTTGGA | 191 | ```
     AA  GAAC
TCCAA TGC    CCAGATTG
||||| |||    ||||||||
AGGTT ACG    GGTCTGAC
     CC  ACCA
``` |
| GAM24 | 477 | KCNH8 | 3' | TTGGGTTCACATTCTGGA | 252 | ```
    A    C
TCCA AATG GAACCCAG
|||| |||| ||||||||
AGGT TTAC CTTGGGTT
    C    A
``` |
| GAM24 | 477 | KIAA0870 | 3' | TTGGGTCTGCATTTGGA | 339 | ```
              A
TCCAAAATGCG ACCCAG
||||||||||| ||||||
AGGTTTTACGT TGGGTT
              C
``` |
| GAM24 | 482 | KIAA1157 | 3' | ACAGTATTCCATTTTGGA | 296 | ```
         C  CCCAG
TCCAAAATG GAA    ATTGT
||||||||| |||    |||||
AGGTTTTAC CTT    TGACA
    _         A____
``` |
| GAM24 | 483 | PRO1048 | 3' | ACAATGAGTTTGCATTTT | 163 | ```
              C  GA
AAAATGCGAAC CA   TTGT
||||||||||| ||   ||||
TTTTACGTTTG GT   AACA
              A  __
``` |
| GAM24 | 479 | PRO1787 | 3' | ACAATTCCGCATTTTG | 165 | ```
             AACCCA
CAAAATGCG    GATTGT
|||||||||    ||||||
GTTTTACGC    TTAACA
             C_____
``` |

-continued

| GENE | G-SEQID | TARGET | UTR | SEQUENCE | T-SEQID | BINDING SITE |
|---|---|---|---|---|---|---|
| GAM24 | 484 | UBE2G1 | 3' | TACAGATGATTACGCATTTTG | 67 | ``` AACC  GA<br>CAAAATGCG   CA   TTGTA<br>|||||||||   ||   |||||<br>GTTTTACGC   GT   GACAT<br>            ATTA  A_ ``` |
| GAM24 | 25 | LOC122402 | 3' | TACTTCTTGGTTCACATTTTGGA | 306 | ``` C      C   TT<br>TCCAAAATG GAACC AGA  GTA<br>||||||||| ||||| |||  |||<br>AGGTTTTAC CTTGG TCT  CAT<br>          A     T    T_ ``` |
| GAM24 | 485 | LOC153592 | 3' | GGAATTCAGCATTTTGGA | 355 | ``` _    C_<br>TCCAAAATGC GAA   CC<br>|||||||||| |||   ||<br>AGGTTTTACG CTT   GG<br>           A     AA ``` |
| GAM24 | 482 | LOC256158 | 5' | ACAATCTGAACGTCTGGG | 404 | ``` AAAT     AACC<br>TCCA    GCG    CAGATTGT<br>||||    |||    ||||||||<br>GGGT    TGC    GTCTAACA<br>C____   AA__ ``` |
| GAM25 | 486 | ITGA5 | 3' | CTCAGATCCAGGGACAGAGG | 264 | ``` GTTAGA    A_<br>TCTCTG      CC   GATCTGAG<br>||||||      ||   ||||||||<br>GGAGAC      GG   CTAGACTC<br>     AG____    AC ``` |
| GAM25 | 487 | SF3B3 | 3' | GCTCTAGAATCTAACCAGA | 116 | ``` CCAGA  _<br>TCTGGTTAGA    TCT GAGC<br>||||||||||    ||| ||||<br>AGACCAATCT    AGA CTCG<br>          A_____ T ``` |
| GAM25 | 487 | SLC4A4 | 3' | GCTCAGAGTTGTTAACCAGA | 71 | ``` AC    A<br>TCTGGTTAG  CAG TCTGAGC<br>|||||||||  ||| |||||||<br>AGACCAATT  GTT AGACTCG<br>   ___      G ``` |
| GAM25 | 486 | ZNF180 | 3' | CTCAGACCTGAATCAGAGA | 120 | ``` AGAC    A<br>TCTCTGGTT    CAG TCTGAG<br>|||||||||    ||| ||||||<br>AGAGACTAA    GTC AGACTC<br>         ____     C ``` |
| GAM25 | 487 | AP1G2 | 5' | GCCCAGGCACGCCCGACCAGAGA | 233 | ``` AGACCAGA     A<br>TCTCTGGTT       TCTG GC<br>|||||||||       |||| ||<br>AGAGACCAG       GGAC CG<br>         CCCGCAC_   C ``` |
| GAM25 | 488 | BCL2L1 | 3' | GCCCAGATCTGGTCCCTTGCAG | 241 | ``` GTTA_          A<br>CTG     GACCAGATCTG GC<br>|||     |||||||||||| ||<br>GAC     CTGGTCTAGAC CG<br>   GTTCC            C ``` |
| GAM25 | 486 | FLJ25012 | 5' | CTCAGATCTGAAAAGCACAAGA | 250 | ``` C       AGAC<br>TCT TG GTT    CAGATCTGAG<br>||| || |||    ||||||||||<br>AGA AC CGA    GTCTAGACTC<br>  _    A    AAA_ ``` |
| GAM25 | 489 | FLJ31952 | 3' | CAAATCTGGTTCTGAAAG | 253 | ``` GG    _        C<br>CT  TTAGA CCAGAT TG<br>||  ||||| |||||| ||<br>GA  AGTCT GGTCTA AC<br>A_      T      A ``` |
| GAM25 | 490 | MDS025 | 3' | CTCAGACCTGGTTTGAGATAGA | 184 | ``` G_        A<br>TCTG  TTAGACCAG TCTGAG<br>||||  ||||||||| ||||||<br>AGAT  AGTTTGGTC AGACTC<br>  AG            C ``` |

-continued

| GENE | G-SEQID | TARGET | UTR | SEQUENCE | T-SEQID | BINDING SITE |
|---|---|---|---|---|---|---|
| GAM25 | 487 | MGC32043 | 3' | GCTCAGATCTGATGCTTCAAGA | 249 | <pre>    GGTT  AC_<br>TCT    AG   CAGATCTGAGC<br>|||    ||   |||||||||||<br>AGA    TC   GTCTAGACTCG<br>   ACT_ GTA</pre> |
| GAM25 | 486 | MSI2 | 3' | CTCCCCATCCCAACCAGAGA | 245 | <pre>         AGACCA    CT_<br>TCTCTGGTT      GAT  GAG<br>|||||||||      |||  |||<br>AGAGACCAA      CTA  CTC<br>         CC____    CCC</pre> |
| GAM25 | 487 | ZNF271 | 5' | GCTCAGATCTGGTTAAACATCAGAGA | 395 | <pre>        __   A<br>TCTCTG GTT GACCAGATCTGAGC<br>|||||| ||| |||||||||||||<br>AGAGAC CAA TTGGTCTAGACTCG<br>       TA  A</pre> |
| GAM25 | 487 | LOC144508 | 5' | GCTCAGATCCATGTGCCAGGGA | 362 | <pre>        TAGACCA<br>TCTCTGGT       GATCTGAGC<br>||||||||       |||||||||<br>AGGGACCG       CTAGACTCG<br>        TGTAC__</pre> |
| GAM25 | 486 | LOC145845 | 3' | CTCAAATCCCACCAGAGA | 346 | <pre>         TAGACCA   C<br>TCTCTGGT       GAT TGAG<br>||||||||       ||| ||||<br>AGAGACCA       CTA ACTC<br>         CC____   A</pre> |
| GAM26 | 491 | CDH19 | 3' | GAAAATTTAAAGGAGCAA | 182 | <pre>    A_<br>TTGC  CTTTAAATTTTC<br>||||  ||||||||||||<br>AACG  GAAATTTAAAAG<br>    AG</pre> |
| GAM26 | 492 | CRYGS | 5' | TGGGAAAACCAGTCTATGCACCAA | 152 | <pre>       T   CTTTAAA_<br>TTGGT GCA          TTTTCCCA<br>||||| |||          ||||||||<br>AACCA CGT          AAAAGGGT<br>    _    ATCTGACC</pre> |
| GAM26 | 493 | CYP1B1 | 3' | GAAAATTGAAAAGTACAACTAA | 33 | <pre>       C    A_<br>TTGGTTG ACTTT  AATTTTC<br>||||||| |||||  |||||||<br>AATCAAC TGAAA  TTAAAAG<br>       A    AG</pre> |
| GAM26 | 494 | GLI3 | 3' | GGAAAAAAGACTGCAACCAA | 35 | <pre>         C   AAA<br>TTGGTTGCA TTT   TTTTCC<br>||||||||| |||   ||||||<br>AACCAACGT AGA   AAAAGG<br>         C   AA_</pre> |
| GAM26 | 493 | PCLO | 3' | GAAGATAATGCAACCAA | 391 | <pre>         CTTTAA<br>TTGGTTGCA      ATTTTC<br>|||||||||      ||||||<br>AACCAACGT      TAGAAG<br>         AA____</pre> |
| GAM26 | 492 | PPP2R5A | 3' | TGGGAAAGTAAACCAA | 102 | <pre>      GC   TAAATTT<br>TTGGTT ACTT       TCCCA<br>|||||| ||||       |||||<br>AACCAA TGAA       AGGGT<br>      A_        _____</pre> |
| GAM26 | 492 | PTER | 3' | TGAGAAAATTTAAAGTGTTTCTAG | 207 | <pre>    TT              C<br>TTGG  GCACTTTAAATTTTC CA<br>||||  |||||||||||||||| ||<br>GATC  TGTGAAATTTAAAAG GT<br>    TT              A</pre> |
| GAM26 | 495 | RFX5 | 3' | GGGAAAAGCAGTAAACCAA | 39 | <pre>      GC   TTAAA<br>TTGGTT ACT      TTTTCCC<br>|||||| |||      |||||||<br>AACCAA TGA      AAAAGGG<br>      A_  CG___</pre> |

| GENE | G-SEQID | TARGET | UTR | SEQUENCE | T-SEQID | BINDING SITE |
|---|---|---|---|---|---|---|
| GAM26 | 494 | CSMD1 | 3' | GGAGTATTAAAGTGGAACCAA | 301 | ```
       G        ATT
TTGGTT CACTTTAA    TTCC
|||||| ||||||||    ||||
AACCAA GTGAAATT    GAGG
       G        AT_
``` |
| GAM26 | 493 | MGC15438 | 3' | GAAAGAAAGCGCAGCCAA | 220 | ```
         A    AAA
TTGGTTGC CTTT    TTTTC
|||||||| ||||    |||||
AACCGACG GAAA    GAAAG
         C
``` |
| GAM26 | 494 | NYD-SP18 | 3' | GGAGAAAACTGCAACCAA | 217 | ```
         C   AAAT
TTGGTTGCA TTT    TTTCC
||||||||| |||    |||||
AACCAACGT AAA    AGAGG
         C
``` |
| GAM26 | 494 | OLFM3 | 3' | GGAAAAATAATGTAACCAA | 340 | ```
         C  TAAA
TTGGTTGCA TT     TTTTCC
||||||||| ||     ||||||
AACCAATGT AA     AAAAGG
         _  TA__
``` |
| GAM26 | 495 | RPL13A | 3' | GGGAAGATGCACAACCAA | 115 | ```
       CACTTTAA
TTGGTTG         ATTTTCCC
|||||||         ||||||||
AACCAAC         TAGAAGGG
       ACG_____
``` |
| GAM26 | 496 | LOC129452 | 3' | AGAATGGACAAGCGCAACCAA | 310 | ```
         A   TAA_
TTGGTTGC CTT     ATTTT
|||||||| |||     |||||
AACCAACG GAA     TAAGA
         C   CAGG
``` |
| GAM26 | 494 | LOC150197 | 3' | GGATTAAAGTGGAACCAA | 335 | ```
       G        ATTT
TTGGTT CACTTTAA     TCC
|||||| ||||||||     |||
AACCAA GTGAAATT     AGG
       G        ____
``` |
| GAM26 | 494 | LOC162239 | 3' | GGAAATTATAAATGGCAACCAA | 344 | ```
         AC    AAT
TTGGTTGC  TTTA    TTTCC
||||||||  ||||    |||||
AACCAACG  AAAT    AAAGG
         GT    ATT
``` |
| GAM26 | 496 | LOC219972 | 3' | GAAATGGCAAGTGCAACCAA | 379 | ```
            TAA
TTGGTTGCACTT    ATTTT
||||||||||||    |||||
AACCAACGTGAA    TAAAG
            CGG
``` |
| GAM27 | 497 | DDX6 | 3' | ATTGTGACAAGAATTGTTACC | 80 | ```
   C    CCC  C
GG AACGA   CT GTCACAAT
|| |||||   || ||||||||
CC TTGTT   GA CAGTGTTA
   A    AA_  A
``` |
| GAM27 | 498 | LOC126917 | 3' | GCAGTGGGTCTGTTGCCA | 309 | ```
       _       C
TGGCAAC GACCC CT GT
||||||| ||||| || ||
ACCGTTG CTGGG GA CG
       T       T  _
``` |
| GAM27 | 499 | LOC170395 | 3' | TATTGTTTCTGGGTGTTGCCA | 316 | ```
       G    CTCGTC
TGGCAAC ACCC      ACAATA
||||||| ||||      ||||||
ACCGTTG TGGG      TGTTAT
       _    TCTT__
``` |
| GAM28 | 500 | ABCC3 | 3' | TGCCCCTGGCTGTGCTCTAC | 170 | ```
    C  A   T
GTG AG ACA CCAGGGGCA
||| || ||| |||||||||
CAT TC TGT GGTCCCCGT
    C  G   C
``` |

-continued

| GENE | G-SEQID | TARGET | UTR | SEQUENCE | T-SEQID | BINDING SITE |
|---|---|---|---|---|---|---|
| GAM28 | 500 | CASP3 | 3' | TGCCCCTGGATCTACCAGCAT | 225 | ``` AGAAC_ GTGC        ATCCAGGGGCA ||||        ||||||||||| TACG        TAGGTCCCCGT ACCATC ``` |
| GAM28 | 500 | CASP3 | 3' | TGCCCCTGGATCTACCAGCAT | 79 | ``` AGAAC_ GTGC        ATCCAGGGCA ||||        |||||||||| TACG        TAGGTCCCGT ACCATC ``` |
| GAM28 | 501 | EMS1 | 3' | CCCTGGATCCTCACACTA | 90 | ``` CA  AC TAGTG  GA  ATCCAGGG |||||  ||  |||||||| ATCAC  CT  TAGGTCCC A_  CC ``` |
| GAM28 | 501 | EMS1 | 3' | CCCTGGATCCTCACACTA | 240 | ``` CA  AC TAGTG  GA  ATCCAGGG |||||  ||  |||||||| ATCAC  CT  TAGGTCCC A_  CC ``` |
| GAM28 | 500 | MLLT2 | 3' | TGCCCCTGGACATGTTCCTAC | 97 | ``` CA      __ GTG  GAACA  TCCAGGGGCA |||  |||||  |||||||||| CAT  TTTGT  AGGTCCCCGT CC      AC ``` |
| GAM28 | 502 | TACC1 | 3' | TGCCCCCAGATGTTCCTGGGCTG | 104 | ``` G    _   CA TAGT CAG AACATC  GGGCA |||| ||| ||||||  ||||| GTCG GTC TTGTAG  CCCCGT G    _     AC ``` |
| GAM28 | 503 | TNFSF6 | 3' | CCAGGTGTTCTACACTCA | 42 | ``` T    C       CA A AGTG AGAACATC  GG | ||||  ||||||||  || A TCAC TCTTGTGG  CC C    A       A_ ``` |
| GAM28 | 504 | UBB | 3' | TGGCATTACTCTGCACTATA | 166 | ``` AC_  __CCA TATAGTGCAGA   AT CCA |||||||||||   || ||| ATATCACGTAT   TA GGT CAT  C ``` |
| GAM28 | 505 | AKAP10 | 3' | TGCCCCTTTGGAATTCTGCACT | 113 | ``` CA    __ AGTGCAGGA  TCCA   GGGCA |||||||||  ||||   |||||| TCACGTCTT  AGGT   CCCCGT A_     TT ``` |
| GAM28 | 506 | DECR2 | 3' | GCCCCTCTGTCTCTGCAC | 176 | ``` _   TCC GTGCAGA ACA   AGGGGC |||||||  |||   ||||| CACGTCT  TGT   TCCCCG C    C__ ``` |
| GAM28 | 507 | KIAA0240 | 3' | GCCCCTGTGTCCACTA | 383 | ``` CA  A  TC TAGTG  GA CA  CAGGGGC |||||  || ||  ||||||| ATCAC  CT GT  GTCCCCG C_  _   __ ``` |
| GAM28 | 506 | MGC16385 | 5' | GCCCCTGGACGTTTCTGCCGC | 255 | ``` _     _A GTG  CAGAA  C  TCCAGGGGC |||  |||||  |  |||||||||| CGC  GTCTT  G  AGGTCCCCG C     T C ``` |
| GAM28 | 508 | MGC5139 | 5' | GCCCCTGGGCACACTGTA | 305 | ``` CAGAACA TATAGTG       TCCAGGGGC |||||||       ||||||||| ATGTCAC       GGGTCCCCG AC_____ ``` |

-continued

| GENE | G-SEQID | TARGET | UTR | SEQUENCE | T-SEQID | BINDING SITE |
|------|---------|--------|-----|----------|---------|--------------|
| GAM28 | 509 | P5-1 | 3' | CCCCTGGATGCCCCTAACCACT | 110 | ```
    C___  AA__
AGTG   AG    CATCCAGGGG
||||   ||    ||||||||||
TCAC   TC    GTAGGTCCCC
    CAA   CCC
``` |
| GAM28 | 510 | TED | 3' | CCCCTGGGCCCTGCCTA | 143 | ```
    A    AACA
TAG GCAG    TCCAGGGG
||| ||||    ||||||||
ATC CGTC    GGGTCCCC
        CC__
``` |
| GAM28 | 502 | LOC133418 | 3' | TGCTCTAAAGCTCTGCACTA | 311 | ```
            ACATCCA
TAGTGCAGA          GGGGCA
|||||||||          ||||||
ATCACGTCT          TCTCGT
         CGAAA__
``` |
| GAM28 | 511 | LOC152402 | 3' | GCCCTTACATTCTGCACT | 353 | ```
            CATCC
AGTGCAGAA        AGGGC
|||||||||        |||||
TCACGTCTT        TTCCCG
         ACA__
``` |
| GAM28 | 512 | LOC158677 | 3' | TGCCCCTGGATATCAGCAATATA | 360 | ```
     G   A  AC
TATA TGC GA  ATCCAGGGGCA
|||| ||| ||  |||||||||||
ATAT ACG CT  TAGGTCCCGT
     A   A  A_
``` |
| GAM28 | 501 | LOC221715 | 3' | CCACTGTGCTTGCACTA | 390 | ```
         AA  TC  __
TAGTGCAG  CA  CAG GG
||||||||  ||  ||| ||
ATCACGTT  GT  GTC CC
        C_ __   A
``` |
| GAM28 | 504 | LOC254746 | 3' | TGGCATTACTCTGCACTATA | 394 | ```
           AC__     __
TATAGTGCAGA    AT CCA
|||||||||||    || |||
ATATCACGTCT    TA GGT
           CAT  C
``` |
| GAM28 | 502 | LOC255098 | 3' | TGCTCTAAAGCTCTGCACTA | 396 | ```
            ACATCCA
TAGTGCAGA          GGGGCA
|||||||||          ||||||
ATCACGTCT          TCTCGT
         CGAAA__
``` |
| GAM29 | 513 | ADAM19 | 3' | CTGATGGAGATGCTCAAGGC | 228 | ```
        AG       TATGG
GCCTT  GCATCTCC       CAG
|||||  ||||||||       |||
CGGAA  CGTAGAGG       GTC
    CT         TA___
``` |
| GAM29 | 514 | LFG | 3' | TGCCACAGGCCTAAGGCT | 319 | ```
           ATCTC  A
AGCCTTAGGC     CT TGGCA
||||||||||     || |||||
TCGGAATCCG     GA ACCGT
              _____  C
``` |
| GAM29 | 515 | NOLA2 | 5' | GGAAGTGATGCCTAAAGCT | 393 | ```
    C
AGC TTAGGCATC__ TCC
||| |||||||||   |||
TCG AATCCGTAG   AGG
    A         TGA
``` |
| GAM29 | 514 | FLJ10751 | 3' | CCAGAGACACCTGAGGC | 158 | ```
          CA   CTA
GCCTTAGG   TCTC    TGG
||||||||   ||||    |||
CGGAGTCC   AGAG    ACC
        AC      ____
``` |
| GAM29 | 514 | FLJ10751 | 3' | CCAGAGACACCTGAGGC | 159 | ```
          CA   CTA
GCCTTAGG   TCTC    TGG
||||||||   ||||    |||
CGGAGTCC   AGAG    ACC
        AC      ____
``` |

-continued

| GENE | G-SEQID | TARGET | UTR | SEQUENCE | T-SEQID | BINDING SITE |
|------|---------|--------|-----|----------|---------|--------------|
| GAM29 | 513 | FLJ10925 | 5' | CTGCCCCCAGGGACACCTAAGGC | 160 | ``` CA  T    AT_ GCCTTAGG  TC CCT    GGCAG ||||||||  || |||    ||||| CGGAATCC  AG GGA    CCGTC AC   _    CCC ``` |
| GAM29 | 517 | KIAA1118 | 3' | GTGGTTGAGATGCCCACGGCT | 289 | ``` TTA        CT  G AGCC    GGCATCTC  AT GC ||||    ||||||||  || || TCGG    CCGTAGAG  TG TG CAC        T   G ``` |
| GAM29 | 518 | KIAA1649 | 3' | CTGCCATTTCTGTGCCTAGGCT | 215 | ``` T       CTCCT AGCCT AGGCAT     ATGGCAG ||||| ||||||     ||||||| TCGGA TCCGTG     TACCGTC            TCTT_ ``` |
| GAM29 | 513 | LILMR | 3' | CTGCCATCTGCTGCCTAGGC | 157 | ``` T      TCTCCT GCCT AGGCA     ATGGCAG |||| |||||     ||||||| CGGA TCCGT     TACCGTC  _        CGTC__ ``` |
| GAM29 | 516 | MGC14161 | 5' | CCAGAGAGATGCCCAAAGGC | 221 | ``` A         CTA GCCTT GGCATCTC    TGG ||||| ||||||||    ||| CGGAA CCGTAGAG    ACC A           AG_ ``` |
| GAM29 | 519 | NJMU-R1 | 3' | CATGAAGAAATGCCTGAAGC | 188 | ``` C           C  C_ GC TTAGGCAT TC  TATG || ||||||||| ||  |||| CG AGTCCGTA AG  GTAC A           A  AA ``` |
| GAM29 | 518 | SEMA3E | 3' | CTGTTGTGAGAAATGCCCAGGCT | 119 | ``` TA    C  C  TG AGCCT GGCAT TC TA GCAG ||||| ||||| || || |||| TCGGA CCGTA AG GT TGTC C_    A  A  GT ``` |
| GAM29 | 520 | YKT6 | 3' | CTGCCATAGATACCCTAAG | 106 | ``` CATCTC CTTAGG    CTATGGCAG ||||||    ||||||||| GAATCC    GATACCGTC CATA__ ``` |
| GAM29 | 521 | LOC142972 | 5' | GCCACAGGAGATGCCCAAAGC | 271 | ``` C  A           A GC TT GGCATCTCCT TGGC || || |||||||||| |||| CG AA CCGTAGAGGA ACCG A  C           C ``` |
| GAM29 | 514 | LOC143689 | 3' | TGCCATAAGCTCAAGGCT | 318 | ``` AG ATCTCC AGCCTT GC    TATGGCA |||||| ||    ||||||| TCGGAA CG    ATACCGT CT A_____ ``` |
| GAM29 | 522 | LOC148930 | 5' | CCATAGGGAGCCTAAG | 332 | ``` A  T CTTAGGC TC CCTATGG ||||||| || ||||||| GAATCCG AG GGATACC  _       _ ``` |
| GAM29 | 516 | LOC220469 | 3' | CCAAGGGATGCCCAAAGC | 317 | ``` C  A    T  A GC TT GGCATC CCT TGG || || |||||| ||| ||| CG AA CCGTAG GGA ACC A  C    _  _ ``` |
| GAM29 | 519 | LOC253782 | 3' | CATAAGAGCACCTAAGGC | 398 | ``` CAT     C GCCTTAGG CTC TATG |||||||| ||| |||| CGGAATCC GAG ATAC AC_     A ``` |

| GENE | G-SEQID | TARGET | UTR | SEQUENCE | T-SEQID | BINDING SITE |
|---|---|---|---|---|---|---|
| GAM29 | 514 | LOC92078 | 5' | TGCCCAGAGGCCTAAGGCT | 282 | AGCCTTAGGC TCT   A   CCTAT GGCA<br>\|\|\|\|\|\|\|\|\|\| \|\|\|           \|\|\|\|<br>TCGGAATCCG AGA           CCGT |

The invention claimed is:

1. An isolated nucleic acid consisting of 77 up to 120 nucleotides, wherein the nucleic acid comprises the sequence of SEQ ID NO: 14.

2. An isolated nucleic acid wherein the sequence of the nucleic acid consists of the sequence of SEQ ID NO: 14.

3. A vector comprising an HIV nucleic acid insert, wherein the nucleic acid insert consists of the nucleic acid of claim 1 or claim 2, and wherein said vector does not comprise an HIV nucleic acid insert other than the nucleic acid of claim 1 or claim 2.

4. A probe comprising an HIV nucleic acid insert, wherein the nucleic acid insert consists of the nucleic acid of claim 1 or claim 2, and wherein said probe does not comprise an HIV nucleic acid insert other than the nucleic acid of claim 1 or claim 2.

5. An isolated nucleic acid complement of the nucleic acid of claim 1 or claim 2, wherein said isolated nucleic acid complement is identical in length to the nucleic acid of claim 1 or 2.

* * * * *